(12) United States Patent
Myers et al.

(10) Patent No.: US 6,599,916 B2
(45) Date of Patent: Jul. 29, 2003

(54) QUINUCLIDINE-SUBSTITUTED HETEROARYL MOIETIES FOR TREATMENT OF DISEASE

(75) Inventors: Jason K. Myers, Kalamazoo, MI (US); Bruce N. Rogers, Portage, MI (US); Vincent E. Groppi, Jr., Kalamazoo, MI (US); David W. Piotrowski, Portage, MI (US); Alice L. Bodnar, Kalamazoo, MI (US); Eric Jon Jacobsen, Richland, MI (US); Jeffrey W. Corbett, Portage, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/932,299

(22) Filed: Aug. 17, 2001

(65) Prior Publication Data

US 2002/0091135 A1 Jul. 11, 2002

Related U.S. Application Data

(60) Provisional application No. 60/226,652, filed on Aug. 21, 2000, and provisional application No. 60/284,841, filed on Apr. 19, 2001.

(51) Int. Cl.$^7$ ..................... A61K 31/439; C07D 453/02
(52) U.S. Cl. ...................... 514/305; 546/133; 546/135
(58) Field of Search .................. 514/305, 299; 546/133

(56) References Cited

U.S. PATENT DOCUMENTS

| | | | |
|---|---|---|---|
| 3,702,324 A | 11/1972 | Skinner et al. | 260/293.53 |
| 4,605,652 A | 8/1986 | Welstead, Jr. | 514/214 |
| 4,657,911 A | 4/1987 | Imbert et al. | 514/272 |
| 4,721,720 A | 1/1988 | Wootton et al. | 514/304 |
| 4,789,673 A | 12/1988 | Donatsch et al. | 514/214 |
| 4,798,829 A | 1/1989 | King et al. | 514/214 |
| 4,803,199 A | 2/1989 | Donatsch et al. | 514/214 |
| 4,822,795 A | 4/1989 | King | 514/214 |
| 4,835,162 A | 5/1989 | Abood | 514/305 |
| 4,921,982 A | 5/1990 | Cohen et al. | 549/462 |
| 4,988,691 A | 1/1991 | Benelli et al. | 514/214 |
| 5,017,580 A | 5/1991 | Naylor et al. | 514/299 |
| 5,025,022 A | 6/1991 | Naylor et al. | 514/305 |
| 5,039,680 A | 8/1991 | Impoerato et al. | 514/304 |
| 5,057,519 A | 10/1991 | Suberg | 514/282 |
| 5,070,095 A | 12/1991 | Jagdmann, Jr. et al. | 514/305 |
| 5,106,843 A | 4/1992 | Ward et al. | 514/213 |
| 5,175,173 A | 12/1992 | Sun | 514/305 |
| 5,183,822 A | 2/1993 | Van Wijngaarden et al. | 514/305 |
| 5,206,246 A | 4/1993 | Langlois et al. | 514/272 |
| 5,217,975 A | 6/1993 | Wadsworth et al. | 514/299 |
| 5,236,931 A | 8/1993 | Jagdmann et al. | 514/305 |
| 5,237,066 A | 8/1993 | Dorme et al. | 546/133 |
| 5,246,942 A | 9/1993 | Youssefyeh et al. | 514/305 |
| 5,273,972 A | 12/1993 | Jagdmann et al. | 514/210 |
| 5,342,845 A | 8/1994 | Chokai et al. | 514/305 |
| 5,364,863 A | 11/1994 | Cohen et al. | 514/304 |
| 5,510,478 A | 4/1996 | Sabb | 540/585 |
| 5,561,149 A | 10/1996 | Azria et al. | 514/397 |
| 5,624,941 A | 4/1997 | Barth et al. | 514/326 |
| 5,712,270 A | 1/1998 | Sabb | 514/212 |
| 5,837,489 A | 11/1998 | Elliott et al. | 435/69.1 |
| 5,977,144 A | 11/1999 | Meyer et al. | 514/334 |

FOREIGN PATENT DOCUMENTS

| | | | | |
|---|---|---|---|---|
| DE | 3810552 A1 | 10/1989 | | C07D/451/12 |
| EP | 327335 A1 | 8/1989 | | A61K/31/435 |
| EP | 378111 A1 | 7/1990 | | C07D/413/12 |
| EP | 512350 A2 | 11/1992 | | C07D/453/02 |
| FR | 2625678 | 7/1989 | | A61K/31/435 |
| JP | 04-247081 | 9/1992 | | |
| WO | WO 90/14347 | 11/1990 | | C07D/453/02 |
| WO | WO 92/11259 | 7/1992 | | C07D/451/04 |
| WO | WO 92/15579 | 9/1992 | | C07D/451/00 |
| WO | WO 97/30998 | 8/1997 | | C07D/453/02 |
| WO | WO 98/54189 | 12/1998 | | C07D/491/20 |
| WO | WO 00/73431 A2 | 12/2000 | | C12N/15/00 |
| WO | WO 01/36417 A1 | 5/2001 | | C07D/451/04 |
| WO | WO01/60821 A1 | 8/2001 | | C07D/453/02 |

OTHER PUBLICATIONS

Bannon, A. W., et. al., *Science*, "Broad–Spectrum, Non–Opioid Analgesic Activity by Selective Modulation on Neuronal Nicotinic Acetylcholine Receptors." vol. 279, Jan. 2, 1998.

Holladay, Mark W., et. al., *Journal of Medicinal Chemistry* "Neuronal Nicotinic Acetylcholine Receptors as Targets for Drug Discovery" vol. 40, No. 26. Dec. 19, 1997.

Macor, JE. *Bioorganic & Medicinal Chemistry Letters*. "The 5–HT$_3$ Antagonist Tropisetron (ICS 205–930) is a Potent and Selective α7 Nicotinic Receptor Partial Agonist." 11(2001) 319–321.

Kem, William R. *Behavioural Brain Research*. "The brain α7 nicotinic receptor may be an important therapeutic target for the treatment of Alzheimers's disease: studies with DMXBA (GTS–21)." 113 (2000) 169–181.

*Primary Examiner*—Charanjit S. Aulakh
(74) *Attorney, Agent, or Firm*—Mary J. Hosley

(57) ABSTRACT

The invention provides compounds of Formula I:

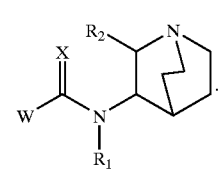

Formula I

These compounds may be in the form of pharmaceutical salts or compositions, and racemic mixtures or pure enantiomers thereof. The compounds of Formula I are useful in pharmaceuticals in which α7 is known to be involved.

52 Claims, No Drawings

QUINUCLIDINE-SUBSTITUTED HETEROARYL MOIETIES FOR TREATMENT OF DISEASE

CROSS REFERENCE TO RELATED APPLICATIONS

This application claims the benefit of U.S. provisional application Ser. No. 60/226,652 filed on Aug. 21, 2000, under 35 USC 119(e)(i) and U.S. provisional application Ser. No. 60/284,841 filed on Apr. 19, 2001, under 35 USC 119(e)(i), which are incorporated herein by reference in their entirety.

FIELD OF INVENTION

Nicotinic acetylcholine receptors (nAChRs) play a large role in central nervous system (CNS) activity. Particularly, they are known to be involved in cognition, learning, mood, emotion, and neuroprotection. There are several types of nicotinic acetylcholine receptors, and each one appears to have a different role in regulating CNS function. Nicotine affects all such receptors, and has a variety of activities. Unfortunately, not all of the activities are desirable. In fact, one of the least desirable properties of nicotine is its addictive nature and the low ratio between efficacy and safety. The present invention relates to molecules that have a greater effect upon the α7 nAChRs as compared to other closely related members of this large ligand-gated receptor family. Thus, the invention provides compounds that are active drug molecules with fewer side effects.

BACKGROUND OF THE INVENTION

U.S. Pat. No. 5,977,144 discloses compositions for benzylidene- and cinnamylidene-anabaseines and methods for using these compositions for treating conditions associated with defects or malfunctioning of nicotinic subtypes brain receptors. These compositions target the α7 receptor subtype with little or no activation of the (x4p2 or other receptor subtypes.

U.S. Pat. No. 5,837,489 discloses human neuronal nicotinic acetylcholine receptor and cells transformed with same DNA and mRNA encoding subunits.

U.S. Pat. No. 5,712,270 discloses a group of 2-aroylaminothiazole derivatives which bind to and stimulate central muscarinic acetylcholine receptors and are useful agents for treating symptoms of cognitive disorders, specifically the impaired memory associated with a decrease in the neurotransmitter, acetylcholine. Some of the compounds of this invention also bind to $5HT_{1A}$ receptors and dopamine $D_2$ receptors, making them useful as antipsychotic agents.

U.S. Pat. No. 5,624,941 discloses pyrazole derivatives useful in pharmaceuticals in which cannabis is known to be involved.

U.S. Pat. No. 5,561,149 discloses the use of a mono or bicyclic carbocyclic, or heterocyclic carboxylic, acid ester or amide or an imidazolyl carbazol in the manufacture of a medicament suitable for the treatment of stress-related psychiatric disorders, for increasing vigilance, for the treatment of rhinitis or serotonin-induced disorders and/or coadministration with another active agent to increase the bioavailability thereof, or for nasal administration.

U.S. Pat. No. 5,510,478 discloses a group of 2-aroylaminothiazole derivatives which bind to and stimulate central muscarinic acetylcholine receptors and are useful agents for treating symptoms of cognitive disorders, specifically the impaired memory associated with a decrease in the neurotransmitter, acetylcholine. Some of the compounds of this invention also bind to 5HTIA receptors and dopamine $D_2$ receptors, making them useful as antipsychotic agents.

U.S. Pat. No. 5,364,863 discloses bicyclic carboxylic esters and amides, their pharmaceutical formulations, and a method for their use in treating migraine, emesis, gastrointestinal disorders, schizophrenia, or anxiety in mammals.

U.S. Pat. No. 5,342,845 discloses indole derivatives and drugs effective as gastrointestinal motor activity regulator, antimigraine, antipsychotic or antianxiety drugs.

U.S. Pat. No. 5,273,972 discloses novel 2-substituted-3-quinuclidinyl arylcarboxamides and arylthiocarboxamides and corresponding arylcarboxylates which have utility as therapeutic agents which exhibit gastric prokinetic, antiemetic, anxiolytic and 5-HT (serotonin) antagonist effects in warm blooded animals.

U.S. Pat. No. 5,246,942 discloses certain dibenzofurancarboxamides and their use as $5\text{-HT}_3$ antagonists having unique CNS, antimetic and gastric prokinetic activity void of any significant $D_2$ receptor binding properties.

U.S. Pat. No. 5,237,066 discloses enantiomers of absolute configuration S of amide derivatives of 3-aminoquinuclidine, the process for preparing them and their use as medicinal products having activity in respect of gastric movements and antiemetic activity.

U.S. Pat. No. 5,236,931 discloses novel 3-quinuclidinyl benzamides and benzoates which have utility as therapeutical agents which exhibit anxiolytic, antipsychotic, cognition improvement, antiemetic and gastric prokinetic effects in warm blooded animals.

U.S. Pat. No. 5,217,975 discloses azabicyclic compounds for treating dementia.

U.S. Pat. No. 5,206,246 discloses anxiolytic-R-N-(1-azabicyclo[2.2.2]oct-3-yl) benzamides and thiobenzamides, their N-oxides and pharmaceutically acceptable salts thereof. A preferred compound is R-(+)-4-amino-N-(1-azabicyclo[2.2.2]oct-3-yl)-5-chloro-2-methoxybenzamide.

U.S. Pat. No. 5,183,822 discloses new heterocyclic compounds (3,4-annelated benzimidazole-2(11)-ones) having an antagonistic activity on 5-hydroxytryptamine (5-HT) receptors.

U.S. Pat. No. 5,175,173 discloses carboxamides useful as antiemetic or antipsychotic agents.

U.S. Pat. No. 5,106,843 discloses heterocyclic compounds useful as 5-1T3 antagonists.

U.S. Pat. No. 5,070,095 discloses novel 1-(azabicyclo [2.2.2]oct-3- or 4-yl)benzamides substituted on the benzene ring with the basic substituted aminomethyleneamino group which have been found to be useful in treating emesis, including emesis due to chemical and radiation anticancer therapy, anxiety, and impaired gastric emptying.

U.S. Pat. No. 5,057,519 discloses $5\text{-HT}_3$ antagonists as being useful in reducing opiate tolerance.

U.S. Pat. No. 5,039,680 discloses $5\text{-HT}_3$ antagonists in preventing or reducing dependency on dependency-inducing agents.

U.S. Pat. No. 5,025,022 discloses a method of treating or preventing schizophrenia and/or psychosis using S-N-(1-azabicyclo[2.2.2]oct-3-yl)benzamides and thiobenzamides, their N-oxides and pharmaceutically acceptable salts thereof. A preferred compound is S(-)-4-amino-N-(1-azabicyclo[2.2.2]oct-3-yl)-5-chloro-2-methoxybenzamide.

U.S. Pat. No. 5,017,580 discloses memory enhancing R-N-(1-azabicyclo[2.2.2]oct-3-yl)benzamides and thiobenzamides, their N-oxides and pharmaceutically acceptable salts thereof. A preferred compound is R-(+)-4-amino-N-(1-azabicyclo[2.2.2]oct-3-yl)-5-chloro-2-methoxybenzamide.

U.S. Pat. No. 4,988,691 discloses isoxazole-containing compounds exhibiting anti-serotonin activity.

U.S. Pat. No. 4,921,982 discloses 5-halo-2,3-dihydro-2,2-dimethylbenzofuran-7-carboxylic acids which are useful as intermediates for 5-HT$_3$ antagonists.

U.S. Pat. No. 4,835,162 discloses agonists and antagonists to nicotine as smoking deterrents.

U.S. Pat. No. 4,822,795 discloses pharmaceutically useful esters and amides having 5-HT$_3$ antagonist activity.

U.S. Pat. No. 4,803,199 discloses pharmaceutically useful heterocyclic acid esters and amides or alkylene bridged peperidines as serotonin M antagonists.

U.S. Pat. No. 4,798,829 discloses 1-azabicyclo[3.2.2] nonane derivatives having gastric motility enhancing activity and/or anti-emetic activity and/or 5-HT receptor antagonist activity.

U.S. Pat. No. 4,789,673 discloses dicarboxylic, heterocyclic and substituted benzoic acid alkylene-bridged piperidyl amides and esters as being serotonin M antagonists.

U.S. Pat. No. 4,721,720 discloses a method of treating emesis, anxiety and/or irritable bowel syndrome.

U.S. Pat. No. 4,657,911 discloses 3-amino quinuclidine derivatives and the application thereof as accelerators of gastrointestinal motor function and as medicament potentiators.

U.S. Pat. No. 4,605,652 discloses a method of enhancing memory or correcting memory deficiency with arylamido (and arylthioamido)-azabicycloalkanes, and the pharmaceutically acceptable acid addition salts, hydrates and alcoholates thereof.

U.S. Pat. No. 3,702,324 discloses 3,4,5-trimethoxybenzamides of substituted anilines and of alkylpiperidines which exert a specific effect on the central nervous system and a somewhat lesser effect on muscle function, and thus have utility as tranquilizers.

WO 01/36417 A1 discloses novel N-azabicyclo-amide derivatives and use in therapy, especially in the treatment of prophylaxis of psychotic disorders and intellectual impairment disorders.

WO 00/73431 A2 discloses two binding assays to directly measure the affinity and selectivity of compounds at the α7 nAChR and the 5-HT$_3$R. The combined use of these functional and binding assays may be used to identify compounds that are selective agonists of the α7 nAChR.

WO 92/15579 discloses multicyclic tertiary amine polyaromatic squalene synthase inhibitors and method of treatment for lowering serum cholesterol levels using the compounds.

WO 92/11259 discloses azabicyclic amides or esters of halogenated benzoic acids having 5-HT$_3$ receptor antagonist activity.

WO 90/14347 A as abstracted in chemical abstract 1991:143, 158 discloses N-quinuclidinyl-indolecarboxamide derivatives as being antiemetics.

EP 512 350 A2 discloses 3-(indolyl-2-carboxamido) quinuclidines useful for treating diseases characterized by an excess or enhanced sensitivity to serotonin, e.g., psychosis, nausea, vomiting, dementia or other cognitive diseases, migraine, diabetes. The compound may be used to control anxiety, aggression, depression, and pain. The compounds are disclosed as serotonin 5-HT$_3$ antagonists DE 3810552 A1 discloses esters and amides of indolyl-, benzo[b]thiophenyl-, benzo[b]furancarboxylic acids or 4-amino-2 methoxy-benzoic acids with N-heterocyclic or N-heterobicyclic alcohols or amines. The compounds disclosed have activity against pain especially migraine, as an anti-arrhythmic for gastrointestinal disturbances, stomach disturbances, gastritis ulcer, gall bladder, spastic colon, Crohn's disease, ulcerative colitis, carcinoid syndrome, diarrhea of various types. The compounds are also disclosed as speeding stomach emptying, controlling gastro duodenal and gastro esophageal reflux, disturbances of esophageal motility, hiatal hernia, cardiac insufficiency, hypotonic stomach, paralytic ileus, manic depressive psychosis and other psychoses. The compounds are also disclosed as useful for stress related diseases, senility, and enhancement of nasal absorption of other agents, e.g., in the treatment of emesis.

FR 2 625 678 discloses N-(quinuclidin-3-yl)-benzamides and thiobenzamides useful as diet-control agents.

In *Bioorg. & Med. Chem. Lett.* 11 (2001) 319–321, the 5-HI3 antagonist tropisetron (ICS 205–930) is discussed as a potent and selective α7 Nicotinic receptor partial agonist.

In *Behavioral Brain Res.*, 113 (2000) 169–181, it is discussed that the brain α7 nicotinic receptor may be an important therapeutic target for the treatment of Alzheimer's disease using DMXBA which is known as GTS-21.

SUMMARY OF THE INVENTION

A compound of Formula I:

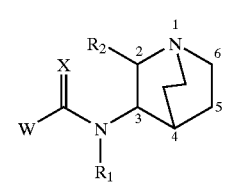

Formula I or pharmaceutically acceptable salts thereof wherein $R_1$ is selected from —H, alkyl, cycloalkyl, halogenated alkyl, or aryl;

Alkyl is both straight and branched-chain moieties having from 1–6 carbon atoms;

Halogenated alkyl is an alkyl moiety having from 1–6 carbon atoms and having 1 to (2n+1) substituent(s) independently selected from —F, —Cl, —Br, or —I where n is the maximum number of carbon atoms in the moiety;

Cycloalkyl is a cyclic alkyl moiety having from 3–6 carbon atoms;

Aryl is phenyl, substituted phenyl, naphthyl, or substituted naphthyl;

Substituted phenyl is a phenyl either having 14 substituents independently selected from —F, —Cl, —Br, or —I, or having 1 substituent selected from —$R_{12}$ and 0–3 substituents independently selected from —F, —Cl, —Br, or —I;

Substituted naphthyl is a naphthalene moiety either having 14 substituents independently selected from —F, —Cl, —Br, or —I, or having 1 substituent selected from —$R_{12}$ and 0–3 substituents independently selected from —F, —Cl, —Br, or —I, where the substitution can be independently on either the same ring or different rings of said naphthalene moiety;

$R_2$ is —H, alkyl, halogenated alkyl, substituted alkyl, cycloalkyl, benzyl, substituted benzyl, or aryl;

Substituted alkyl is an alkyl moiety having from 1–6 carbon atoms and having 0–3 substituents independently selected from —F, —Cl, —Br, or —I, and further having 1 substituent selected from —$R_7$, —$R_9$, —$OR_{10}$, —$SR_{10}$, —$NR_{10}R_{10}$, —$C(O)R_{10}$, —$NO_2$, —$C(O)NR_{10}R_{10}$, —CN, —$NR_{10}C(O)R_{10}$, —$S(O)_2NR_{10}R_{10}$, —$NR_{10}S(O)_2R_{10}$, phenyl, or substituted phenyl;

Substituted benzyl is a benzyl either having 1–4 substituents independently selected from —F, —Cl, —Br, or —I, or having 1 substituent selected from —$R_{12}$ and 0–3 substituents independently selected from —F, —Cl, —Br, or —I, provided that all substitution is on the phenyl ring of the benzyl;

X is O or S;

W is a cyclic heteroaromatic moiety where the heteroatoms can be from 1–3 atoms selected from oxygen, sulfur, or nitrogen of the following structures:

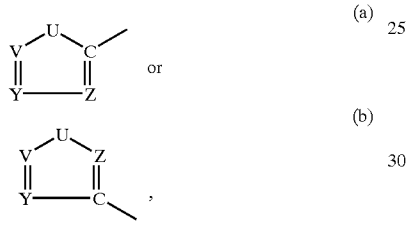

wherein U is —O—, —S—, or —N($R_3$)—;

V and Y are independently selected from =N—, or =C($R_5$)—;

Z is =N—, or =CH—, provided that when both V and Y are =C($R_5$)—and Z is =CH—, only one =C($R_5$)— can be =CH—, and further provided that when U is —O—, Y is =C($R_5$)—and Z is =C($R_5$)—, V cannot be =N—, $R_3$ is —H, alkyl, cycloalkyl, heterocycloalkyl, halogenated alkyl, halogenated cycloalkyl, halogenated heterocycloalkyl, substituted alkyl, limited substituted alkyl, substituted cycloalkyl, substituted heterocycloalkyl, or aryl, and provided that when W is (b) and Z is =N— and U is N($R_3$), $R_3$ cannot be phenyl or substituted phenyl;

Limited substituted alkyl is a substituted alkyl having from 1–6 carbon atoms and having 0–3 substituents independently selected from —F, —Cl, —Br, or —I, and further having 1 substituent on either only the ω carbon and selected from —$OR_{11}$, —$SR_{11}$, —$NR_{11}R_{11}$, —$C(O)R_{11}$, —$NO_2$, —$C(O)NR_{11}R_{11}$, —CN, —$NR_{10}C(O)R_{11}$, —$S(O)_2NR_{10}R_{10}$, or —$NR_{10}S(O)_2R_{10}$, or on any carbon with sufficient valency but not on the ω carbon and selected from —$R_7$, —$R_9$, —$OR_{10}$, —$SR_{10}$, —$NR_{10}R_{10}$, —$C(O)R_{10}$, —$NO_2$, —$C(O)NR_{10}R_{10}$, —CN, —$NR_{10}C(O)R_{10}$, —$S(O)_2NR_{10}R_{10}$, —$NR_{10}S(O)_2R_{10}$, phenyl, or substituted phenyl;

Alkenyl is straight and branched-chain moieties having from 2–6 carbon atoms and having at least one carbon—carbon double bond;

Halogenated alkenyl is an unsaturated alkenyl moiety having from 2–6 carbon atoms and having 1 to (2n–1) substituent(s) independently selected from —F, —Cl, —Br, or —I where n is the maximum number of carbon atoms in the moiety;

Substituted alkenyl is an unsaturated alkenyl moiety having from 2–6 carbon atoms and having 0–3 substituents independently selected from —F, or —Cl, and further having 1 substituent selected from —$R_7$, —$R_9$, —$OR_{10}$, —$SR_{10}$, —$NR_{10}R_{10}$, —$C(O)R_{10}$, —$C(O)NR_{10}R_{10}$, —CN, —$NR_{10}C(O)R_{10}$, —$S(O)_2NR_{10}R_{10}$, —$NR_{10}S(O)_2R_{10}$, phenyl, or substituted phenyl;

Alkynyl is straight and branched-chain moieties having from 2–6 carbon atoms and having at least one carbon—carbon triple bond;

Halogenated alkynyl is an unsaturated alkynyl moiety having from 3–6 carbon atoms and having 1 to (2n–3) substituent(s) independently selected from —F, —Cl, —Br, or —I where n is the maximum number of carbon atoms in the moiety;

Substituted alkynyl is an unsaturated alkynyl moiety having from 3–6 carbon atoms and having 0–3 substituents independently selected from —F, or —Cl, and further having 1 substituent selected from —$R_7$, —$R_9$, —$OR_{10}$, —$SR_{10}$, —$NR_{10}R_{10}$, —$C(O)R_{10}$, —CN, —$C(O)NR_{10}R_{10}$, —$NR_{10}C(O)R_{10}$, —$S(O)_2NR_{10}R_{10}$, —$NR_{10}S(O)_2R_{10}$, phenyl, or substituted phenyl;

Halogenated cycloalkyl is a cyclic moiety having from 3–6 carbon atoms and having 14 substituents independently selected from —F, or —Cl;

Substituted cycloalkyl is a cyclic moiety having from 3–6 carbon atoms and having 0–3 substituents independently selected from —F, or —Cl, and further having 1 substituent selected from —$OR_{10}$, —$SR_{10}$, —$NR_{10}R_{10}$, —$C(O)R_{10}$, —$C(O)NR_{10}R_{10}$, —CN, —$NR_{10}C(O)R_{10}$, —$S(O)_2NR_{10}R_{10}$, —$NR_{10}S(O)_2R_{10}$, —$NO_2$, phenyl, or substituted phenyl;

Heterocycloalkyl is a cyclic moiety having 4–7 atoms with 1–2 atoms within the ring being —S—, —N($R_3$)—, or —O—;

Halogenated heterocycloalkyl is a cyclic moiety having from 4–7 atoms with 1–2 atoms within the ring being —S—, —N($R_3$)—, or —O—, and having 14 substituents independently selected from —F, or —Cl;

Substituted heterocycloalkyl is a cyclic moiety having from 4–7 atoms with 1–2 atoms within the ring being —S—, —N($R_3$)—, or —O— and having 0–3 substituents independently selected from —F, or —Cl, and further having 1 substituent selected from —$OR_{10}$, —$SR_{10}$, —$NR_{10}R_{10}$, —$C(O)R_{10}$, —$C(O)NR_{10}R_{10}$, —CN, —$NR_{10}C(O)R_{10}$, —$NO_2$, —$S(O)_2NR_{10}R_{10}$, —$NR_{10}S(O)_2R_{10}$, phenyl, or substituted phenyl;

$R_5$ is independently selected from the group consisting of —H, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, limited substituted alkyl, limited substituted alkenyl, limited substituted alkynyl, aryl, —$OR_8$, —$OR_{14}$, —$SR_8$, —$SR_{14}$, —F, —Cl, —Br, —I, —$NR_8R_8$, —$NR_{14}R_{14}$, —$C(O)R_8$, —$C(O)R[_4$, —$C(O)NR_8R_8$, —$C(O)NR_{14}R_{14}$, —CN, —$NR_8C(O)R_{11}$, —$S(O)_2NR_8R_8$, —$OS(O)_2R_{11}$, —$S(O)_2R_9$, —$S(O)_2R_{14}$, —$NR_8S(O)_2R_8$, —N(H)C(O)N(H)$R_8$, —$NO_2$, —$R_7$, and —$R_9$;

Limited substituted alkenyl is a substituted alkenyl having from 1–6 carbon atoms and having 0–3 substituents independently selected from —F, —Cl, —Br, or 4, and further having 1 substituent on either only the ω carbon and selected from —OR$_{11}$, —SR$_{11}$, —NR$_{11}$R$_{11}$, —C(O)R$_{11}$, —NO$_2$, —C(O)NR$_{11}$R$_{11}$, —CN, —NR$_{10}$C(O)R$_{11}$, —S(O)$_2$NR$_{10}$R$_{10}$, or —NR$_{10}$S(O)$_2$R$_{10}$, or on any carbon with sufficient valency but not on the ω carbon and selected from —R$_7$, —R$_9$, —OR$_{10}$, —SR$_{10}$, —NR$_{10}$R$_{10}$, —C(O)R$_{10}$, —NO$_2$, —C(O)NR$_{10}$R$_{10}$, —CN, —NR$_{10}$C(O)R$_{10}$, —S(O)$_2$NR$_{10}$R$_{10}$, —NR$_{10}$S(O)$_2$R$_{10}$, phenyl, or substituted phenyl;

Limited substituted alkynyl is a substituted alkynyl having from 1–6 carbon atoms and having 0–3 substituents independently selected from —F, —Cl, —Br, or —I, and further having 1 substituent on either only the (carbon and selected from —OR$_{11}$, —SR$_{11}$, —NR$_{11}$R$_{11}$, —C(O)R$_{11}$, —NO$_2$, —C(O)NR$_{11}$R$_{11}$, —CN, —NR$_{10}$C(O)R$_{11}$, —S(O)$_2$NR$_{10}$R$_{10}$, or —NR$_{10}$S(O)$_2$R$_{10}$, or on any carbon with sufficient valency but not on the ω carbon and selected from —R$_7$, —R$_9$, —OR$_{10}$, —SR$_{10}$, —NR$_{10}$R$_{10}$, —C(O)R$_{10}$, —NO$_2$, —C(O)NR$_{10}$R$_{10}$, —CN, —NR$_{10}$C(O)R$_{10}$, —S(O)$_2$NR$_{10}$R$_{10}$, —NR$_{10}$S(O)$_2$R$_{10}$, phenyl, or substituted phenyl;

R$_7$ is 5-membered heteroaromatic mono-cyclic moieties containing within the ring 1–3 heteroatoms independently selected from the group consisting of —O—, =N—, —N(R$_3$)—, and —S—, and having 0–1 substituent selected from —R$_{12}$ and 0–3 substituents independently selected from —F, —Cl, —Br, or —I, or R$_7$ is a 9-membered fused-ring moiety having a 6-membered ring fused to a 5-membered ring and having the formula

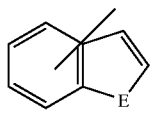

wherein E is O, S, or NR$_3$,

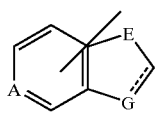

wherein E and G are independently selected from CR$_{18}$, O, S, or NR$_3$, and A is CR$_{18}$ or N, or

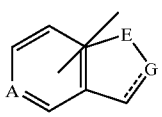

wherein E and G are independently selected from CR$_{81}$, O, S, or NR$_3$, and A is CR$_{18}$ or N, each 9-membered fused-ring moiety having 0–1 substituent selected from —R$_{12}$ and 0–3 substituent(s) independently selected from —F, —Cl, —Br, or —I, and having a bond directly or indirectly attached to the core molecule where valency allows in either the 6-membered or the 5-membered ring of the fused-ring moiety;

Each R$_8$ is independently selected from —H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, —R$_7$, —R$_9$, phenyl, or substituted phenyl;

R$_9$ is 6-membered heteroaromatic mono-cyclic moieties containing within the ring 1–3 heteroatoms selected from =N— and having 0–1 substituent selected from —R$_{12}$ and 0–3 substituent(s) independently selected from —F, —Cl, —Br, or —I, or 10-membered heteroaromatic bi-cyclic moieties containing within one or both rings 1–3 heteroatoms selected from =N—, including, but not limited to, quinolinyl or isoquinolinyl, each 10-membered fused-ring moiety having 0–1 substituent selected from —R$_{12}$ and 0–3 substituent(s) independently selected from —F, —Cl, —Br, or —I, and having a bond directly or indirectly attached to the core molecule where valency allows;

Each R$_{10}$ is independently selected from —H, alkyl, cycloalkyl, heterocycloalkyl, alkyl substituted with 1 substituent selected from R$_{13}$, cycloalkyl substituted with 1 substituent selected from R$_{13}$, heterocycloalkyl substituted with 1 substituent selected from R$_{13}$, halogenated alkyl, halogenated cycloalkyl, halogenated heterocycloalkyl, phenyl, substituted phenyl, —R$_7$, or —R$_9$;

Each R$_{11}$ is independently selected from —H, alkyl, cycloalkyl, heterocycloalkyl, halogenated alkyl, halogenated cycloalkyl, or halogenated heterocycloalkyl;

R$_{12}$ is selected from —OR$_{11}$, —SR$_{11}$, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —NR$_{11}$R$_{11}$, —C(O)R$_{11}$, —NO$_2$, —C(O)NR$_{11}$R$_{11}$, —CN, —NR$_{11}$C(O)R$_{11}$, —S(O)$_2$NR$_{11}$R$_{11}$, or —NR$_{11}$S(O)$_2$R$_{11}$;

R$_{13}$ is selected from —OR$_{11}$, —SR$_{11}$, —NR$_{11}$R$_{11}$, —C(O)R$_{11}$, —C(O)NR$_{11}$R$_{11}$, —CN, —NR$_{11}$C(O)R$_{11}$, —S(O)$_2$NR$_{11}$R$_{11}$, —NR$_{11}$S(O)$_2$R$_{11}$, —CF$_3$, or —NO$_2$;

R$_{14}$ is independently selected from —H, alkyl, halogenated alkyl, limited substituted alkyl, cycloalkyl, halogenated cycloalkyl, substituted cycloalkyl, heterocycloalkyl, halogenated heterocycloalkyl, substituted heterocycloalkyl; and Each R$_{18}$ is independently selected from —H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_{11}$, —SR$_{11}$, —NR$_{11}$R$_{11}$, —C(O)R$_{11}$, —NO$_2$, —C(O)NR$_{11}$R$_{11}$, —CN, —NR$_{11}$C(O)R$_{11}$, —S(O)$_2$NR$_{11}$R$_{11}$, or —NR$_{11}$S(O)$_2$R$_{11}$, —F, —Cl, —Br, or —I, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_{11}$, —SR$_{11}$, —NR$_{11}$R$_{11}$, —C(O)R$_{11}$, —NO$_2$, —C(O)NR$_{11}$R$_{11}$, CN, —NR$_{11}$C(O)R$_{11}$, —S(O)$_2$NR$_{11}$R$_{11}$, or —NR$_{11}$S(O)$_2$R$_{11}$, and further provided that the fused-ring moiety has 0–3 substituent(s) selected from —F, —Cl, —Br, or —I.

Compounds of Formula I are useful to treat any one of or combination of cognitive and attention deficit symptoms of Alzheimer's, neurodegeneration associated with diseases such as Alzheimer's disease, pre-senile dementia (mild cognitive impairment), or senile dementia.

DETAILED DESCRIPTION OF THE INVENTION

Surprisingly, we have found that compounds of Formula I:

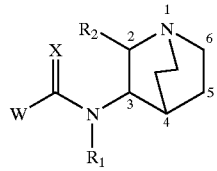

Formula I wherein $R_1$ is selected from —H, alkyl, cycloalkyl, halogenated alkyl, or aryl;

Alkyl is both straight and branched-chain moieties having from 1–6 carbon atoms;

Halogenated alkyl is an alkyl moiety having from 1–6 carbon atoms and having 1 to (2n+1) substituent(s) independently selected from —F, —Cl, —Br, or —I where n is the maximum number of carbon atoms in the moiety;

Cycloalkyl is a cyclic alkyl moiety having from 3–6 carbon atoms;

Aryl is phenyl, substituted phenyl, naphthyl, or substituted naphthyl;

Substituted phenyl is a phenyl either having 14 substituents independently selected from —F, —Cl, —Br, or —I, or having 1 substituent selected from —$R_{12}$ and 0–3 substituents independently selected from —F, —Cl, —Br, or —I;

Substituted naphthyl is a naphthalene moiety either having 14 substituents independently selected from —F, —Cl, —Br, or —I, or having 1 substituent selected from —$R_{12}$ and 0–3 substituents independently selected from —F, —Cl, —Br, or —I, where the substitution can be independently on either the same ring or different rings of said naphthalene moiety;

$R_2$ is —H, alkyl, halogenated alkyl, substituted alkyl, cycloalkyl, benzyl, substituted benzyl, or aryl;

Substituted alkyl is an alkyl moiety having from 1–6 carbon atoms and having 0–3 substituents independently selected from —F, —Cl, —Br, or —I, and further having 1 substituent selected from —$R_7$, —$R_9$, —$OR_{10}$, —$SR_{10}$, —$NR_{10}R_{10}$, —$C(O)R_{10}$, —$NO_2$, —$C(O)NR_{10}R_{10}$, —CN, —$NR_{10}C(O)R_{10}$, —$S(O)_2NR_{10}R_{10}$, —$NR_{10}S(O)_2R_{10}$, phenyl, or substituted phenyl;

Substituted benzyl is a benzyl either having 14 substituents independently selected from —F, —Cl, —Br, or —I, or having 1 substituent selected from —$R_{12}$ and 0–3 substituents independently selected from —F, —Cl, —Br, or —I, provided that all substitution is on the phenyl ring of the benzyl;

X is O or S;

W is a cyclic heteroaromatic moiety where the heteroatoms can be from 1–3 atoms selected from oxygen, sulfur, or nitrogen of the following structures:

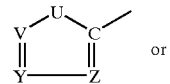 (a)

or

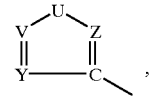 (b)

wherein U is —O—, —S—, or —N($R_3$)—;

V and Y are independently selected from =N—, or =C($R_5$)—;

Z is =N—, or =CH—, provided that when both V and Y are =C($R_5$)— and Z is =CH—, only one =C($R_5$)— can be =CH—, and further provided that when U is —O—, Y is =C($R_5$)— and Z is =C($R_5$)—, V cannot be =N—, $R_3$ is —H, alkyl, cycloalkyl, heterocycloalkyl, halogenated alkyl, halogenated cycloalkyl, halogenated heterocycloalkyl, substituted alkyl, limited substituted alkyl, substituted cycloalkyl, substituted heterocycloalkyl, or aryl, and provided that when W is (b) and Z is =N— and U is N($R_3$), $R_3$ cannot be phenyl or substituted phenyl;

Limited substituted alkyl is a substituted alkyl having from 1–6 carbon atoms and having 0–3 substituents independently selected from —F, —Cl, —Br, or —I, and further having 1 substituent on either only the c carbon and selected from —$OR_{11}$, —$SR_{11}$, —$NR_{11}R_{11}$, —$C(O)R_{11}$, —$NO_2$, —$C(O)NR_{11}R_{11}$, —CN, —$NR_{10}C(O)R_{11}$, —$S(O)_2NR_{10}R_{10}$, or —$NR_{10}S(O)_2R_{10}$, or on any carbon with sufficient valency but not on the X carbon and selected from —$R_7$, —$R_9$, —$OR_{10}$, —$SR_{10}$, —$NR_{10}R_{10}$, —$C(O)R_{10}$, —$NO_2$, —$C(O)NR_{10}R_{10}$, —CN, —$NR_{10}C(O)R_{10}$, —$S(O)_2NR_{10}R_{10}$, —$NR_{10}S(O)_2R_{10}$, phenyl, or substituted phenyl;

Alkenyl is straight and branched-chain moieties having from 2–6 carbon atoms and having at least one carbon—carbon double bond;

Halogenated alkenyl is an unsaturated alkenyl moiety having from 2–6 carbon atoms and having 1 to (2n−1) substituent(s) independently selected from —F, —Cl, —Br, or —I where n is the maximum number of carbon atoms in the moiety;

Substituted alkenyl is an unsaturated alkenyl moiety having from 2–6 carbon atoms and having 0–3 substituents independently selected from —F, or —Cl, and further having 1 substituent selected from —$R_7$, —$R_9$, —$OR_{10}$, —$SR_{10}$, —$NR_{10}R_{10}$, —$C(O)R_{10}$, —$C(O)NR_{10}R_{10}$, —CN, —$NR_{10}C(O)R_{10}$, —$S(O)_2NR_{10}R_{10}$, —$NR_{10}S(O)_2R_{10}$, phenyl, or substituted phenyl;

Alkynyl is straight and branched-chain moieties having from 2–6 carbon atoms and having at least one carbon—carbon triple bond;

Halogenated alkynyl is an unsaturated alkynyl moiety having from 3–6 carbon atoms and having 1 to (2n−3) substituent(s) independently selected from —F, —Cl, —Br, or —I where n is the maximum number of carbon atoms in the moiety;

Substituted alkynyl is an unsaturated alkynyl moiety having from 3–6 carbon atoms and having 0–3 substituents independently selected from —F, or —Cl, and further having 1 substituent selected from —$R_7$, —$R_9$, —OR$_{10}$, —SR$_{10}$, —NR$_{10}$R$_{10}$, —C(O)R$_{10}$, —CN, —C(O)NR$_{10}$R$_{10}$, —NR$_{10}$C(O)R$_{10}$, —S(O)$_2$NR$_{10}$R$_{10}$, —NR$_{10}$S(O)$_2$R$_{10}$, phenyl, or substituted phenyl;

Halogenated cycloalkyl is a cyclic moiety having from 3–6 carbon atoms and having 14 substituents independently selected from —F, or —Cl;

Substituted cycloalkyl is a cyclic moiety having from 3–6 carbon atoms and having 0–3 substituents independently selected from —F, or —Cl, and further having 1 substituent selected from —OR$_{10}$, —SR$_{10}$, —NR$_{10}$R$_{10}$, —C(O)R$_{10}$, —C(O)NR$_{10}$R$_{10}$, —CN, —NR$_{10}$C(O)R$_{10}$, —S(O)$_2$NR$_{10}$R$_{10}$, —NR$_{10}$S(O)$_2$R$_{10}$, —NO$_2$, phenyl, or substituted phenyl;

Heterocycloalkyl is a cyclic moiety having 4–7 atoms with 1–2 atoms within the ring being —S—, —N(R$_3$)—, or —O—;

Halogenated heterocycloalkyl is a cyclic moiety having from 4–7 atoms with 1–2 atoms within the ring being —S—, —N(R$_3$)—, or —O—, and having 14 substituents independently selected from —F, or —Cl;

Substituted heterocycloalkyl is a cyclic moiety having from 4–7 atoms with 1–2 atoms within the ring being —S—, —N(R$_3$)—, or —O— and having 0–3 substituents independently selected from —F, or —Cl, and further having 1 substituent selected from —OR$_{10}$, —SR$_{10}$, —NR$_{10}$R$_{10}$, —C(O)R$_{10}$, —C(O)NR$_{10}$R$_{10}$, —CN, —NR$_{10}$C(O)R$_{10}$, —NO$_2$, —S(O)$_2$NR$_{10}$R$_{10}$, —NR$_{10}$S(O)$_2$R$_{10}$ phenyl, or substituted phenyl;

R$_5$ is independently selected from the group consisting of —H, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, limited substituted alkyl, limited substituted alkenyl, limited substituted alkynyl, aryl, —OR$_8$, —OR$_{14}$, —SR$_8$, —SR$_{14}$, —F, —Cl, —Br, I, —NR$_8$R$_8$, —NR$_{14}$R$_{14}$, —C(O)R, —C(O)R$_{14}$, —C(O)NR$_8$R, C(O)NR$_{14}$R$_{14}$, —CN, —NR$_8$C(O)R$_{11}$, —S(O)$_2$NR$_8$R$_8$, —OS(O)$_2$R$_{11}$, —S(O)$_2$R$_8$, —S(O)$_2$R$_{14}$, —NR$_8$S(O)$_2$R$_8$, —N(H)C(O)N(H)R$_8$, —NO$_2$, —R$_7$, and —R$_9$;

Limited substituted alkenyl is a substituted alkenyl having from 1–6 carbon atoms and having 0–3 substituents independently selected from —F, —Cl, —Br, or —I, and further having 1 substituent on either only the ω carbon and selected from —OR$_{11}$, —SR$_{11}$, —NR$_{11}$R$_{11}$, —C(O)R$_{11}$, —NO$_2$, —C(O)NR$_{11}$R$_{11}$, —CN, —NR$_{10}$C(O)R$_{11}$, —S(O)$_2$NR$_{10}$R$_{10}$, or —NR$_{10}$S(O)$_2$R$_{10}$, or on any carbon with sufficient valency but not on the ω carbon and selected from —R$_7$, —R$_9$, —OR$_{10}$, —SR$_{10}$, —NR$_{10}$R$_{10}$, —C(O)R$_{10}$, —NO$_2$, —C(O)NR$_{10}$R$_{10}$, —CN, —NR$_{10}$C(O)R$_{10}$, —S(O)$_2$NR$_{10}$R$_{10}$, —NR$_{10}$S(O)$_2$R$_{10}$, phenyl, or substituted phenyl;

Limited substituted alkynyl is a substituted alkynyl having from 1–6 carbon atoms and having 0–3 substituents independently selected from —F, —Cl, —Br, or —I, and further having 1 substituent on either only the ω carbon and selected from —OR$_{11}$, —SR$_{11}$, —NR$_{11}$R$_{11}$, —C(O)R$_{11}$, —NO$_2$, —C(O)NR$_{11}$R$_{11}$, —CN, —NR$_{10}$C(O)R$_{11}$, —S(O)$_2$NR$_{10}$R$_{10}$, or —NR$_{10}$S(O)$_2$R$_{10}$, or on any carbon with sufficient valency but not on the ω carbon and selected from —R$_7$, —R$_9$, —OR$_{10}$, —SR$_{10}$, —NR$_{10}$R$_{10}$, —C(O)R$_{10}$, —NO$_2$, —C(O)NR$_{10}$R$_{10}$, —CN, —NR$_{10}$C(O)R$_{10}$, —S(O)$_2$NR$_{10}$R$_{10}$, —NR$_{10}$S(O)$_2$R$_{10}$, phenyl, or substituted phenyl;

R$_7$ is 5-membered heteroaromatic mono-cyclic moieties containing within the ring 1–3 heteroatoms independently selected from the group consisting of —O—, =N—, —N(R$_3$)—, and —S—, and having 0–1 substituent selected from —R$_{12}$ and 0–3 substituents independently selected from —F, —Cl, —Br, or —I, or R$_7$ is a 9-membered fused-ring moiety having a 6-membered ring fused to a 5-membered ring and having the formula

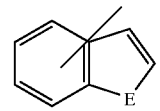

wherein E is O, S, or NR$_3$,

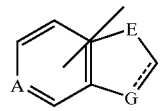

wherein E and G are independently selected from CR$_{18}$, O, S, or NR$_3$, and A is CR$_{18}$ or N, or

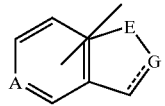

wherein E and G are independently selected from CR$_{18}$, O, S, or NR$_3$, and A is CR$_{18}$ or N, each 9-membered fused-ring moiety having 0–1 substituent selected from —R$_{12}$ and 0–3 substituent(s) independently selected from —F, —Cl, —Br, or —I, and having a bond directly or indirectly attached to the core molecule where valency allows in either the 6-membered or the 5-membered ring of the fused-ring moiety;

Each R$_8$ is independently selected from —H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, —R$_7$, —R$_9$, phenyl, or substituted phenyl;

R$_9$ is 6-membered heteroaromatic mono-cyclic moieties containing within the ring 1–3 heteroatoms selected from =N— and having 0–1 substituent selected from —R$_{12}$ and 0–3 substituent(s) independently selected from —F, —Cl, —Br, or —I, or 10-membered heteroaromatic bi-cyclic moieties containing within one or both rings 1–3 heteroatoms selected from =N—, including, but not limited to, quinolinyl or isoquinolinyl, each 10-membered fused-ring moiety having 0–1 substituent selected from —R$_{12}$ and 0–3 substituent(s) independently selected from —F, —Cl, —Br, or —I and having a bond directly or indirectly attached to the core molecule where valency allows;

Each R$_{10}$ is independently selected from —H, alkyl, cycloalkyl, heterocycloalkyl, alkyl substituted with 1 substituent selected from R$_{13}$, cycloalkyl substituted with 1 substituent selected from R$_{13}$, heterocycloalkyl substituted with 1 substituent selected from R$_{13}$, halogenated alkyl, halogenated cycloalkyl, halogenated heterocycloalkyl, phenyl, substituted phenyl, —R$_7$, or —R$_9$;

Each $R_{11}$ is independently selected from —H, alkyl, cycloalkyl, heterocycloalkyl, halogenated alkyl, halogenated cycloalkyl, or halogenated heterocycloalkyl;

$R_{12}$ is selected from —$OR_{11}$, —$SR_{11}$, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, or —$NR_{11}S(O)_2R_{11}$;

$R_{13}$ is selected from —$OR_{11}$, —$SR_{11}$, —$NR_{11}R_{11}$, —$C(O)R_{11}$, —$C(O)NR_{11}R_{11}$, —CN, —$NR_{11}C(O)R_{11}$, —$S(O)_2NR_{11}R_{11}$, —$NR_{11}S(O)_2R_{11}$, —$CF_3$, or —$NO_2$;

$R_{14}$ is independently selected from —H, alkyl, halogenated alkyl, limited substituted alkyl, cycloalkyl, halogenated cycloalkyl, substituted cycloalkyl, heterocycloalkyl, halogenated heterocycloalkyl, substituted heterocycloalkyl;

Each $R_{18}$ is independently selected from —H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, or —$NR_{11}S(O)_2R_{11}$, —F, —Cl, —Br, or —I, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, or —$NR_{11}S(O)_2R_{11}$, and further provided that the fused-ring moiety has 0–3 substituent(s) selected from —F, —Cl, —Br, or —I; and pharmaceutically acceptable salts are useful to treat any one of or combination of cognitive and attention deficit symptoms of Alzheimer's, neurodegeneration associated with diseases such as Alzheimer's disease, pre-senile dementia (mild cognitive impairment), or senile dementia.

Abbreviations which are well known to one of ordinary skill in the art may be used (e.g., "Ph" for phenyl, "Me" for methyl, "Et" for ethyl, "h" for hour or hours, min for minute or minutes, and "rt" for room temperature).

All temperatures are in degrees Centigrade.

Room temperature is within the range of 15–25 degrees Celsius.

Eq refers to equivalents.

Satd refers to saturated.

ACHR refers to acetylcholine receptor.

"Pre-senile dementia" and "mild cognitive impairment" refer to the same disease state.

nAChR refers to nicotinic acetylcholine receptor.

$5HT_3R$ refers to the serotonin-type 3 receptor.

FLIPR refers to a device marketed by Molecular Devices, Inc. designed to precisely measure cellular fluorescence in a high throughput whole-cell assay. (Schroeder et. al., *J. Biomolecular Screening*, 1(2), p 75–80, 1996).

TLC refers to thin-layer chromatography.

HPLC refers to high pressure liquid chromatography.

MeOH refers to methanol.

EtOH refers to ethanol.

WPA refers to isopropyl alcohol.

THF refers to tetrahydrofuran.

DMSO refers to dimethylsulfoxide.

DMF refers to dimethylformamide.

EtOAc refers to ethyl acetate.

TMS refers to tetramethylsilane.

TEA refers to triethylamine.

HATU refers to O—(7-azabenzotriazol-1-yl)-N,N,N',N'-tetramethyluronium hexafluorophosphate.

DIEA refers to N,N-diisopropylethylamine.

MLA refers to methyllycaconitine.

Ether refers to diethyl ether.

$KH_2PO_4$ refers to potassium phosphate, monobasic.

$NaClO_2$ refers to sodium chlorite.

t-BuOH refers to tert-butanol.

$Na_2SO_4$ refers to sodium sulfate.

$MgSO_4$ refers to magnesium sulfate.

$K_2CO_3$ refers to potassium carbonate.

NHOH refers to ammonium hydroxide.

$NaHCO_3$ refers to sodium bicarbonate.

$CH_3CN$ refers to acetonitrile.

The ω carbon is determined by counting the longest carbon chain of the alkyl moiety with the C-1 carbon being the carbon attached to the W moiety of the core molecule and the a) carbon being the carbon furthest, e.g., separated by the greatest number of carbon atoms in the chain, from said C-1 carbon;

The core molecule is the quinuclidinyl-(carboxamide-type moiety)-W:

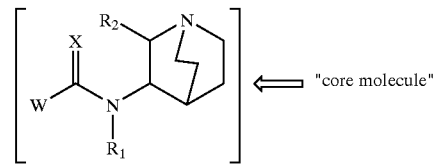  ⇐ "core molecule"

Therefore, when speaking of the ω carbon, the ω carbon is the carbon furthest from the core molecule and the C-1 carbon is the carbon attached to the core molecule by attachment to the W moiety of the core molecule.

One of the most conventionally accepted ways of naming the compound pictured below is 5-(2-aminophenyl)-N-[(3R)-1-azabicyclo[2.2.2]oct-3-yl]thiophene-2-carboxamide, but for one ordinarily skilled in the art, the following name also describes the same compound, N-[(3R)-1-azabicyclo[2.2.2]oct-3-yl]-5-(2-aminophenyl)-thiophene-2-carboxamide:

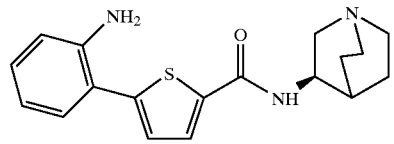

The two are used interchangeably in this patent.

The carbon atom content of various hydrocarbon-containing moieties is indicated by a prefix designating the minimum and maximum number of carbon atoms in the moiety, i.e., the prefix $C_{i-j}$ indicates a moiety of the integer 'i' to the integer "j" carbon atoms, inclusive. Thus, for example, $C_{1-6}$ alkyl refers to alkyl of one to six carbon atoms, inclusive.

Halogen is F, Cl, Br, or I.

Alkyl is both straight and branched-chain moieties having from 1–6 carbon atoms.

Halogenated alkyl is an alkyl moiety having from 1–6 carbon atoms and having 1 to (2n+1) halogen atom(s)

independently selected from —F, —Cl, —Br, or —I where n is the maximum number of carbon atoms in the moiety.

Substituted alkyl is an alkyl moiety having from 1–6 carbon atoms and having 0–3 substituents independently selected from —F, —Cl, —Br, or —I, and further having 1 substituent selected from —$R_7$, —$R_9$, —$OR_{10}$, —$SR_{10}$, —$NR_{10}R_{10}$, —$C(O)R_{10}$, —$NO_2$, —$C(O)NR_{10}R_{10}$, —CN, —$NR_{10}C(O)R_{10}$, —$S(O)_2NR_{10}R_{10}$, —$NR_{10}S(O)_2R_{10}$, phenyl, or substituted phenyl.

Limited substituted alkyl is a substituted alkyl having from 1–6 carbon atoms and having 0–3 substituents independently selected from —F, —Cl, —Br, or —I, and further having 1 substituent on either only the (1 carbon and selected from —$OR_{11}$, —$SR_{11}$, —$NR_{11}R_{11}$, —$C(O)R_{11}$, —$NO_2$, —$C(O)NR_{11}R_{11}$, —CN, —$NR_{10}C(O)R_{11}$, —$S(O)_2NR_{10}R_{10}$, or —$NR_{10}S(O)_2R_{10}$, or on any carbon with sufficient valency but not on the ω carbon and selected from —$R_7$, —$R_9$, —$OR_{10}$, —$SR_{10}$, —$NR_{10}R_{10}$, —$C(O)R_{10}$, —$NO_2$, —$C(O)NR_{10}R_{10}$, —CN, —$NR_{10}C(O)R_{10}$, —$S(O)_2NR_{10}R_{10}$, —$NR_{10}S(O)_2R_{10}$, phenyl, or substituted phenyl.

Alkenyl is straight and branched-chain moieties having from 2–6 carbon atoms and having at least one carbon—carbon double bond.

Halogenated alkenyl is an unsaturated alkenyl moiety having from 2–6 carbon atoms and having 1 to (2n−1) halogen atom(s) independently selected from —F, —Cl, —Br, or —I where n is the maximum number of carbon atoms in the moiety.

Substituted alkenyl is an unsaturated alkenyl moiety having from 2–6 carbon atoms and having 0–3 substituents independently selected from —F, or —Cl, and further having 1 substituent selected from —$R_7$, —$R_8$, —$OR_{10}$, —$SR_{10}$, —$NR_{10}R_{10}$, —$C(O)R_{10}$, —$C(O)NR_{10}R_{10}$, —CN, —$NR_{10}C(O)R_{10}$, —$S(O)_2NR_{10}R_{10}$, —$NR_{10}S(O)_2R_{10}$ phenyl, or substituted phenyl.

Limited substituted alkenyl is a substituted alkenyl having from 1–6 carbon atoms and having 0–3 substituents independently selected from —F, —Cl, —Br, or —I, and further having 1 substituent on either only the (o carbon and selected from —$OR_{11}$, —$SR_{11}$, —$NR_{11}R_{11}$, —$C(O)R_{11}$, —$NO_2$, —$C(O)NR_{11}R_{11}$, —CN, —$NR_{10}C(O)R_{11}$, —$S(O)_2NR_{10}R_{10}$, or —$NR_{10}S(O)_2R_{10}$, or on any carbon with sufficient valency but not on the (carbon and selected from —$R_7$, —$R_9$, —$OR_{10}$, —$SR_{10}$, —$NR_{10}R_{10}$, —$C(O)R_{10}$, —$NO_2$, —$C(O)NR_{10}R_{10}$, —CN, —$NR_{10}C(O)R_{10}$, —$S(O)_2NR_{10}R_{10}$, —$NR_{10}S(O)_2R_{10}$, phenyl, or substituted phenyl.

Alkynyl is straight and branched-chain moieties having from 2–6 carbon atoms and having at least one carbon—carbon triple bond.

Halogenated alkynyl is an unsaturated alkynyl moiety having from 3–6 carbon atoms and having 1 to (2n−3) halogen atom(s) independently selected from —F, —Cl, —Br, or —I where n is the maximum number of carbon atoms in the moiety.

Substituted alkynyl is an unsaturated alkynyl moiety having from 3–6 carbon atoms and having 0–3 substituents independently selected from —F, or —Cl, and further having 1 substituent selected from —$R_7$, —$R_9$, —$OR_{10}$, —$SR_{10}$, —$NR_{10}R_{10}$, —$C(O)R_{10}$, —CN, —$C(O)NR_{10}R_{10}$, —$NR_{10}C(O)R_{10}$, —$S(O)_2NR_{10}R_{10}$, —$NR_{10}S(O)_2R_{10}$, phenyl, or substituted phenyl.

Limited substituted alkynyl is a substituted alkynyl having from 1–6 carbon atoms and having 0–3 substituents independently selected from —F, —Cl, —Br, or —I, and further having 1 substituent on either only the ω carbon and selected from —$OR_{11}$, —$SR_{11}$, —$NR_{11}R_{11}$, —$C(O)R_{11}$, —$NO_2$, —$C(O)NR_{11}R_{11}$, —CN, —$NR_{10}C(O)R_{11}$, —$S(O)_2NR_{10}R_{10}$, or —$NR_{10}S(O)_2R_{10}$, or on any carbon with sufficient valency but not on the (carbon and selected from —$R_7$, —$R_9$, —$OR_{10}$, —$SR_{10}$, —$NR_{10}R_{10}$, —$C(O)R_{10}$, —$NO_2$, —$C(O)NR_{10}R_{10}$, —CN, —$NR_{10}C(O)R_{10}$, —$S(O)_2NR_{10}R_{10}$, —$NR_{10}S(O)_2R_{10}$, phenyl, or substituted phenyl.

Cycloalkyl is a cyclic alkyl moiety having from 3–6 carbon atoms.

Halogenated cycloalkyl is a cyclic moiety having from 3–6 carbon atoms and having 14 substituents independently selected from —F, or —Cl.

Substituted cycloalkyl is a cyclic moiety having from 3–6 carbon atoms and having 0–3 substituents independently selected from —F, or —Cl, and further having 1 substituent selected from —$OR_{10}$, —$SR_{10}$, —$NR_{10}R_{10}$, —$C(O)R_{10}$, —$C(O)NR_{10}R_{10}$, —CN, —$NR_{10}C(O)R_{10}$, —$S(O)_2NR_{10}R_{10}$, —$NR_{10}S(O)_2R_{10}$, —$NO_2$, phenyl, or substituted phenyl.

Heterocycloalkyl is a cyclic moiety having 4–7 atoms with 1–2 atoms within the ring being —S—, —N($R_3$)— or —O—.

Halogenated heterocycloalkyl is a cyclic moiety having from 4–7 atoms with 1–2 atoms within the ring being —S—, —N($R_3$)—, or —O—, and having 14 substituents independently selected from —F, or —Cl.

Substituted heterocycloalkyl is a cyclic moiety having from 4–7 atoms with 1–2 atoms within the ring being —S—, —N($R_3$)—, or —O— and having 0–3 substituents independently selected from —F, or —Cl, and further having 1 substituent selected from —$OR_{10}$, —$SR_{10}$, —$NR_{10}R_{10}$, —$C(O)R_{10}$, —$C(O)NR_{10}R_{10}$, —CN, —$NR_{10}C(O)R_{10}$, —$NO_2$, —$S(O)_2NR_{10}R_{10}$, —$NR_{10}S(O)_2R_{10}$, phenyl, or substituted phenyl.

Substituted benzyl is a benzyl either having 14 substituents independently selected from —F, —Cl, —Br, or —I, or having 1 substituent selected from —$R_{12}$ and 0–3 substituents independently selected from —F, —Cl, —Br, or —I, provided that all substitution is on the phenyl ring of the benzyl.

Aryl is phenyl, substituted phenyl, naphthyl, or substituted naphthyl.

Substituted phenyl is a phenyl either having 14 substituents independently selected from —F, —Cl, —Br, or —I, or having 1 substituent selected from —$R_{12}$ and 0–3 substituents independently selected from —F, —Cl, —Br, or —I.

Substituted naphthyl is a naphthalene moiety either having 14 substituents independently selected from —F, —Cl, —Br, or —I, or having 1 substituent selected from —$R_{12}$ and 0–3 substituents independently selected from —F, —Cl, —Br, or —I, where the substitution can be independently on either the same ring or different rings of said naphthalene moiety.

Mammal denotes human and other mammals.

Compounds of the present invention may be in a form of pharmaceutically acceptable salts.

Brine refers to an aqueous saturated sodium chloride solution.

IR refers to infrared spectroscopy.

Lv refers to leaving groups within a molecule, including Br, Cl, OH, or mixed anhydride.

NMR refers to nuclear (proton) magnetic resonance spectroscopy, chemical shifts are reported in ppm (5) downfield from TMS.

MS refers to mass spectrometry expressed as m/e or mass/charge unit. HRMS refers to high resolution mass spectrometry expressed as m/e or mass/charge unit. $M+H^+$ refers to the positive ion of a parent plus a hydrogen atom. $M-H^-$ refers to the negative ion of a parent minus a hydrogen atom. $M+Na^+$ refers to the positive ion of a parent plus a sodium atom. $M+K^+$ refers to the positive ion of a parent plus a potassium atom. EI refers to electron impact. ESI refers to electrospray ionization. CI refers to chemical ionization. FAB refers to fast atom bombardment.

Compounds of the present invention may be in the form of pharmaceutically acceptable salts. The term "pharmaceutically acceptable salts" refers to salts prepared from pharmaceutically acceptable non-toxic bases including inorganic bases and organic bases, and salts prepared from inorganic acids, and organic acids. Salts derived from inorganic bases include aluminum, ammonium, calcium, ferric, ferrous, lithium, magnesium, potassium, sodium, zinc, and the like. Salts derived from pharmaceutically acceptable organic non-toxic bases include salts of primary, secondary, and tertiary amines, substituted amines including naturally occurring substituted amines, cyclic amines, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and the like. Salts derived from inorganic acids include salts of hydrochloric acid, hydrobromic acid, hydroiodic acid, sulfuric acid, phosphoric acid, phosphorous acid and the like. Salts derived from pharmaceutically acceptable organic non-toxic acids include salts of $C_{1-6}$ alkyl carboxylic acids, di-carboxylic acids, and tri-carboxylic acids such as acetic acid, propionic acid, fumaric acid, succinic acid, tartaric acid, maleic acid, adipic acid, and citric acid, and aryl and alkyl sulfonic acids such as toluene sulfonic acids and the like.

By the term "effective amount" of a compound as provided herein is meant a nontoxic but sufficient amount of the compound(s) to provide the desired effect. As pointed out below, the exact amount required will vary from subject to subject, depending on the species, age, and general condition of the subject, the severity of the disease that is being treated, the particular compound(s) used, the mode of administration, and the like. Thus, it is not possible to specify an exact "effective amount." However, an appropriate effective amount may be determined by one of ordinary skill in the art using only routine experimentation.

The compounds of Formula I have optically active center (s) on the quinuclidine ring. Although it is desirable that the stereochemical purity be as high as possible, absolute purity is not required. This invention involves racemic mixtures and compositions of varying degrees of streochemical purities. It is preferred to carry out stereoselective syntheses and/or to subject the reaction product to appropriate purification steps so as to produce substantially optically pure materials. Suitable stereoselective synthetic procedures for producing optically pure materials are well known in the art, as are procedures for purifying racemic mixtures into optically pure fractions.

The preferred compounds of the present invention have the R configuration at the C3 position of the quinuclidine ring. It is also preferred for the compounds of the present invention that X is O. Another group of compounds of Formula I includes compounds wherein X is O and $R_1$ is H. Another group of compounds of Formula I includes compounds wherein X is O and $R_2$ is H. Another group of compounds of Formula I includes compounds wherein X is O and $R_2$ is alkyl, halogenated alkyl, substituted alkyl, cycloalkyl, benzyl, substituted benzyl, or aryl.

The amount of therapeutically effective compound(s) that is administered and the dosage regimen for treating a disease condition with the compounds and/or compositions of this invention depends on a variety of factors, including the age, weight, sex and medical condition of the subject, the severity of the disease, the route and frequency of administration, and the particular compound(s) employed, and thus may vary widely. The compositions contain well know carriers and excipients in addition to a therapeutically effective amount of compounds of Formula I. The pharmaceutical compositions may contain active ingredient in the range of about 0.001–100 mg/kg/day for an adult, preferably in the range of about 0.1–50 mg/kg/day for an adult. A total daily dose of about 1–1000 mg of active ingredient may be appropriate for an adult. The daily dose can be administered in 14 doses per day.

In addition to the compound(s) of Formula I, the composition for therapeutic use may also comprise one or more non-toxic, pharmaceutically acceptable carrier materials or excipients. The term "carrier" material or "excipient" herein means any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable excipients include lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose, or other methods known to those skilled in the art. For oral administration, the pharmaceutical composition may be in the form of, for example, a tablet, capsule, suspension or liquid. If desired, other active ingredients may be included in the composition.

In addition to the oral dosing, noted above, the compositions of the present invention may be administered by any suitable route, in the form of a pharmaceutical composition adapted to such a route, and in a dose effective for the treatment intended. The compositions may, for example, be administered parenterally, e.g., intravascularly, intraperitoneally, subcutaneously, or intramuscularly. For parenteral administration, saline solution, dextrose solution, or water may be used as a suitable carrier. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The serotonin type 3 receptor ($5HT_3R$) is a member of a superfamily of ligand-gated ion channels, which includes the muscle and neuronal nAChR, the glycine receptor, and the γ-aminobutyric acid type A receptor. Like the other members of this receptor superfamily, the $5HT_3R$ exhibits a large degree of sequence homology with a α7 nAChR but functionally the two ligand-gated ion channels are very different. For example, α7 nAChR is rapidly inactivated, is highly permeable to calcium and is activated by acetylcholine and nicotine. On the other hand, $5HT_3R$ is inactivated slowly, is relatively impermeable to calcium and is activated by serotonin. These experiments suggest that the α7 nAChR and $5HT_3R$ proteins have some degree of homology, but function very differently. Indeed the pharmacology of the channels is very different. For example, Ondansetron, a highly selective $5HT_3R$ antagonist, has little activity at the α7 nAChR. The converse is also true. For example, GTS-21, a highly selective α7 nAChR agonist, has little activity at the $5HT_3R$.

α7 nAChR is a ligand-gated $Ca^{++}$ channel formed by a homopentamer of α7 subunits. Previous studies have established that a-bungarotoxin (α-btx) binds selectively to this homopetameric, α7 nAChR subtype, and that α7 nAChR has a high affinity binding site for both cc-btx and methyllycaconitine (MLA). α7 nAChR is expressed at high levels in the hippocampus, ventral tegmental area and ascending cholinergic projections from nucleus basilis to thalamocortical areas. (x7 nAChR agonists increase neurotransmitter release, and increase cognition, arousal, attention, learning and memory.

Data from human and animal pharmacological studies establish that nicotinic cholinergic neuronal pathways control many important aspects of cognitive function including attention, learning and memory (Levin, E. D., *Psychopharmacology,* 108:417–31, 1992; Levin, E. D. and Simon B. B., Psychopharmacology, 138:217–30, 1998). For example, it is well known that nicotine increases cognition and attention in humans. ABT418, a compound that activates α4β2 and α7 nAChR, improves cognition and attention in clinical trials of Alzheimer's disease and attention-deficit disorders (Potter, A. et. al., *Psychopharmacology (Berl).,* 142(4):33442, Mar. 1999; Wilens, T. E. et. al., *Am. J. Psychiatry,* 156(12):1931–7, Dec. 1999). It is also clear that nicotine and selective but weak α7 nAChR agonists increase cognition and attention in rodents and non-human primates.

Selective α7 nAChR agonists may be found using a functional assay on FLIPR (see WO 00/73431 A2). FLIPR is designed to read the fluorescent signal from each well of a 96 or 384 well plate as fast as twice a second for up to 30 minutes. This assay may be used to accurately measure the functional pharmacology of 0:7 nAChR and $5HT_3R$. To conduct such an assay, one uses cell lines that expressed functional forms of the α7 nAChR using the α7/5-HT3 channel as the drug target and cell lines that expressed functional $5HT_3R$. In both cases, the ligand-gated ion channel was expressed in SH-EP1 cells. Both ion channels can produce robust signal in the FLIPR assay.

The compounds of the present invention are α7 nAChR agonists and may be used to treat a wide variety of diseases. For example, they may be used in treating cognitive and attention deficit symptoms of Alzheimer's, neurodegeneration associated with diseases such as Alzheimer's disease, pre-senile dementia (also known as mild cognitive impairment), and senile dementia.

Alzheimer's disease has many aspects, including cognitive and attention deficits. Currently, these deficits are treated with cholinesterase inhibitors. These inhibitors slow the break down of acetylcholine, and thereby provide a general nonspecific increase in the activity of the cholinergic nervous system. Since the drugs are nonspecific, they have a wide variety of side effects. Thus, there is a need for a drug that stimulates a portion of the cholinergic pathways and thereby provides improvement in the cognitive and attention deficits associated with Alzheimer's disease without the side effects created by nonspecific stimulation of the cholinergic pathways.

Neurodegeneration is a common problem associated with diseases such as Alzheimer's disease. While the current drugs treat some of the symptoms of this disease, they do not control the underlying pathology of the disease. Accordingly, it would be desirable to provide a drug that can slow the progress of Alzheimer's disease.

Pre-senile dementia (mild cognitive impairment) concerns memory impairment rather than attention deficit problems and otherwise unimpaired cognitive functioning. Mild cognitive impairment is distinguished from senile dementia in that mild cognitive impairment involves a more persistent and troublesome problem of memory loss for the age of the patient. There currently is no medication specifically identified for treatment of mild cognitive impairment, due somewhat to the newness of identifying the disease. Therefore, there is a need for a drug to treat the memory problems associated with mild cognitive impairment.

Senile dementia is not a single disease state. However, the conditions classified under this name frequently include cognitive and attention deficits. Generally, these deficits are not treated. Accordingly, there is a need for a drug that provides improvement in the cognitive and attention deficits associated with senile dementia.

Finally, the compounds of the present invention may be used in combination therapy with typical and atypical antipsychotic drugs. All compounds within the present invention are useful for and may also be used in combination with each other to prepare pharmaceutical compositions. Such combination therapy lowers the effective dose of the anti-psychotic drug and thereby reduces the side effects of the antipsychotic drugs. Some typical anti-psychotic drugs that may be used in the practice of the invention include Haldol. Some atypical anti-psychotic drugs include Ziprasidone, Olanzapine, Resperidone, and Quetiapine.

Compounds of Formula I can be prepared as shown in Scheme 1. The key step in the preparation of this class of compounds is the coupling of commercially available 3-aminoquinuclidine ($R_2$=H) with the requisite acid chloride (Lv=Cl), mixed anhydride (e.g., Lv=diphenyl phosphoryl or acyloxy of the general formula of —O—C(O)—$R_{Lv}$ where $R_{Lv}$ includes phenyl or t-butyl), ester (Lv=OMe or OEt), or carboxylic acid (Lv=OH) in the presence of an activating reagent. Suitable activating reagents are well known in the art, for examples see Kiso, Y.; Yajima, H. "Peptides" pp. 39–91, San Diego, Calif., Academic Press, (1995), and include, but are not limited to, agents such as a carbodiimides, phosphonium and uronium salts (such as uronium salt HATU).

Scheme 1

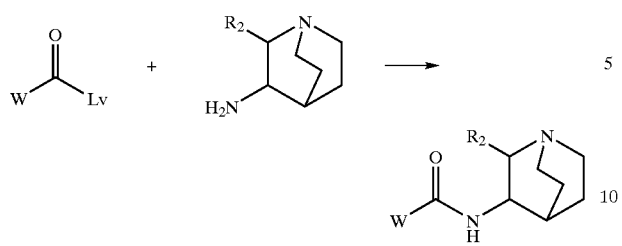

One of ordinary skill in the art will recognize that the methods described for the reaction of the unsubstituted 3-aminoquinuclidine ($R_2$=H) are equally applicable to substituted compounds ($R_2 \neq$H). Such compounds can be prepared by reduction of the oxime of the corresponding 3-quinuclidinone (see *J. Labelled Compds. Radiopharm.*, 53–60 (1995) and *J. Med. Chem.* 988–995, (1998)). The oximes can be prepared by treatment of the 3-quinuclidinones with hydroxylamine hydrochloride in the presence of a base. The 3-quinuclidinones, where $R_2$=substituted alkyl, cycloalkyl, substituted benzyl, can be prepared by known procedures (see *Tet. Lett.* 1015–1018, (1972), *J. Am. Chem. Soc.* 1278–1291 (1994), *J. Am. Chem. Soc.* 4548–4552 (1989), *Tetrahedron,* 1139–1146 (2000)). The 3-quinuclidinones, where $R_2$=aryl, can be prepared by palladium catalyzed arylation as described in *J. Am. Chem. Soc.* 1473–1478 (1999) and *J. Am. Chem. Soc.* 1360–1370 (2000).

Preferably, when W is a thiophene or in some furan cases, the acid is converted into a mixed anhydride by treatment with diphenylchlorophosphate in the presence of TEA and $CH_2Cl_2$ as the solvent. The resulting anhydride solution is directly reacted with aminoquinuclidine using aqueous DMF as the solvent. When W is furan, oxazole, oxadiazole, pyrrole, 5-thiazole, thiophene, or triazole, the acid is activated with a uronium salt, preferably HATU (see *J. Am. Chem. Soc.,* 4397 (1993)), in the presence of a base such as DIEA in DMF, and reacted directly with aminoquinuclidine to afford the desired amides. In the case where W is a 2-thiazole, 2-oxazole, or a thiadiazole, the amide bond is formed by the reaction of the amine and ester (Lv=OEt) in an alcoholic solvent (see *Liebigs Ann. Chem.,* 1216–1231 (1980)).

It will be apparent to those skilled in the art that the requisite carboxylic acids can be obtained commercially or can be synthesized by known procedures. The thiophene acids required in Examples 1–11, 13, and 41–42 can be synthesized from the corresponding aldehydes by oxidation with $NaClO_2$ as described in *J. Chem. Soc. Perkin Trans. I.,* 789–794 (1999). The requisite aldehydes can be made as described in *J. Med. Chem.,* 1585–1599 (1997). An aryl boronic acid is reacted with a bromothiophene in the presence of a palladium (O) source, such as tetrakis-(triphenylphosphine)palladium (O), and a base, preferably aqueous sodium carbonate. The reaction works best if heated at reflux in THF/water for 24 hours. The thiophene acids of Examples 14–19 are prepared by similar methods as in Example 1 with modifications as described herein. The furan and thiophene acids required for Examples 20–30 are available commercially.

Scheme 2

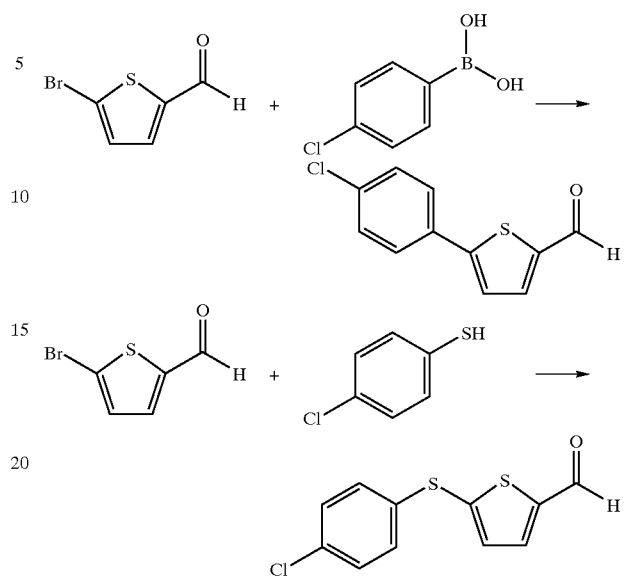

The thiophene acids for Examples 3140 are synthesized from the corresponding esters by base catalyzed hydrolysis. Typical hydrolysis procedures are well known in the art. Preferably, the thiophene ester is treated with aqueous lithium hydroxide in a solvent such as dioxane. The esters are either commercially available or synthesized by reaction of a bromothiophene ester with the appropriate thiophenol or phenol as described in *Coll. Czech. Chem. Comm.,* 2360–2363 (1980). Namely, the sodium salt of the thiophenol or phenol is formed by treatment with a strong base like sodium hydride. The sodium salt is then reacted with a bromothiophene in a solvent such as acetone.

When W is thiazole, the required acids for Examples 4449 are prepared by nucleophilic addition of the requisite phenol or thiophenol to 2-bromo-1,3-thiazole-5-carboxylic ethyl ester according to the procedure described in *Helv. Chim. Acta.,* 2002–2022 (1997). Preferably, in EtOH utilizing $K_2CO_3$ as a base (Scheme 3). The esters are hydrolyzed to the corresponding acids by procedures well known in the art. The 2-bromo-1,3-thiazole is prepared by the method described in *Roczniki Chemii Ann. Soc. Chim. Polonorum,* 1647–1658 (1972). The aryl 1,3-thiazole for Example 50 is prepared according to the procedure of Huntress and Pfister in *J. Am. Chem. Soc.,* 2167–2169 (1943). The requisite 1,3-thiazoles-5-acids for Examples 51 and 58–62 are commercially available. The 1,3-thiazole-5-acids required in Examples 52–57 can be synthesized from the corresponding esters by base hydrolysis via procedures well known in the art. The requisite esters can be prepared by a Suzuki reaction as described in *J. Med. Chem.,* 4985–92 (1995). An aryl boronic acid is reacted with a bromothiazole ester in the presence of a palladium (O) source, such as tetrakis-(triphenylphosphine)palladium (O), and a base, preferably aqueous sodium carbonate. The 1,3,4-thiadiazole esters for Examples 64–72 are synthesized by nucleophilic addition of the requisite phenol or thiophenol to 2-bromo-1,3,4-thiadiazolezole-5-carboxylic ethyl ester as described in *Can. J. Chem.,* 243–250 (1977) (Scheme 3).

Scheme 3

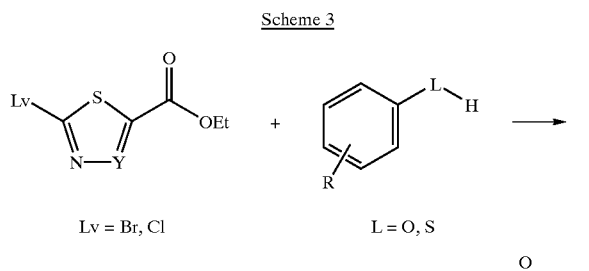

Lv = Br, Cl    L = O, S

The triazole for Example 75 and the oxadiazole for Example 76 are prepared by the methods of McKillop et al., *Tetrahedron Lett.* 23, 3357–3360 (1982) with modifications as described herein. The oxadiazole for Example 77 is prepared following the procedures of Snyder in *J. Org. Chem.* 3257–3269 (1990), Muchowski in *Can. J. Chem.* 3079–3082 (1972), and Crenshaw in U.S. Pat. No. 4,001,238.

The 5-substituted-1,3-oxazole-2-esters for Examples 79–88 are synthesized according to procedures described in *J. Pharm. Soc. Japan,* 305–7 (1956) as shown in Scheme 4. The 5-substituted-1,3-thiazole-2-esters for Examples 89–102 are synthesized according to procedures described in *Chem. Pharm. Bull.,* 4195–4198 (1982).

Scheme 4

U = O, S

The furans for Examples 103–130 are commercially available or can be prepared from their corresponding aldehydes or esters as described for the thiophenes (Examples 1–11). In the event that the furan is not commercially available, it can be prepared by the method of Bussolari and Rehborn described in *Org. Lett.* 965–7 (1999). Furan Examples 131–146 are prepared in a convergent means by a direct palladium catalyzed Suzuki coupling N-[(3R)-1-azabicyclo[2.2.2]oct-3-yl]-5-bromo-furan-2-carboxamide with the requisite boronic acid by the method described in *Org. Lett.* 965–7 (1999), to yield directly the desired aryl amides (Scheme 5).

Scheme 5

One of ordinary skill in the art would recognize that Examples 12, and 147–149 are prepared by reduction of the corresponding aryl nitro compounds by methods well known in the art, preferably by reduction with Pd/C in an alcoholic solvent such as EtOH under $H_2$. The acid for example 150 is prepared by a Pd(O) catalyzed Sonogashira coupling of 5-bromo-2-furanal and phenyl acetylene as described in *Tetrathedron Lett.,* 4467–70 (1975). The resulting aldehyde is converted to the desired analog by methods as described for Example 103. Example 151 is prepared by addition of the sodium salt of phenol to N-[(3R)-1-azabicyclo[2.2.2]oct-3-yl]-5-bromo-furan-2-carboxamide. The requisite acid for Example 152 is prepared by bromination of methyl-5-bromo-1-methyl-1H-pyrrole-2-carboxylate, followed by similar Pd-catalyzed coupling as described for Example 1.

The 1,3-oxazole-2-carboxylic acid required for Example 153 is prepared by the method described in *J. Pharm. Sci. Japan* 305–7, (1956). 3-Phenyl-1,2,4-oxadiazole-5-carboxylic acid required for Example 154 is prepared by the method of Wurm as described in *Chem. Ber.,* 3133, (1889). The 2-phenyl-1,3-oxazole-5-carboxylic acid required for Example 155 is prepared by the method described in Chem.

Heterocycl. Compd. (Engl.Transl.), 654–663, (1986). 2-Phenyl-1,3-oxazole-4-carboxylic acid required for Example 156 is prepared as described by Korte and Stoeriko, in *Chem. Ber.*, 1033–1042, (1960). The 5-phenylisoxazole-3-carboxylic acid for Example 157 is prepared by the method of Vaughan and Spencer as described in *J. Org. Chem.* 1160–4, (1960).

Thioamides, such as Example 159, can be prepared from the requisite thioester by direct displacement of the thioester with aminoquinuclidine (Scheme 6). The thioester can be prepared as described in *J. Organometallic Chem.*, 95–98 (1987). One of ordinary skill in the art would quickly identify that compounds such as Example 159 could also be prepared directly from the amides exemplified throughout this patent by direct treatment with a reagent such as Lawesson's reagent (see Lawesson et. al. in *Bull. Soc. Chim. Belg.*, 229 (1978)) or $P_4S_{10}$ (see Chem. Rev., 45 (1961)).

Scheme 6

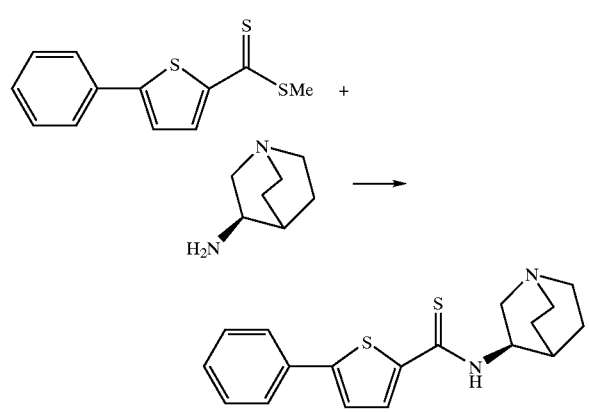

The following examples are provided as examples and are not intended to limit the scope of this invention to only those provided examples and named compounds. Also, the salts made in the examples are only exemplary and are not intended to limit the invention. Any pharmaceutically acceptable salt can be made by one of ordinary skill in the art. Further, the naming of specific stereoisomers is for exemplification, and is not intended to limit in anyway the scope of the invention. The invention includes the following examples in pure stereoisomeric form or as racemic mixtures.

EXAMPLE 1

N-[(3R)-1-azabicyclo[2.2.2]oct-3-yl]-5-phenyl-thiophene-2-carboxamide Hydrochloride:

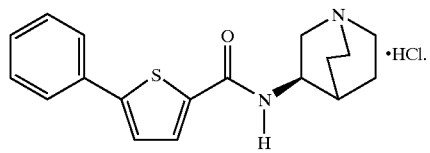

Step 1a: Preparation of 5-phenylthiophene-2-carboxaldehyde.

5-Bromothiophene-2-carboxaldehyde (10 g, 5.2 mmol) is added to a solution of tetrakis(triphenylphosphine)palladium (O) (180 mg, 0.16 mmol) in degassed THF (10 mL). The resulting solution is stirred for 5 minutes. A solution of phenylboronic acid (760 mg, 6.2 mmol) in THF (10 mL) is added followed by aqueous $Na_2CO_3$ (2M, 5.2 mL). The mixture is heated at reflux for 24 hours. The reaction mixture is allowed to cool, poured into ether, and washed twice with water. The ether layer is dried over $Na_2SO_4$ and concentrated in vacuo. The crude product is purified by flash column chromatography (1:1 hexanes:$CH_2Cl_2$) to yield the desired product (900 mg, 91%). 1H NMR (300 MHz, $CDCl_3$) δ 7.38–7.45, 7.65–7.68, 7.73, 9.88.

Step 1b: Preparation of 5-phenylthiophene-2-carboxylic Acid.

The product of Step 1a (750 mg, 4 mmol) is dissolved in a mixture of THF, t-BuOH, and water (2:1:1, 60 mL). $KH_2PO_4$ (1.36 g, 10 mmol) is added followed by $NaClO_2$ (900 mg, 10 mmol). The mixture is stirred at room temperature for 5 days. Aqueous NaOH (2M, 10 mL) is added, and a majority of the organic solvents are removed in vacuo yielding an aqueous suspension. This suspension is diluted with water and washed three times with $CH_2Cl_2$. The aqueous layer is acidified to pH<6 with 25% $H_2SO_4$ and the product is extracted three times with $CH_2Cl_2$. The combined organic washes are dried over $Na_2SO_4$, filtered and concentrated in vacuo to yield the desired product (417 mg, 51%). MS for $C_{11}H_8O_2S$ (ESI) (M–H)$^-$ m/z 203.

Step 1c Preparation of N-[(3R)-1-azabicyclo[2.2.2]oct-3-yl]-5-phenylthiophene-2-carboxamide Hydrochloride.

TEA (210 pb, 1.5 mmol) is added to a suspension of the product of Step 1b (304 mg, 1.5 mmol) in $CH_2C_{12}$ (5 mL). Diphenylchlorophosphate (290PL, 1.4 mmol) is added and the resulting solution is stirred at room temperature for 30 minutes. This solution is added to a solution of (R)-3-aminoquinuclidine dihydrochloride (279 mg, 1.4 mmol) and TEA (580 µL, 4.2 mmol) in DMF/water (5:1, 10 mL). The resulting solution is allowed to stir overnight. MeOH is added and the mixture is poured through a column of AG50Wx2 ion exchange resin (H$^+$ form). The resin is washed with MeOH then the product is eluted with 5% TEA in MeOH. The eluent is evaporated to dryness. The hydrochloride salt is formed and crystallized from MeOH/IPA to yield the desired product (280 mg, 57%). MS for $C_{18}H_{20}N_2OS$ (ESI) (M+H)$^+$ m/z 313.

EXAMPLES 2–11

The following compounds are made from the corresponding boronic acids according to the procedure of Example 1, making non-critical variations.

Example 2

N-[(3R)-1-azabicyclo[2.2.2]oct-3-yl]-5-(4-chlorophenyl)-thiophene-2-carboxamide hydrochloride (from 4-chlorophenylboronic acid). Yield 24% for 3 steps. MS for $C_{18}H_{19}ClN_2OS$ (ESI) (M+H)$^+$ nm/z 347.

Example 3

N-[(3R)-1-azabicyclo[2.2.2]oct-3-yl]-5-(3-chlorophenyl)-thiophene-2-carboxamide hydrochloride (from 3-chlorophenylboronic acid). Yield 16%. MS for $C_{18}H_{19}ClN_2OS$ (ESI) (M+H)$^+$ m/z 347.

Example 4

N-[(3R)-1-azabicyclo[2.2.2]oct-3-yl]-5-(2-chlorophenyl)-thiophene-2-carboxamide hydrochloride (from 2-chlorophenylboronic acid). Yield 48%. MS for $C_{18}H_{19}ClN_2OS$ (ESI) (M+H)$^+$ m/z 347.

Example 5

N-[(3R)-1-azabicyclo[2.2.2]oct-3-yl]-2,3'-bithiophene-5-carboxamide hydrochloride (from 3-thiopheneboronic acid).

Yield 49%. HRMS (FAB) calculated for $C_{16}H_{18}N_2OS_{2+}H$ 319.0939, found 319.0939.

Example 6

N-[(3R)-1-azabicyclo[2.2.2]oct-3-yl]-5-(2-nitrophenyl)-thiophene-2-carboxamide hydrochloride (from 2-nitrophenylboronic acid). Yield 45%. HRMS (FAB) calculated for $C_{18}H_{19}N_3O_3S+H$ 358.1225, found 358.1224.

Example 7

N-[(3R)-1-azabicyclo[2.2.2]oct-3-yl]-5-(3-nitrophenyl)-thiophene-2-carboxamide (from 3-nitrophenylboronic acid). Yield 25%. HRMS (FAB) calculated for $C_{18}H_{19}N_3O_3S+H$ 358.1225, found 358.1217.

Example 8

N-[(3R)-1-azabicyclo[2.2.2]oct-3-yl]-4-phenyl-thiophene-2-carboxamide hydrochloride (starting with phenyl boronic acid and 4-bromothiophene-2-carboxaldehyde in place of 5-bromothiophene-2-carboxaldehyde). Yield 35%. MS for $C_{18}H_{20}N_2OS$ (ESI) (M+H)$^+$ m/z 313.

Example 9

N-[(3R)-1-azabicyclo[2.2.2]oct-3-yl]-5-(3-benzyloxyphenyl)-thiophene-2-carboxamide hydrochloride (from 3-benzyloxyphenylboronic acid). Yield 35%. MS for $C_{25}H_{26}N_2O_2S$ (ESI) (M+H)$^+$ m/z 419.

Example 10

N-[(3R)-1-azabicyclo[2.2.2]oct-3-yl]-5-(4-benzyloxyphenyl)-thiophene-2-carboxamide hydrochloride (from 4-benzyloxyphenylboronic acid). Yield 34%. MS for $C_{25}H_{26}N_2O_2S$ (ESI) (M+H)$^+$ m/z 419.

Example 11

N-[(3R)-1-azabicyclo[2.2.2]oct-3-yl]-5-(3-fluoro-4-benzyloxyphenyl)-thiophene-2-carboxamide hydrochloride (from 3-fluoro-4-benzyloxyphenylboronic acid). Yield 41%. MS for $C_{25}H_{25}FN_2O_2S$ (ESI) (M+H)$^+$ m/z 436.

EXAMPLE 12

5-(2-Aminophenyl)-N-[(3R)-1-azabicyclo[2.2.2]oct-3-yl]-thiophene-2-carboxamide:

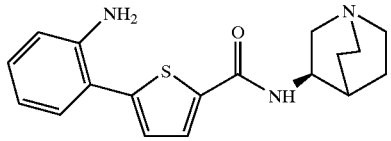

Step 12a: Preparation of 5-(2-aminophenyl)-N-[(3R)-1-azabicyclo[2.2.2]oct-3-yl]thiophene-2-carboxamide.

In a 200 mL Parr flask is placed the compound Example 6 (0.200 g, 0.51 mmol), EtOH (5 m]L) and $CH_2Cl_2$ (5 mL). The flask is shaken under 30 psi $H_2$ for 16 hours. The contents are then filtered through a pad of celite with 10% MeOH—$CH_2Cl_2$ (150 mL). The solvents are removed in vacuo. This lot is then combined with a second lot prepared in a similar manner on the scale of 0.25 mmol. The product is re-dissolved in MeOH and loaded onto a column of AG50Wx2 ion exchange resin (H+ form). The resin is washed with MeOH then the product is eluted with 5% TEA in MeOH. The eluent is evaporated to dryness to yield the desired product (0.17 g, 69%). MS for $C_{18}H_{21}N_3OS$ (EI) m/z (rel. intensity) 327 (M+, 78), 327 (78), 203 (23), 202 (94), 130 (44), 125 (21), 117 (23), 109 (58), 96 (24), 83 (26), 70 (99).

EXAMPLE 13

N-[(3R)-1-azabicyclo[2.2.2]oct-3-yl]-5-pyridin-3-yl-thiophene-2-carboxamide Dihydrochloride:

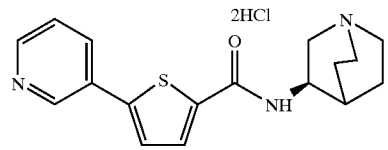

Step 13a: Preparation of 5-(3-pyridinyl)-2-thiophenecarboxaldehyde.

In a flask are placed 3-pyridinediethylborane (0.81 g, 5.5 mmol), 2-bromothiophene-5-carboxaldehyde (0.59 mL, 5.0 mmol), and Pd(PPh$_3$)$_4$ (0.17 g, 0.15 mmol). The flask is vacuum purged and nitrogen filled three times followed by addition of a 4:1 mixture of toluene-EtOH (8.3 mL) by syringe. After careful vacuum purge/nitrogen fill (3×), a solution of Na$_2$CO$_3$ (2M, 5 mL, 10.0 mmol) is added by syringe, and the flask is vacuum purged and nitrogen filled (3×). The reaction mixture is heated to 90° C. and stirred for 22 h. The reaction mixture is cooled to rt and diluted with $H_2O$. The aqueous solution is extracted with ether (3×). The combined ether layers are then washed with water (3×) and brine (2×). The organic layer is dried over MgSO$_4$, diluted with EtOAc for solubility, then filtered and concentrated. The crude product is then chromatographed over silica gel (10/30/50% EtOAc-heptane gradient) to provide the product as a yellow solid (0.34 g, 35%). NMR (400 MHz, CDCl$_3$): 9.97, 9.05, 8.68, 8.13, 7.83, 7.59–7.54.

Step 13b: Preparation of N-[(3R)-1-azabicyclo[2.2.2]oct-3-yl]-5-pyridin-3-yl-thiophene-2-carboxamide Dihydrochloride.

This compound is made from the product of Step 13a by using the procedure discussed in Steps 1b and 1c, making non-critical variations. The yield from 2 steps is 20%. MS for $C_{17}H_{19}N_3OS$ (ESI) (M+H)$^+$ m/z 314.

EXAMPLE 14

N-[(3R)-1-azabicyclo[2.2.2]oct-3-yl]-5'-methyl-2,2'-bithiophene-5-carboxamide Hydrochloride:

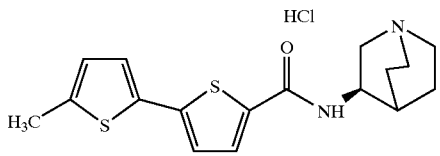

Step 14a: Preparation of methyl 5'-methyl-2,2'-bithiophene-5-carboxylate.

In a flask are placed 2-bromothiophene-5-carboxylic acid (1.20 g, 5.81 mmol), 5-methylthiophene-2-boronic acid (0.99 g, 6.97 mmol), and Pd(PPh$_3$)$_4$ (0.20 g, 0.17 mmol). The flask is then vacuum purged and nitrogen filled (3×). THF (12 ml) is then added by syringe followed by vacuum purge and nitrogen fill (3×). A solution of Na$_2$CO$_3$ (2M, 5.8 mL, 11.6 mmol) is added followed by vacuum purge and nitrogen fill (3×). The reaction mixture is heated to reflux for 19 h then cooled to rt and diluted with water. The aqueous solution is extracted with ether (3x). The aqueous layer is then acidified and extracted with EtOAc (3x). The combined organic layers are dried over MgSO$_4$, filtered, and concentrated to provide an inseparable 3:1 mixture of 2-bromothiophene-5-carboxylic acid and bithiophene product. To separate the compounds the methyl esters are formed: In a flask are placed the aforementioned mixture, MeOH (50 mL) and conc H$_2$SO$_4$ (5 drops) and heated to reflux for 24 h. The solution is concentrated and chromatographed over silica gel (2% acetone-heptane) to provide the product as a solid (0.37 g, 26% 2 steps). $^1$H NMR (400 MHz, CDCl$_3$) δ 7.69, 7.10, 7.07, 6.73, 3.91, 2.52.

Step 14b: Preparation of 5'-methyl-2,2'-bithiophene-5-carboxylic Acid.

The product of Step 14a (0.37 g, 1.54 mmol), dioxane (5 mL) and LiOH (1N, 3.1 mL, 3.1 mmol) are placed in a flask. Additional dioxane (5 mL) is then added for solubility and stirred for 24 h at rt. 1N HCl is added slowly until pH<6, whereupon a precipitate forms. The precipitate is then collected by filtration, rinsed with water, and dried in a 70° C. vacuum oven to provide the product as a yellow solid (0.30 g, 86%). MS for C$_{10}$H$_8$O$_2$S$_2$ (ESI) (M−H)$^+$ m/z 223.

Step 14c: Preparation of N-[(3R)-1-azabicyclo[2.2.2]oct-3-yl]-5'-methyl-2,2'-bithiophene-5-carboxamide Hydrochloride.

This compound is made using the product of Step 14b as the starting material and using the procedure discussed in Step 1c, making non-critical variations. Yield 84%. MS C$_{17}$H$_{20}$N$_2$OS$_2$ (EI) m/z (rel. intensity) 332 (M+, 90), 332 (90), 207 (99), 135 (90), 125 (55), 109 (86), 108 (43), 96 (52), 84 (52), 83 (48), 70 (88).

EXAMPLE 15

N-[(3R)-1-azabicyclo[2.2.2]oct-3-yl]-5'-chloro-2,2'-bithiophene-5-carboxamide Hydrochloride:

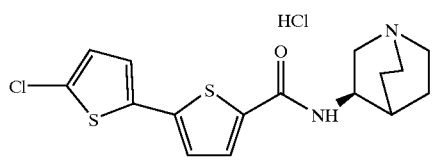

Step 15a: Preparation of 5'-chloro-2,2'-bithiophene-5-carboxaldehyde.

In a flask are placed 2-bromo-5-chlorothiophene (0.55 mL, 5.0 mmol) and Pd(PPh$_3$)$_4$ (0.17 g, 0.15 mmol), and the flask is vacuum purged and nitrogen filled (3x). THF (10 mL) is added by syringe and stirred 10 min. In a separate flask is placed 5-formyl-2-thiopheneboronic acid (0.94 g, 6.0 mmol) and EtOH (2 mL) and stirred until dissolved. This mixture is added by syringe to the first flask followed by vacuum purge and nitrogen fill (3x). A solution of Na$_2$CO$_3$ (2M, 5.0 mL, 10.0 mmol) is added by syringe followed by vacuum purge and nitrogen fill (3x). The reaction mixture is heated at 85° C. for 20 h. The reaction is cooled to rt and diluted with water. The aqueous solution is extracted with ether (3x). The combined ether layers are washed with water (3x) then brine (2x). The ether is dried over MgSO$_4$, filtered, and concentrated. The crude product is purified over silica gel (5% EtOAc-heptane) to provide the product as an orange solid (0.27 g, 24%). $^1$NMR (400 MHz, CDCl$_3$) δ 9.89, 7.69, 7.20, 7.16, 6.93.

Step 15b: Preparation of N-[(3R)-1-azabicyclo[2.2.2]oct-3-yl]-5'-chloro-2,2'-bithiophene-5-carboxamide hydrochloride.

This compound is made from the product of Step 15a as the starting material by using the procedures discussed in Steps 1b and 1c, making non-critical variations. Yield for 2 steps 34%. HRMS (FAB) calculated for C$_{16}$H$_{17}$ClN$_2$OS$_2$+H 353.0549, found 353.0545.

EXAMPLE 16

N-[(3R)-1-azabicyclo[2.2.2]oct-3-yl]-5-nitro-thiophene-2-carboxamide Hydrochloride:

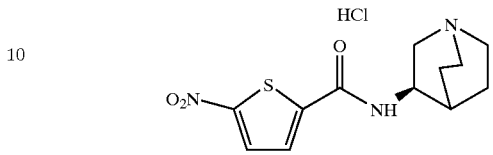

Step 16a: Preparation of N-[(3R)-1-azabicyclo[2.2.2]oct-3-yl]-5-nitrothiophene-2-carboxamide Hydrochloride.

This compound is made from 2-nitrothiophene-5-carboxaldehyde by using the procedure discussed in Steps 1b and 1c, making non-critical variations. Yield for 2 steps 48%. MS for C$_{12}$H$_{15}$N$_3$O$_3$S (EI) m/z (rel. intensity) 281 (M+, 16), 156 (37), 125 (37), 110 (34), 109 (80), 96 (33), 84 (29), 82 (41), 81 (16), 70 (99), 55 (17).

EXAMPLE 17

5-(Aminomethyl)-N-[(3R)-1-azabicyclo[2.2.2]oct-3-yl]-thiophene-2-carboxamide Dihydrochloride:

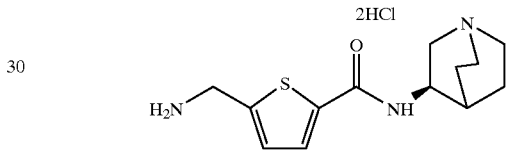

Step 17a: Preparation of tert-butyl 2-thienylmethylcarbamate.

A 500 mL receiving flask is placed in an ice bath, and to the flask is added thiophene-2-methylamine (5.0 mL, 48.7 mmol), CH$_2$Cl$_2$ (250 mL) then di-tert-butyl dicarbonate (12.7 g, 73.0 mmol) in 2–3 g portions over 5 min. The reaction mixture is stirred for 3 h then washed with 1N HCl (3x), 1N NaOH (3x) and brine (2x). The organic layer is dried over MgSO$_4$, filtered and concentrated to a yellow oil. The oil is chromatographed over silica gel (2.5–5% EtOAc-heptane gradient) to provide 8.70 g (84%) of the desired product as a clear oil. MS for C$_{10}$H$_{15}$NO$_2$S (ESI) (M+H)$^+$ m/z 214.

Step 17b: Preparation of 5-{[(tert-butoxycarbonyl)amino]methyl}-2-thiophenecarboxylic Acid.

In a flask is placed the product of Step 17a (3.50 g, 16.4 mmol) and dry THF (80 mL) then cooled in an acetone/solid CO$_2$ bath. Lithium diisopropylamide (18.0 mL, 36.1 mmol, 2.0 M solution in heptane/THF/ethylbenzene) is added in a slow stream by syringe. The resulting orange solution is stirred for 10 min and then quenched with excess dry ice. The solution is warmed over 1 h and the THF removed in vacuo. The crude product is diluted with CH$_2$Cl$_2$ and washed with 1N HCl (3x). The CH$_2$Cl$_2$ is removed in vacuo and replaced with EtOAc due to insolubility. The organic solution is dried over MgSO$_4$, filtered, and concentrated to provide a dark orange oil, which is chromatographed over silica gel (25–90% EtOAc-heptane gradient) to provide 0.873 g (21%) of the product as an off-white foam. $^1$NMR (400 MHz, CDCl$_3$) δ 12.96, 7.60, 7.56, 6.97, 4.28, 1.40.

Step 17c: Preparation of 5-(aminomethyl)-N-[(3R)-1-azabicyclo[2.2.2]oct-3-yl]thiophene-2-carboxamide Dihydrochloride.

This compound is made by using the product of Step 17b as a starting material and using the procedure discussed in Step 1c, making non-critical variations. Yield 55%. MS for $C_{13}H_{19}N_3OS$ (EI) m/z (rel. intensity) 265 (M+, 6), 140 (24), 109 (79), 96 (24), 80 (31), 78 (99), 70 (80), 65 (28), 63 (99), 62 (39), 61 (77).

EXAMPLE 18

N-[(3R)-1-azabicyclo[2.2.2]oct-3-yl]-5-cyano-thiophene-2-carboxamide Hydrochloride:

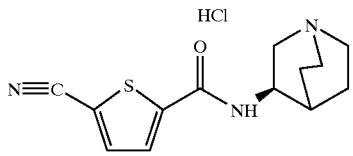

Step 18a: Preparation of 5-cyano-thiophene-2-carboxylic Acid.

In a 500 mL receiving flask are placed thiophene-2-carbonitrile (5.0 mL, 53.8 mmol) and THF (270 mL) and cooled in an acetone/solid $CO_2$ bath. Lithium diisopropylamide (40.3 mL, 80.7 mmol, 2.0M solution in heptane/THF/ethylbenzene) is added in a slow stream via syringe. The solution is stirred for 10 min then quenched with an excess of dry ice. The reaction mixture is warmed in a water bath and the THF removed in vacuo. The slurry is taken up in 1N NaOH and extracted with ether (3×). The aqueous layer is then acidified to pH<6 with conc. HCl, whereupon a brown precipitate forms. This precipitate is filtered off and to the resulting eluent is added 1N HCl which results in precipitation of the product. The product is collected by filtration then triturated with $CH_2Cl_2$. Purification over silica gel (1:2.5:100 formic acid:MeOH:$CH_2Cl_2$) provides the product as a solid (1.79 g, 22%). $^1$NMR (400 MHz, $CDCl_3$) δ 14.10, 8.00, 7.80.

Step 18b: Preparation of N-[(3R)-1-azabicyclo[2.2.2]oct-3-yl]-5-cyanothiophene-2-carboxamide Hydrochloride.

This compound is made by using the product of Step 18a as a starting material and using the procedure discussed in Step 1c, making non-critical variations. Yield 57%. HRMS (FAB) calculated for $C_{13}H_{15}N_3O_2S$+H 262.1014, found 262.1003.

EXAMPLE 19

N-[(3R)-1-azabicyclo[2.2.2]oct-3-yl]-5-methoxy-thiophene-2-carboxamide Hydrochloride:

This compound is prepared from 2-methoxythiophene according to the procedure used to make the compound of Example 18, making non-critical variations. Yield for 2 steps 33%. HRMS (FAB) calculated for $C_{13}H_{18}N_2O_2S$+H 267.1167, found 267.1167.

EXAMPLE 20

N-[(3R)-1-azabicyclo[2.2.2]oct-3-yl]-5-(pyridin-2-yl)-thiophene-2-carboxamide:

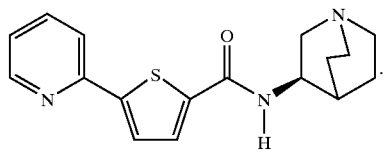

Step 20a: TEA (50 μL, 0.35 mmol) is added to a suspension of 5-(pyridin-2-yl)-2-thiophenecarboxylic acid (72 mg, 0.35 mmol) in $CH_2Cl_2$:DMF (2:1, 1.5 mL). Diphenylchlorophosphate (62 μL, 0.3 mmol) is added and the resulting solution is stirred at room temperature for 30 minutes. A solution of (R)-3-aminoquinuclidine (1M, 0.2 mmol, 0.2 mL) in DMF is added and the resulting solution is stirred overnight at room temperature. MeOH is added and the mixture is poured through a column of AG50Wx2 ion exchange resin (H+form). The resin is washed with MeOH then the product is eluted with 5% TEA in MeOH. The eluent is evaporated to dryness to yield the desired product (15 mg, 24%). MS for $C_{17}H_{19}N_3OS$ (ESI) (M+H)$^+$ m/z 314.

EXAMPLES 21–30

The following compounds are made from the corresponding carboxylic acids according to the procedure of Example 20, making non-critical variations.

Example 21

N-[(3R)-1-azabicyclo[2.2.2]oct-3-yl]-[2,2]bithiophenyl-5-carboxamide (from 2,2'-bithiophene-5-carboxylic acid). Yield 13%. MS for $C_{16}H_{18}N_2OS_2$ (ESI) (M+H)$^+$ m/z 319.

Example 22

N-[(3R)-1-azabicyclo[2.2.2]oct-3-yl]-5-(methylsulfanyl)-thiophene-2-carboxamide (from 5-methylsulfanylthiophene-2-carboxylic acid). Yield 84%. MS for $C_{13}H_{18}N_2OS_2$ (ESI) (M+H)$^+$ m/z 283.

Example 23

N-[(3R)-1-azabicyclo[2.2.2]oct-3-yl]-5-chloro-thiophene-2-carboxamide (from 5-chlorothiophene-2-carboxylic acid). Yield 6%. MS for $C_{12}H_{15}ClN_2OS$ (ESI) (M+H)$^+$ m/z 271.

Example 24

N-[(3R)-1-azabicyclo[2.2.2]oct-3-yl]-5-acetyl-thiophene-2-carboxamide (from 5-acetylthiophene-2-carboxylic acid). Yield 7%. MS for $C_{14}H_{18}N_2O_2S$ (ESI) (M+H)$^+$ m/z 279.

Example 25

N-[(3R)-1-azabicyclo[2.2.2]oct-3-yl]-5-methyl-thiophene-2-carboxamide (from 5-methylthiophene-2-carboxylic acid). Yield 6%. MS for $C_{13}H_{18}N_2OS$ (ESI) (M+H)$^+$ m/z 251.

Example 26

N-[(3R)-1-azabicyclo[2.2.2]oct-3-yl]-5-bromo-thiophene-2-carboxamide (from 5-bromothiophene-2-carboxylic acid). Yield 8%. MS for $C_{12}H_{15}BrN_2OS$ (ESI) (M+H)$^+$ m/z 315/317.

Example 27

N-[(3R)-1-azabicyclo[2.2.2]oct-3-yl]-5-(phenylsulfanyl)-thiophene-2-carboxamide (from 5-phenylsulfanylthiophene- 2-carboxylic acid). Yield 68%. MS for $C_{18}H_{20}N_2OS_2$ (ESI) (M+H)$^+$ m/z 345.

Example 28

N-[(3R)-1-azabicyclo[2.2.2]oct-3-yl]-5-(acetylamino)-furan-2-carboxamide (from 5-acetylaminofuran-2-carboxylic acid). Yield 16%. MS for $C_{14}H_{19}N_3O_3$ (ESI) (M+H)$^+$ m/z 278.

Example 29

N-[(3R)-1-azabicyclo[2.2.2]oct-3-yl]-5-trifluoromethyl-furan-2-carboxamide (from 5-trifluoromethylfuran-2-carboxylic acid). Yield 11%. MS for $C_{13}H_{15}F_3N_2O_2$ (ESI) (M+H)$^+$ m/z 289.

Example 30

N-[(3R)-1-azabicyclo[2.2.2]oct-3-yl]-5-(2-methyl-5-trifluoromethyl-2H-pyrazole-3-yl)-thiophene-2-carboxamide (from 5-(2-methyl-5-trifluoromethyl-2H-pyrazole-3-yl)-thiophene-2-carboxylic acid). Yield 9%. MS for $C_{17}H_{19}F_3N_4OS$ (ESI) (M+H)$^+$ m/z 385.

EXAMPLE 31

N-[(3R)-1-azabicyclo[2.2.2]oct-3-yl]-5-(2-methylthiazol-4-yl)-thiophene-2-carboxamide:

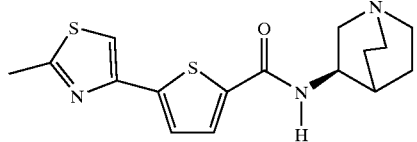

Step 31a: Preparation of 5-(2-methylthiazol-4-yl)-thiophene-2-carboxylic Acid.

Aqueous LiOH (1N, 1.5 mL) is added to a solution of methyl 5-(2-methylthiazol-4-yl)-thiophene-2-carboxylate (81 mg, 0.34 mmol) in dioxane (1 mL). The reaction is stirred at room temperature for 2 hours. Aqueous HCl (1N, 4 mL) is added and the resultant precipitate is collected by filtration, washed with water, and dried to give the desired product (53 mg, 69%). $^1$NMR (300 MHz, DMSO) δ 8.03, 7.69, 7.59, 2.70.

Step 31b: Preparation of N-[(3R)-1-azabicyclo[2.2.2]oct-3-yl]-5-(2-methylthiazol-4-yl)-thiophene-2-carboxamide.

This compound is made by using the product of Step 31a as a starting material and using the procedure discussed in Step 20a, making non-critical variations. Yield 16%. MS for $C_{16}H_{19}N_3OS_2$ (ESI) (M+H)$^+$ m/z 334.

EXAMPLE 32
N-[(3R)-1-azabicyclo[2.2.2]oct-3-yl]-5-[2-(3-chlorophenyl)-vinyl]-thiophene-2-carboxamide:

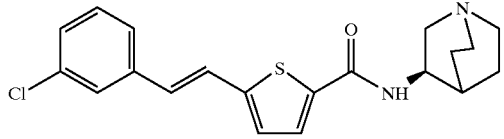

This compound is prepared from methyl 5-[2-(3-chlorophenyl) vinyl]-thiophene-2-carboxylate according to the procedure used to make the compound of Example 31, making non-critical variations. Yield 19%. MS for $C_{20}H_{21}ClN_2OS$ (ESI) (M+H)$^+$ m/z 373.

EXAMPLE 33

N-[(3R)-1-azabicyclo[2.2.2]oct-3-yl]-5-(4-chlorophenylsulfanyl)-thiophene-2-carboxamide:

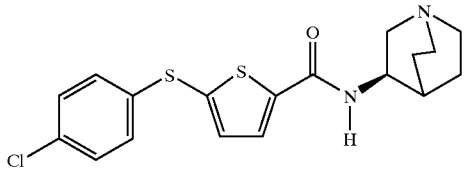

Step 33a: Preparation of 5-(4-chlorophenylsulfanyl)-thiophene-2-carboxaldehyde.

Sodium hydride (60%, 1.2 g, 30 mmol) is added to a solution of 4-chlorothiophenol (4.3 g, 30 mmol) in THF (30 mL). The resulting solution is stirred for 10 minutes then the solvent is removed in vacuo. Acetone (60 mL) is added followed by 5-bromothiophene-2-carboxaldehyde (3.0 mL, 25 mmol). The mixture is stirred at room temperature for 2 hours. The solvent is removed in vacuo and the resulting slurry diluted with $CH_2Cl_2$. This solution is washed three times with 1N NaOH then dried over $MgSO_4$, filtered and concentrated in vacuo. The crude product is purified by flash column chromatography (gradient of 1 to 5% EtOAc in heptane) to give the desired product (6.2 g, 98%). $^1$NMR (300 MHz, CDCl$_3$) 87.13, 7.31–7.39, 7.63, 9.78.

Step 33b: Preparation of 5-(4-chlorophenylsulfanyl)-thiophene-2-carboxylic Acid.

The product of Step 33a (6. lg, 24 mmol) is dissolved in a mixture of THF, t-BuOH, and water (3:3:1, 255 mL). 2-Methyl-2-butene (20.3 mL, 192 mmol) is added followed by $KH_2PO_4$ (9.8 g, 72 mmol) and then $NaClO_2$ (80%, 8.17 g, 72.3 mmol). The mixture is stirred at room temperature for 2 hours. Aqueous $KHSO_4$ (0.5M, 200 mL) is added and the organic solvents are removed in vacuo to produce an aqueous suspension of the product. The precipitate is collected by filtration, dissolved in 1N NaOH and washed two times with ether. The aqueous solution is then acidified to pH<6 with concentrated HCl and a precipitate formed. The precipitate is collected by filtration and washed with 0.5M $KHSO_4$ then water. The solid is dried in vacuo to give the product (5.7 g, 87%). MS for $C_{11}H_7ClO_2S_2$ (ESI) (M–H)$^-$ m/z 269.

Step 33c: Preparation of N-[(3R)-1-azabicyclo[2.2.2]oct-3-yl]-5-(4-chlorophenylsulfanyl)-thiophene-2-carboxamide.

TEA (1.5 mL, 10.9 mmol) was added to a suspension of the product of Step 33b (2.7 g, 10 mmol) in $CH_2Cl_2$ (100 mL). Diphenylchlorophosphate (2.08 mL, 10 mmol) was added and the resulting solution is stirred at room temperature for 30 minutes. To this solution is added a solution of (R)-3-aminoquinuclidine (1M in DMF, 9.1 mL, 9.1 mmol). The resulting solution is stirred overnight at room temperature. MeOH is added and the mixture is poured through a column of AG50Wx2 ion exchange resin (H+form). The resin is washed with MeOH, then the product is eluted with 5% TEA in MeOH. The eluent is evaporated to dryness and the resulting solid is triturated with ether and dried in vacuo to yield the desired product (2.4 g, 71%). Alternatively, these compounds can be converted to their hydrochloride salts and crystallized from MeOH/IPA. MS for $C_{18}H_{19}ClN_2OS_2$ (ESI) (M+H)$^+$ m/z 379.

EXAMPLES 34–39

The following compounds are made from the corresponding carboxylic acids according to the procedure of Example 33, making non-critical variations.

Example 34

N-[(3R)-1-azabicyclo[2.2.2]oct-3-yl]-5-(2,4-difluorophenyl-sulfanyl)-thiophene-2-carboxamide hydrochloride (from 2,4-difluorothiophenol). Yield for 3 steps 9%. MS for $C_{18}H_{18}F_2N_2OS_2$ (ESI) (M+H)$^+$ m/z 381.

Example 35

N-[(3R)-1-azabicyclo[2.2.2]oct-3-yl]-5-(3-chlorophenyl-sulfanyl)-thiophene-2-carboxamide (from 3-chlorothiophenol). Yield 50%. MS for $C_{18}H_{18}ClN_2OS_2$ (ESI) (M+H)$^+$ m/z 379.

Example 36

N-[(3R)-1-azabicyclo[2.2.2]oct-3-yl]-5-(3-chloro-4-fluoro-phenylsulfanyl)-thiophene-2-carboxamide (from 3-chloro-4-fluorothiophenol). Yield 29%. MS for $C_{18}H_{18}ClFN_2OS_2$ (ESI) (M+H)$^+$ m/z 397.

Example 37

N-[(3R)-1-azabicyclo[2.2.2]oct-3-yl]-5-(2,3-dichlorophenyl-sulfanyl)-thiophene-2-carboxamide hydrochloride (from 2,3-dichlorothiophenol). Yield 44%. MS for $C_{18}H_{18}Cl_2N_2OS_2$ (ESI) (M+H)$^+$ m/z 413.

Example 38

N-[(3R)-1-azabicyclo[2.2.2]oct-3-yl]-5-(2,4,5-trichlorophenyl-sulfanyl)-thiophene-2-carboxamide (from 2,4,5-trichlorothiophenol). Yield 53%. MS for $C_{18}H_{17}C_{13}N_2OS_2$ (ESI) (M+H)$^+$ m/z 449.

Example 39

N-[(3R)-1-azabicyclo[2.2.2]oct-3-yl]-5-(3,4-dichlorophenyl-sulfanyl)-thiophene-2-carboxamide (from 3,4-dichlorothiophenol). Yield 21%. MS for $C_{18}H_{18}Cl_2N_2OS_2$ (ESI) (M+H)$^+$ m/z 413.

EXAMPLE 40

N-[(3R)-1-azabicyclo[2.2.2]oct-3-yl]-5-phenoxy-thiophene-2-carboxamide Hydrochloride:

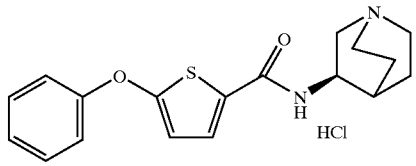

Step 40a: 5-Phenoxy-thiophene-2-carboxaldehyde.

Phenol (3.3 g, 35 mmol) is added in portions to a suspension of 60% NaH (1.3 g, 35 mmol) in DMSO (100 mL). The resulting mixture is stirred for 30 minutes then 5-nitrothiophene-2-carboxaldehyde (5 g, 32 mmol) is added. After 1 hour the reaction mixture is poured into water (1 L) and washed with ether (4×500 mL). The combined organic layers are dried over $Na_2SO_4$, filtered and evaporated to dryness. The resulting material is dissolved in MeOH and passed through a column (2.5 cm×20 cm) of Amberjet 4400 (OH form). The eluent is dried in vacuo then evaporated twice from $CH_3CN$. The crude product is purified by column chromatography in EtOAc-hexanes (1:1) to yield the desired aldehyde (304 mg, 5%). $^1$H NMR (300 MHz, CDCl$_3$) δ 6.52, 7.20, 7.27, 7.45, 7.55, 9.75.

Step 40b: 5-Phenoxy-thiophene-2-carboxylic Acid.

5-Phenoxy-thiophene-2-carboxaldehyde (325 mg, 1.6 mmol) is dissolved in a mixture of THF (10 mL), t-BuOH (5 mL) and water (5 mL). $NaH_2PO_4$ (650 mg, 4.8 mmol) is added followed by $NaClO_2$ (432 mg, 4.8 mmol). The resulting mixture is stirred for 24 hours at room temperature. Aqueous NaOH (2M, 5 mL) is added, and the organic solvents are removed in vacuo. The resulting aqueous suspension is poured into water (10 mL) and washed with ether (3×50 mL). The aqueous layer is acidified to pH<2 with 25% $H_2SO_4$ then washed with $CH_2Cl_2$ (3×50 mL). The combined organic washes are dried over $Na_2SO_4$, filtered and concentrated in vacuo. The crude product is dissolved in hot aqueous acetone and filtered. The solvents are gradually removed until a precipitate forms. The solid is collected by filtration and dried in vacuo to yield the desired product (192 mg, 55%). MS for $C_{11}H_7O_3S$ (ESI) (M–H)$^+$ m/z 219.

Step 40c: N-[(3R)-1-azabicyclo[2.2.2]oct-3-yl]-5-phenoxy-thiophene-2-carboxamide Hydrochloride.

The compound is made according to the procedure of Step 1c, starting with 5-phenoxy-thiophene-2-carboxylic acid and making non-critical variations. Yield (66%). MS for $C_{18}H_{21}N_2O_2S$ (ESI) (M+H)$^+$ m/z 329.

EXAMPLE 41

N-[(3R)-1-azabicyclo[2.2.2]oct-3-yl]-5-(2-hydroxyphenyl)-thiophene-2-carboxamide Hydrochloride:

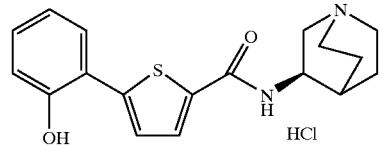

Step 41a: 5-(2-Hydroxyphenyl)-thiophene-2-carboxylic Acid.

Tetrakis(triphenylphosphine)palladium(O) (133 mg, 0.12 mmol) is added to a solution of 5-bromothiophene-2-carboxylic acid (850 mg, 4.1 mmol) in degassed THF (10 mL). The resulting solution is stirred for 5 minutes and then 2,4,4,5,5-tetramethyl)-1,3,2-dioxaborolan-2-yl) phenol (1 g, 4.6 mmol) is added followed by aqueous $Na_2CO_3$ (2M, 6.9 mL). The mixture is heated at reflux overnight. The reaction mixture is allowed to cool, poured into water (50 mL), and washed with ether (3×50 mL). The aqueous layer is acidified with concentrated HCl to pH<2. The resulting precipitate is collected by filtration, washed with water and dried in vacuo to yield the desired product (761 mg, 83%). MS for $C_{11}H_7O_3S$ (ESI) (M–H)$^+$ m/z 219.

Step 41b: N-[(3R)-1-azabicyclo[2.2.2]oct-3-yl]-5-(2-hydroxyphenyl)-thiophene-2-carboxamide Hydrochloride.

5-(2-Hydroxyphenyl)-thiophene-2-carboxylic acid (650 mg, 2.95 mmol) is dissolved in DMF (30 mL). (R)-3-Aminoquinuclidine dihydrochloride (587 mg, 2.95 mmol) is added followed by DIEA (1.6 mL, 8.85 mmol) and HATU (1.12 g, 2.95 mmol). The reaction is allowed to stir for 96 hours. The reaction mixture is diluted with MeOH and poured through a column of AG50Wx2. The column is washed with MeOH and then the product is eluted with 5% TEA in MeOH. The solvents are removed in vacuo and the resulting material is dissolved in $CH_3CN$, concentrated and then dried in vacuo. The hydrochloride salt is formed and triturated with MeOH to yield the desired product (784 mg, 73%). MS for $C_{18}H_{21}N_2O_2S$ (ESI) (M+H)$^+$ m/z 329.

EXAMPLE 42

N-[(3R)-1-azabicyclo[2.2.2]oct-3-yl]-5-(3-hydroxyphenyl)-thiophene-2-carboxamide Hydrochloride:

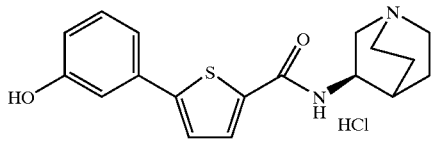

The compound is made from the 3-hydroxyphenylboronic acid according to the procedure of Example 41, making non-critical variations. Yield 46%. MS for $C_{18}H_{21}N_2O_2S$ (ESI) $(M+H)^+$ m/z 329.

EXAMPLE 43

N-[(3R)-1-azabicyclo[2.2.2]oct-3-yl]-5-(3-fluoro-4-hydroxyphenyl)-thiophene-2-carboxamide Hydrochloride:

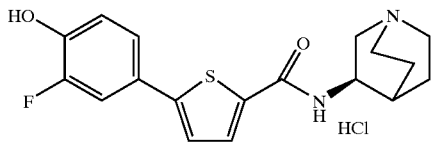

Step 43a: The compound Example 11 (165 mg, 0.38 mmol) is dissolved in MeOH and poured through a plug of Amberjet 4400 (OH⁻ form). The solvent is removed in vacuo and the product is redissolved in EtOH (2 mL). This solution is added to a suspension of Pd/C (10%, 165 mg) in EtOH (2 mL). Cyclohexadiene (360 mL, 3.8 mmol) is added, and the reaction is heated at 60° C. for 6 hours. The reaction mixture is diluted with MeOH and filtered through celite. The solvents are removed in vacuo then the hydrochloride salt is formed and crystallized from MeOH/CH₃CN to yield the desired product (52 mg, 36%). MS for $C_{18}H_{20}FN_2O_2S$ (ESI) $(M+H)^+$ m/z 347.

EXAMPLE 44

N-[(3R)-1-azabicyclo[2.2.2]oct-3-yl]-2-(phenylsulfanyl)-1,3-thiazole-5-carboxamide Fumarate:

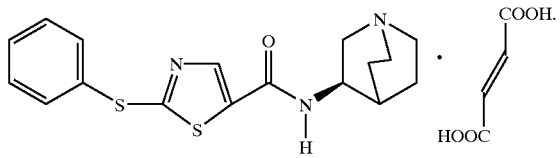

Step 44a: Preparation of 2-phenylsulfanyl-thiazole-5-carboxylic Acid Ethyl Ester.

A suspension of 2-bromo-1,3-thiazole-5-carboxylic acid ethyl ester (1.5 g, 6.15 mmol, 1 eq) and K₂CO₃ (1.7 g, 12.3 mmol, 2 eq) in EtOH (60 mL) is cooled in an ice bath, and thiophenol (0.631 mL, 6.15 mmol, 1 eq) is added. The reaction is monitored by HPLC until the starting material is consumed. The reaction mixture is filtered (to remove a solid by-product), and the solvent is removed in vacuo. The crude mixture is purified by silica gel chromatography using a Biotage Flash 40S column using 2% EtOAc in hexanes to afford the product as an oil (0.784 g, 46%). MS (ESI) for $C_2H_{11}NO_2S_2$ m/z 266.1 $(M+H)^+$.

Step 44b: Preparation of 2-phenylsulfanyl-thiazole-5-carboxylic Acid.

Potassium hydroxide (1.58 g, 28.2 mmol, 10 eq) is added to a solution of 2-phenylsulfanyl-thiazole-5-carboxylic acid ethyl ester (0.748 g, 2.82 mmol, 1 eq) in EtOH (15 mL) and water (10.5 mL). The reaction is stirred for 1.5 hours, diluted with water (30 mL) and EtOH (30 mL), and acidified by addition of 3 N HCl until a white precipitate forms. The precipitate is filtered and purified by recrystallization from water and EtOH to give the product as a white crystalline solid (0.307 g). MS (ESI) for $C_{10}H_7NO_2S_2$ m/z 235.9 $(M-H)^-$.

Step 44c: N-[(3R)-1-azabicyclo[2.2.2]oct-3-yl]-2-(phenylsulfanyl)-1,3-thiazole-5-carboxamide Fumarate.

HATU (0.493 g, 1.30 mmol, 1 eq) is added to a solution of 2-phenylsulfanyl-thiazole-5-carboxylic acid (0.307 g, 1.30 mmol, 1 eq), (R)-(+)-3-aminoquinuclidine dihydrochloride (0.258 g, 1.30 mmol, 1 eq), and DIEA (0.677 mL, 3.89 mmol, 3 eq) in DMF (9.8 mL), the flask containing which was in an ice bath. The reaction is stirred overnight. CH₂Cl₂ is added, and the mixture is washed with water three times. The organic layer is dried over MgSO₄, and the solvent removed in vacuo. The product is purified using a Biotage Flash 40M column (1% NH₄OH/9% MeOH/90%CH₂Cl₂), affording a clear oil. The fumaric acid salt of the product is made, and recrystallized from MeOH and ether to give the product as a white crystalline solid (0.408 g, 72%). MS (ESI) for $C_{17}H_{19}N_3OS_2$ m/z 346.1 $(M+H)^+$.

EXAMPLES 45–49

The following compounds are prepared from the requisite phenols or thiophenols according to the procedures for Example 44, making non-critical variations.

Example 45

N-[(3R)-1-azabicyclo[2.2.2]oct-3-yl]-2-[(4-chlorophenyl)-sulfanyl]-1,3-thiazole-5-carboxamide fumarate (from 4-chlorothiophenol). Yield 39%. HRMS (FAB) calculated for $C_{17}H_{18}ClN_3OS_2+H_1$ 380.0658, found 380.0659.

Example 46

N-[(3R)1-azabicyclo[2.2.2]oct-3-yl]-2-phenoxy-1,3-thiazole-5-carboxamide fumarate (from phenol). Yield 81%. HRMS (FAB) calculated for $C_{17}H_{19}N_3O_2S+H_1$ 330.1276, found 330.1269.

Example 47

N-[(3R)-1-azabicyclo[2.2.2]oct-3-yl]-2-[(4-fluorophenyl)-sulfanyl]-1,3-thiazole-5-carboxamide fumarate (from 4-fluorothiophenol). Yield 43%. HRMS (FAB) calculated for $C_{17}H_{18}FN_3OS_2+H_1$ 363.0875, found 364.0945.

Example 48

N-[(3R)-1-azabicyclo[2.2.2]oct-3-yl]-2-(methylsulfanyl)-1,3-thiazole-5-carboxamide fumarate (from methanethiol). Yield 28%. HRMS (FAB) calculated for $C_{12}H_{17}N_3OS_2+H_1$ 284.0891, found 284.0894.

Example 49

N-[(3R) 1-azabicyclo[2.2.2]oct-3-yl]-2-(4-chlorophenoxy)-1,3-thiazole-5-carboxamide fumarate (from 4-chlorophenol). Yield 42%. HRMS (FAB) calculated for $C_{17}H_{18}ClN_3O_2S+H_1$ 364.0886, found 364.0885.

EXAMPLE 50

N-[(3R)-1-azabicyclo[2.2.2]oct-3-yl]-2-phenyl-1,3-thiazole-5-carboxamide Fumarate:

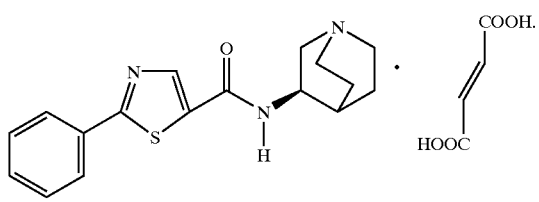

Step 50a: Preparation of 2-phenyl-thiazole-5-carboxylic Acid Ethyl Ester.

A solution of α-formyl-α-chloroacetate (9.34 g, 49.5 mmol, 1 eq) and thiobenzamide (6.79 g, 49.5 mmol, 1 eq) in EtOH (37.0 mL) is refluxed for 1 hour. The solution changes from an orange/brown color to a deep green. This solution is washed with water and extracted with $CH_2Cl_2$. The organic fraction is dried over $Na_2SO_4$, filtered, and the solvent removed in vacuo. The product is purified by column chromatography using a Biotage Flash 40M column (20% hexanes/EtOAc) to give the product as a deep orange oil (1.82 g, 15%). MS (ESI) for $C_{12}H_{13}NO_3S$ m/z 252.1 $(M+H)^+$.

Step 50b: Preparation of N-[(3R)-1-azabicyclo[2.2.2]oct-3-yl]-2-phenyl-1,3-thiazole-5-carboxamide Fumarate.

Making non-critical variations, the 2-phenyl-thiazole-5-carboxylic acid (1-azabicyclo[2.2.2]oct-3-yl)-amide is prepared using Steps 44b and 44c, starting with 2-phenyl-thiazole-5-carboxylic acid ethyl ester. The fumaric acid salt of the product is made and recrystallized from MeOH and ether to give the product as a white crystalline salt (77.4 mg, 22%). HRMS (FAB) calculated for $C_{17}H_{19}N_3OS+H_1$ 314.1327, found 314.1336.

EXAMPLE 51

N-[(3R)-1-azabicyclo[2.2.2]oct-3-yl]-2,4-dimethyl-1,3-thiazole-5-carboxamide (from 2,3-dimethyl-thiazole-5-carboxylic acid as described in Step 1c). Yield 18%. HRMS (FAB) calculated for $C_{13}H_{19}N_3OS+H_1$ 266.1327, found 266.1332.

EXAMPLE 52

N-[(3R)-1-azabicyclo[2.2.2]oct-3-yl]-2-(2-fluorophenyl)-1,3-thiazole-5-carboxamide Citrate:

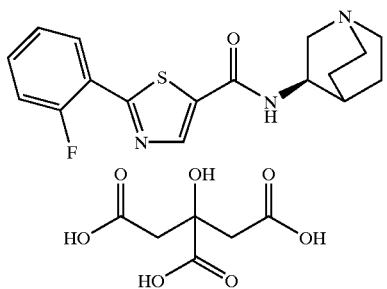

Step 52a: Preparation of ethyl 2-(2-fluorophenyl)-1,3-thiazole-5-carboxylate.

Tetrakis(triphenylphosphine)palladium (O) (0.58 g, 0.5 mmol), and a degassed solution of 2.0M $Na_2CO_3$ (10 mL) are added to a degassed solution of 2-bromo-1,3-thiazole-5-carboxylic ethyl ester (1.18 g, 5.0 mmol) and 2-fluorophenylboronic acid (0.77 g, 5.5 mmol) in DME (10 mL). The resulting suspension is stirred under argon at 80° C. for 4 hours. The reaction mixture is cooled, diluted with EtOAc, and then washed with two portions of 1.0 M NaOH, then one portion of brine. The combined organic phases are concentrated in vacuo and the resulting oil purified with flash chromatography. Yield 37%. HRMS (FAB) calculated for $C_{12}H_{10}FNO_2S+H$ 252.0495, found 252.0496.

Step 52b: Preparation of N-[(3R)-1-azabicyclo[2.2.2]oct-3-yl]-2-(2-fluorophenyl)-1,3-thiazole-5-carboxamide Citrate.

This compound is hydrolyzed and coupled according to Steps 44b and 44c, making non-critical variations. The citrate is prepared from the crude reaction mixture without chromatography, and crystallized. Yield 27%. HRMS (FAB) calculated for $C_{17}H_{18}FN_3OS+H$ 332.1233, found 332.1239.

EXAMPLES 53–57

The following compounds are prepared from their requisite boronic acids according to the procedures for Example 52. The desired salt form is prepared directly from the crude reaction mixture without chromatography, and crystallized until the product is of analytical purity.

Example 53

N-[(3R)-1-azabicyclo[2.2.2]oct-3-yl]-2-(3-fluorophenyl)-1,3-thiazole-5-carboxamide 4-methylbenzenesulfonate (from 3-fluorophenylboronic acid). Yield 20%. HRMS (FAB) calculated for $C_{17}H_{18}FN_3OS+H$ 332.1233, found 332.1225.

Example 54

N-[(3R)-1-azabicyclo[2.2.2]oct-3-yl]-2-(4-fluorophenyl)-1,3-thiazole-5-carboxamide 4-methylbenzenesulfonate (from 4-fluorophenylboronic acid). Yield 51%. HRMS (FAB) calculated for $C_{17}H_{18}FN_3OS+H$ 332.1233, found 332.1239.

Example 55

N-[(3R)-1-azabicyclo[2.2.2]oct-3-yl]-2-(2-hydroxyphenyl)-1,3-thiazole-5-carboxamide hydrochloride (from 2-(4,4,5,5-tetramethyl-1,3,2-dioxaborolan-2-yl) phenol). This compound was purified by reverse-phase preparative chromatography prior to the formation of the salt. Yield 0.5%. HRMS (FAB) calculated for $C_{17}H_{19}N_3O_2S+H$ 330.1276, found 330.1268.

Example 56

N-[(3R)-1-azabicyclo[2.2.2]oct-3-yl]-2-(4-methylphenyl)-1,3-thiazole-5-carboxamide hydrochloride (from 4-tolylphenylboronic acid). Yield 50%. MS (ESI) for $C_{18}H_{21}N_3OS$ m/z 328.2 $(M+H)^+$.

Example 57

N-[(3R)-1-azabicyclo[2.2.2]oct-3-yl]-2-[4-(benzyloxy)phenyl]-1,3-thiazole-5-carboxamide hydrochloride (from (4-benzyloxyphenyl)boronic acid). Yield 98%. MS (ESI) for $C_{24}H_{25}N_3O_2S$ m/z 420.3 $(M+H)^+$.

EXAMPLES 58–62

The following compounds are prepared from their requisite carboxylic acids according the procedures from Step 44c. The desired salt form is prepared directly from the crude reaction mixture without chromatography, and crystallized.

Example 58

N-[(3R)-1-azabicyclo[2.2.2]oct-3-yl]-2-pyridin-3-yl-1,3-thiazole-4-carboxamide dihydrochloride (from (2-pyrid-3-yl)thiazole-4-carboxylic acid). HRMS (FAB) calculated for $C_{16}H_{18}N_4OS+H$ 315.1279, found 315.1289.

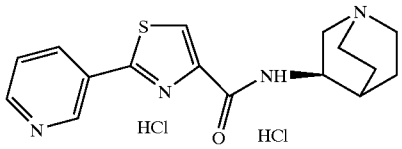

Example 59

N-[(3R)-1-azabicyclo[2.2.2]oct-3-yl]-4-methyl-2-phenyl-1,3-thiazole-5-carboxamide dihydrochloride (from 4-methyl-2-phenyl-1,3-thiazole-5-carboxylic acid). Yield 61%. HRMS (EI) calculated for $C_{18}H_{21}N_3OS$ 327.1405, found 327.1403.

Example 60

N-[(3R)-1-azabicyclo[2.2.2]oct-3-yl]-2-(4-chlorophenyl)-4-methyl-1,3-thiazole-5-carboxamide 4-methylbenzenesulfonate (from 2-(4-chlorophenyl)4-methyl-1,3-thiazole-5-carboxylic acid). Yield 85%. MS (ESI) for $C_{18}H_{21}N_3OS$ m/z 328.2 $(M+H)^+$.

Example 61

N-[(3R)-1-azabicyclo[2.2.2]oct-3-yl]-4-methyl-2-pyridin-2-yl-1,3-thiazole-5-carboxamide hydrochloride (from 4-methyl-2-pyridin-2-yl-1,3-thiazole-5-carboxylic acid). Yield 57%. MS (ESI) for $C_{18}H_{20}ClN_3OS$ m/z 362.2 $(M+H)^+$.

Example 62

N-[(3R)-1-azabicyclo[2.2.2]oct-3-yl]-4-methyl-2-pyridin-4-yl-1,3-thiazole-5-carboxamide dihydrochloride (from 4-methyl-2-pyridin-4-yl-1,3-thiazole-5-carboxylic acid). Yield 87%. MS (ESI) for $C_{17}H_{20}N_4OS$ m/z 329.2 $(M+H)^+$.

EXAMPLE 63

N-[(3R)-1-azabicyclo[2.2.2]oct-3-yl]-2-(methylamino)-1,3-thiazole-5-carboxamide Hydrochloride:

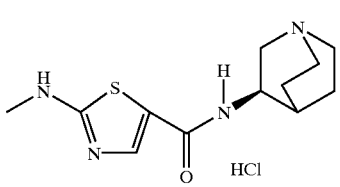

Step 63a: Preparation of Ethyl 2-[(tert-butoxycarbonyl)amino]-1,3-thiazole-5-carboxylate:

A flask is charged with a solution of ethyl 2-amino-1,3-thiazole-5-carboxylate (2.65 g, 15.4 mmol) and 4-dimethylaminopyridine (10 mg) in THF (75 mL). Di(tert-butyl) dicarbonate (3.6 mL, 15.4 mmol, 1.0 eq) and TEA (4.3 mL, 30.8 2.0 eq) are added, and the resulting solution is stirred at room temperature for 90 minutes. The reaction mixture is concentrated to dryness, and the crude product is crystallized from CHCl$_3$/hexanes to give a light brown solid. Yield 68%. HRMS (FAB) calculated for $C_{11}H_{16}N_2O_4S+H$ 273.0909, found 273.0897.

Step 63b: Preparation of Ethyl 2-[(tert-butoxycarbonyl)(methyl)amino]-1,3-thiazole-5-carboxylate.

A flask is charged with a suspension of sodium hydride (60% in mineral oil) (0.109 g, 2.72 mmol) in THF (5 mL). The ethyl 2-[(tert-butoxycarbonyl)amino]-1,3-thiazole-5-carboxylate (0.735 g, 2.70 mmol) is added, followed by iodomethane (175 µL, 2.70 mmol) and the resulting suspension is heated to reflux for 3 hours, then cooled to room temperature. Water is added, followed by 1.0 N NaOH. The basic phase is extracted with 3 portions of EtOAc. The combined organic phases are washed with brine, dried over Na$_2$SO$_4$, filtered, and concentrated to give a clear oil purified with flash chromatography. Yield 45%. HRMS (FAB) calculated for $C_{12}H_{18}N_2O_4S+H$ 287.1065, found 287.1068.

Step 63c: Preparation of 2-[(tert-butoxycarbonyl)(methyl)amino]-1,3-thiazole-5-carboxylic Acid.

The product of Step 63b is hydrolyzed according to Step 44b, making non-critical variations. Yield 49%. HRMS (FAB) calculated for $C_{10}H_{14}N_2O_4S+H$ 259.0752, found 259.0750.

Step 63d: Preparation of tert-butyl 5-{[[(3R)-1-azabicyclo[2.2.2]oct-3-ylamino]carbonyl}-1,3-thiazol-2-yl(methyl)carbamate.

This compound is coupled according to Step 44c. The citrate is prepared from the crude reaction mixture without chromatography, and crystallized until the product is of analytical purity. Yield 32%. MS (ESI) for $C_{17}H_{21}N_4O_3S$ m/z 367.2 $(M+H)^+$.

Step 63e: Preparation of N-[(3R)-1-azabicyclo[2.2.2]oct-3-yl]-2-(methylamino)-1,3-thiazole-5-carboxamide Hydrochloride.

A flask is charged with tert-butyl 5-{[[(3R)-1-azabicyclo[2.2.2]oct-3-ylamino]carbonyl}-1,3-thiazol-2-yl(methyl)carbamate (72 mg, 0.18 mmol) in MeOH (5 mL). To this suspension is added a solution of 4.0 N HCl/dioxane (10 mL) and the reaction mixture is stirred at room temperature for 3.5 hours. The solvents are removed in vacuo and the residue crystallized from IPA/ether. Yield 63%. MS (ESI) for $C_{12}H_{18}N_4OS$ m/z 267.2 $(M+H)^+$.

EXAMPLE 64

N-[(3R)-1-azabicyclo[2.2.2]oct-3-yl]-5-(phenylsulfanyl)-1,3,4-thiadiazole-2-carboxamide:

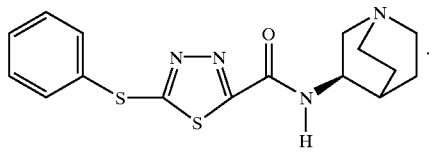

Step 64a: Preparation of 5-phenylsulfanyl-[1,3,4]thiadiazole-2-carboxylic Acid Ethyl Ester.

To a solution of 5-chloro-[1,3,4]thiadiazole-2-carboxylic acid ethyl ester (1.0 g, 5.2 mmol, 1 eq), and K$_2$CO$_3$ (1.44 g, 104 mmol, 2 eq) in CH$_3$CN (50 mL), thiophenol (0.53 mL, 5.2 mmol, 1 eq) is added. The reaction is stirred overnight at room temperature. The reaction is filtered to remove the salts, and the filtrate is washed with CH$_3$CN. The solvents are removed under reduced pressure, and the product is recrystallized from EtOH to give 5-phenylsulfanyl-[1,3,4]thiadiazole-2-carboxylic acid ethyl ester (1.03 g, 74%). MS (ESI) for $C_{11}H_{10}N_2O_2S_2$ m/z 267.0 $(M+H)^+$.

Step 64b: Preparation of 5-phenylsulfanyl-[1,3,4] thiadiazole-2-carboxylic Acid.

The 5-phenylsulfanyl-[1,3,4]thiadiazole-2-carboxylic acid ethyl ester from Step 64a (1.0 g, 3.76 mmol, 1 eq) is dissolved in EtOH (40 mL), and cooled in an ice bath. To this, 2N NaOH (1.88 mL, 3.76 mmol, 1 eq) is added drop wise. The sodium salt of the acid precipitates out of solution. The reaction mixture is concentrated in vacuo to give a white crystalline product. The reaction mixture is carried through to the next step in its crude form to make the acid chloride. MS (ESI) for $C_9H_6N_2S_2O_2$ m/z 237.0 (M–H)$^-$.

Step 64c: Preparation of N-[(3R)-1-azabicyclo[2.2.2]oct-3-yl]-5-(phenyl-sulfanyl)-1,3,4-thiadiazole-2-carboxamide.

5-Phenylsulfanyl-[1,3,4]thiadiazole-2-carboxylic acid (3.76 mmol) is placed in a flask and put under nitrogen. The acid is chilled in an ice bath. Oxalyl chloride (9 mL) that has also been cooled in an ice bath is added drop wise to the acid. The excess oxalyl chloride is removed under reduced pressure. The acid chloride is dissolved in about 5 mL $CH_2Cl_2$. The freebase of (R)-3-aminoquinuclidine (0.5 g, 2.52 mmol, 0.67 eq) is also dissolved in $CH_2Cl_2$ (5 mL), and the solution containing the acid chloride is cannulated into the flask containing the aminoquinuclidine. The reaction is stirred overnight at room temperature. The reaction mixture is diluted with MeOH, and poured through a Dowex 50AGWX2 CH+ column. The impurities are removed by washing the column with MeOH, and the product is eluted by washing the column with a solution containing 5% TEA in MeOH. The solvent is removed under reduced pressure, and the product is further purified by silica gel chromatography using a Biotage Flash 40M column (5% MeOH/$CH_2Cl_2$). This gives Example 64 (0.289 g, 22%) as a tan oil. MS (ESI) for $C_{16}H_{18}N_4OS_2$ m/z 347.2 (M+H)$^+$.

EXAMPLE 65

N-[(3R)-1-azabicyclo[2.2.2]oct-3-yl]-5-phenoxy-1,3,4-thiadiazole-2-carboxamide. This compound is prepared from phenol according to the procedures for Example 64, making non-critical variations. Yield 16%. HRMS (FAB) calculated for $C_{16}H_{17}N_3O_3S$ 331.0991, found 331.1229 (M)$^+$.

EXAMPLE 66

N-[(3R)-1-azabicyclo[2.2.2]oct-3-yl]-5-[(4-chlorophenyl)-sulfanyl]-1,3,4-thiadiazole-2-carboxamide:

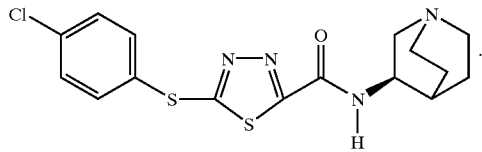

5-(4-Chloro-phenylsulfanyl)-[1,3,4]thiadiazole-2-carboxylic acid ethyl ester (0.1 g, 0.33 mmol, 1 eq), the free base of (R)-(+)-3-aminoquinuclidine (0.041 g, 0.33 mmol, 1 eq), and EtOH (0.66 mL) are added to a vial, and the solution is heated at 80° C. The reaction is complete after 4 hours as determined by HPLC. The product is purified by silica gel chromatography using a Biotage Flash 40S column (0.5% $NH_4OH$/9.5% $MeOH/CH_2Cl_2$) to give Example 66 (0.0254 g, 20%) as a pale oil. HRMS (FAB) calculated for $C_{16}H_{17}ClN_4OS_2+H_1$ 381.0610, found 381.0617.

EXAMPLES 67–72

The following compounds are prepared from the requisite phenols or thiophenols according to the procedures for Example 66, making non-critical variations.

Example 67

N-[(3R)-1-azabicyclo[2.2.2]oct-3-yl]-5-(4-fluorophenoxy)-1,3,4-thiadiazole-2-carboxamide (from 4-fluorophenol). Yield 27%. HRMS (FAB) calculated for $C_{16}H_{17}FN_4OS_2+H_1$ 365.0906, found 365.0899.

Example 68

N-[(3R)-1-azabicyclo[2.2.2]oct-3-yl]-5-(4-chlorophenoxy)-1,3,4-thiadiazole-2-carboxamide (from 4-chlorophenol). Yield 18%. HRMS (FAB) calculated for $C_{16}H_{17}ClN_4O_2S+H_1$ 365.0839, found 365.0826.

Example 69

N-[(3R)-1-azabicyclo[2.2.2]oct-3-yl]-5-[(3-fluorophenyl)-sulfanyl]-1,3,4-thiadiazole-2-carboxamide (from 3-fluorothiophenol). Yield 16%. HRMS (FAB) calculated for $C_{16}H_{17}FN_4OS_2+H_1$ 365.0906, found 365.0899.

Example 70

N-[(3R)-1-azabicyclo[2.2.2]oct-3-yl]-5-[(2-chlorophenyl)-sulfanyl]-1,3,4-thiadiazole-2-carboxamide (from 2-chlorothiophenol). Yield 44%. HRMS (FAB) calculated for $C_{16}H_{17}ClN_4OS_2+H_1$ 381.0610, found 381.0625.

Example 71

N-[(3R)-1-azabicyclo[2.2.2]oct-3-yl]-5-[(4-fluorophenyl)-sulfanyl]-1,3,4-thiadiazole-2-carboxamide (from 4-fluorothiophenol). Yield 34%. HRMS (FAB) calculated for $C_{16}H_{17}FN_4OS_2+H_1$ 365.0906, found 365.0921.

Example 72

N-[(3R)-1-azabicyclo[2.2.2]oct-3-yl]-5-[(3-chlorophenyl)-sulfanyl]-1,3,4-thiadiazole-2-carboxamide (from 3-chlorothiophenol). Yield 34%. HRMS (FAB) calculated for $C_{16}H_{17}ClN_4OS_2+H_1$ 381.0610, found 381.0603.

EXAMPLE 75

N-[(3R)-1-azabicyclo[2.2.2]oct-3-yl]-5-phenyl-1H-1,2,4-triazole-3-carboxamide Dihydrochloride:

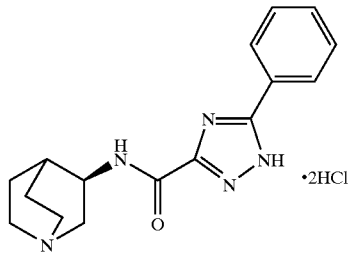

Step 75a: Preparation of Ethyl (2Z)-amino(benzoylhydrazono)ethanoate.

Ethyl thioxamate (0.6 g, 4.5 mmol) and benzyl hydrazide 0.68 g, 5.0 mmol) in EtOH (20 mL) are heated at reflux for 2 hours according to the procedure described in McKillop et al., *Tetrahedron Lett.* 23, 3357–3360 (1982). The resulting solids are collected and washed with EtOH, and dried in vacuo to afford the desired product (0.5 g, 50%).

Step 75b: Preparation of Ethyl 5-phenyl-1,3,4-oxadiazole-2-carboxylate and Ethyl 5-phenyl-1H-1,2,4-triazole-3-carboxylate.

Modification of the procedure described in McKillop et al., *Tetrahedron Lett.* 23, 3357–3360 (1982) affords a mixture of two products. In particular, heating ethyl (2Z)-amino(benzoylhydrazono)ethanoate (0.5 g, 2.1 mmol) in mesitylene (15 mL) at reflux overnight affords a clear solution that was concentrated in vacuo. The resultant material is purified by silica gel chromatography (20% EtOAc/hexanes) to afford a 2.2:1 mixture of ethyl 5-phenyl-1,3,4-oxadiazole-2-carboxylate (310 mg, 67%) and ethyl 5-phenyl-1H-1,2,4-triazole-3-carboxylate (140 mg, 30%), respectively. MS for $C_{11}H_{10}N_2O_3$ (ethyl 5-phenyl-1,3,4-oxadiazole-2-carboxylate) (ESI) (M+H)$^+$ m/z 219 and MS for $C_{11}H_{10}N_2O_3$ (ethyl 5-phenyl-1H-1,2,4-triazole-3-carboxylate) (ESI) (M+H)$^+$ m/z 218.

Step 75c: Preparation of N-[(3R)-1-azabicyclo[2.2.2]oct-3-yl]-5-phenyl-1H-1,2,4-triazole-3-carboxamide Dihydrochloride.

This material is prepared using ethyl 5-phenyl-1H-1,2,4-triazole-3-carboxylate prepared in Step 75b and coupled to (R)-(+)-3-aminoquinuclidine. The product is purified as described in Example 66, making non-critical variations, to afford the desired product (13 mg, 7.3%). MS for $C_{16}H_{19}N_5O$ (ESI) (M+H)$^+$ m/z 298.

EXAMPLE 76

N-[(3R)-1-azabicyclo[2.2.2]oct-3-yl]-5-phenyl-1,3,4-oxadiazole-2-carboxamide Hydrochloride:

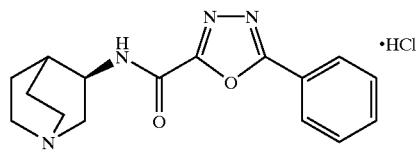

This material is prepared using ethyl 5-phenyl-1,3,4-oxadiazole-2-carboxylate prepared in Step 75b and coupled to (R)-(+)-3-aminoquinuclidine and the product is purified as described in Example 66, making non-critical variations. 7.3% Yield. MS for $C_{16}H_{18}N_4O_2$ (ESI) (M+H)$^+$ m/z 299.

EXAMPLE 77

N-[(3R)-1-azabicyclo[2.2.2]oct-3-yl]-5-(methylthio)-1,3,4-oxadiazole-2-carboxamide Hydrochloride:

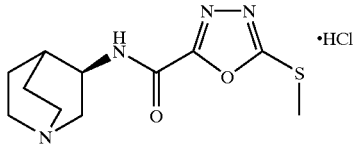

Step 77a: Preparation of Ethyl-1,3,4-oxadiazole-2-thione-5-carboxylate Potassium Salt Dimethylsulfoxide Solvate.

A mixture of ethyl hydrazino(oxo)acetate (3.7 g, 28 mmol), prepared as described by Benson, Gross, and Snyder in *J. Org. Chem.* 3257–3269 (1990), EtOH (25 mL), carbon disulfide (8.5 g, 6.6 mL, 112 mmol), DMSO (6 mL) and a solution of KOH (1.57 g, 28 mmol) in water (2 mL) are heated at reflux overnight, as described by Homing and Muchowski in *Can. J. Chem.* 3079–3082 (1972). The resultant solid is collected by vacuum filtration and washed to afford the desired product as a DMSO solvate that was used without further purification (8.2 g of a semi-solid).

Step 77b: Preparation of Methyl Ethyl-1,3,4-oxadiazole-2-thione-5-carboxylate.

Following the procedure of Partyka and Crenshaw in U.S. Pat. No. 4,001,238, a solution of ethyl-1,3,4-oxadiazole-2-thione-5-carboxylate potassium salt dimethylsulfoxide solvate (4.1 g, 24 mmol) and iodomethane (6.7 g, 47 mmol) are heated for 1 hour at reflux in EtOH (20 mL). A solid is removed by vacuum filtration, and the filtrate is concentrated. Water (40 mL) is added to the resultant material, a solid is isolated by vacuum filtration, dried at 50° C./0.5 mmHg overnight to afford the desired product (2.3 g, 50%).

Step 77c: N-[(3R)-1-azabicyclo[2.2.2]oct-3-yl]-5-(methylthio)-1,3,4-oxadiazole-2-carboxamide Hydrochloride:

This material is prepared using methyl ethyl-1,3,4-oxadiazole-2-thione-5-carboxylate prepared in Step 77b and coupled to (R)-(+)-3-aminoquinuclidine as described in Example 66, making non-critical variations, to afford material that is purified by silica gel chromatography (10% MeOH/CHCl$_3$+0.5% NH$_4$OH). The hydrochloride salt is prepared upon crystallization of the desired product from 1M HCl/Et$_2$O (65 mg, 42%). MS for $C_{11}H_{16}N_4O_2S$ (ESI) (M+H)$^+$ m/z 269.

EXAMPLE 79

N-[(3R)-1-azabicyclo[2.2.2]oct-3-yl]-5-(3-chlorophenyl)-1,3-oxazole-2-carboxamide 4-methylbenzenesulfonate:

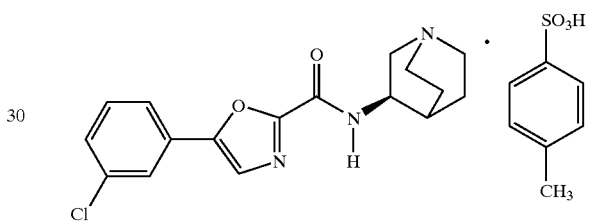

Step 79a: Preparation of 2-amino-1-(3-chlorophenyl)ethanone Hydrochloride.

A mixture of 3-chlorophenylacyl bromide (5.18 g, 22.2 mmol, 1 eq), sodium diformylimide (2.11 g, 22.2 mmol, 1 eq) and CH$_3$CN (125 mL) is heated in an 80° C. oil bath. After 3.5 h, the mixture is filtered and evaporated. The residue is treated with EtOH (40 mL) and HCl (10 mL, 12 N). The mixture was then heated in a 50° C. water bath for 30 min and evaporated. The resulting solid is triturated with acetone and collected by filtration to afford the title compound (2.86 g, 62%). MS (ESI) for C$_8$H$_8$ClNO m/z 170 (M+H)$^+$.

Step 79b: Preparation of Ethyl [[2-(3-chlorophenyl)-2-oxoethyl]amino](oxo) Acetate.

A mixture of 2-amino-1-(3-chlorophenyl)ethanone hydrochloride from Step 79a (2.83 g, 13.7 mmol, 1 eq), ethyl chlorooxoacetate (1.87 g, 13.7 mmol, 1 eq), and CH$_2$Cl$_2$ (40 mL) is cooled in an ice-H$_2$O bath. The mixture is treated with a solution of TEA (4.0 mL, 29 mmol, 2.1 eq) in CH$_2$Cl$_2$ (20 mL), and the reaction is warmed to room temperature overnight. Water is added and the organic layer is separated, dried over MgSO$_4$, filtered, and evaporated. The resulting solid is triturated with hexane/2-propanol and dried in vacuo to provide the title compound (2.70 g, 72%). MS (ESI) for C$_{12}$H$_{12}$ClNO$_4$ m/z 270 (M+H)$^+$.

Step 79c: Preparation of Ethyl 5-(3-chlorophenyl)-1,3-oxazole-2-carboxylate.

A mixture of the product from Step 79b (1.28 g, 4.70 mmol, 1 eq), benzene (8 mL), and POCl$_3$ (2.0 mL, 21 mmol) is heated under reflux for 65 h and cooled. The mixture is then evaporated and extracted between CHCl$_3$ and water. The organic layer is separated, dried over MgSO$_4$, filtered, and evaporated. The residue is crystallized from EtOH to give the title product (0.61 g, 51%). MS (ESI) for $C_{12}H_{10}ClNO_3$ m/z 252 (M+H)$^+$.

Step 79d: Preparation of N-[(3R)-1-azabicyclo[2.2.2]oct-3-yl]-5-(3-chlorophenyl)-1,3-oxazole-2-carboxamide 4-methylbenzenesulfonate.

A mixture of the product from Step 79c (0.419 g, 1.66 mmol, 1.0 eq), (R)-(+)-3-aminoquinuclidine (0.221 g, 1.75 mmol, 1.05 eq) and EtOH (4.0 mL) is heated under reflux. After 64 h, the mixture is cooled and the contents are filtered through glass wool into p-toluenesulfonic acid monohydrate (0.315 g, 1.65 mmol, 1.0 eq). The resulting solid is filtered and dried in vacuo to afford the title compound (0.59 g, 65%). HRMS (FAB) calculated for $C_{17}H_{18}ClN_3O_2+H_1$ 332.1165, found 332.1180.

EXAMPLES 80–88

The following compounds are prepared from the requisite acylhalides according to the procedures for Example 79, making non-critical variations. For some examples, the product of Step 79a is commercially available.

Example 80

N-[(3R)-1-azabicyclo[2.2.2]oct-3-yl]-5-(3-methoxyphenyl)-1,3-oxazole-2-carboxamide 4-methylbenzenesulfonate (from 2-bromo-1-(3-methoxyphenyl)ethanone). Yield 20%. HRMS (FAB) calculated for $C_{18}H_{21}N_3O_3+H_1$ 328.1661, found 328.1660.

Example 81

N-[(3R)-1-azabicyclo[2.2.2]oct-3-yl]-5-(3-nitrophenyl)-1,3-oxazole-2-carboxamide 4-methylbenzenesulfonate (from 2-amino-1-(3-nitrophenyl)ethanone hydrochloride). Yield 8%. HRMS (FAB) calculated for $C_{17}H_{18}N_4O_4+H_1$ 343.1406, found 343.1405.

Example 82

N-[(3R)-1-azabicyclo[2.2.2]oct-3-yl]-5-(4-methoxyphenyl)-1,3-oxazole-2-carboxamide 4-methylbenzenesulfonate (from 2-amino-1-(4-methoxyphenyl)ethanone hydrochloride). Yield 23%. HRMS (FAB) calculated for $C_{18}H_{21}N_3O_3+H_1$ 328.1661, found 328.1662.

Example 83

N-[(3R)-1-azabicyclo[2.2.2]oct-3-yl]-5-(2-nitrophenyl)-1,3-oxazole-2-carboxamide 4-methylbenzenesulfonate (from 2-bromo-1-(2-nitrophenyl)ethanone). Yield 4%. HRMS (FAB) calculated for $C_{17}H_{18}N_4O_4+H_1$ 343.1406, found 343.1405.

Example 84

N-[(3R)-1-azabicyclo[2.2.2]oct-3-yl]-5-(2-methoxyphenyl)-1,3-oxazole-2-carboxamide 4-methylbenzenesulfonate (from 2-bromo-1-(2-methoxyphenyl)ethanone). Yield 13%. HRMS (FAB) calculated for $C_{18}H_{21}N_3O_3+H_1$ 328.1661, found 328.1661.

Example 85

N-[(3R)-1-azabicyclo[2.2.2]oct-3-yl]-5-(4-fluorophenyl)-1,3-oxazole-2-carboxamide 4-methylbenzenesulfonate (from 2-bromo-1-(4-fluorophenyl)-ethanone). Yield 5%. HRMS (FAB) calculated for $C_{17}H_{18}FN_3O_2+H_1$ 316.1461, found 316.1470.

Example 86

N-[(3R)-1-azabicyclo[2.2.2]oct-3-yl]-5-(2-chlorophenyl)-1,3-oxazole-2-carboxamide 4-methylbenzenesulfonate (from 2-bromo-1-(2-chlorophenyl)-ethanone). Yield 10%. HRMS (FAB) calculated for $C_{17}H_{18}ClN_3O_2+H_1$ 332.1165, found 332.1168.

Example 87

N-[(3R)-1-azabicyclo[2.2.2]oct-3-yl]-5-(3-cyanophenyl)-1,3-oxazole-2-carboxamide 4-methylbenzenesulfonate (from 3-(bromoacetyl)-benzonitrile). Yield 3%. HRMS (FAB) calculated for $C_{18}H_{21}N_3O_3+H_1$ 323.1508, found 323.1516.

Example 88

N-[(3R)-1-azabicyclo[2.2.2]oct-3-yl]-5-(4-bromophenyl)-1,3-oxazole-2-carboxamide 4-methylbenzenesulfonate (from 2-amino-1-(4-bromophenyl)-ethanone hydrochloride). Yield 6%. HRMS (FAB) calculated for $C_{17}H_{18}BrN_3O_2+H_1$ 376.0661, found 376.0660.

EXAMPLE 89

N-[(3R)-1-azabicyclo[2.2.2]oct-3-yl]-4-methyl-5-phenyl-1,3-thiazole-2-carboxamide 4-methylbenzenesulfonate:

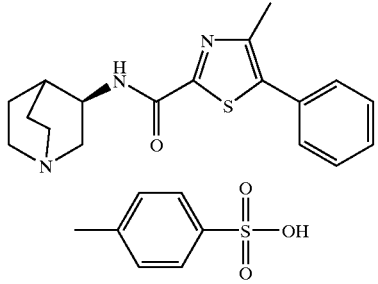

Step 89a: Preparation of 2-amino-1-phenylpropan-1-one Hydrochloride.

2-Bromo-1-phenylpropan-1-one (8.97 g, 42.1 mmol, 1 eq) is added dropwise to a suspension of diformylimide sodium salt (4.80 g, 50.5 mmol, 1.2 eq) in 80 mL $CH_3CN$. The reaction is stirred for 60 h at 70–75° C. The hot mixture is filtered to remove the salts and the solids are washed with $CH_3CN$. The combined filtrates are concentrated in vacuo, dissolved in 40 mL 6N HCl and heated under reflux for 0.75 h. The solvents are removed under reduced pressure and the product is recrystallized from IPA to give 2-amino-1-phenylpropan-1-one hydrochloride (6.15 g, 79%). MS (ESI) for $C_9H_{11}NO$ m/z 150.2 (M+H)$^+$.

Step 89b: Preparation of ethyl [(1-methyl-2-oxo-2-phenylethyl)amino](oxo)acetate.

TEA (3.22 mL, 0.0231 mol, 2.1 eq) is added dropwise to a suspension of the product from Step 89a (2.05 g, 11.0 mmol, 1 eq) and ethyl oxalyl chloride (1.24 mL, 11.0 mmol, 1 eq) in 50 mL $CH_2Cl_2$ in an ice/water bath. The mixture is allowed to slowly warn to room temperature. After stirring overnight, water and 20 mL 1N HCl are added. The aqueous layer is extracted with $CH_2Cl_2$. The combined organic layers are dried over $MgSO_4$, filtered and concentrated to give ethyl [(1-methyl-2-oxo-2-phenylethyl)amino](oxo)acetate as a yellow oil (2.58 g, 94%). MS (ESI) for $C_{13}H_{15}NO_4$ m/z 250.2 (M+H)$^+$.

Step 89c: Preparation of Ethyl 4-methyl-5-phenyl-1,3-thiazole-2-carboxylate.

The product from Step 89b (2.58 g, 10.4 mmol, 1 eq) and $P_2S_5$ (4.83 g, 10.9 mmol, 1.05 eq) are suspended in 30 mL $CHCl_3$. The mixture is heated under reflux. After 12 h, water and solid $K_2CO_3$ are carefully added until all material dissolves. The aqueous layer is made sufficiently basic with 1N NaOH (pH more than 10) and extracted with EtOAc. The combined organic layers are washed with 1N NaOH and brine, dried over $MgSO_4$, filtered and concentrated to give ethyl 4-methyl-5-phenyl-1,3-thiazole-2-carboxylate as a yellow oil (2.51 g, 98%). MS (ESI) for $C_{13}H_{13}NO_2S$ m/z 248.1 $(M+H)^+$.

Step 89d: Preparation of N-[(3R)-1-azabicyclo[2.2.2]oct-3-yl]-4-methyl-5-phenyl-1,3-thiazole-2-carboxamide 4-methylbenzenesulfonate.

The freebase of (R)-3-aminoquinuclidine (1.0 g, 5.02 mmol, 2.26 eq) dissolved in THF (5 mL) is added to a solution of the product from Step 89c (0.55 g, 2.22 mmol, 1 eq) in 10 mL EtOH. The mixture is heated under reflux. After 48 h, the mixture is cooled and concentrated in vacuo. The residue is purified by silica gel chromatography using a Biotage Flash 40S column (90:9:1 $CHCl_3/MeOH/NH_4OH$) to provide N-[(3R)-1-azabicyclo[2.2.2]oct-3-yl]-4-methyl-5-phenyl-1,3-thiazole-2-carboxamide (0.40 g, 55%) as a yellow oil. The p-toluenesulfonic acid salt of the product is made and recrystallized from IPA/ether to give the product as light yellow solid. MS (ESI) for $C_{18}H_{21}N_3OS$ m/z 328.2 $(M+H)^+$.

EXAMPLES 90–102

The following compounds are prepared from the requisite ethyl 5-substituted-1,3-thiazole-2-carboxylates according to the procedures outlined in Example 79 or Example 66 (thiadiazole amide), making non-critical variations.

Example 90

N-[(3R)-1-azabicyclo[2.2.2]oct-3-yl]-5-phenyl-1,3-thiazole-2-carboxamide (from 2-amino-1-phenylethanone hydrochloride). Yield 36%. HRMS (FAB) calculated for $C_{17}H_{19}N_3OS+H_1$ 314.1327, found 314.1330.

Example 91

N-[(3R)-1-azabicyclo[2.2.2]oct-3-yl]-5-(4-bromophenyl)-1,3-thiazole-2-carboxamide 4-methylbenzenesulfonate (from 2-amino-1-(4-bromophenyl)-ethanone hydrochloride). Yield 18%. HRMS (FAB) calculated for $C_{17}H_{18}BrN_3OS+H_1$ 392.0432, found 392.0423.

Example 92

N-[(3R)-1-azabicyclo[2.2.2]oct-3-yl]-5-(3-nitrophenyl)-1,3-thiazole-2-carboxamide 4-methylbenzenesulfonate (from 2-amino-1-(3-nitrophenyl)-ethanone hydrochloride). Yield 47%. HRMS (FAB) calculated for $C_{17}H_{18}N_4O_3S+H_1$ 359.1178, found 359.1165.

Example 93

N-[(3R)-1-azabicyclo[2.2.2]oct-3-yl]-5-(3-methoxyphenyl)-1,3-thiazole-2-carboxamide 4-methylbenzenesulfonate (from 2-bromo-1-(3-methoxyphenyl)-ethanone). Yield 14%. HRMS (FAB) calculated for $C_{18}H_{21}N_3O_2S+H_1$ 344.1432, found 344.1423.

Example 94

N-[(3R)-1-azabicyclo[2.2.2]oct-3-yl]-5-(2-chlorophenyl)-1,3-thiazole-2-carboxamide 4-methylbenzenesulfonate (from 2-bromo-1-(2-chlorophenyl)-ethanone. Yield 28%. HRMS (FAB) calculated for $C_{17}H_{18}ClN_3OS+H_1$ 348.0937, found 348.0947.

Example 95

N-[(3R)-1-azabicyclo[2.2.2]oct-3-yl]-5-(4-fluorophenyl)-1,3-thiazole-2-carboxamide 4-methylbenzenesulfonate (from 2-bromo-1-(4-fluorophenyl)-ethanone). Yield 16%. HRMS (FAB) calculated for $C_{17}H_{18}FN_3OS+H$, 332.1233, found 332.1233.

Example 96

N-[(3R)-1-azabicyclo[2.2.2]oct-3-yl]-5-(2-methoxyphenyl)-1,3-thiazole-2-carboxamide 4-methylbenzenesulfonate (from 2-bromo-1-(2-methoxyphenyl)ethanone). Yield 14%. HRMS (FAB) calculated for $C_{18}H_{21}N_3O_2S+H_1$ 344.1432, found 344.1436.

Example 97

N-[(3R)-1-azabicyclo[2.2.2]oct-3-yl]-5-(4-chlorophenyl)-1,3-thiazole-2-carboxamide 4-methylbenzenesulfonate (from 2-bromo-1-(4-chlorophenyl)-ethanone). Yield 12%. HRMS (FAB) calculated for $C_{17}H_{18}ClN_3OS+H_1$ 348.0937, found 348.0934.

Example 98

N-[(3R)-1-azabicyclo[2.2.2]oct-3-yl]-5-methyl-1,3-thiazole-2-carboxamide 4-methylbenzenesulfonate (from 1-chloroacetone). Yield 2%. HRMS (FAB) calculated for $Cl_2H_{17}N_3OS+H_1$ 252.1171, found 252.1171.

Example 99

N-[(3R)-1-azabicyclo[2.2.2]oct-3-yl]-5-(3-chlorophenyl)-1,3-thiazole-2-carboxamide 4-methylbenzenesulfonate (from 2-bromo-1-(3-chlorophenyl)-ethanone). Yield 10%. HRMS (FAB) calculated for $C_{17}H_{18}ClN_3OS+H_1$ 348.0937, found 348.0936.

Example 100

N-[(3R)-1-azabicyclo[2.2.2]oct-3-yl]-5-(2-fluorophenyl)-1,3-thiazole-2-carboxamide 4-methylbenzenesulfonate (from 2-bromo-1-(2-fluorophenyl)-ethanone). Yield 0.4%. MS (ESI) for $C_{17}H_{18}FN_3OS$ m/z 332.2 $(M+H)^+$.

Example 101

N-[(3R)-1-azabicyclo[2.2.2]oct-3-yl]-5-(3-fluorophenyl)-1,3-thiazole-2-carboxamide 4-methylbenzenesulfonate (from 2-bromo-1-(3-fluorophenyl)-ethanone). Yield 6%. MS (ESI) for $C_{17}H_{18}FN_3OS$ m/z 332.2 $(M+H)^+$.

Example 102

N-[(3R)-1-azabicyclo[2.2.2]oct-3-yl]-5-thien-2-yl-1,3-thiazole-2-carboxamide 4-methylbenzenesulfonate (from 2-bromo-1-thien-2-yl-ethanone). Yield 10%. MS (ESI) for $C_{15}H_{17}N_3OS_2$ m/z 320.2 $(M+H)^+$.

EXAMPLE 103

N-[(3R)-1-azabicyclo[2.2.2]oct-3-yl]-5-phenyl-furan-2-carboxamide 4-methylbenzenesulfonate:

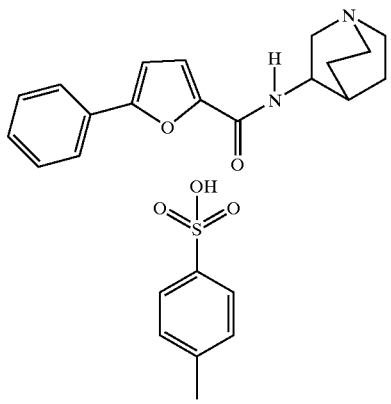

Step 103a: Synthesis of 5-phenyl-furan-2-carbaldehyde.

A solution of 5-bromo-furan-2-carbaldehyde (1.08 g, 6.16 mmol, 1 eq), phenylboronic acid (0.90 g, 7.39 mmol, 1.1 eq), tetrabutylammonium bromide (1.99 g, 6.16 mmol, 1 eq), palladium acetate (30 mg, 0.0.12 mmol 0.02 eq), $K_2CO_3$ (2.13 g, 15.4 mmol, 2.5 eq) in water (10 mL) is stirred under nitrogen at room temperature overnight. Upon completion, the reaction mixture turns into a black mass floating in the solution. The reaction is diluted with 40 ML water and extracted with EtOAc (3×100 mL). The organic layers are combined and stirred with charcoal for 30 min, then dried over $MgSO_4$ and filtered. The solvent is removed under reduced pressure to give an oil. The product is purified by silica gel chromatography using a Biotage Flash 40M column (10% EtOAc/heptane). Yield 70.1%. HRMS (FAB) calculated for $C_{11}H_8O_2$+H 173.0603, found 173.0607.

Step 103b: Synthesis of 5-phenyl-furan-2-carboxylic Acid.

To a solution of the product from Step 103a (0.650 g, 3.78 mmol, 1 eq) in water (5.5 mL), t-BuOH (18.0 mL), and THF (18.0 mL) is added 2-methyl-2-butene (3.2 mL, 30.2 mmol, 8 eq), potassium phosphate monobasic (1.54 g, 11.3 mmol, 3 eq), then $NaClO_2$ (1.03 g, 11.3 mmol, 3 eq) in that order. After four hours, the reaction is complete and diluted with 1 N NaOH (100 mL). The aqueous solution is extracted with ether (2×100 mL), and the aqueous layer is acidified with conc. HCl. The resulting solution is extracted with $CH_2Cl_2$ (3×100 mL). The organic layers are dried over $MgSO_4$, and the solvent removed. The product is purified by silica gel chromatography using a Biotage Flash 40M column (10% EtOAc/1% formic acid/heptane). The solid remaining after removal of the solvent is filtered and recrystallized from EtOH and water to give the acid as a white crystalline solid (0.499 g, 70.2%). HRMS (FAB) calculated for $C_{11}H_8O_3$+H 189.0473, found 189.0403.

Step 103c: Preparation of N-[(3R)-1-azabicyclo[2.2.2]oct-3-yl]-5-phenyl-2-furamide 4-methylbenzenesulfonate.

The product of Step 103b (0.499 g, 2.65 mmol, 1 eq) and the dihydrochloride salt of R-(+)-aminoquinuclidine (0.528 g, 2.65 mmol, 1 eq) in DIEA (1.38 mL, 7.96 mmol, 3 eq), in THF (17.6 mL) are cooled to 0° C. and HATU (1.01 g, 2.65 mmol, 1 eq) is added. The reaction is stirred overnight. The reaction is diluted with $CH_2Cl_2$ (150 mL). The organic is washed with 1N NaOH, satd $NaHCO_3$, and water. The organic layer is dried over $MgSO_4$, and the solvent is removed under reduced pressure. The product is purified by silica gel chromatography using a Biotage Flash 40M column (8%MeOH/1%$NH_4OH$/$CH_2Cl_2$). The p-toluene sulfonic acid salt is made, which gave an amorphous solid (1.06 g, 42%). HRMS (FAB) calculated for $C_{18}H_{20}N_2O_2$+H, 297.1603, found 297.1602.

EXAMPLES 104–130

The following compounds are prepared from the requisite boronic acid, furaldehyde, or furan-carboxylic acid according to the procedures for Example 103, making non-critical variations.

Example 104

N-[(3R)-1-azabicyclo[2.2.2]oct-3-yl]-5-(2-chlorophenyl)-furan-2-carboxamide toluene sulfonate (from 5-(2-chlorophenyl)-2-furaldehyde). Yield 46%. HRMS (FAB) calculated for $C_{18}H_{18}ClN_2O_2$+$H_1$ 331.1213, found 331.1208.

Example 105

N-[(3R)-1-azabicyclo[2.2.2]oct-3-yl]-5-(3-chlorophenyl)-furan-2-carboxamide toluene sulfonate (from 5-(3-chlorophenyl)-2-furaldehyde). Yield 72%. HRMS (FAB) calculated for $C_{18}H_{19}ClN_2O_2$+$H_1$ 331.1213, found 331.1212.

Example 106

N-[(3R)-1-azabicyclo[2.2.2]oct-3-yl]-5-(4-chlorophenyl)-furan-2-carboxamide fumarate (from 5-(4-chlorophenyl)-2-furoic acid). Yield 43%. HRMS (FAB) calculated for $C_{18}H_{18}ClN_2O_2$+$H_1$ 331.1213, found 331.1216.

Example 107

N-[(3R)-1-azabicyclo[2.2.2]oct-3-yl]-5-(4-bromophenyl)-furan-2-carboxamide toluene sulfonate (from 5-(4-bromophenyl)-2-furaldehyde). Yield 38%. HRMS (FAB) calculated for $C_{18}H_{19}BrN_2O_2$+$H_1$ 375.0708, found 375.0713.

Example 108

N-[(3R)-1-azabicyclo[2.2.2]oct-3-yl]-5-[2-(trifluoromethyl)-phenyl]-furan-2-carboxamide fumarate (from 5-(2-(trifluoromethyl)-phenyl)-furan-2-carboxylic acid). Yield 78%. HRMS (FAB) calculated for $C_{19}H_{19}F_3N_2O_2$+$H_1$ 365.1477, found 365.1468.

Example 109

N-[(3R)-1-azabicyclo[2.2.2]oct-3-yl]-5-[3-(trifluoromethyl)-phenyl]-furan-2-carboxamide fumarate (from 5-(3-(trifluoromethyl)-phenyl)-furan-2-carboxaldehyde). Yield 31%. MS (ESI) for $C_{19}H_{19}F_3N_2O_2$ m/z 365.2 (M+H)$^+$.

Example 110

N-[(3R)-1-azabicyclo[2.2.2]oct-3-yl]-5-(2-nitrophenyl)-furan-2-carboxamide 4-methylbenzenesulfonate (from 5-(2-nitro-phenyl)-furan-2-carboxylic acid). Yield 82%. HRMS (FAB) calculated for $C_{18}H_{19}N_3O_4$+$H_1$ 342.1454, found 342.1469.

Example 111

N-[(3R)-1-azabicyclo[2.2.2]oct-3-yl]-5-(3-nitrophenyl)-furan-2-carboxamide 4-methylbenzenesulfonate (from 5-(3-nitro-phenyl)-furan-2-carboxylic acid). Yield 66%. HRMS (FAB) calculated for $C_18H_{19}N_3O_4$+$H_1$ 342.1454, found 342.1463.

Example 112

N-[(3R)-1-azabicyclo[2.2.2]oct-3-yl]-5-(4-nitrophenyl)-furan-2-carboxamide 4-methylbenzenesulfonate (from 5-(4- nitro-phenyl)-furan-2-carboxylic acid). Yield 52%. HRMS (FAB) calculated for $C_{18}H_{19}N_3O_4+H_1$ 342.1454, found 342.1465.

Example 113

N-[(3R)-1-azabicyclo[2.2.2]oct-3-yl]-5-(2-fluorophenyl)-furan-2-carboxamide 4-methylbenzenesulfonate (from 2-fluorophenylboronic acid). Yield 12%. HRMS (FAB) calculated for $C_{18}H_{19}FN_2O_2+Hl$ 315.1508, found 315.1519.

Example 114

N-[(3R)-1-azabicyclo[2.2.2]oct-3-yl]-5-(3-fluorophenyl)-furan-2-carboxamide 4-methylbenzenesulfonate (from 3-fluorophenylboronic acid). Yield 29%. HRMS (FAB) calculated for $C_{18}H_{19}FN_2O_2+H_1$ 315.1508, found 315.1519.

Example 115

N-[(3R)-1-azabicyclo[2.2.2]oct-3-yl]-5-(4-fluorophenyl)-furan-2-carboxamide 4-methylbenzenesulfonate (from 4-fluorophenylboronic acid). Yield 16%. HRMS (FAB) calculated for $C_{18}H_{19}FN_2O_2+H_1$ 315.1508, found 315.1500.

Example 116

N-[(3R)-1-azabicyclo[2.2.2]oct-3-yl]-5-(2,4-difluorophenyl)-furan-2-carboxamide hydrochloride (from 2,4-difluorophenylboronic acid). Yield 46%. MS (ESI) for $C_{18}H_{18}F_2N_2O_2$ m/z 333.2 (M+H)$^+$.

Example 117

N-[(3R)-1-azabicyclo[2.2.2]oct-3-yl]-5-(2,5-difluorophenyl)-furan-2-carboxamide hydrochloride (from 2,5-difluorophenylboronic acid). Yield 33%. MS (ESI) for $C_{18}H_{18}F_2N_2O_2$ m/z 333.2 (M+H)$^+$.

Example 118

N-[(3R)-1-azabicyclo[2.2.2]oct-3-yl]-5-(2-methoxyphenyl)-furan-2-carboxamide 4-methylbenzenesulfonate (from 2-methoxyphenylboronic acid). Yield 63%. HRMS (FAB) calculated for $C_{19}H_{22}N_2O_3+H_1$ 327.1708, found 327.1717.

Example 119

N-[(3R)-1-azabicyclo[2.2.2]oct-3-yl]-5-(3-methoxyphenyl)-furan-2-carboxamide 4-methylbenzenesulfonate (from 3-methoxyphenylboronic acid). Yield 83%. HRMS (FAB) calculated for $C_{19}H_{22}N_2O_3+H_1$ 327.1708, found 327.1714.

Example 120

N-[(3R)-1-azabicyclo[2.2.2]oct-3-yl]-5-[3-(trifluoromethoxy)phenyl]-furan-2-carboxamide 4-methylbenzenesulfonate (from 3-trifluoromethoxyphenylboronic acid). Yield 58%. HRMS (FAB) calculated for $C_{19}H_{19}F_3N_2O_3+H_1$ 381.1426, found 381.1440.

Example 121

N-[(3R)-1-azabicyclo[2.2.2]oct-3-yl]-5-[2-chloro-5-(trifluoromethyl)-phenyl]-furan-2-carboxamide fumaric acid (from 2-chloro-5-trifluoromethylphenylboronic acid). Yield 55%. HRMS (FAB) calculated for $C_{19}H_{18}ClF_3N_2O_2+H_1$ 399.1087, found 399.1097.

Example 122

N-[(3R)-1-azabicyclo[2.2.2]oct-3-yl]-5-(4-fluoro-3-methylphenyl)-furan-2-carboxamide 4-methylbenzenesulfonate (from 4-fluoro-3-methylphenylboronic acid). Yield 77%. HRMS (FAB) calculated for $Cl_9H_2,FN_2O_2+H_1$ 329.1665, found 329.1661.

Example 123

N-[(3R)-1-azabicyclo[2.2.2]oct-3-yl]-5-(4-cyanophenyl)-furan-2-carboxamide hydrochloride (from 4-cyanophenylboronic acid). Yield 31%. MS (ESI) for $C_{18}H_{19}N_3O_2$ m/z 322.2 (M+H)$^+$.

Example 124

N-[(3R)-1-azabicyclo[2.2.2]oct-3-yl]-5-thien-2-yl-furan-2-carboxamide 4-methylbenzenesulfonate (from 2-thiophene-boronic acid). MS (ESI) for $C_{16}H_{18}N_2O_2S$ m/z 303.2 (M+H)$^+$.

Example 125

N-[(3R)-1-azabicyclo[2.2.2]oct-3-yl]-5-thien-3-yl-furan-2-carboxamide 4-methylbenzenesulfonate (from 3-thiophene-boronic acid). MS (ESI) for $C_{16}H_{18}N_2O_2S$ m/z 303.2 (M+H)$^+$.

Example 126

N-[(3R)-1-azabicyclo[2.2.2]oct-3-yl]-5-bromo-furan-2-carboxamide 4-methylbenzenesulfonate (from 5-bromo-furan-2-carboxylic acid). Yield 75%. MS (ESI) for $C_{12}H_{15}N_2O_2Br$ m/z 299.0 (M+H)$^+$.

Example 127

N-[(3R)-1-azabicyclo[2.2.2]oct-3-yl]-5-nitro-furan-2-carboxamide hydrochloride (from 5-nitro-furan-2-carboxylic acid). Yield 63%. MS (ESI) for $C_{12}H_{15}N_3O_4$ m/z 265.1 (M+H)$^+$.

Example 128

N-[(3R)-1-azabicyclo[2.2.2]oct-3-yl]-4,5-dimethyl-furan-2-carboxamide hydrochloride (from 4,5-dimethyl-furan-2-carboxylic acid). Yield 75%. HRMS (FAB) calculated for $C_{14}H_{20}N_2O_2+H$ 249.1603, found 249.1593.

Example 129

N-[(3R)-1-azabicyclo[2.2.2]oct-3-yl]-5-(4-chloro-2-nitrophenyl)-furan-2-carboxamide hydrochloride (from 4-chloro-2-nitrophenyl)-furan-2-carboxylic acid). Yield 7%. HRMS (FAB) calculated for $C_{18}H_{18}ClN_3O_4+H$ 376.1064, found 376.1067.

Example 130

N-[(3R)-1-azabicyclo[2.2.2]oct-3-yl]-5-(4-methyl-2-nitrophenyl)-furan-2-carboxamide hydrochloride (from 4-methyl-2-nitrophenyl)-furan-2-carboxylic acid). Yield 56%. MS (ESI) for $C_{19}H_{21}N_3O_4$ m/z 356.2 (M+H)$^+$.

EXAMPLE 131

N-[(3R)-1-azabicyclo[2.2.2]oct-3-yl]-5-(2,3-difluorophenyl)-furan-2-carboxamide 4-methylbenzenesulfonate:

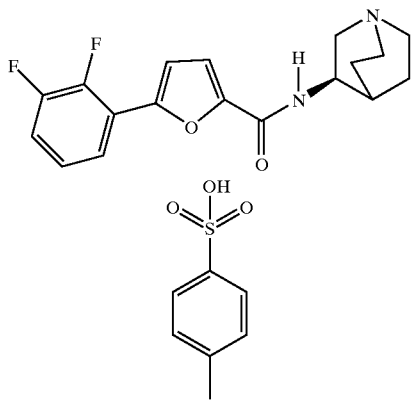

Step 131a: A solution of N-[(3R)-1-azabicyclo[2.2.2]oct-3-yl]-5-bromo-furan-2-carboxamide (0.258 g, 0.85 mmol, 1 eq), 2,3-difluorophenylboronic acid (0.147 g, 0.93 mmol, 1.1 eq), tetrabutylammonium bromide (0.244 g, 0.85 mmol, 1 eq), palladium acetate (3.8 mg, 0.017 mmol, 0.02 eq), $K_2CO_3$ (0.41 g, 2.97 mmol, 3.5 mmol) and water 1.4 mL is stirred under argon overnight. The reaction forms a brownish insoluble lump, but is complete by HPLC. The reaction is purified by silica gel chromatography using a Biotage Flash 40 M column (10%MeOH(1%TEA/$CH_2Cl_2$). The p-toluenesulfonic acid salt of 5-(2,3-difluoro-phenyl)-furan-2-carboxylic acid (1-aza-bicyclo[2.2.2]oct-3-yl)-amide is synthesized and recrystallized from IPA/MeOH/ether, and the product is recovered as a crystalline solid (0.135 g, 31%). HRMS (FAB) calculated for $C_{18}H_{18}F_2N_2O_2+H_1$ 333.1414, found 333.1418.

EXAMPLES 132–146

The following compounds are prepared from the requisite boronic acid and N-[(3R)-1-azabicyclo[2.2.2]oct-3-yl]-5-bromo-furan-2-carboxamide as stated for Example 131, making non-critical variations.

Example 132

N-[(3R)-1-azabicyclo[2.2.2]oct-3-yl]-5-(3,4-difluorophenyl)-furan-2-carboxamide hydrochloride (from 3,4-difluorophenyl-boronic acid). Yield 24%. HRMS (FAB) calculated for $C_{18}H_{18}F_2N_2O_2+H_1$ 333.1414, found 333.1418.

Example 133

N-[(3R)-1-azabicyclo[2.2.2]oct-3-yl]-5-(3,5-difluorophenyl)-furan-2-carboxamide hydrochloride (from 3,5-difluorophenyl-boronic acid). Yield 60%. HRMS (FAB) calculated for $C_{18}H_{18}F_2N_2O_2+H_1$ 333.1414, found 333.1424.

Example 134

N-[(3R)-1-azabicyclo[2.2.2]oct-3-yl]-5-(4-methoxyphenyl)-furan-2-carboxamide hydrochloride (from 4-methoxy-phenyl-boronic acid). Yield 17%. HRMS (FAB) calculated for $C_{19}H_{22}N_2O_3+H_1$ 327.1708, found 327.1707.

Example 135

N-[(3R)-1-azabicyclo[2.2.2]oct-3-yl]-5-(2-methylphenyl)-furan-2-carboxamide 4-methylbenzenesulfonate (from o-tolylboronic acid). Yield 26%. HRMS (FAB) calculated for $C_{19}H_{22}N_2O_2+H_1$ 311.1759, found 311.1763.

Example 136

N-[(3R)-1-azabicyclo[2.2.2]oct-3-yl]-5-(3-methylphenyl)-furan-2-carboxamide 4-methylbenzenesulfonate (from m-tolylboronic acid). HRMS (FAB) calculated for $C_{19}H_{22}N_2O_2+H_1$ 311.1759, found 311.1752.

Example 137

N-[(3R)-1-azabicyclo[2.2.2]oct-3-yl]-5-(4-methylphenyl)-furan-2-carboxamide 4-methylbenzenesulfonate (from p-tolylboronic acid). Yield 10%. HRMS (FAB) calculated for $C_{19}H_{22}N_2O_2+H_1$ 311.1759, found 311.1752.

Example 138

N-[(3R)-1-azabicyclo[2.2.2]oct-3-yl]-5-[2-(trifluoromethoxy)phenyl]-furan-2-carboxamide 4-methylbenzenesulfonate (from 2-(trifluoromethoxy)phenylboronic acid). Yield 19%. MS (ESI) for $C_{19}H_{19}F_3N_2O_3$ m/z 381.3 $(M+H)^+$.

Example 139

N-[(3R)-1-azabicyclo[2.2.2]oct-3-yl]-5-[4-(trifluoromethoxy)phenyl]-furan-2-carboxamide 4-methylbenzenesulfonate (from 4-trifluoromethoxyphenylboronic acid). Yield 61%. HRMS (FAB) calculated for $C_{19}H_{19}F_3N_2O_3+H_1$ 381.1426, found 381.1434.

Example 140

N-[(3R)-1-azabicyclo[2.2.2]oct-3-yl]-5-(4-tert-butylphenyl)-furan-2-carboxamide 4-methylbenzenesulfonate (from 4-tert-butylphenyl-boronic acid). Yield 73%. HRMS (FAB) calculated for $C_{22}H_{28}N_2O_2+H$, 353.2229, found 353.2218.

Example 141

N-[(3R)-1-azabicyclo[2.2.2]oct-3-yl]-5-(1-benzothien-2-yl)-furan-2-carboxamide 4-methylbenzenesulfonate (from benzothiophene-2-boronic acid). Yield 17%. HRMS (FAB) calculated for $C_{20}H_{20}N_2O_2S+H_1$ 353.1324, found 353.1326.

Example 142

N-[(3R)-1-azabicyclo[2.2.2]oct-3-yl]-5-quinolin-3-yl-furan-2-carboxamide 4-methylbenzenesulfonate (from 3-quinoline-boronic acid). Yield 9%. MS (ESI) for $C_{21}H_{21}N_3O_2$ m/z 348.3 $(M+H)^+$.

Example 143

N-[(3R)-1-azabicyclo[2.2.2]oct-3-yl]-5-(4-ethylphenyl)-furan-2-carboxamide hydrochloride (from 4-ethylphenyl-boronic acid). MS (ESI) for $C_{20}H_{24}N_2O_2$ m/z 325.3 (M+H).

Example 144

N-[(3R)-1-azabicyclo[2.2.2]oct-3-yl]-5-(4-isopropylphenyl)-furan-2-carboxamide hydrochloride (from 4-isopropylphenyl-boronic acid). MS (ESI) for $C_{21}H_{26}N_2O_2$ m/z 339.3 $(M+H)^+$.

Example 145

N-[(3R)-1-azabicyclo[2.2.2]oct-3-yl]-5-(3-fluoro-4-methoxyphenyl)-furan-2-carboxamide hydrochloride (from 3-fluoro-4-methoxy-boronic acid). MS (ESI) for $C_{19}H_{21}FN_2O_2$ m/Z 345.2 (M+H)+.

Example 146

N-[(3R)-1-azabicyclo[2.2.2]oct-3-yl]-5-(1-benzofuran-2-yl)-furan-2-carboxamide 4-methylbenzenesulfonate (from benzofuran-2-boronic acid). MS (ESI) for $C_{20}H_{20}N_2O_3$ m/z 337.2 (M+H)+.

EXAMPLE 147

5-(2-Aminophenyl)-N-[(3R)-1-azabicyclo[2.2.2]oct-3-yl]-furan-2-carboxamide bis(4-methylbenzenesulfonate):

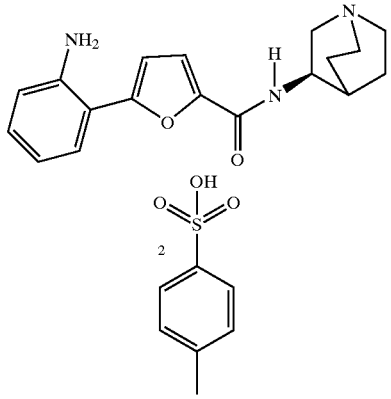

Step 147a: To a solution of N-[(3R)-1-aza-bicyclo[2.2.2]oct-3-yl]-5-(2-nitrophenyl)-furan-2-carboxamide (1.65 g, 3.22 mmol, 1 eq) in 100 mL EtOH was added Pd/C (50 mg). This mixture was placed on a Parr shaker under 40 psi hydrogen overnight. The palladium is removed by filtration over a pad of celite, and the solvent is removed. The p-toluenesulfonic acid salt of 5-(2-amino-phenyl)-furan-2-carboxylic acid (1-aza-bicyclo[2.2.2]oct-3-yl)-amide is purified by recrystallization from IPA/MeOH/ether to give a crystalline solid (0.783 g, 50%). HRMS (FAB) calculated for $C_{18}H_{21}N_3O_2$+ $H_1$ 312.1712, found 312.1717.

EXAMPLES 148–149

The following compounds are prepared from the requisite nitro amide according to the procedures for Example 147, making non-critical variations.

Example 148

5-(4-aminophenyl)-N-[(3R)-1-azabicyclo[2.2.2]oct-3-yl]-furan-2-carboxamide tris(4-methylbenzenesulfonate) (from N-[(3R)-1-azabicyclo[2.2.2]oct-3-yl]-5-(4-nitrophenyl)-2-furamide). Yield 84%. HRMS (FAB) calculated for $C_{18}H_{21}N_3O_2$+$H_1$ 312.1712, found 312.1727.

Example 149

5-(2-amino-4-methylphenyl)-N-[(3R)-1-azabicyclo[2.2.2]oct-3-yl]-furan-2-carboxamide dihydrochloride (from 5-(4-methyl-2-nirophenyl)-N-[(3R)-1-azabicyclo[2.2.2]oct-3-yl]-2-furamide dihydrochloride). Yield 55%. HRMS (FAB) calculated for $C_{19}H_{23}N_3O_2$+H 326.1868, found 326.1871.

EXAMPLE 150

N-[(3R)-1-azabicyclo[2.2.2]oct-3-yl]-5-(phenylethynyl)-furan-2-carboxamide 4-methylbenzenesulfonate:

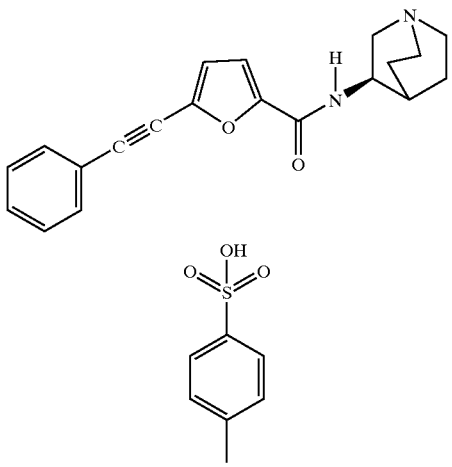

Step 150a: Preparation of 5-phenylethylnyl-furan-2-aldehyde.

To a solution of 5-bromofuraldehyde (1.0 g, 5.71 mmol, 1 eq), copper (I) iodide (0.163 g, 0.857 mmol, 0.15 eq), trans-dichlorobis(triphenylphosphine) palladium(II) (0.20 g, 0.287 mmol, 0.05 eq), and TEA (3.98 mL, 28.6 mmol, 5 eq) in THF (45 mL) is added dropwise phenyl acetylene (1.25 mL, 11.4 mmol, 2 eq). After 48 hours, the reaction appears complete. The reaction is filtered over a pad of celite, and the solvent is removed under reduced pressure. The reaction is purified by silica gel chromatography using a Biotage Flash 40M column (10% EtOAc/heptane) to give a yellow orange crystalline solid (0.765 g, 68.3%). MS (ESI) for $C_{13}H_8O_2$ m/z 197.1 (M+H)+.

Step 150b: Preparation of N-[(3R)-1-azabicyclo[2.2.2]oct-3-yl]-5-(phenylethynyl)-furan-2-carboxamide 4-methylbenzenesulfonate.

Following the general procedure of Example 103, making non-critical variations but starting with 5-phenylethylnyl-furan-2-aldehyde, N-[(3R)-1-azabicyclo[2.2.2]oct-3-yl]-5-(phenylethynyl)-furan-2-carboxamide 4-methylbenzenesulfonate is synthesized and recovered as a crystalline solid (0.692 g, 74%). HRMS (FAB) calculated for $C_{20}H_{20}N_2O_2$+Hl 321.1603, found 321.1595.

EXAMPLE 151

N-[(3R)-1-azabicyclo[2.2.2]oct-3-yl]-5-phenoxy-furan-2-carboxamide 4-methylbenzenesulfonate:

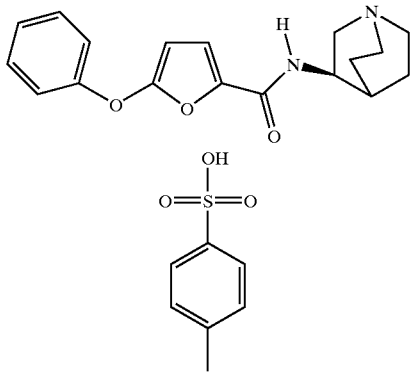

Step 151a: Preparation of N-[(3R)-1-azabicyclo[2.2.2]oct-3-yl]-5-phenoxy-furan-2-carboxamide 4-methylbenzenesulfonate.

A solution of N-[(3R)-1-aza-bicyclo[2.2.2]oct-3-yl]-5-bromo-furan-2-carboxamide (0.200 g, 0.42 mmol, 1 eq), sodium phenoxide (0.500 g, 4.3 mmol, 10.1 eq), in DMSO (5 mL) is stirred under nitrogen at room temperature overnight. The reaction is diluted with 25 mL water and extracted with $CH_2Cl_2$ (50 mL). The organic layer is washed with water (3×25 mL), satd $NaHCO_3$, brine, and dried over $MgSO_4$. The p-toluenesulfonic acid salt is prepared and recrystallized from IPA/MeOH/ether, and the product is recovered as a crystalline solid (70%). HRMS (FAB) calculated for $C_{18}H_{20}N_2O_3+H$ 313.1552, found 313.1558.

EXAMPLE 152

N-[(3R)-1-azabicyclo[2.2.2]oct-3-yl]-1-methyl-5-phenyl-1H-pyrrole-2-carboxamide:

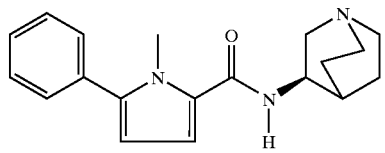

Step 152a: Preparation of methyl 5-bromo-1-methyl-1H-pyrrole-2-carboxylate.

To a dry flask is added methyl 1-methyl-1H-pyrrole-2-carboxylate (12.0 g, 86.4 mmol) and 150 mL of dry $CH_2Cl_2$, and the flask is wrapped in foil and purged with nitrogen. N-bromosuccinimide (16.2 g, 90.7 mmol) is added in one portion and the mixture is stirred at room temperature for 0.5 h. The reaction mixture is washed with water (50 mL) and brine (50 mL), dried over $MgSO_4$, filtered, and concentrated under reduced pressure. Fractional distillation gives 12.0 g of methyl 5-bromo-1-methyl-1H-pyrrole-2-carboxylate as a yellow oil (64% yield). MS for $C_7H_8NO_2Br$ (ESI) $(M)^+$ m/z 217.1.

Step 152b: Preparation of methyl 1-methyl-5-phenyl-1H-pyrrole-2-carboxylate.

The product from step 152a is added to a solution of tetrakis(triphenylphosphine)palladium(O) (0.530 g, 0.459 mmol) in 90 mL of ethylene glycol dimethyl ether. The resulting solution is stirred under nitrogen for 5 min and then phenylboronic acid (1.34 g, 11.0 mmol) is added followed by a solution of $Na_2CO_3$ (19.5 g, 183 mmol) in 90 mL of $H_2O$. The mixture is heated at reflux for 24 hours. The reaction mixture is allowed to cool to rt, 100 mL of $CH_2Cl_2$ is added, and the layers are separated. The aqueous layer is extracted with $CH_2Cl_2$ (3×50 mL) and combined organic layers are dried over $MgSO_4$, filtered, and concentrated in vacuo. The crude product is purified by flash column chromatography (5% EtOAc in hexane) to give 1.89 g of methyl 1-methyl-5-phenyl-1H-pyrrole-2-carboxylate as a yellow oil (96% yield). MS for $Cl_3H_{13}NO_2$ (ESI) $(M+H)^+$ m/z 216.1.

Step 152c: Preparation of 1-methyl-5-phenyl-1H-pyrrole-2-carboxylic Acid.

Lithium hydroxide (1.39 g, 33.2 mmol) is added to a solution of the product from Step 152b (1.43 g, 6.64 mmol) in 96 mL of a 1.25:1:1 $H_2O$:MeOH:THF solvent mixture. The reaction is stirred at 50° C. for 2 h. Aqueous HCl (1N, 50 mL) is added and the resultant precipitate is collected by filtration, washed with water, and dried to give 0.851 g of 1-methyl-5-phenyl-1H-pyrrole-2-carboxylic acid as a tan solid (64% yield). MS for $C_{12}H_{11}NO_2$ (ESI) $(M-H)^+$ m/z 200.1.

Step 152d: Preparation of N-[(3R)-1-azabicyclo[2.2.2]oct-3-yl]-1-methyl-5-phenyl-1H-pyrrole-2-carboxamide.

To a solution of (R)-(+)-3-aminoquinuclidine dihydrochloride (0.831 g, 4.17 mmol) in 55 mL of dry THF is added DIEA (2.08 mL, 11.9 mmol). After allowing the mixture to stir under nitrogen for 15 min, the product from Step 152c (0.800 g, X 3.98 mmol) is added. The mixture is allowed to stir for another 15 min, cooled in an A ice bath, and HATU (1.59 g, 4.17 mmol) is added. The reaction mixture is stirred on >an ice bath for 0.5 h, then at rt for an additional 2 h. The mixture is diluted with 60 mL $CH_2Cl_2$, washed with 50 mL of 1N NaOH and 50 mL of satd $NaHCO_3$ solution, dried over $MgSO_4$, filtered, and concentrated in vacuo. The crude product is purified by flash column chromatography (10% EtOAc, 1% $NH_4OH$ in $CH_2Cl_2$) to give 0.383 grams of N-[(3R)-1-azabicyclo[2.2.2]oct-3-yl]-1-methyl-5-phenyl-1H-pyrrole-2-carboxamide (31%) as a white solid. MS for $C_{19}H_{23}N_3O$ (ESI) $(M+H)^+$ m/z 310.3.

EXAMPLES 153–157

These examples are prepared using the coupling procedure for Example 103c, making non-critical variations and using the appropriate carboxylic acids.

Example 153

N-[(3R)-1-azabicyclo[2.2.2]oct-3-yl]-5-phenyl-1,3-oxazole-2-carboxamide 4-methylbenzenesulfonate (from 5-phenyl-1,3-oxazole-2-carboxylic acid, see Saito, S.; Tanaka, C. J. Pharm. Sci. Japan 76, 1956, 305–7). Yield 77%. HRMS (FAB) calculated for $C_{17}H_{19}N_3O_2+H_1$ 298.1555, found 298.1558.

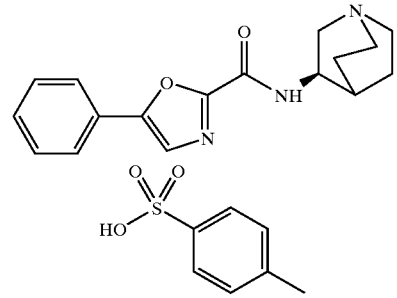

Example 154

N-[(3R)-1-azabicyclo[2.2.2]oct-3-yl]-3-phenyl-1,2,4-oxadiazole-5-carboxamide 4-methylbenzenesulfonate (from 3-phenyl-1,2,4-oxadiazole-5-carboxylic acid, see Wurm. Chem. Ber.; 22; 1889; 3133). Yield 54%. HRMS (FAB) calculated for $C_{16}H_{18}N_4O_2+H_1$ 299.1508, found 299.1512.

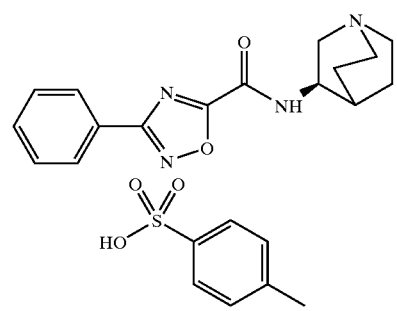

Example 155

N-[(3R)-1-azabicyclo[2.2.2]oct-3-yl]-2-phenyl-1,3-oxazole-5-carboxamide 4-methylbenzenesulfonate (from 2-phenyl-1,3-oxazole-5-carboxylic acid, see Belen'kii, L. I.; Cheskis, M. A.; Zvolinskii, V. P.; Obukhov, A. E. *Chem. Heterocycl. Compd. (Engl.Transl.)*; 22; 1986; 654–663). Yield 16%. HRMS (FAB) calculated for $C_{17}H_{19}N_3O_2+H_1$ 298.1555, found 298.1555.

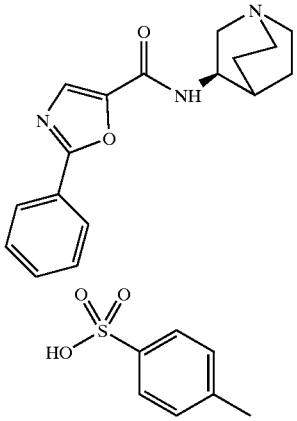

Example 156

N-[(3R)-1-azabicyclo[2.2.2]oct-3-yl]-2-phenyl-1,3-oxazole-4-carboxamide 4-methylbenzenesulfonate (from 2-phenyl-1,3-oxazole-4-carboxylic acid, see Korte, F.; Stoeriko, K. *Chem. Ber.*; 93; 1960; 1033–1042). Yield 22%. HRMS (FAB) calculated for $C_{17}H_{19}N_3O_2+H_1$ 298.1555, found 298.1559.

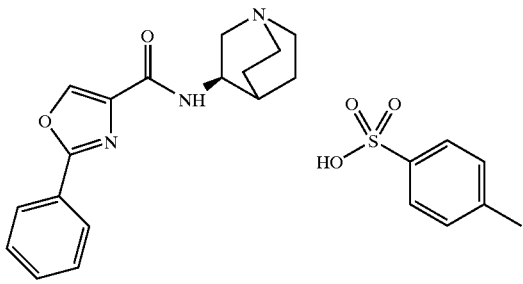

Example 157

N-[(3R)-1-azabicyclo[2.2.2]oct-3-yl]-5-phenylisoxazole-3-carboxamide 4-methylbenzenesulfonate (from 5-phenylisoxazole-3-carboxylic acid, see Vaughan, W. R.; Spencer, J. L. *J. Org. Chem.*; 25; 1960; 1160–1164). Yield 76%. HRMS (FAB) calculated for $C_{17}H_{19}N_3O_2+H_1$ 298.1555, found 298.1556.

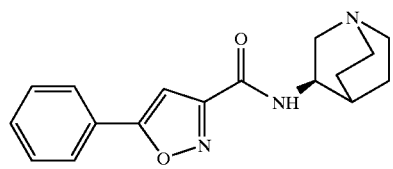

-continued

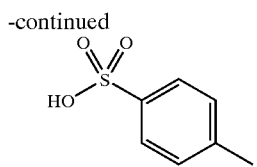

EXAMPLE 158

5-Bromo-N-(2-methyl-1-azabicyclo[2.2.2]oct-3-yl)-thiophene-2-carboxamide 4-methylbenzenesulfonate:

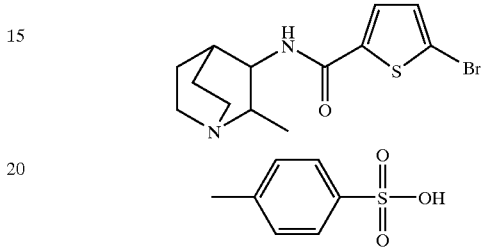

Step 158a: Preparation of 2-methylenequinuclidin-3-one.

A mixture of 2-methylene-3-quinuclidinone dihydrate hydrochloride (25.7 g, 0.1225 mol, 1 eq) and $K_2CO_3$ (67.0 g, 0.4848 mol, 4 eq) is dissolved in 125 mL water and 200 mL $CH_2Cl_2$ and is stirred vigorously. After 16 h, the layers are separated and the aqueous layer is extracted with $CH_2Cl_2$. The combined organic layers are dried over $MgSO_4$, filtered and concentrated to give 14.75 g (88%) of 2-methylenequinuclidin-3-one as a yellow oil. MS (ESI) for $C_8H_{11}NO$ m/z 138.1 $(M+H)^+$.

Step 158b: Preparation of 2-methylquinuclidin-3-one Hydrochloride.

The product from Step 158a (14.75 g, 0.1075 mol, 1 eq), formic acid (10.4 g, 0.2150 mol, 2 eq) and $(Ph_3P)_3RuCl_2$ (0.21 g, 0.21 mmol) are dissolved in 100 mL THF. The mixture is heated under reflux. Fresh portions of catalyst (0.58 g, 0.59 mmol, (total)) and formic acid (1.2 g, 0.026 mol) are added periodically over the course of the reaction. After 72 h, the mixture is concentrated in vacuo. The residue is taken up in ether and excess HCl in dioxane (27 mL, 4.0M) is added. The solids are washed with ether and recrystallized from EtOH to afford 14.4 g (76%) of 2-methylquinuclidin-3-one hydrochloride as a white solid. MS (ESI) for $C_8H_{13}NO$ m/z 140.2 $(M+H)^+$.

Step 158c: Preparation of (3E/Z)-2-methyl-1-azabicyclo [2.2.2]octan-3one Oxime.

The product from Step 158b (3.2 g, 23.0 mmol, 1 eq) and hydroxylamine hydrochloride (1.6 g, 23.0 mmol, 1 eq) are dissolved in 20 mL EtOH/pyridine (4:1) and stirred at room temperature. After 5 days, water and solid NaOH are added to adjust pH to pH 11. The mixture is extracted with several portions of $CHCl_3$. The combined organic layers are dried over $MgSO_4$, filtered and concentrated to give 3.42 g (96%) of 2-methyl-1-azabicyclo[2.2.2]octan-3-one oxime as a 1:2.6 mixture of oxime isomers. Partial $^1$NMR ($CDCl_3$, 300 MHz) δ 1.53 ppm (d, 2-$CH_3$, 0.8H), 1.38 (d, 2-$CH_3$. 2.2H). MS (ESI) for $C_8H_{14}N_2O$ m/z 154.8 $(M+H)^+$.

Step 158d: Preparation of 2-methylquinuclidin-3-amine Dihydrochloride

Sodium (7.0 g, 0.303 mol, 10 eq) is added in portions to a solution of 2-methyl-1-azabicyclo[2.2.2]octan-3-one oxime from Step 158c (4.65 g, 30.2 mmol, 1 eq) in 100 mL n-propanol. The mixture is heated under reflux. After about 12 h, the mixture is cooled and 80 mL of water is added. The layers are separated, and the aqueous layer is extracted with CHCl$_3$. The combined organic layers are dried over MgSO$_4$ and filtered. An excess of HCl in dioxane (15 mL, 4.0 M) is added to the solution and the solvent is removed to give 6.0 g (93%) of 2-methylquinuclidin-3-amine dihydrochloride as an oil. A hygroscopic solid was obtained by trituration of the oil in hot IPA. MS (ESI) for C$_8$H$_{16}$N$_2$ m/Z 141.3 (M+H)$^+$.

Step 158e: Preparation of 5-bromo-N-(2-methyl-1-azabicyclo[2.2.2]oct-3-yl)-thiophene-2-carboxamide 4-methylbenzenesulfonate.

5-Bromothiophene-2-carboxylic acid (1.63 g, 7.88 mmol, 1 eq), the product from Step 158d (1.68 g, 7.88 mmol, 1 eq) and HATU (2.97 g, 7.81 mmol, 1 eq) are suspended in 60 mL CH$_3$CN. The mixture is cooled in an ice bath and DIEA (8.2 mL, 47.28 mmol, 6 eq) is added dropwise. The mixture is allowed to warm to room temperature and stirred overnight. EtOAc and satd NaHCO$_3$ are added. The aqueous layer is extracted with EtOAc. The combined organic layers are washed with 1N NaOH, dried over MgSO$_4$, filtered and concentrated. The residue is purified by silica gel chromatography using a Biotage Flash 40S column (90:9:1 CHCl$_3$/MeOH/NH$_4$OH) to provide 1.26 g (49%) of 5-bromo-N-(2-methyl-1-azabicyclo[2.2.2]oct-3-yl)-thiophene-2-carboxamide as a trans/cis mixture of isomers. The p-toluenesulfonic acid salt of the product is made and recrystallized from IPA/ether to give the product as light yellow solid. MS (ESI) for C$_{13}$H$_{17}$BrN$_2$OS m/z 328.9/330.9 (M+H)$^+$. Reverse phase HPLC (ZORBAX Eclipse XDB-C8, 4.6 mm×15 cm, 80:12:8 H$_2$O/CH$_3$CN/IPA) revealed a 95:5 trans/cis mixture of isomers.

EXAMPLE 159

N-[(3R)-1-azabicyclo[2.2.2]oct-3-yl]-5-phenyl-thiophene-2-carbothioamide Fumarate:

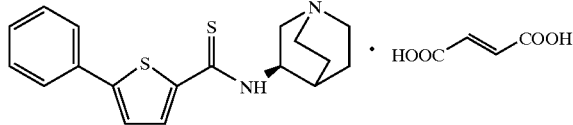

Step 159a: Preparation of methyl 5-phenyl-thiophene-2-carbodithioate.

To a cooled (−10 to 0° C.) solution of n-BuLi (22.7 mL, 33.4 mmol) in THF (10 mL) is added dropwise a solution of 2-phenyl-thiophene (5.46 g, 34.0 mmol) in THF (15 mL). The resulting green solution is stirred at 0° C. After 30 minutes, a solution of copper (1) bromide (0.87 g, 6.1 mmol) and lithium bromide (1.29 g, 14.9 mmol) in THF (20 mL) is added to the cooled reaction solution over several minutes. The resulting dark green solution is stirred at 0° C. for 15 minutes, at which time, carbon disulfide (2.0 mL, 34.0 mmol) is added dropwise over 15 minutes. The resulting dark brown solution is stirred for 30 minutes, then iodomethane (2.9 mL, 46.4 mmol) is added dropwise to the reaction solution over 5 minutes. The resulting dark brown solution is allowed to warm to room temperature and stirred for 1 hour, then is quenched with a solution of potassium cyanide in water (100 mL). The biphasic mixture was diluted with EtOAc and washed with brine, dried over MgSO$_4$, filtered, and concentrated to give a dark orange solid (8.5 grams) which is purified with flash chromatography on silica gel (eluent: gradient of heptane to 2% THF/heptane) to give an orange solid. Yield 34%. HRMS (FAB) calculated for C$_{12}$H$_{10}$S$_3$+H 251.0023, found 251.0023.

Step 159b: Preparation of N-[(3R)-1-azabicyclo[2.2.2]oct-3-yl]-5-phenyl-thiophene-2-carbothioamide Fumarate.

A solution of the product of Step 159a (0.49 g, 2.0 mmol) and (R)-3-aminoquinulidine (0.55 g, 4.4 mmol) in THF is stirred at 50° C. for 19 hours. The crude reaction mixture is absorbed on to silica gel and purified by flash chromatography (gradient of 7% [9:1 MeOH/NH$_4$OH]/CH$_2$Cl$_2$ to 9%[9:1 MeOH/NH$_4$OH]/CH$_2$Cl$_2$). The fumarate salt is prepared and crystallized. Yield 75%. HRMS (FAB) calculated for Cl$_8$H$_{20}$N$_2$S$_2$+H 329.1146, found 329.1151.

The present invention also includes, by representation but not limitation, any one of the following or combination of the following compounds and pharmaceutically acceptable salts thereof, both of which can be made by one of ordinary skill in the art using the procedures provided making non-critical changes:

N-[(2S,3R)-2-methyl-1-azabicyclo[2.2.2]oct-3-yl]-5-phenyl-thiophene-2-carboxamide; N-[(2S,3R)-2-methyl-1-azabicyclo[2.2.2]oct-3-yl]-5-(4-chlorophenyl)-thiophene-2-carboxamide; N-[(2S,3R)-2-methyl-1-azabicyclo[2.2.2]oct-3-yl]-5-(3-chlorophenyl)-thiophene-2-carboxamide; N-[(2S,3R)-2-methyl-1-azabicyclo[2.2.2]oct-3-yl]-5-(2-chlorophenyl)-thiophene-2-carboxamide; N-[(2S,3R)-2-methyl-1-azabicyclo[2.2.2]oct-3-yl]-2,3'-bithiophene-5-carboxamide; N-[(2S,3R)-2-methyl-1-azabicyclo[2.2.2]oct-3-yl]-5-(2-nitrophenyl)-thiophene-2-carboxamide; N-[(2S,3R)-2-methyl-1-azabicyclo[2.2.2]oct-3-yl]-5-(3-nitrophenyl)-thiophene-2-carboxamide; N-[(2S,3R)-2-methyl-1-azabicyclo[2.2.2]oct-3-yl]-4-phenyl-thiophene-2-carboxamide; N-[(2S,3R)-2-methyl-1-azabicyclo[2.2.2]oct-3-yl]-5-(3-benzyloxyphenyl)-thiophene-2-carboxamide; N-[(2S,3R)-2-methyl-1-azabicyclo[2.2.2]oct-3-yl]-5-(4-benzyloxyphenyl)-thiophene-2-carboxamide; N-[(2S,3R)-2-methyl-1-azabicyclo[2.2.2]oct-3-yl]-5-(3-fluoro-4-benzyloxyphenyl)-thiophene-2-carboxamide; 5-(2-aminophenyl)-N-[(2S,3R)-2-methyl-1-azabicyclo[2.2.2]oct-3-yl]-thiophene-2-carboxamide; N-[(2S,3R)-2-methyl-1-azabicyclo[2.2.2]oct-3-yl]-5-pyridin-3-yl-thiophene-2 carboxamide; N-[(2S,3R)-2-methyl-1-azabicyclo[2.2.2]oct-3-yl]-5'-methyl-2,2'-bithiophene-5-carboxamide; N-[(2S3R)-2-methyl-1-azabicyclo[2.2.2]oct-3-yl]-5'-methyl-2,2'-bithiophene-5-carboxamide; N-[(2S,3R)-2-methyl-1-azabicyclo[2.2.2]oct-3-yl]-5-nitro-thiophene-2-carboxamide; 5-(aminomethyl)-N-[(2S,3R)-2-methyl-azabicyclo[2.2.2]oct-3-yl]-thiophene-2;carboxamide; N-[(2S,3R)-2-methyl-1-azabicyclo[2.2.2]oct-3-yl]-5-cyanothiophene-2-carboxamide; N-[(2S,3R)-2-methyl-azabicyclo[2.2.2]oct-3-yl]-5-methoxy-thiophene-2-carboxamide; N-[(2S,3R)-2-methyl-1-azabicyclo[2.2.2]oct-3-yl]-5-(pyridin-2-yl)-thiophene-2-carboxamide; N-[(2S,3R)-2-methyl-1-azabicyclo[2.2.2]oct-3-yl]-[2,2']bithiophenyl-5-carboxamide; N-[(2S,3R)-2-methyl-1-azabicyclo[2.2.2]oct-3-yl]-5-(methylsulfanyl)-thiophene-2-carboxamide; N-[(2S,3R)-2-methyl-1-azabicyclo[2.2.2]oct-3-yl]-5-chloro-thiophene-2-carboxamide; N-[(2S,3R)-2-methyl-1-azabicyclo[2.2.2]oct-3-yl]-5-acetyl-thiophene-2-carboxamide; N-[(2S,3R)-2-methyl-1-azabicyclo[2.2.2]oct-3-yl]-5-methyl-thiophene-2-carboxamide; N-[(2S,3R)-2-methyl-1-azabicyclo[2.2.2]oct-3-yl]-5-bromo-thiophene-2-carboxamide; N-[(2S,3R)-2-methyl-1-azabicyclo[2.2.2]oct-3-yl]-5-(phenylsulfanyl)-thiophene-2-carboxamide; N-[(2S,3R)-2-methyl-1-azabicyclo[2.2.2]oct-3-yl]-5-(acetylamino)-furan-2-carboxamide; N-[(2S,3R)-2-methyl-1-azabicyclo[2.2.2]oct-3-yl]-5-trifluoromethyl-furan-2-carboxamide; N-[(2S,3R)-2-methyl-1-azabicyclo[2.2.2]oct-3-yl]-5-(2-methyl-5-trifluoromethyl-2H-pyrazole-3-yl)-thiophene-2-carboxamide; N-[(2S,3R)-2-methyl-1- azabicyclo[2.2.2]oct-3-yl]-5-(2-methylthiazol-4-yl)-thiophene-2-carboxamide; N-[(2S,3R)-2-methyl-1-azabicyclo[2.2.2]oct-3-yl]-5-[2-(3-chlorophenyl)-vinyl]-thiophene-2-carboxamide; N-[(2S,3R)-2-methyl-1-azabicyclo[2.2.2]oct-3-yl]-5-(4-chlorophenylsulfanyl)-thiophene-2-carboxamide; N-[(2S,3R)-2-methyl-1-azabicyclo[2.2.2]oct-3-yl]-5-(2,4-difluorophenyl-sulfanyl)-thiophene-2-carboxamide; N-[(2S,3R)-2-methyl-1-azabicyclo[2.2.2]oct-3-yl]-5-(3-chlorophenyl-sulfanyl)-thiophene-2-carboxamide; N-[(2S,3R)-2-methyl-1-azabicyclo[2.2.2]oct-3-yl]-5-(3-chloro-4-fluoro-phenylsulfanyl)-thiophene-2-carboxamide; N-[(2S,3R)-2-methyl-1-azabicyclo[2.2.2]oct-3-yl]-5-(2,3-dichlorophenyl-sulfanyl)-thiophene-2-carboxamide; N-[(2S,3R)-2-methyl-1-azabicyclo[2.2.2]oct-3-yl]-5-(2,4,5-trichlorophenyl-sulfanyl)-thiophene-2-carboxamide; N-[(2S,3R)-2-methyl-1-azabicyclo[2.2.2]oct-3-yl]-5-(3,4-dichlorophenyl-sulfanyl)-thiophene-2-carboxamide; N-[(2S,3R)-2-methyl-1-azabicyclo[2.2.2]oct-3-yl]-5-phenoxy-thiophene-2-carboxamide; N-[(2S,3R)-2-methyl-1-azabicyclo[2.2.2]oct-3-yl]-5-(2-hydroxyphenyl)-thiophene-2-carboxamide; N-[(2S,3R)-2-methyl-1-azabicyclo[2.2.2]oct-3-yl]-5-(3-hydroxyphenyl)-thiophene-2-carboxamide; N-[(2S,3R)-2-methyl-1-azabicyclo[2.2.2]oct-3-yl]-5-3-fluoro-4-hydroxyphenyl)-thiophene-2-carboxamide; N-[(2S,3R)-2-methyl-1-azabicyclo[2.2.2]oct-3-yl]-2-(phenylsulfanyl)-1,3-thiazole-5-carboxamide; N-[(2S,3R)-2-methyl-1-azabicyclo[2.2.2]oct-3-yl]-2-[(4-chlorophenyl)-sulfanyl]-1,3-thiazole-5-carboxamide; N-[(2S,3R)-2-methyl-1-azabicyclo[2.2.2]oct-3-yl]-2-phenoxy-1,3-thiazole-5-carboxamide; N-[(2S,3R)-2-methyl-1-azabicyclo[2.2.2]oct-3-yl]-2-[(4-fluorophenyl)-sulfanyl]-1,3-thiazole-5-carboxamide; N-[(2S,3R)-2-methyl-1-azabicyclo[2.2.2]oct-3-yl]-2-(methylsulfanyl)-1,3-thiazole-5-carboxamide; N-[(2S,3R)-2-methyl-1-azabicyclo[2.2.2]oct-3-yl]-2-(4-chlorophenoxy)-1,3-thiazole-5-carboxamide; N-[(2S,3R)-2-methyl-1-azabicyclo[2.2.2]oct-3-yl]-2-phenyl-1,3-thiazole-5-carboxamide; N-[(2S,3R)-2-methyl-1-azabicyclo[2.2.2]oct-3-yl]-2,4-dimethyl-1,3-thiazole-5-carboxamide; N-[(2S,3R)-2-methyl-1-azabicyclo[2.2.2]oct-3-yl]-2-(2-fluorophenyl)-1,3-thiazole-5-carboxamide; N-[(2S,3R)-2-methyl-1-azabicyclo[2.2.2]oct-3-yl]-2-(3-fluorophenyl)-1,3-thiazole-5-carboxamide; N-[(2S,3R)-2-methyl-1-azabicyclo[2.2.2]oct-3-yl]-2-(4-fluorophenyl)-1,3-thiazole-5-carboxamide; N-[(2S,3R)-2-methyl-1-azabicyclo[2.2.2]oct-3-yl]-2-(2-hydroxyphenyl)-1,3-thiazole-5-carboxamide; N-[(2S,3R)-2-methyl-1-azabicyclo[2.2.2]oct-3-yl]-2-(4-methylphenyl)-1,3-thiazole-5-carboxamide; N-[(2S,3R)-2-methyl-1-azabicyclo[2.2.2]oct-3-yl]-2-[4-(benzyloxy)phenyl]-1,3-thiazole-5-carboxamide; N-[(2S,3R)-2-methyl-1-azabicyclo[2.2.2]oct-3-yl]-2-pyridin-3-yl-1,3-thiazole-4-carboxamide; N-[(2S,3R)-2-methyl-1-azabicyclo[2.2.2]oct-3-yl]-4-methyl-2-phenyl-1,3-thiazole-5-carboxamide; N-[(2S,3R)-2-methyl-1-azabicyclo[2.2.2]oct-3-yl]-2-(4-chlorophenyl)-4-methyl-1,3-thiazole-5-carboxamide; N-[(2S,3R)-2-methyl-1-azabicyclo[2.2.2]oct-3-yl]-4-methyl-2-pyridin-2-yl-1,3-thiazole-5-carboxamide; N-[(2S,3R)-2-methyl-1-azabicyclo[2.2.2]oct-3-yl]-4-methyl-2-pyridin-4-yl-1,3-thiazole-5-carboxamide; N-[(2S,3R)-2-methyl-1-azabicyclo[2.2.2]oct-3-yl]-2-(methylamino)-1,3-thiazole-5-carboxamide; N-[(2S,3R)-2-methyl-1-azabicyclo[2.2.2]oct-3-yl]-5-(phenylsulfanyl)-1,3,4-thiadiazole-2-carboxamide; N-[(2S,3R)-2-methyl-1-azabicyclo[2.2.2]oct-3-yl]-5-phenoxy-1,3,4-thiadiazole-2-carboxamide; N-[(2S,3R)-2-methyl-1-azabicyclo[2.2.2]oct-3-yl]-5-[(4-chlorophenyl)-sulfanyl]-1,3,4-thiadiazole-2-carboxamide; N-[(2S,3R)-2-methyl-1-azabicyclo[2.2.2]oct-3-yl]-5-(4-fluorophenoxy)-1,3,4-thiadiazole-2-carboxamide; N-[(2S,3R)-2-methyl-1-azabicyclo[2.2.2]oct-3-yl]-5-(4-chlorophenoxy)-1,3,4-thiadiazole-2-carboxamide; N-[(2S,3R)-2-methyl-1-azabicyclo[2.2.2]oct-3-yl]-5-[(3-fluorophenyl)-sulfanyl]-1,3,4-thiadiazole-2-carboxamide; N-[(2S,3R)-2-methyl-1-azabicyclo[2.2.2]oct-3-yl]-5-[(2-chlorophenyl)-sulfanyl]-1,3,4-thiadiazole-2-carboxamide; N-[(2S,3R)-2-methyl-1-azabicyclo[2.2.2]oct-3-yl]-5-[(4-fluorophenyl)-sulfanyl]-1,3,4-thiadiazole-2-carboxamide; N-[(2S,3R)-2-methyl-1-azabicyclo[2.2.2]oct-3-yl]-5-[(3-chlorophenyl)-sulfanyl]-1,3,4-thiadiazole-2-carboxamide; N-[(2S,3R)-2-methyl-1-azabicyclo[2.2.2]oct-3-yl]-5-phenyl-1H-1,2,4-triazole-3-carboxamide; N-[(2S,3R)-2-methyl-1-azabicyclo[2.2.2]oct-3-yl]-5-phenyl-1,3,4-oxadiazole-2-carboxamide; N-[(2S,3R)-2-methyl-1-azabicyclo[2.2.2]oct-3-yl]-5-(methylthio)-1,3,4-oxadiazole-2-carboxamide; N-[(2S,3R)-2-methyl-1-azabicyclo[2.2.2]oct-3-yl]-5-(3-chlorophenyl)-1,3-oxazole-2 carboxamide; N-[(2S,3R)-2-methyl-1-azabicyclo[2.2.2]oct-3-yl]-5-(3-methoxyphenyl)-1,3-oxazole-2-carboxamide; N-[(2S,3R)-2-methyl-1-azabicyclo[2.2.2]oct-3-yl]-5-(3-nitrophenyl)-1,3-oxazole-2-carboxamide; N-[(2S,3R)-2-methyl- N-[(2S,3R)-2-methyl-1-azabicyclo[2.2.2]oct-3-yl]-5-(4-bromophenyl)-1,3-thiazole-2-carboxamide; N-[(2S,3R)-2-methyl-1-azabicyclo[2.2.2]oct-3-yl]-5-(3-nitrophenyl)-1,3-thiazole-2-carboxamide; N-[(2S,3R)-2-methyl-1-azabicyclo[2.2.2]oct-3-yl]-5-(3-methoxyphenyl)-1,3-thiazole-2-carboxamide; N-[(2S,3R)-2-methyl-1-azabicyclo[2.2.2]oct-3-yl]-5-(2-chlorophenyl)-1,3-thiazole-2-carboxamide; N-[(2S,3R)-2-methyl-1-azabicyclo[2.2.2]oct-3-yl]-5-(4-fluorophenyl)-1,3-thiazole-2-carboxamide; N-[(2S,3R)-2-methyl-1-azabicyclo[2.2.2]oct-3-yl]-5-(2-methoxyphenyl)-1,3-thiazole-2-carboxamide; N-[(2S,3R)-2-methyl-1-azabicyclo[2.2.2]oct-3-yl]-5-(4-chlorophenyl)-1,3-thiazole-2-carboxamide; N-[(2S,3R)-2-methyl-1-azabicyclo[2.2.2]oct-3-yl]-5-methyl-1,3-thiazole-2-carboxamide; N-[(2S,3R)-2-methyl-1-azabicyclo[2.2.2]oct-3-yl]-5-(3-chlorophenyl)-1,3-thiazole-2-carboxamide; N-[(2S,3R)-2-methyl-1-azabicyclo[2.2.2]oct-3-yl]-5-(2-fluorophenyl)-1,3-thiazole-2-carboxamide; N-[(2S,3R)-2-methyl-1-azabicyclo[2.2.2]oct-3-yl]-5-(3-fluorophenyl)-1,3-thiazole-2-carboxamide; N-[(2S,3R)-2-methyl-1-azabicyclo[2.2.2]oct-3-yl]-5-thien-2-yl-1,3-thiazole-2-carboxamide; N-[(2S,3R)-2-methyl-1-azabicyclo[2.2.2]oct-3-yl]-5-phenyl-furan-2-carboxamide; N-[(2S,3R)-2-methyl-1-azabicyclo[2.2.2]oct-3-yl]-5-(2-chlorophenyl)-furan-2-carboxamide; N-[(2S,3R)-2-methyl-1-azabicyclo[2.2.2]oct-3-yl]-5-(3-chlorophenyl)-furan-2-carboxamide; N-[(2S,3R)-2-methyl-1-azabicyclo[2.2.2]oct-3-yl]-5-4-chlorophenyl)-furan-2-carboxamide; N-[(2S,3R)-2-methyl-1-azabicyclo[2.2.2]oct-3-yl]-5-(4-bromophenyl)-furan-2-carboxamide; N-[(2S,3R)-2-methyl-1-azabicyclo[2.2.2]oct-3-yl]-5-[2-(trifluoromethyl)-phenyl]-furan-2-carboxamide; N-[(2S,3R)-2-methyl-1-azabicyclo[2.2.2]oct-3-yl]-5-[3-(trifluoromethyl)-phenyl]-furan-2-carboxamide; N-[(2S,3R)-2-methyl-1-azabicyclo[2.2.2]oct-3-yl]-5-(2-nitrophenyl)-furan-2-carboxamide; N-[(2S,3R)-2-methyl-1-azabicyclo[2.2.2]oct-3-yl]-5-(3-nitrophenyl)-furan-2-carboxamide; N-[(2S,3R)-2-methyl-1-azabicyclo[2.2.2]oct-3-yl]-5-(4-nitrophenyl)-furan-2-carboxamide; N-[(2S,3R)-2-methyl-1-azabicyclo[2.2.2]oct-3-yl]-5-(2-fluorophenyl)-furan-2-carboxamide; N-[(2S,3R)-2-methyl-1-azabicyclo[2.2.2]oct-3-yl]-5-(3-fluorophenyl)-furan-2-carboxamide; N-[(2S,3R)-2-methyl-1-azabicyclo[2.2.2]oct-3-yl]-5-(4-fluorophenyl)-furan-2-carboxamide; N-[(2S,3R)-2-methyl-1-azabicyclo[2.2.2]oct-3-yl]-5-(2,4-difluorophenyl)-furan-2-carboxamide; N-[(2S,3R)-2-methyl-1-azabicyclo[2.2.2]

oct-3-yl]-5-(2,5-difluorophenyl)-furan-2-carboxamide; N-[(2S,3R)-2-methyl-1-azabicyclo[2.2.2]oct-3-yl]-5-(2-methoxyphenyl)-furan-2-carboxamide; N-[(2S,3R)-2-methyl-1-azabicyclo[2.2.2]oct-3-yl]-5-(3-methoxyphenyl)-furan-2-carboxamide; N-[(2S,3R)-2-methyl-1-azabicyclo[2.2.2]oct-3-yl]-5-[3-(trifluoromethoxy)phenyl]-furan-2-carboxamide; N-[(2S,3R)-2-methyl-1-azabicyclo[2.2.2]oct-3-yl]-5-[2-chloro-5-(trifluoromethyl)phenyl]-furan-2-carboxamide; N-[(2S,3R)-2-methyl-1-azabicyclo[2.2.2]oct-3-yl]-5-(4-fluoro-3-methylphenyl)-furan-2-carboxamide; N-[(2S,3R)-2-methyl-1-azabicyclo[2.2.2]oct-3-yl]-5-(4-cyanophenyl)-furan-2-carboxamide; N-[(2S,3R)-2-methyl-1-azabicyclo[2.2.2]oct-3-yl]-5-thien-2-yl-furan-2-carboxamide; N-[(2S,3R)-2-methyl-1-azabicyclo[2.2.2]oct-3-yl]-5-thien-3-yl-furan-2-carboxamide; N-[(2S,3R)-2-methyl-1-azabicyclo[2.2.2]oct-3-yl]-5-bromo-furan-2-carboxamide; N-[(2S,3R)-2-methyl-1-azabicyclo[2.2.2]oct-3-yl]-5-nitro-furan-2-carboxamide; N-[(2S,3R)-2-methyl-1-azabicyclo[2.2.2]oct-3-yl]-4,5-dimethyl-furan-2-carboxamide; N-[(2S,3R)-2-methyl-1-azabicyclo[2.2.2]oct-3-yl]-5-(4-chloro-2-nitrophenyl)-furan-2-carboxamide; N-[(2S,3R)-2-methyl-1-azabicyclo[2.2.2]oct-3-yl]-5-(4-methyl-2-nitrophenyl)-furan-2-carboxamide; N-[(2S,3R)-2-methyl-1-azabicyclo[2.2.2]oct-3-yl]-5-(2,3-difluorophenyl)-furan-2-carboxamide; N-[(2S,3R)-2-methyl-1-azabicyclo[2.2.2]oct-3-yl]-5-(3,4-difluorophenyl)-furan-2-carboxamide; N-[(2S,3R)-2-methyl-1-azabicyclo[2.2.2]oct-3-yl]-5-(3,5-difluorophenyl)-furan-2-carboxamide; N-[(2S,3R)-2-methyl-1-azabicyclo[2.2.2]oct-3-yl]-5-(4-methoxy-phenyl)-furan-2-carboxamide; N-[(2S,3R)-2-methyl-1-azabicyclo[2.2.2]oct-3-yl]-5-(2-methylphenyl)-furan-2-carboxamide; N-[(2S,3R)-2-methyl-1-azabicyclo[2.2.2]oct-3-yl]-5-(3-methylphenyl)-furan-2-carboxamide; N-[(2S,3R)-2-methyl-1-azabicyclo[2.2.2]oct-3-yl]-5-(4-methylphenyl)-furan-2-carboxamide; N-[(2S,3R)-2-methyl-1-azabicyclo[2.2.2]oct-3-yl]-5-[2-(trifluoromethoxy)phenyl]-furan-2-carboxamide; N-[(2S,3R)-2-methyl-1-azabicyclo[2.2.2]oct-3-yl]-5-[4-(trifluoromethoxy)phenyl]-furan-2-carboxamide; N-[(2S,3R)-2-methyl-1-azabicyclo[2.2.2]oct-3-yl]-5-(4-tert-butylphenyl)-furan-2-carboxamide; N-[(2S,3R)-2-methyl-1-azabicyclo[2.2.2]oct-3-yl]-5-(1-benzothien-2-yl)-furan-2-carboxamide; N-[(2S,3R)-2-methyl-1-azabicyclo[2.2.2]oct-3-yl]-5-quinolin-3-yl-furan-2-carboxamide; N-[(2S,3R)-2-methyl-1-azabicyclo[2.2.2]oct-3-yl]-5-(4-ethylphenyl)-furan-2-carboxamide; N-[(2S,3R)-2-methyl-1-azabicyclo[2.2.2]oct-3-yl]-5-(4-isopropylphenyl)-furan-2-carboxamide; N-[(2S,3R)-2-methyl-1-azabicyclo[2.2.2]oct-3-yl]-5-(3-fluoro-4-methoxyphenyl)-furan-2-carboxamide; N-[(2S,3R)-2-methyl-1-azabicyclo[2.2.2]oct-3-yl]-5-(1-benzofuran-2-yl)-furan-2-carboxamide; 5-(2-aminophenyl)-N-[(2S,3R)-2-methyl-1-azabicyclo[2.2.2]oct-3-yl]-furan-2-carboxamide; 5-(4-aminophenyl)-N-[(2S,3R)-2-methyl-1-azabicyclo[2.2.2]oct-3-yl]-furan-2-carboxamide; 5-(2-amino-4-methylphenyl)-N-[(2S,3R)-2-methyl-1-azabicyclo[2.2.2]oct-3-yl]-furan-2-carboxamide; N-[(2S,3R)-2-methyl-1-azabicyclo[2.2.2]oct-3-yl]-5-(phenylethynyl)-furan-2-carboxamide; N-[(2S,3R)-2-methyl-1-azabicyclo[2.2.2]oct-3-yl]-5-phenoxy-furan-2-carboxamide; N-[(2S,3R)-2-methyl-1-azabicyclo[2.2.2]oct-3-yl]-1-methyl-5-phenyl-1H-pyrrole-2-carboxamide; N-[(2S,3R)-2-methyl-1-azabicyclo[2.2.2]t-3-yl]-5-phenyl-1,3-oxazole-2-carboxamide; N-[(2S,3R)-2-methyl-1-azabicyclo[2.2.2]oct-3-yl]-3-phenyl-1,2,4-oxadiazole-5-carboxamide; N-[(2S,3R)-2-methyl-1-azabicyclo[2.2.2]oct-3-yl]-2-phenyl-1,3-oxazole-5-carboxamide; N-[(2S,3R)-2-methyl-1-azabicyclo[2.2.2]oct-3-yl]-2-phenyl-1,3-oxazole-4-carboxamide; N-[(2S,3R)-2-methyl-1-azabicyclo[2.2.2]oct-3-yl]-5-phenylisoxazole-3-carboxamide; 5-bromo-N-[(2S,3R)-2-methyl-1-azabicyclo[2.2.2]oct-3-yl]-thiophene-2-carboxamide; N-[(2S,3R)-2-methyl-1-azabicyclo[2.2.2]oct-3-yl]-5-phenyl-thiophene-2-carbothioamide;

N-[(3R)-1-azabicyclo[2.2.2]oct-3-yl]-5-(2-acetamidophenyl)-thiophene-2-carboxamide; N-[(3R)-1-azabicyclo[2.2.2]oct-3-yl]-5-(3-acetamidophenyl)-thiophene-2-carboxamide; N-[(3R)-1-azabicyclo[2.2.2]oct-3-yl]-5-(4-acetamidophenyl)-thiophene-2-carboxamide; N-[(3R)-1-azabicyclo[2.2.2]oct-3-yl]-5-(2-trifluoroacetamidophenyl)-thiophene-2-carboxamide; N-[(3R)-1-azabicyclo[2.2.2]oct-3-yl]-5-(3-trifluoroacetamidophenyl)-thiophene-2-carboxamide; N-[(3R)-1-azabicyclo[2.2.2]oct-3-yl]-5-(4-trifluoroacetamidophenyl)-thiophene-2-carboxamide; N-[(3R)-1-azabicyclo[2.2.2]oct-3-yl]-5-(2-methanesulfonylaminophenyl)-thiophene-2-carboxamide; N-[(3R)-1-azabicyclo[2.2.2]oct-3-yl]-5-(3-methanesulfonylaminophenyl)-thiophene-2-carboxamide; N-[(3R)-1-azabicyclo[2.2.2]oct-3-yl]-5-(4-methanesulfonylaminophenyl)-thiophene-2-carboxamide; N-[(3R)-1-azabicyclo[2.2.2]oct-3-yl]-5-(2-trifluoromethanesulfonylaminophenyl)-thiophene-2-carboxamide; N-[(3R)-1-azabicyclo[2.2.2]oct-3-yl]-5-(3-trifluoromethanesulfonylaminophenyl)-thiophene-2-carboxamide; N-[(3R)-1-azabicyclo[2.2.2]oct-3-yl]-5-(4-trifluoromethanesulfonylaminophenyl)-thiophene-2-carboxamide; N-[(3R)-1-azabicyclo[2.2.2]oct-3-yl]-5-(2-difluoroacetamidophenyl)-thiophene-2-carboxamide; N-[(3R)-1-azabicyclo[2.2.2]oct-3-yl]-5-(3-difluoroacetamidophenyl)-thiophene-2-carboxamide; N-[(3R)-1-azabicyclo[2.2.2]oct-3-yl]-5-(4-difluoroacetamidophenyl)-thiophene-2-carboxamide; N-[(3R)-1-azabicyclo[2.2.2]oct-3-yl]-5-(2-carbamoylphenyl)-thiophene-2-carboxamide; N-[(3R)-1-azabicyclo [2.2.2]oct-3-yl]-5-(3-carbamoylphenyl)-thiophene-2-carboxamide; N-[(3R)-1-azabicyclo[2.2.2]oct-3-yl]-5-(4-carbamoylphenyl)-thiophene-2-carboxamide; N-[(3R)-1-azabicyclo[2.2.2]oct-3-yl]-5-(2-sulfamoylphenyl)-thiophene-2-carboxamide; N-((3R)-1-azabicyclo[2.2.2]oct-3-yl]-5-(3-sulfamoylphenyl)-thiophene-2-carboxamide; N-[(3R)-1-azabicyclo[2.2.2]oct-3-yl]-5-(4-sulfamoylphenyl)-thiophene-2-carboxamide; N-[(3R)-1-azabicyclo[2.2.2]oct-3-yl]-5-(2-acetamidophenylsulfanyl)-thiophene-2-carboxamide; N-[(3R)-1-azabicyclo[2.2.2]oct-3-yl]-5-(3-acetamidophenylsulfanyl)-thiophene-2-carboxamide; N-[(3R)-1-azabicyclo[2.2.2]oct-3-yl]-5-(4-acetamidophenylsulfanyl)-thiophene-2-carboxamide; N-[(3R)-1-azabicyclo[2.2.2]oct-3-yl]-5-(2-trifluoroacetamidophenylsulfanyl)-thiophene-2-carboxamide; N-[(3R)-1-azabicyclo[2.2.2]oct-3-yl]-5-(3-trifluoroacetamidophenylsulfanyl)-thiophene-2-carboxamide; N-[(3R)-1-azabicyclo[2.2.2]oct-3-yl]-5-(4-trifluoroacetamidophenylsulfanyl)-thiophene-2-carboxamide; N-[(3R)-1-azabicyclo[2.2.2]oct-3-yl]-5-(2-methanesulfonylaminophenylsulfanyl)-thiophene-2-carboxamide; N-[(3R)-1-azabicyclo[2.2.2]oct-3-yl]-5-(3-methanesulfonylaminophenylsulfanyl)-thiophene-2-carboxamide; N-[(3R)-1-azabicyclo[2.2.2]oct-3-yl]-5-(4-methanesulfonylaminophenylsulfanyl)-thiophene-2-carboxamide; N-[(3R)-1-azabicyclo[2.2.2]oct-3-yl]-5-(2-trifluoromethanesulfonylaminophenylsulfanyl)-thiophene-2-carboxamide; N-[(3R)-1-azabicyclo[2.2.2]oct-3-yl]-5-(3-trifluoromethanesulfonylaminophenylsulfanyl)-thiophene-2-carboxamide; N-[(3R)-1-azabicyclo[2.2.2]oct-3-yl]-5-(4- trifluoromethanesulfonylaminophenylsulfanyl)-thiophene-2-carboxamide; N-[(3R)-1-azabicyclo[2.2.2]oct-3-yl]-5-(2-difluoroacetamidophenylsulfanyl)-thiophene-2-carboxamide; N-[(3R)-1-azabicyclo[2.2.2]oct-3-yl]-5-(3-difluoroacetamidophenylsulfanyl)-thiophene-2-carboxamide; N-[(3R)-1-azabicyclo[2.2.2]oct-3-yl]-5-(4-difluoroacetamidophenylsulfanyl)-thiophene-2-carboxamide; N-[(3R)-1-azabicyclo[2.2.2]oct-3-yl]-5-(2-carbamoylphenylsulfanyl)-thiophene-2-carboxamide; N-[(3R)-1-azabicyclo[2.2.2]oct-3-yl]-5-(3-carbamoylphenylsulfanyl)-thiophene-2-carboxamide; N-[(3R)-1-azabicyclo[2.2.2]oct-3-yl]-5-(4-carbamoylphenylsulfanyl)-thiophene-2-carboxamide; N-[(3R)-1-N-[(3R)-1-azabicyclo[2.2.2]oct-3-yl]-5-(3-sulfamoylphenylsulfanyl)-thiophene-2-carboxamide; N-[(3R)-1-azabicyclo[2.2.2]oct-3-yl]-5-(4-sulfamoylphenylsulfanyl)-thiophene-2-carboxamide; N-[(3R)-1-azabicyclo[2.2.2]oct-3-yl]-5-(2-hydroxyphenylsulfanyl)-thiophene-2-carboxamide; N-[(3R)-1-azabicyclo[2.2.2]oct-3-yl]-5-(3-hydroxyphenylsulfanyl)-thiophene-2-carboxamide; N-[(3R)-1-azabicyclo[2.2.2]oct-3-yl]-5-(4-hydroxyphenylsulfanyl)-thiophene-2-carboxamide; N-[(3R)-1-azabicyclo[2.2.2]oct-3-yl]-5-(2-aminophenylsulfanyl)-thiophene-2-carboxamide; N-[(3R)-1-azabicyclo[2.2.2]oct-3-yl]-5-(3-aminophenylsulfanyl)-thiophene-2-carboxamide; N-[(3R)-1-azabicyclo[2.2.2]oct-3-yl]-5-(4-aminophenylsulfanyl)-thiophene-2-carboxamide; N-[(3R)-1-azabicyclo[2.2.2]oct-3-yl]-5-(2-acetamidophenoxy)-thiophene-2-carboxamide; N-[(3R)-1-azabicyclo[2.2.2]oct-3-yl]-5-(3-acetamidophenoxy)-thiophene-2-carboxamide; N-[(3R)-1-azabicyclo[2.2.2]oct-3-yl]-5-(4-acetamidophenoxy)-thiophene-2-carboxamide; N-[(3R)-1-azabicyclo[2.2.2]oct-3-yl]-5-(2-trifluoroacetamidophenoxy)-thiophene-2-carboxamide; N-[(3R)-1-azabicyclo[2.2.2]oct-3-yl]-5-(3-trifluoroacetamidophenoxy)-thiophene-2-carboxamide; N-[(3R)-1-azabicyclo[2.2.2]oct-3-yl]-5-(4-trifluoroacetamidophenoxy)-thiophene-2-carboxamide; N-[(3R)-1-azabicyclo[2.2.2]oct-3-yl]-5-(2-methanesulfonylaminophenoxy)-thiophene-2-carboxamide; N-[(3R)-1-azabicyclo[2.2.2]oct-3-yl]-5-(3-methanesulfonylaminophenoxy)-thiophene-2-carboxamide; N-[(3R)-1-azabicyclo[2.2.2]oct-3-yl]-5-(4-methanesulfonylaminophenoxy)-thiophene-2-carboxamide; N-[(3R)-1-azabicyclo[2.2.2]oct-3-yl]-5-(2-trifluoromethanesulfonylaminophenoxy)-thiophene-2-carboxamide; N-[(3R)-1-azabicyclo[2.2.2]oct-3-yl]-5-(3-trifluoromethanesulfonylaminophenoxy)-thiophene-2-carboxamide; N-[(3R)-1-azabicyclo[2.2.2]oct-3-yl]-5-(4-trifluoromethanesulfonylaminophenoxy)-thiophene-2-carboxamide; N-[(3R)-1-azabicyclo[2.2.2]oct-3-yl]-5-(2-difluoroacetamidophenoxy)-thiophene-2-carboxamide; N-[(3R)-1-azabicyclo[2.2.2]oct-3-yl]-5-(3-difluoroacetamidophenoxy)-thiophene-2-carboxamide; N-[(3R)-1-azabicyclo[N-[(3R)-1-azabicyclo[2.2.2]oct-3-yl]-5-(4-chlorophenoxy)-thiophene-2-carboxamide; N-[(3R)-1-azabicyclo[2.2.2]oct-3-yl]-5-(2-cyanophenoxy)-thiophene-2-carboxamide; N-[(3R)-1-azabicyclo[2.2.2]oct-3-yl]-5-(3-cyanophenoxy)-thiophene-2-carboxamide; N-[(3R)-1-azabicyclo[2.2.2]oct-3-yl]-5-(4-cyanophenoxy)-thiophene-2-carboxamide; N-[(3R)-1-azabicyclo[2.2.2]oct-3-yl]-5-(2-methoxyphenyl)-thiophene-2-carboxamide; N-[(3R)-1-azabicyclo[2.2.2]oct-3-yl]-5-(3-methoxyphenyl)-thiophene-2-carboxamide; N-[(3R)-1-azabicyclo[2.2.2]oct-3-yl]-5-(4-methoxyphenyl)-thiophene-2-carboxamide; N-[(3R)-1-azabicyclo[2.2.2]oct-3-yl]-5-(2-methylphenyl)-thiophene-2-carboxamide; N-[(3R)-1-azabicyclo[2.2.2]oct-3-yl]-5-(3-methylphenyl)-thiophene-2-carboxamide; N-[(3R)-1-azabicyclo[2.2.2]oct-3-yl]-5-(4-methylphenyl)-thiophene-2-carboxamide; N-[(3R)-1-azabicyclo[2.2.2]oct-3-yl]-5-(2-trifluoromethylphenyl)-thiophene-2-carboxamide; N-[(3R)-1-azabicyclo[2.2.2]oct-3-yl]-5-(3-trifluoromethylphenyl)-thiophene-2-carboxamide; N-[(3R)-1-azabicyclo[2.2.2]oct-3-yl]-5-(4-trifluoromethylphenyl)-thiophene-2-carboxamide; N-[(3R)-1-azabicyclo[2.2.2]oct-3-yl]-5-(2-acetylphenyl)-thiophene-2-carboxamide; N-[(3R)-1-azabicyclo[2.2.2]oct-3-yl]-5-(3-acetylphenyl)-thiophene-2-carboxamide; N-[(3R)-1-azabicyclo[2.2.2]oct-3-yl]-5-(4-acetylphenyl)-thiophene-2-carboxamide; N-[(3R)-1-azabicyclo[2.2.2]oct-3-yl]-5-(2-cyanophenyl)-thiophene-2-carboxamide; N-[(3R)-1-azabicyclo[2.2.2]oct-3-yl]-5-(2-cyanophenyl)-thiophene-2-carboxamide; N-[(3R)-1-azabicyclo[2.2.2]oct-3-yl]-5-(3-cyanophenyl)-thiophene-2-carboxamide; N-[(3R)-1-azabicyclo[2.2.2]oct-3-yl]-5-(2-morpholin-4-yl-phenyl)-thiophene-2-carboxamide; N-[(3R)-1-azabicyclo[2.2.2]oct-3-yl]-5-(3-morpholin-4-yl-phenyl)-thiophene-2-carboxamide; N-[(3R)-1-azabicyclo[2.2.2]oct-3-yl]-5-(4-morpholin-4-yl-phenyl)-thiophene-2-carboxamide; N-[(3R)-1-azabicyclo[2.2.2]oct-3-yl]-5-(2-methoxyphenoxy)-thiophene-2-carboxamide; N-[(3R)-1-azabicyclo[2.2.2]oct-3-yl]-5-(3-methoxyphenoxy)-thiophene-2-carboxamide; N-[(3R)-1-azabicyclo[2.2.2]oct-3-yl]-5-(4-methoxyphenoxy)-thiophene-2-carboxamide; N-[(3R)-1-azabicyclo[2.2.2]oct-3-yl]-5-(2-methylphenoxy)-thiophene-2-carboxamide; N-[(3R)-1-azabicyclo[2.2.2]oct-3-yl]-5-(3-methylphenoxy)-thiophene-2-carboxamide; N-[(3R)-1-azabicyclo[2.2.2]oct-3-yl]-5-(4-methylphenoxy)-thiophene-2-carboxamide; N-[(3R)-1-azabicyclo[2.2.2]oct-3-yl]-5-(2-trifluoromethylphenoxy)-thiophene-2-carboxamide; N-[(3R)-1-azabicyclo[2.2.2]oct-3-yl]-5-(3-trifluoromethylphenoxy)-thiophene-2-carboxamide; N-[(3R)-1-azabicyclo[2.2.2]oct-3-yl]-5-(4-trifluoromethylphenoxy)-thiophene-2-carboxamide; N-[(3R)-1-azabicyclo[2.2.2]oct-3-yl]-5-(2-acetylphenoxy)-thiophene-2-carboxamide; N-[(3R)-1-azabicyclo[2.2.2]oct-3-yl]-5-(3-acetylphenoxy)-thiophene-2-carboxamide; N-[(3R)-1-azabicyclo[2.2.2]oct-3-yl]-5-(4-acetylphenoxy)-thiophene-2-carboxamide; N-[(3R)-1-azabicyclo[2.2.2]oct-3-yl]-5-(2-cyanophenoxy)-thiophene-2-carboxamide; N-[(3R)-1-azabicyclo[2.2.2]oct-3-yl]-5-(3-cyanophenoxy)-thiophene-2-carboxamide; N-[(3R)-1-azabicyclo[2.2.2]oct-3-yl]-5-(4-cyanophenoxy)-thiophene-2-carboxamide; N-[(3R)-1-azabicyclo[2.2.2]oct-3-yl]-5-(2-morpholin-4-yl-phenoxy)-thiophene-2-carboxamide; N-[(3R)-1-azabicyclo[2.2.2]oct-3-yl]-5-(3-morpholin-4-yl-phenoxy)-thiophene-2-carboxamide; N-[(3R)-1-azabicyclo[2.2.2]oct-3-yl]-5-(4-morpholin-4-yl-phenoxy)-thiophene-2-carboxamide; N-[(3R)-1-azabicyclo[2.2.2]oct-3-yl]-5-(2-methoxyphenylsulfanyl)-thiophene-2-carboxamide; N-[(3R)-1-azabicyclo[2.2.2]oct-3-yl]-5-(3-methoxyphenylsulfanyl)-thiophene-2-carboxamide; N-[(3R)-1-azabicyclo[2.2.2]oct-3-yl]-5-(4-methoxyphenylsulfanyl)-thiophene-2-carboxamide; N-[(3R)-1-azabicyclo[2.2.2]oct-3-yl]-5-(2-methylphenylsulfanyl)-thiophene-2-carboxamide; N-[(3R)-1-azabicyclo[2.2.2]oct-3-yl]-5-(3-methylphenylsulfanyl)thiophene-2-carboxamide; N-[(3R)-1-azabicyclo[2.2.2]oct-3-yl]-5-(4-methylphenylsulfanyl)-thiophene-2-carboxamide; N-[(3R)-1-azabicyclo[2.2.2]oct-3-yl]-5-(2-trifluoromethylphenylsulfanyl)-thiophene-2-carboxamide; N-[(3R)-1-azabicyclo[2.2.2]oct-3-yl]-5-(4-trifluoromethylphenylsulfanyl)-thiophene-2- carboxamide; N-[(3R)-1-azabicyclo[2.2.2]oct-3-yl]-5-(2-acetylphenylsulfanyl)-thiophene-2-carboxamide; N-[(3R)-1-azabicyclo[2.2.2]oct-3-yl]-5-(3-acetylphenylsulfanyl)-thiophene-2-carboxamide; N-[(3R)-1-azabicyclo[2.2.2]oct-3-yl]-5-(4-acetylphenylsulfanyl)-thiophene-2-carboxamide; N-[(3R)-1-azabicyclo[2.2.2]oct-3-yl]-5-(2-cyanophenylsulfanyl)-thiophene-2-carboxamide; N-[(3R)-1-azabicyclo[2.2.2]oct-3-yl]-5-(32-cyanophenylsulfanyl)-thiophene-2-carboxamide; N-[(3R)-1-azabicyclo[2.2.2]oct-3-yl]-5-(4-cyanophenylsulfanyl)-thiophene-2-carboxamide; N-[(3R)-1-azabicyclo[2.2.2]oct-3-yl]-5-(2-morpholin-4-yl-phenylsulfanyl)-thiophene-2-carboxamide; N-[(3R)-1-azabicyclo[2.2.2]oct-3-yl]-5-(3-morpholin-4-yl-phenylsulfanyl)-thiophene-2-carboxamide; N-[(3R)-1-azabicyclo[2.2.2]oct-3-yl]-5-(4-morpholin-4-yl-phenylsulfanyl)-thiophene-2-carboxamide; N-[(3R)-1-azabicyclo[2.2.2]oct-3-yl]-5-(pyridin-4-yl)-thiophene-2-carboxamide; N-[(3R)-1-azabicyclo[2.2.2]oct-3-yl]-5-(2-methylpyridin-4-yl)-thiophene-2-carboxamide; N-[(3R)-1-azabicyclo[2.2.2]oct-3-yl]-5-(6-methylpyridin-3-yl)-thiophene-2-carboxamide; N-[(3R)-1-azabicyclo[2.2.2]oct-3-yl]-5-(5-methylpyridin-2-yl)-thiophene-2-carboxamide; N-[(3R)-1-azabicyclo[2.2.2]oct-3-yl]-5-(2-methoxypyridin-4-yl)-thiophene-2-carboxamide; N-[(3R)-1-azabicyclo[2.2.2]oct-3-yl]-5-(6-methoxypyridin-3-yl)-thiophene-2-carboxamide; N-[(3R)-1-azabicyclo[2.2.2]oct-3-yl]-5-(5-methoxypyridin-2-yl)-thiophene-2-carboxamide; N-[(3R)-1-azabicyclo[2.2.2]oct-3-yl]-5-(2-chloropyridin-4-yl)-thiophene-2-carboxamide; N-[(3R)-1-azabicyclo[2.2.2]oct-3-yl]-5-(6-chloropyridin-3-yl)-thiophene-2-carboxamide; N-[(3R)-1-azabicyclo[2.2.2]oct-3-yl]-5-(5-chloropyridin-2-yl)-thiophene-2-carboxamide; N-[(3R)-1-azabicyclo[2.2.2]oct-3-yl]-5-(5-chloropyridin-3-yl)-thiophene-2-carboxamide; N-[(3R)-1-azabicyclo[2.2.2]oct-3-yl]-5-(6-chloropyridin-2-yl)-thiophene-2-carboxamide; N-[(3R)-1-azabicyclo[2.2.2]oct-3-yl]-5-(4-chloropyridin-2-yl)-thiophene-2-carboxamide; N-[(3R)-1-azabicyclo[2.2.2]oct-3-yl]-5-(pyridin-4-yloxy)-thiophene-2-carboxamide; N-[(3R)-1-azabicyclo[2.2.2]oct-3-yl]-5-(pyridin-3-yloxy)-thiophene-2-carboxamide; N-[(3R)-1-azabicyclo[2.2.2]oct-3-yl]-5-(pyridin-2-yloxy)-thiophene-2-carboxamide; N-[(3R)-1-azabicyclo[2.2.2]oct-3-yl]-5-(2-methylpyridin-4-yloxy)-thiophene-2-carboxamide; N-[(3R)-1-azabicyclo[2.2.2]oct-3-yl]-5-(6-methylpyridin-3-yloxy)-thiophene-2-carboxamide; N-[(3R)-1-azabicyclo[2.2.2]oct-3-yl]-5-(5-methylpyridin-2-yloxy)-thiophene-2-carboxamide; N-[(3R)-1-azabicyclo[2.2.2]oct-3-yl]-5-(2-methoxypyridin-4-yloxy)-thiophene-2-carboxamide; N-[(3R)-1-azabicyclo[2.2.2]oct-3-yl]-5-(6-methoxypyridin-3-yloxy)-thiophene-2-carboxamide; N-[(3R)-1-azabicyclo[2.2.2]oct-3-yl]-5-(5-methoxypyridin-2-yloxy)-thiophene-2-carboxamide; N-[(3R)-1-azabicyclo[2.2.2]oct-3-yl]-5-(2-chloropyridin-4-yloxy)-thiophene-2-carboxamide; N-[(3R)-1-azabicyclo[2.2.2]oct-3-yl]-5-(6-chloropyridin-3-yloxy)-thiophene-2-carboxamide; N-[(3R)-1-azabicyclo[2.2.2]oct-3-yl]-5-(5-chloropyridin-2-yloxy)-thiophene-2-carboxamide; N-[(3R)-1-azabicyclo[2.2.2]oct-3-yl]-5-(2-chloropyridin-4-yloxy)-thiophene-2-carboxamide; N-[(3R)-1-azabicyclo[2.2.2]oct-3-yl]-5-(6-chloropyridin-3-yloxy)-thiophene-2-carboxamide; N-[(3R)-1-azabicyclo[2.2.2]oct-3-yl]-5-(5-chloropyridin-2-yloxy)-thiophene-2-carboxamide; N-[(3R)-1-azabicyclo[2.2.2]oct-3-yl]-5-(5-chloropyridin-3-yloxy)-thiophene-2-carboxamide; N-[(3R)-1-azabicyclo[2.2.2]oct-3-yl]-5-(6-chloropyridin-2-yloxy)-thiophene-2-carboxamide; N-[(3R)-1-azabicyclo[2.2.2]oct-3-yl]-5-(4-chloropyridin-2-yloxy)-thiophene-2-carboxamide; N-[(3R)-1-azabicyclo[2.2.2]oct-3-yl]-5-(pyridin-4-ylsulfanyl)-thiophene-2-carboxamide; N-[(3R)-1-azabicyclo[2.2.2]oct-3-yl]-5-(pyridin-3-ylsulfanyl)-thiophene-2-carboxamide; N-[(3R)-1-azabicyclo[2.2.2]oct-3-yl]-5-(pyridin-2-ylsulfanyl)-thiophene-2-carboxamide; N-[(3R)-1-azabicyclo[2.2.2]oct-3-yl]-5-(2-methylpyridin-4-ylsulfanyl)-thiophene-2-carboxamide; N-[(3R)-1-azabicyclo[2.2.2]oct-3-yl]-5-(6-methylpyridin-3-ylsulfanyl)-thiophene-2-carboxamide; N-[(3R)-1-azabicyclo[2.2.2]oct-3-yl]-5-(5-methylpyridin-2-ylsulfanyl)-thiophene-2-carboxamide; N-[(3R)-1-azabicyclo[2.2.2]oct-3-yl]-5-(2-methoxypyridin-4-ylsulfanyl)-thiophene-2-carboxamide; N-[(3R)-1-azabicyclo[2.2.2]oct-3-yl]-5-(6-methoxypyridin-3-ylsulfanyl)-thiophene-2-carboxamide; N-[(3R)-1-azabicyclo[2.2.2]oct-3-yl]-5-(5-methoxypyridin-2-ylsulfanyl)-thiophene-2-carboxamide; N-[(3R)-1-azabicyclo[2.2.2]oct-3-yl]-5-(2-chloropyridin-4-ylsulfanyl)-thiophene-2-carboxamide; N-[(3R)-1-azabicyclo[2.2.2]oct-3-yl]-5-(6-chloropyridin-3-ylsulfanyl)-thiophene-2-carboxamide; N-[(3R)-1-azabicyclo[2.2.2]oct-3-yl]-5-(5-chloropyridin-2-ylsulfanyl)-thiophene-2-carboxamide; N-[(3R)-1-azabicyclo[2.2.2]oct-3-yl]-5-(2-chloropyridin-4-ylsulfanyl)-thiophene-2-carboxamide; N-[(3R)-1-azabicyclo[2.2.2]oct-3-yl]-5-(6-chloropyridin-3-ylsulfanyl)-thiophene-2-carboxamide; N-[(3R)-1-azabicyclo[2.2.2]oct-3-yl]-5-(5-chloropyridin-2-ylsulfanyl)-thiophene-2-carboxamide; N-[(3R)-1-azabicyclo[2.2.2]oct-3-yl]-5-(5-chloropyridin-3-ylsulfanyl)-thiophene-2-carboxamide; N-[(3R)-1-azabicyclo[2.2.2]oct-3-yl]-5-(6-chloropyridin-2-ylsulfanyl)-thiophene-2-carboxamide; N-[(3R)-1-azabicyclo[2.2.2]oct-3-yl]-5-(4-chloropyridin-2-ylsulfanyl)-thiophene-2-carboxamide; N-[(3R)-1-azabicyclo[2.2.2]oct-3-yl]-5-(thiophene-4-yl)-thiophene-2-carboxamide; N-[(3R)-1-azabicyclo[2.2.2]oct-3-yl]-5-(5-methylthiophen-2-yl)-thiophene-2-carboxamide; N-[(3R)-1-azabicyclo[2.2.2]oct-3-yl]-5-(5-methoxythiophen-2-yl)-thiophene-2-carboxamide; N-[(3R)-1-azabicyclo[2.2.2]oct-3-yl]-5-(5-chlorothiophen-2-yl)-thiophene-2-carboxamide; N-[(3R)-1-azabicyclo[2.2.2]oct-3-yl]-5-(furan-4-yl)-thiophene-2-carboxamide; N-[(3R)-1-azabicyclo[2.2.2]oct-3-yl]-5-(5-methylfuran-2-yl)-thiophene-2-carboxamide; N-[(3R)-1-azabicyclo[2.2.2]oct-3-yl]-5-(5-methoxyfuran-2-yl)-thiophene-2-carboxamide; N-[(3R)-1-azabicyclo[2.2.2]oct-3-yl]-5-(5-chlorofuran-2-yl)-thiophene-2-carboxamide; N-[(3R)-1-azabicyclo[2.2.2]oct-3-yl]-5-(oxazol-2-yl)-thiophene-2-carboxamide; N-[(3R)-1-azabicyclo[2.2.2]oct-3-yl]-5-(5-methyloxazol-2-yl)-thiophene-2-carboxamide; N-[(3R)-1-azabicyclo[2.2.2]oct-3-yl]-5-(5-methoxyoxazol-2-yl)-thiophene-2-carboxamide; N-[(3R)-1-azabicyclo[2.2.2]oct-3-yl]-5-(5-chlorooxazol-2-yl)-thiophene-2-carboxamide; N-[(3R)-1-azabicyclo[2.2.2]oct-3-yl]-5-(oxazol-5-yl)-thiophene-2-carboxamide; N-[(3R)-1-azabicyclo[2.2.2]oct-3-yl]-5-(2-methyloxazol-5-yl)-thiophene-2-carboxamide; N-[(3R)-1-azabicyclo[2.2.2]oct-3-yl]-5-(2-methoxyoxazol-5-yl)-thiophene-2-carboxamide; N-[(3R)-1-azabicyclo[2.2.2]oct-3-yl]-5-(2-chlorooxazol-5-yl)-thiophene-2-carboxamide; N-[(3R)-1-azabicyclo[2.2.2]oct-3-yl]-5-(thiazol-2-yl)-thiophene-2-carboxamide; N-[(3R)-1-azabicyclo[2.2.2]oct-3-yl]-5-(5-methylthiazol-2-yl)-thiophene-2-carboxamide; N-[(3R)-1-azabicyclo[2.2.2]oct-3-yl]-5-(5-methoxythiazol-2-yl)-thiophene-2-carboxamide; N-[(3R)-1-azabicyclo[2.2.2]oct-3-yl]-5-(5-chlorothiazol-2-yl)-thiophene-2-carboxamide; N-[(3R)-1-azabicyclo[2.2.2]oct-3-yl]-5-(thiazol-5-yl)-thiophene-2-carboxamide; N-[(3R)-1-azabicyclo[2.2.2]oct-3-yl]-5-(2- methylthiazol-5-yl)-thiophene-2-carboxamide; N-[(3R)-1-azabicyclo[2.2.2]oct-3-yl]-5-(2-methoxythiazol-5-yl)-thiophene-2-carboxamide; N-[(3R)-1-azabicyclo[2.2.2]oct-3-yl]-5-(2-chlorothiazol-5-yl)-thiophene-2-carboxamide; N-[(3R)-1-azabicyclo[2.2.2]oct-3-yl]-5-(4-methylthiazol-2-yl)-thiophene-2-carboxamide; N-[(3R)-1-azabicyclo[2.2.2]oct-3-yl]-5-(4-methoxythiazol-2-yl)-thiophene-2-carboxamide; N-[(3R)-1-azabicyclo[2.2.2]oct-3-yl]-5-(4-chlorothiazol-2-yl)-thiophene-2-carboxamide; N-[(3R)-1-azabicyclo[2.2.2]oct-3-yl]-5-(4-methyloxazol-2-yl)-thiophene-2-carboxamide; N-[(3R)-1-azabicyclo[2.2.2]oct-3-yl]-5-(4-methoxyoxazol-2-yl)-thiophene-2-carboxamide; N-[(3R)-1-azabicyclo[2.2.2]oct-3-yl]-5-(4-chlorooxazol-2-yl)-thiophene-2-carboxamide; N-[(3R)-1-azabicyclo[2.2.2]oct-3-yl]-5-([1,3,4]thiadiazol-2-yl)-thiophene-2-carboxamide; N-[(3R)-1-azabicyclo[2.2.2]oct-3-yl]-5-(5-methyl[1,3,4]thiadiazol-2-yl)-thiophene-2-carboxamide; N-[(3R)-1-azabicyclo[2.2.2]oct-3-yl]-5-(5-methoxy[1,3,4]thiadiazol-2-yl)-thiophene-2-carboxamide; N-[(3R)-1-azabicyclo[2.2.2]oct-3-yl]-5-(5-chloro[1,3,4]thiadiazol-2-yl)-thiophene-2-carboxamide; N-[(3R)-1-azabicyclo[2.2.2]oct-3-yl]-5-([1,3,4]oxadiazol-2-yl)-thiophene-2-carboxamide; N-[(3R)-1-azabicyclo[2.2.2]oct-3-yl]-5-(5-methyl[1,3,4]oxadiazol-2-yl)-thiophene-2-carboxamide; N-[(3R)-1-azabicyclo[2.2.2]oct-3-yl]-5-(5-methoxy[1,3,4]oxadiazol-2-yl)-thiophene-2-carboxamide; N-[(3R)-1-azabicyclo[2.2.2]oct-3-yl]-5-(5-chloro[1,3,4]oxadiazol-2-yl)-thiophene-2-carboxamide; N-[(3R)-1azabicyclo[2.2.2]oct-3-yl]-5-(thiophen-4-yloxy)-thiophene-2-carboxamide; N-[(3R)-1-azabicyclo[2.2.2]oct-3-yl]-5-(5-meth N-[(3R)-1-azabicyclo[2.2.2]oct-3-yl]-5-(5-methoxythiophen-2-yloxy)-thiophene-2-carboxamide; N-[(3R)-1-azabicyclo[2.2.2]oct-3-yl]-5-(5-chlorothiophen-2-yloxy)-thiophene-2-carboxamide; N-[(3R)-1-azabicyclo[2.2.2]oct-3-yl]-5-(furan-4-yloxy)-thiophene-2-carboxamide; N-[(3R)-1-azabicyclo[2.2.2]oct-3-yl]-5-(5-methylfuran-2-yloxy)-thiophene-2-carboxamide; N-[(3R)-1-azabicyclo[2.2.2]oct-3-yl]-5-(5-methoxyfuran-2-yloxy)-thiophene-2-carboxamide; N-[(3R)-1-azabicyclo[2.2.2]oct-3-yl]-5-(5-chlorofuran-2-yloxy)-thiophene-2-carboxamide; N-[(3R)-1-azabicyclo[2.2.2]oct-3-yl]-5-(oxazol-2-yloxy)-thiophene-2-carboxamide; N-[(3R)-1-azabicyclo[2.2.2]oct-3-yl]-5-(5-methyloxazol-2-yloxy)-thiophene-2-carboxamide; N-[(3R)-1-azabicyclo[2.2.2]oct-3-yl]-5-(5-methoxyoxazol-2-yloxy)-thiophene-2-carboxamide; N-[(3R)-1-azabicyclo[2.2.2]oct-3-yl]-5-(5-chlorooxazol-2-yloxy)-thiophene-2-carboxamide; N-[(3R)-1-azabicyclo[2.2.2]oct-3-yl]-5-(oxazol-5-yloxy)-thiophene-2-carboxamide; N-[(3R)-1-azabicyclo[2.2.2]oct-3-yl]-5-(2-methyloxazol-5-yloxy)-thiophene-2-carboxamide; N-[(3R)-1-azabicyclo[2.2.2]oct-3-yl]-5-(2-methoxyoxazol-5-yloxy)-thiophene-2-carboxamide; N-[(3R)-1-azabicyclo[2.2.2]oct-3-yl]-5-(2-chlorooxazol-5-yloxy)-thiophene-2-carboxamide; N-[(3R)-1-azabicyclo[2.2.2]oct-3-yl]-5-(thiazol-2-yloxy)-thiophene-2-carboxamide; N-[(3R)-1-azabicyclo[2.2.2]oct-3-yl]-5-(5-methylthiazol-2-yloxy)-thiophene-2-carboxamide; N-[(3R)-1-azabicyclo[2.2.2]oct-3-y l]-5-(5-methoxythiazol-2-yloxy)thiophene-2-carboxamide; N-[(3R)-1-azabicyclo[2.2.2]oct-3-yl]-5-(5-chlorothiazol-2-yloxy)-thiophene-2-carboxamide; N-[(3R)-1-azabicyclo[2.2.2]oct-3-yl]-1-5-(thiazol-5-yloxy)-thiophene-2-carboxamide; N-[(3R)-1-azabicyclo[2.2.2]oct-3-yl]-5-(2-methylthiazol-5-yloxy)-thiophene-2-carboxamide; N-[(3R)-1-azabicyclo[2.2.2]oct-3-yl]-5-(2-methoxythiazol-5-yloxy)-thiophene-2-carboxamide; N-[(3R)-1-azabicyclo[2.2.2]oct-3-yl]-5-(2-chlorothiazol-5-yloxy)-thiophene-2-carboxamide; N-[(3R)-1-azabicyclo[2.2.2]oct-3-yl]-5-(4-methylthiazol-2-yloxy)-thiophene-2-carboxamide; N-[(3R)-1-azabicyclo[2.2.2]oct-3-yl]-5-(4-methoxythiazol-2-yloxy)-thiophene-2-carboxamide; N-[(3R)-1-azabicyclo[2.2.2]oct-3-yl]-5-(4-chlorothiazol-2-yloxy)-thiophene-2-carboxamide; N-[(3R)-1-azabicyclo[2.2.2]oct-3-yl]-5-(4-methyloxazol-2-yloxy)-thiophene-2-carboxamide; N-[(3R)-1-azabicyclo[2.2.2]oct-3-yl]-5-(4-methoxyoxazol-2-yloxy)-thiophene-2-carboxamide; N-[(3R)-1-azabicyclo[2.2.2]oct-3-yl]-5-(4-chlorooxazol-2-yloxy)-thiophene-2-carboxamide; N-[(3R)-1-azabicyclo[2.2.2]oct-3-yl]-5-([1,3,4]thiadiazol-2-yloxy)-thiophene-2-carboxamide; N-[(3R)-1-azabicyclo[2.2.2]oct-3-yl]-5-(5-methyl[1,3,4]thiadiazol-2-yloxy)-thiophene-2-carboxamide; N-[(3R)-1-azabicyclo[2.2.2]oct-3-yl]-5-(5-methoxy[1,3,4]thiadiazol-2-yloxy)-thiophene-2-carboxamide; N-[(3R)-1-azabicyclo[2.2.2]oct-3-yl]-5-(5-chloro[1,3,4]thiadiazol-2-yloxy)-thiophene-2-carboxamide; N-[(3R)-1-azabicyclo[2.2.2]oct-3-yl]-5-([1,3,4]oxadiazol-2-yloxy)-thiophene-2-carboxamide; N-[(3R)-1-azabicyclo[2.2.2]oct-3-yl]-5-(5-methyl[1,3,4]oxadiazol-2-yloxy)-thiophene-2-carboxamide; N-[(3R)-1-azabicyclo[2.2.2]oct-3-yl]-5-(5-methoxy[1,3,4]oxadiazol-2-yloxy)-thiophene-2-carboxamide; N-[(3R)-1-azabicyclo[2.2.2]oct-3-yl]-5-(5-chloro[1,3,4]oxadiazol-2-yloxy)-thiophene-2-carboxamide; N-[(3R)-1-azabicyclo[2.2.2]oct-3-yl]-5-(thiophen-4-ylsulfanyl)-thiophene-2-carboxamide; N-[(3R)-1-azabicyclo[2.2.2]oct-3-yl]-5-(5-methylthiophen-2-ylsulfanyl)-thiophene-2-carboxamide; N-[(3R)-1-azabicyclo[2.2.2]oct-3-yl]-5-(5-methoxythiophen-2-ylsulfanyl)-thiophene-2-carboxamide; N-[(3R)-1-azabicyclo[2.2.2]oct-3-yl]-5-(5-chlorothiophen-2-ylsulfanyl)-thiophene-2-carboxamide; N-[(3R)-1-azabicyclo[2.2.2]oct-3-yl]-5-(furan-4-ylsulfanyl)-thiophene-2-carboxamide; N-[(3R)-1-azabicyclo[2.2.2]oct-3-yl]-5-(5-methylfuran-2-ylsulfanyl)-thiophene-2-carboxamide; N-[(3R)-1-azabicyclo[2.2.2]oct-3-yl]-5-(5-methoxyfuran-2-ylsulfanyl)-thiophene-2-carboxamide; N-[(3R)-1-azabicyclo[2.2.2]oct-3-yl]-5-(5-chlorofuran-2-ylsulfanyl)-thiophene-2-carboxamide; N-[(3R)-1-azabicyclo[2.2.2]oct-3-yl]-5-(oxazol-2-ylsulfanyl)-thiophene-2-carboxamide; N-[(3R)-1-azabicyclo[2.2.2]oct-3-yl]-5-(5-methyloxazol-2-ylsulfanyl)-thiophene-2-carboxamide; N-[(3R)-1-azabicyclo[2.2.2]oct-3-yl]-5-(5-methoxyoxazol-2-ylsulfanyl)-thiophene-2-carboxamide; N-[(3R)-1-azabicyclo[2.2.2]oct-3-yl]-5-(5-chlorooxazol-2-ylsulfanyl)-thiophene-2-carboxamide; N-[(3R)-1-azabicyclo[2.2.2]oct-3-yl]-5-(oxazol-5-ylsulfanyl)-thiophene-2-carboxamide; N-[(3R)-1-azabicyclo[2.2.2]oct-3-yl]-5-(2-methyloxazol-5-ylsulfanyl)-thiophene-2-carboxamide; N-[(3R)-1-azabicyclo[2.2.2]oct-3-yl]-5-(2-methoxyoxazol-5-ylsulfanyl)-thiophene-2-carboxamide; N-[(3R)-1-azabicyclo[2.2.2]oct-3-yl]-5-(2-chlorooxazol-5-ylsulfanyl)-thiophene-2-carboxamide; N-[(3R)-1-azabicyclo[2.2.2]oct-3-yl]-5-(thiazol-2-ylsulfanyl)-thiophene-2-carboxamide; N-[(3R)-1-azabicyclo[2.2.2]oct-3-yl]-5-(5-methylthiazol-2-ylsulfanyl)-thiophene-2-carboxamide; N-[(3R)-1-azabicyclo[2.2.2]oct-3-yl]-5-(5-methoxythiazol-2-ylsulfanyl)-thiophene-2-carboxamide; N-[(3R)-1-azabicyclo[2.2.2]oct-3-yl]-5-(5-chlorothiazol-2-ylsulfanyl)-thiophene-2-carboxamide; N-[(3R)-1-azabicyclo[2.2.2]oct-3-yl]-5-(thiazol-5-ylsulfanyl)-thiophene-2-carboxamide; N-[(3R)-1-azabicyclo[2.2.2]oct-3-yl]-5-(2-methylthiazol-5-ylsulfanyl)-thiophene-2-carboxamide; N-[(3R)-1-azabicyclo[2.2.2]oct-3-yl]-5-(2-methoxythiazol-5-ylsulfanyl)-thiophene-2-carboxamide; N-[(3R)-1-azabicyclo[2.2.2]oct-3-yl]-5-(2-chlorothiazol-5-ylsulfanyl)-thiophene-2-carboxamide; N-[(3R)-1-azabicyclo[2.2.2]oct-3-yl]-5-(4-methylthiazol-2- ylsulfanyl)-thiophene-2-carboxamide; N-[(3R)-1-azabicyclo[2.2.2]oct-3-yl]-5-(4-methoxythiazol-2-ylsulfanyl)-thiophene-2-carboxamide; N-[(3R)-1-azabicyclo[2.2.2]oct-3-yl]-5-(4-chlorothiazol-2-ylsulfanyl)-thiophene-2-carboxamide; N-[(3R)-1-azabicyclo[2.2.2]oct-3-yl]-5-(4-methyloxazol-2-ylsulfanyl)-thiophene-2-carboxamide; N-[(3R)-1-azabicyclo[2.2.2]oct-3-yl]-5-(4-methoxyoxazol-2-ylsulfanyl)-thiophene-2-carboxamide; N-[(3R)-1-azabicyclo[2.2.2]oct-3-yl]-5-(4-chlorooxazol-2-ylsulfanyl)-thiophene-2-carboxamide; N-[(3R)-1-azabicyclo[2.2.2]oct-3-yl]-5-([1,3,4]thiadiazol-2-ylsulfanyl)-thiophene-2-carboxamide; N-[(3R)-1-azabicyclo[2.2.2]oct-3-yl]-5-(5-methyl[1,3,4]thiadiazol-2-ylsulfanyl)-thiophene-2-carboxamide; N-[(3R)-1-azabicyclo[2.2.2]oct-3-yl]-5-(5-methoxy[1,3,4]thiadiazol-2-ylsulfanyl)-thiophene-2-carboxamide; N-[(3R)-1-azabicyclo[2.2.2]oct-3-yl]-5-(5-chloro[1,3,4]thiadiazol-2-ylsulfanyl)-thiophene-2-carboxamide; N-[(3R)-1-azabicyclo[2.2.2]oct-3-yl]-5-([1,3,4]oxadiazol-2-ylsulfanyl)-thiophene-2-carboxamide; N-[(3R)-1-azabicyclo[2.2.2]oct-3-yl]-5-(5-methyl[1,3,4]oxadiazol-2-ylsulfanyl)-thiophene-2-carboxamide; N-[(3R)-1-azabicyclo[2.2.2]oct-3-yl]-5-(5-methoxy[1,3,4]oxadiazol-2-ylsulfanyl)-thiophene-2-carboxamide; N-[(3R)-1-azabicyclo[2.2.2]oct-3-yl]-5-(5-chloro[1,3,4]oxadiazol-2-ylsulfanyl)-thiophene-2-carboxamide; N-[(3R)-1-azabicyclo[2.2.2]oct-3-yl]-5-(pyrrole-2-yl)-thiophene-2-carboxamide; N-[(3R)-1-azabicyclo[2.2.2]oct-3-yl]-5-(isothiazol-3-yl)-thiophene-2-carboxamide; N-[(3R)-1-azabicyclo[2.2.2]oct-3-yl]-5-(isoxazol-3-yl)-thiophene-2-carboxamide; N-[(3R)-1-azabicyclo[2.2.2]oct-3-yl]-5-(3H-imidazol4-yl)-thiophene-2-carboxamide; N-[(3R)-1-azabicyclo[2.2.2]oct-3-yl]-4-(4-hydroxyphenylsulfanyl)-thiophene-2-carboxamide; N-[(3R)-1-azabicyclo[2.2.2]oct-3-yl]-4-(3-acetamidophenylsulfanyl)-thiophene-2-carboxamide; N-[(3R)-1-azabicyclo[2.2.2]oct-3-yl]-4-(2-methanesulfonylaminophenyl)-thiophene-2-carboxamide; N-[(3R)-1-azabicyclo[2.2.2]oct-3-yl]-4-(pyridin-2-yloxy)-thiophene-2-carboxamide; N-[(3R)-1-azabicyclo[2.2.2]oct-3-yl]-4-(2-methylpyridin-4-yloxy)-thiophene-2-carboxamide; N-[(3R)-1-azabicyclo[2.2.2]oct-3-yl]-4-(4-trifluoromethylphenyl)-thiophene-2-carboxamide; N-[(3R)-1-azabicyclo[2.2.2]oct-3-yl]-4-(2-acetylphenyl)-thiophene-2-carboxamide; N-[(3R)-1-azabicyclo[2.2.2]oct-3-yl]-4-chloro-5-phenyl-thiophene-2-carboxamide; N-[(3R)-1-azabicyclo[2.2.2]oct-3-yl]-4-methyl-5-phenyl-thiophene-2-carboxamide; N-[(3R)-1-azabicyclo[2.2.2]oct-3-yl]-4-cyano-5-phenyl-thiophene-2-carboxamide; N-[(3R)-1-azabicyclo[2.2.2]oct-3-yl]-4-methoxy-5-phenyl-thiophene-2-carboxamide; N-[(3R)-1-azabicyclo[2.2.2]oct-3-yl]-5-chloro-4-phenyl-thiophene-2-carboxamide; N-[(3R)-1-azabicyclo[2.2.2]oct-3-yl]-5-methyl-4-phenyl-thiophene-2-carboxamide; N-[(3R)-1-azabicyclo[2.2.2]oct-3-yl]-5-cyano-4-phenyl-thiophene-2-carboxamide; N-[(3R)-1-azabicyclo[2.2.2]oct-3-yl]-5-methoxy-4-phenyl-thiophene-2-carboxamide; N-[(3R)-1-azabicyclo[2.2.2]oct-3-yl]-4-chloro-5-bromo-thiophene-2-carboxamide; N-[(3R)-1-azabicyclo[2.2.2]oct-3-yl]-4-chloro-5-methylsulfanyl-thiophene-2-carboxamide; N-[(3R)-1-azabicyclo[2.2.2]oct-3-yl]-4-chloro-5-methyl-thiophene-2-carboxamide; N-[(3R)-1-azabicyclo[2.2.2]oct-3-yl]-4-chloro-5-cyano-thiophene-2-carboxamide; N-[(3R)-1-azabicyclo[2.2.2]oct-3-yl]-5-chloro-4-bromo-thiophene-2-carboxamide; N-[(3R)-1-azabicyclo[2.2.2]oct-3-yl]-5-chloro-4-methylsulfanyl-thiophene-2-carboxamide; N-[(3R)-1-azabicyclo[2.2.2]oct-3-yl]-5-chloro-4-methyl-thiophene-2-carboxamide; N-[(3R)-1-azabicyclo[2.2.2]oct-3-yl]-5-chloro-4-cyano-thiophene-2-carboxamide;

N-[(2S,3R)-2-methyl-1-azabicyclo[2.2.2]oct-3-yl]-5-(2-acetamidophenyl)-thiophene-2-carboxamide; N-[(2S,3R)-2-methyl-1-azabicyclo[2.2.2]oct-3-yl]-5-(3-acetamidophenyl)-thiophene-2-carboxamide; N-[(2S,3R)-2-methyl-1-azabicyclo[2.2.2]oct-3-yl]-5-(4-acetamidophenyl)-thiophene-2-carboxamide; N-[(2S,3R)-2-methyl-1-azabicyclo[2.2.2]oct-3-yl]-5-(2-trifluoroacetamidophenyl)-thiophene-2-carboxamide; N-[(2S,3R)-2-methyl-1-azabicyclo[2.2.2]oct-3-yl]-5-(3-trifluoroacetamidophenyl)-thiophene-2-carboxamide; N-[(2S,3R)-2-methyl-1-azabicyclo[2.2.2]oct-3-yl]-5-(4-trifluoroacetamidophenyl)-thiophene-2-carboxamide; N-[(2S,3R)-2-methyl-1-azabicyclo[2.2.2]oct-3-yl]-5-(2-methanesulfonylaminophenyl)-thiophene-2-carboxamide; N-[(2S,3R)-2-methyl-1-azabicyclo[2.2.2]oct-3-yl]-5-(3-methanesulfonylaminophenyl)-thiophene-2-carboxamide; N-[(2S,3R)-2-methyl-1-azabicyclo[2.2.2]oct-3-yl]-5-(4-methanesulfonylaminophenyl)-thiophene-2-carboxamide; N-[(2S,3R)-2-methyl-1-azabicyclo[2.2.2]oct-3-yl]-5-(2-trifluoromethanesulfonylaminophenyl)-thiophene-2-carboxamide; N-[(2S,3R)-2-methyl-1-azabicyclo[2.2.2]oct-3-yl]-5-(3-trifluoromethanesulfonylaminophenyl)-thiophene-2-carboxamide; N-[(2S,3R)-2-methyl-1-azabicyclo[2.2.2]oct-3-yl]-5-(4-trifluoromethanesulfonylaminophenyl)-thiophene-2-carboxamide; N-[(2S,3R)-2-methyl-1-azabicyclo[2.2.2]oct-3-yl]-5-(2-difluoroacetamidophenyl)-thiophene-2-carboxamide; N-[(2S,3R)-2-methyl-1-azabicyclo[2.2.2]oct-3-yl]-5-(3-difluoroacetamidophenyl)-thiophene-2-carboxamide; N-[(2S,3R)-2-methyl-1-azabicyclo[2.2.2]oct-3-yl]-5-(4-difluoroacetamidophenyl)-thiophene-2-carboxamide; N-[(2S,3R)-2-methyl-1-azabicyclo[2.2.2]oct-3-yl]-5-(2-carbamoylphenyl)-thiophene-2-carboxamide; N-[(2S,3R)-2-methyl-1-azabicyclo[2.2.2]oct-3-yl]-5-(3-carbamoylphenyl)-thiophene-2-carboxamide; N-[(2S,3R)-2-methyl-1-azabicyclo[2.2.2]oct-3-yl]-5-(4-carbamoylphenyl)-thiophene-2-carboxamide; N-[(2S,3R)-2-methyl-1-azabicyclo[2.2.2]oct-3-yl]-5-(2-sulfamoylphenyl)-thiophene-2-carboxamide; N-[(2S,3R)-2-methyl-1-azabicyclo[2.2.2]oct-3-yl]-5-(3-sulfamoylphenyl)-thiophene-2-carboxamide; N-[(2S,3R)-2-methyl-1-azabicyclo[2.2.2]oct-3-yl]-5-(4-sulfamoylphenyl)-thiophene-2-carboxamide; N-[(2S,3R)-2-methyl-1-azabicyclo[2.2.2]oct-3-yl]-5-(2-acetamidophenylsulfanyl)-thiophene-2-carboxamide; N-[(2S,3R)-2-methyl-1-azabicyclo[2.2.2]oct-3-yl]-5-(3-acetamidophenylsulfanyl)-thiophene-2-carboxamide; N-[(2S,3R)-2-methyl-1-azabicyclo[2.2.2]oct-3-yl]-5-(4-acetamidophenylsulfanyl)-thiophene-2-carboxamide; N-[(2S,3R)-2-methyl-1-azabicyclo[2.2.2]oct-3-yl]-5-(2-trifluoroacetamidophenylsulfanyl)-thiophene-2-carboxamide; N-[(2S,3R)-2-methyl-1-azabicyclo[2.2.2]oct-3-yl]-5-(3-trifluoroacetamidophenylsulfanyl)-thiophene-2-carboxamide; N-[(2S,3R)-2-methyl-1-azabicyclo[2.2.2]oct-3-yl]-5-(4-trifluoroacetamidophenylsulfanyl)-thiophene-2-carboxamide; N-[(2S,3R)-2-methyl-1-azabicyclo[2.2.2]oct-3-yl]-5-(2-methanesulfonylaminophenylsulfanyl)-thiophene-2-carboxamide; N-[(2S,3R)-2-methyl-1-azabicyclo[2.2.2]oct-3-yl]-5-(3-methanesulfonylaminophenylsulfanyl)-thiophene-2-carboxamide; N-[(2S,3R)-2-methyl-1-azabicyclo[2.2.2]oct-3-yl]-5-(4-methanesulfonylaminophenylsulfanyl)-thiophene-2-carboxamide; N-[(2S,3R)-2-methyl-1-azabicyclo[2.2.2]oct-3-yl]-5-(2-trifluoromethanesulfonylaminophenylsulfanyl)-thiophene-2-carboxamide; N-[(2S,3R)-2-methyl-1-azabicyclo[2.2.2]oct-3-yl]-5-(3- trifluoromethanesulfonylaminophenylsulfanyl)-thiophene-2-carboxamide; N-[(2S,3R)-2-methyl-1-azabicyclo[2.2.2]oct-3-yl]-5-(4-trifluoromethanesulfonylaminophenylsulfanyl)-thiophene-2-carboxamide; N-[(2S,3R)-2-methyl-1-azabicyclo[2.2.2]oct-3-yl]-5-(2-difluoroacetamidophenylsulfanyl)-thiophene-2-carboxamide; N-[(2S,3R)-2-methyl-1-azabicyclo[2.2.2]oct-3-yl]-5-(3-difluoroacetamidophenylsulfanyl)-thiophene-2-carboxamide; N-[(2S,3R)-2-methyl-1-azabicyclo[2.2.2]oct-3-yl]-5-(4-difluoroacetamidophenylsulfanyl)-thiophene-2-carboxamide; N-[(2S,3R)-2-methyl-1-azabicyclo[2.2.2]oct-3-yl]-5-(2-carbamoylphenylsulfanyl)-thiophene-2-carboxamide; N-[(2S,3R)-2-methyl-1-azabicyclo[2.2.2]oct-3-yl]-5-(3-carbamoylphenylsulfanyl)-thiophene-2-carboxamide; N-[(2S,3R)-2-methyl-1-azabicyclo[2.2.2]oct-3-yl]-5-(4-carbamoylphenylsulfanyl)-thiophene-2-carboxamide; N-[(2S,3R)-2-methyl-1-azabicyclo[2.2.2]oct-3-yl]-5-(2-sulfamoylphenylsulfanyl)-thiophene-2-carboxamide; N-[(2S,3R)-2-methyl-1-azabicyclo[2.2.2]oct-3-yl]-5-(3-sulfamoylphenylsulfanyl)-thiophene-2-carboxamide; N-[(2S,3R)-2-methyl-1-azabicyclo[2.2.2]oct-3-yl]-5-(4-sulfamoylphenylsulfanyl)-thiophene-2-carboxamide; N-[(2S,3R)-2-methyl-1-azabicyclo[2.2.2]oct-3-yl]-5-(2-hydroxyphenylsulfanyl)-thiophene-2-carboxamide; N-[(2S,3R)-2-methyl-1-azabicyclo[2.2.2]oct-3-yl]-5-(3-hydroxyphenylsulfanyl)-thiophene-2-carboxamide; N-[(2S,3R)-2-methyl-1-azabicyclo[2.2.2]oct-3-yl]-5-(4-hydroxyphenylsulfanyl)-thiophene-2-carboxamide; N-[(2S,3R)-2-methyl-1-azabicyclo[2.2.2]oct-3-yl]-5-(2-aminophenylsulfanyl)-thiophene-2-carboxamide; N-[(2S,3R)-2-methyl-1-azabicyclo[2.2.2]oct-3-yl]-5-(3-aminophenylsulfanyl)-thiophene-2-carboxamide; N-[(2S,3R)-2-methyl-1-azabicyclo[2.2.2]oct-3-yl]-5-(4-aminophenylsulfanyl)-thiophene-2-carboxamide; N-[(2S,3R)-2-methyl-1-azabicyclo[2.2.2]oct-3-yl]-5-(2-acetamidophenoxy)-thiophene-2-carboxamide; N-[(2S,3R)-2-methyl-1-azabicyclo[2.2.2]oct-3-yl]-5-(3-acetamidophenoxy)-thiophene-2-carboxamide; N-[(2S,3R)-2-methyl-1-azabicyclo[2.2.2]oct-3-yl]-5-(4-acetamidophenoxy)-thiophene-2-carboxamide; N-[(2S,3R)-2-methyl-1-azabicyclo[2.2.2]oct-3-yl]-5-(2-trifluoroacetamidophenoxy)-thiophene-2-carboxamide; N-[(2S,3R)-2-methyl-1-azabicyclo[2.2.2]oct-3-yl]-5-(3-trifluoroacetamidophenoxy)-thiophene-2-carboxamide; N-[(2S,3R)-2-methyl-1-azabicyclo[2.2.2]oct-3-yl]-5-(4-trifluoroacetamidophenoxy)-thiophene-2-carboxamide; N-[(2S,3R)-2-methyl-1-azabicyclo[2.2.2]oct-3-yl]-5-(2-methanesulfonylaminophenoxy)-thiophene-2-carboxamide; N-[(2S,3R)-2-methyl-1-azabicyclo[2.2.2]oct-3-yl]-5-(3-methanesulfonylaminophenoxy)-thiophene-2-carboxamide; N-[(2S,3R)-2-methyl-1-azabicyclo[2.2.2]oct-3-yl]-5-(4-methanesulfonylaminophenoxy)-thiophene-2-carboxamide; N-[(2S,3R)-2-methyl-1-azabicyclo[2.2.2]oct-3-yl]-5-(2-trifluoromethanesulfonylaminophenoxy)-thiophene-2-carboxamide; N-[(2S,3R)-2-methyl-1-azabicyclo[2.2.2]oct-3-yl]-5-(3-trifluoromethanesulfonylaminophenoxy)-thiophene-2-carboxamide; N-[(2S,3R)-2-methyl-1-azabicyclo[2.2.2]oct-3-yl]-5-(4-trifluoromethanesulfonylaminophenoxy)-thiophene-2-carboxamide; N-[(2S,3R)-2-methyl-1-azabicyclo[2.2.2]oct-3-yl]-5-(2-difluoroacetamidophenoxy)-thiophene-2-carboxamide; N-[(2S,3R)-2-methyl-1-azabicyclo[2.2.2]oct-3-yl]-5-(3-difluoroacetamidophenoxy)-thiophene-2-carboxamide; N-[(2S,3R)-2-methyl-1-azabicyclo[2.2.2]oct-3-yl]-5-(4-difluoroacetamidophenoxy)-thiophene-2-carboxamide; N-[(2S,3R)-2-methyl-1-azabicyclo[2.2.2]oct-3-yl]-5-(2-carbamoylphenoxy)-thiophene-2-carboxamide; N-[(2S,3R)-2-methyl-1-azabicyclo[2.2.2]oct-3-yl]-5-(3-carbamoylphenoxy)-thiophene-2-carboxamide; N-[(2S,3R)-2-methyl-1-azabicyclo[2.2.2]oct-3-yl]-5-(4-carbamoylphenoxy)-thiophene-2-carboxamide; N-[(2S,3R)-2-methyl-1-azabicyclo[2.2.2]oct-3-yl]-5-(2-sulfamoylphenoxy)-thiophene-2-carboxamide; N-[(2S,3R)-2-methyl-1-azabicyclo[2.2.2]oct-3-yl]-5-(3-sulfanoylphenoxy)-thiophene-2-carboxamide; N-[(2S,3R)-2-methyl-1-azabicyclo[2.2.2]oct-3-yl]-5-(4-sulfamoylphenoxy)-thiophene-2-carboxamide; N-[(2S,3R)-2-methyl-1-azabicyclo[2.2.2]oct-3-yl]-5-(2-hydroxyphenoxy)-thiophene-2-carboxamide; N-[(2S,3R)-2-methyl-1-azabicyclo[2.2.2]oct-3-yl]-5-(3-hydroxyphenoxy)-thiophene-2-carboxamide; N-[(2S,3R)-2-methyl-1-azabicyclo[2.2.2]oct-3-yl]-5-(4-hydroxyphenoxy)-thiophene-2-carboxamide; N-[(2S,3R)-2-methyl-1-azabicyclo[2.2.2]oct-3-yl]-5-(2-aminophenoxy)-thiophene-2-carboxamide; N-[(2S,3R)-2-methyl-1-azabicyclo[2.2.2]oct-3-yl]-5-(3-aminophenoxy)-thiophene-2-carboxamide; N-[(2S,3R)-2-methyl-1-azabicyclo[2.2.2]oct-3-yl]-5-(4-aminophenoxy)-thiophene-2-carboxamide; N-[(2S,3R)-2-methyl-1-azabicyclo[2.2.2]oct-3-yl]-5-(2-chlorophenoxy)-thiophene-2-carboxamide; N-[(2S,3R)-2-methyl-1-azabicyclo[2.2.2]oct-3-yl]-5- N-[(2S,3R)-2-methyl-1-azabicyclo[2.2.2]oct-3-yl]-5-(2-cyanophenyl)-thiophene-2-carboxamide; N-[(2S,3R)-2-methyl-1-azabicyclo[2.2.2]oct-3-yl]-5-(3-cyanophenyl)-thiophene-2-carboxamide; N-[(2S,3R)-2-methyl-1-azabicyclo[2.2.2]oct-3-yl]-5-(4-cyanophenyl)-thiophene-2-carboxamide; N-[(2S,3R)-2-methyl-1-azabicyclo[2.2.2]oct-3-yl]-5-(2-morpholin-4-yl-phenyl)-thiophene-2-carboxamide; N-[(2S,3R)-2-methyl-1-azabicyclo[2.2.2]oct-3-yl]-5-(3-morpholin-4-yl-phenyl)-thiophene-2-carboxamide; N-[(2S,3R)-2-methyl-1-azabicyclo[2.2.2]oct-3-yl]-5-(4-morpholin-4-yl-phenyl)-thiophene-2-carboxamide; N-[(2S,3R)-2-methyl-1-azabicyclo[2.2.2]oct-3-yl]-5-(2-methoxyphenoxy)-thiophene-2-carboxamide; N-[(2S,3R)-2-methyl-1-azabicyclo[2.2.2]oct-3-yl]-5-(3-methoxyphenoxy)-thiophene-2-carboxamide; N-[(2S,3R)-2-methyl-1-azabicyclo[2.2.2]oct-3-yl]-5-(4-methoxyphenoxy)-thiophene-2-carboxamide; N-[(2S,3R)-2-methyl-1-azabicyclo[2.2.2]oct-3-yl]-5-(2-methylphenoxy)-thiophene-2-carboxamide; N-[(2S,3R)-2-methyl-1-azabicyclo[2.2.2]oct-3-yl]-) 5-(3-methylphenoxy-thiophene-2-carboxamide; N-[(2S,3R)-2-methyl-1-azabicyclo[2.2.2]oct-3-yl]-5-(4-methylphenoxy)-thiophene-2-carboxamide; N-[(2S,3R)-2-methyl-1-azabicyclo[2.2.2]oct-3-yl]-5-(2-trifluoromethylphenoxy)-thiophene-2-carboxamide; N-[(2S,3R)-2-methyl-1-azabicyclo[2.2.2]oct-3-yl]-5-(3-trifluoromethylphenoxy)-thiophene-2-carboxamide; N-[(2S,3R)-2-methyl-1-azabicyclo[2.2.2]oct-3-yl]-5-(4-trifluoromethylphenoxy)-thiophene-2-carboxamide; N-[(2S,3R)-2-methyl-1-azabicyclo[2.2.2]oct-3-yl]-5-(2-acetylphenoxy)-thiophene-2-carboxamide; N-[(2S,3R)-2-methyl-1-azabicyclo[2.2.2]oct-3-yl]-5-(3-acetylphenoxy)-thiophene-2-carboxamide; N-[(2S,3R)-2-methyl-1-azabicyclo[2.2.2]oct-3-yl]-5-(4-acetylphenoxy)-thiophene-2-carboxamide; N-[(2S,3R)-2-methyl-1-azabicyclo[2.2.2]oct-3-yl]-5-(2-cyanophenoxy)-thiophene-2-carboxamide; N-[(2S,3R)-2-methyl-1-azabicyclo[2.2.2]oct-3-yl]-5-(3-cyanophenoxy)-thiophene-2-carboxamide; N-[(2S,3R)-2-methyl-1-azabicyclo[2.2.2]oct-3-yl]-5-(4-cyanophenoxy)-thiophene-2-carboxamide; N-[(2S,3R)-2-methyl-1-azabicyclo[2.2.2]oct-3-yl]-5-(2-morpholin-4-yl-phenoxy)-thiophene-2-carboxamide; N-[(2S,3R)-2-methyl-1-azabicyclo[2.2.2]oct-3-yl]-5-(3-morpholin-4-yl-phenoxy)- thiophene-2-carboxamide; N-[(2S,3R)-2-methyl-1-azabicyclo[2.2.2]oct-3-yl]-5-(4-morpholin-4-yl-phenoxy)-thiophene-2-carboxamide; N-[(2S,3R)-2-methyl-1-azabicyclo[2.2.2]oct-3-yl]-5-(2-methoxyphenylsulfanyl)-thiophene-2-carboxamide; N-[(2S,3R)-2-methyl-1-azabicyclo[2.2.2]oct-3-yl]-5-(3-methoxyphenylsulfanyl)-thiophene-2-carboxamide; N-[(2S,3R)-2-methyl-1-azabicyclo[2.2.2]oct-3-yl]-5-(4-methoxyphenylsulfanyl)-thiophene-2-carboxamide; N-[(2S,3R)-2-methyl-1-azabicyclo[2.2.2]oct-3-yl]-5-(2-methylphenylsulfanyl)-thiophene-2-carboxamide; N-[(2S,3R)-2-methyl-1-azabicyclo[2.2.2]oct-3-yl]-5-(3-methylphenylsulfanyl)-thiophene-2-carboxamide; N-[(2S,3R)-2-methyl-1-azabicyclo[2.2.2]oct-3-yl]-5-(4-methylphenylsulfanyl)-thiophene-2-carboxamide; N-[(2S,3R)-2-methyl-1-azabicyclo[2.2.2]oct-3-yl]-5-(2-trifluoromethylphenylsulfanyl)-thiophene-2-carboxamide; N-[(2S,3R)-2-methyl-1-azabicyclo[2.2.2]oct-3-yl]-5-(3-trifluoromethylphenylsulfanyl)-thiophene-2-carboxamide; N-[(2S,3R)-2-methyl-1-azabicyclo[2.2.2]oct-3-yl]-5-(4-trifluoromethylphenylsulfanyl)-thiophene-2-carboxamide; N-[(2S,3R)-2-methyl-1-azabicyclo[2.2.2]oct-3-yl]-5-(2-acetylphenylsulfanyl)-thiophene-2-carboxamide; N-[(2S,3R)-2-methyl-1-azabicyclo[2.2.2]oct-3-yl]-5-(3-acetylphenylsulfanyl)-thiophene-2-carboxamide; N-[(2S,3R)-2-methyl-1-azabicyclo[2.2.2]oct-3-yl]-5-(4-acetylphenylsulfanyl)-thiophene-2-carboxamide; N-[(2S,3R)-2-methyl-1-azabicyclo[2.2.2]oct-3-yl]-5-(2-cyanophenylsulfanyl)-thiophene-2-carboxamide; N-[(2S,3R)-2-methyl-1-azabicyclo[2.2.2]oct-3-yl]-5-(3-cyanophenylsulfanyl)-thiophene-2-carboxamide; N-[(2S,3R)-2-methyl-1-azabicyclo[2.2.2]oct-3-yl]-5-(4-cyanophenylsulfanyl)-thiophene-2-carboxamide; N-[(2S,3R)-2-methyl-1-azabicyclo[2.2.2]oct-3-yl]-5-(2-morpholin-4-yl-phenylsulfanyl)-thiophene-2-carboxamide; N-[(2S,3R)-2-methyl-1-azabicyclo[2.2.2]oct-3-yl]-5-(3-morpholin-4-yl-phenylsulfanyl)-thiophene-2-carboxamide; N-[(2S,3R)-2-methyl-1-azabicyclo[2.2.2]oct-3-yl]-5-(4-morpholin-4-yl-phenylsulfanyl)-thiophene-2-carboxamide; N-[(2S,3R)-2-methyl-1-azabicyclo[2.2.2]oct-3-yl]-5-(pyridin-4-yl)-thiophene-2-carboxamide; N-[(2S,3R)-2-methyl-1-azabicyclo[2.2.2]oct-3-yl]-5-(2-methylpyridin-4-yl)-thiophene-2-carboxamide; N-[(2S,3R)-2-methyl-1-azabicyclo[2.2.2]oct-3-yl]-5-(6-methylpyridin-3-yl)-thiophene-2-carboxamide; N-[(2S,3R)-2-methyl-1-azabicyclo[2.2.2]oct-3-yl]-5-(5-methylpyridin-2-yl)-thiophene-2-carboxamide; N-[(2S,3R)-2-methyl-1-azabicyclo[2.2.2]oct-3-yl]-5-(2-methoxypyridin-4-yl)-thiophene-2-carboxamide; N-[(2S,3R)-2-methyl-1-azabicyclo[2.2.2]oct-3-yl]-5-(6-methoxypyridin-3-yl)-thiophene-2-carboxamide; N-[(2S,3R)-2-methyl-1-azabicyclo[2.2.2]oct-3-yl]-5-(5-methoxypyridin-2-yl)-thiophene-2-carboxamide; N-[(2S,3R)-2-methyl-1-azabicyclo[2.2.2]oct-3-yl]-5-(2-chloropyridin-4-yl)-thiophene-2-carboxamide; N-[(2S,3R)-2-methyl-1-azabicyclo[2.2.2]oct-3-yl]-5-6-chloropyridin-3-yl)-thiophene-2-carboxamide; N-[(2S,3R)-2-methyl-1-azabicyclo[2.2.2]oct-3-yl]-5-(5-chloropyridin-2-yl)-thiophene-2-carboxamide; N-[(2S,3R)-2-methyl-1-azabicyclo[2.2.2]oct-3-yl]-5-(5-chloropyridin-3-yl)-thiophene-2-carboxamide; N-[(2S,3R)-2-methyl-1-azabicyclo[2.2.2]oct-3-yl]-5-(6-chloropyridin-2-yl)-thiophene-2-carboxamide; N-[(2S,3R)-2-methyl-1-azabicyclo[2.2.2]oct-3-yl]-5-(4-chloropyridin-2-yl)-thiophene-2-carboxamide; N-[(2S,3R)-2-methyl-1-azabicyclo[2.2.2]oct-3-yl]-5-(pyridin-4-yloxy)-thiophene-2-carboxamide; N-[(2S,3R)-2-methyl-1-azabicyclo[2.2.2]oct-3-yl]-5-(pyridin-3-yloxy)-thiophene-2-carboxamide; N-[(2S,3R)-2-methyl-1-azabicyclo[2.2.2]oct-3-yl]-5-(pyridin-2-yloxy)-thiophene-2-carboxamide; N-[(2S,3R)-2-methyl-1-azabicyclo[2.2.2]oct-3-yl]-5-(2-methylpyridin-4-yloxy)-thiophene-2-carboxamide; N-[(2S,3R)-2-methyl-1-azabicyclo[2.2.2]oct-3-yl]-5-(6-methylpyridin-3-yloxy)-thiophene-2-carboxamide; N-[(2S,3R)-2-methyl-1-azabicyclo[2.2.2]oct-3-yl]-5-(5-methylpyridin-2-yloxy)-thiophene-2-carboxamide; N-[(2S,3R)-2-methyl-1-azabicyclo[2.2.2]oct-3-yl]-5-(2-methoxypyr N-[(2S,3R)-2-methyl-1-azabicyclo[2.2.2]oct-3-yl]-5-(2-chloropyridin-4-yloxy)-thiophene-2-carboxamide; N-[(2S,3R)-2-methyl-1-azabicyclo[2.2.2]oct-3-yl]-5-(6-chloropyridin-3-yloxy)-thiophene-2-carboxamide; N-[(2S,3R)-2-methyl-1-azabicyclo[2.2.2]oct-3-yl]-5-(5-chloropyridin-2-yloxy)-thiophene-2-carboxamide; N-[(2S,3R)-2-methyl-1-azabicyclo[2.2.2]oct-3-yl]-5-(2-chloropyridin-4-yloxy)-thiophene-2-carboxamide; N-[(2S,3R)-2-methyl-1-azabicyclo[2.2.2]oct-3-yl]-5-(6-chloropyridin-3-yloxy)-thiophene-2-carboxamide; N-[(2S,3R)-2-methyl-1-azabicyclo[2.2.2]oct-3-yl]-5-(5-chloropyridin-2-yloxy)-thiophene-2-carboxamide; N-[(2S,3R)-2-methyl-1-azabicyclo[2.2.2]oct-3-yl]-5-(5-chloropyridin-3-yloxy)-thiophene-2-carboxamide; N-[(2S,3R)-2-methyl-1-azabicyclo[2.2.2]oct-3-yl]-5-(6-chloropyridin-2-yloxy)-thiophene-2-carboxamide; N-[(2S,3R)-2-methyl-1-azabicyclo[2.2.2]oct-3-yl]-5-(4-chloropyridin-2-yloxy)-thiophene-2-carboxamide; N-[(2S,3R)-2-methyl-1-azabicyclo[2.2.2]oct-3-yl]-5-(pyridin-4-ylsulfanyl)-thiophene-2-carboxamide; N-[(2S,3R)-2-methyl-1-azabicyclo[2.2.2]oct-3-yl]-5-(pyridin-3-ylsulfanyl)-thiophene-2-carboxamide; N-[(2S,3R)-2-methyl-1-azabicyclo[2.2.2]oct-3-yl]-5-(pyridin-2-ylsulfanyl)-thiophene-2-carboxamide; N-[(2S,3R)-2-methyl-1-azabicyclo[2.2.2]oct-3-yl]-5-(2-methylpyridin-4-ylsulfanyl)-thiophene-2-carboxamide; N-[(2S,3R)-2-methyl-1-azabicyclo[2.2.2]oct-3-yl]-5-(6-methylpyridin-3-ylsulfanyl)-thiophene-2-carboxamide; N-[(2S,3R)-2-methyl-1-azabicyclo[2.2.2]oct-3-yl]-5-(5-methylpyridin-2-ylsulfanyl)-thiophene-2-carboxamide; N-[(2S,3R)-2-methyl-1-azabicyclo[2.2.2]oct-3-yl]-5-(2-methoxypyridin-4-ylsulfanyl)-thiophene-2-carboxamide; N-[(2S,3R)-2-methyl-1-azabicyclo[2.2.2]oct-3-yl]-5-(6-methoxypyridin-3-ylsulfanyl)-thiophene-2-carboxamide; N-[(2S,3R)-2-methyl-1-azabicyclo[2.2.2]oct-3-yl]-5-(5-methoxypyridin-2-ylsulfanyl)-thiophene-2-carboxamide; N-[(2S,3R)-2-methyl-1-azabicyclo[2.2.2]oct-3-yl]-5-(2-chloropyridin-4-ylsulfanyl)-thiophene-2-carboxamide; N-[(2S,3R)-2-methyl-1-azabicyclo[2.2.2]oct-3-yl]-5-(6-chloropyridin-3-ylsulfanyl)-thiophene-2-carboxamide; N-[(2S,3R)-2methyl-1-azabicyclo[2.2.2]oct-3-yl]-5-(5-chloropyridin-2-ylsulfanyl)-thiophene-2-carboxamide; N-[(2S,3R)-2-methyl-1-azabicyclo[2.2.2]oct-3-yl]-5-(2-chloropyridin-4-ylsulfanyl)-thiophene-2-carboxamide; N-[(2S,3R)-2-methyl-1-azabicyclo[2.2.2]oct-3-yl]5-(6-chloropyridin-3-ylsulfanyl)-thiophene-2-carboxamide; N-[(2S,3R)-2-methyl-1-azabicyclo[2.2.2]oct-3-yl]-5-(5-chloropyridin-2-ylsulfanyl)-thiophene-2-carboxamide; N-[(2S,3R)-2-methyl-1-azabicyclo[2.2.2]oct-3-yl]-5-(5-chloropyridin-3-ylsulfanyl)-thiophene-2-carboxamide; N-[(2S,3R)-2-methyl-1-azabicyclo[2.2.2]oct-methyl-1-azabicyclo[2.2.2]oct-3-yl]-5(4-chloropyridin-2-ylsulfanyl)-thiophene-2-carboxamide; N-[(2S,3R)-2-methyl-1-azabicyclo[2.2.2]oct-3-yl]-5-(thiophen-4-yl)-thiophene-2-carboxamide; N-[(2S,3R)-2-methyl-1-azabicyclo[2.2.2]oct-3-yl]-5-(5-methyl-thiophen-2-yl)-thiophene-2-carboxamide; N-[(2S,3R)-2-methyl-1-[(2S,3R)-2-methyl-1-azabicyclo[2.2.2]oct-3-yl]-

5-(5-chlorothiophen-2-yl)-thiophene-2-carboxamide; N-[(2S,3R)-2-methyl-1-azabicyclo[2.2.2]oct-3-yl]-5-(furan-4-yl)-thiophene-2-carboxamide; N-[(2S,3R)-2-methyl-1-azabicyclo[2.2.2]oct-3-yl]-5-(5-methylfuran-2-yl)-thiophene-2-carboxamide; N-[(2S,3R)-2-methyl-1-carboxamide; N-[(2S,3R)-2-methyl-1-azabicyclo[2.2.2]oct-3-yl]-5-(oxazol-2-yl)-thiophene-2-carboxamide; N-[(2S,3R)-2-methyl-1-azabicyclo[2.2.2]oct-3-yl]-5-(5-methyloxazol-2-yl)-thiophene-2-carboxamide; N-[(2S,3R)-2-methyl-1-[(2S,3R)-2-methyl-1-azabicyclo[2.2.2]oct-3-yl]-5(5-cloroooxazol-2-yl)-thiophene-2-carboxamide; N-[(2S,3R)-2-methyl-1-azabicyclo[2.2.2]oct-3-yl]-5-(oxazol-5-yl)-thiophene-2-carboxamide; N-[(2S,3R)-2-methyl-1-azabicyclo[2.2.2]oct-3-yl]-5-(2-methyloxazol-5-yl)-thiophene-2-carboxamide; N-[(2S,3R)-2-methyl-1-[(2S,3R)-2-methyl-1-azabicyclo[2.2.2]oct-3-yl]-5(2-chloroooxazol-5-yl)-thiophene-2-carboxamide; N-[(2S,3R)-2-methyl-1-azabicyclo[2.2.2]oct-3-yl]-5-(thiazol-2-yl)-thiophene-2-carboxamide; N-[(2S,3R)-2-methyl-1-azabicyclo[2.2.2]oct-3-yl]-5-(5-methylthiazol-2-yl)-thiophene-2-carboxamide; N-[(2S,3R)-2-methyl-1-azabicyclo[2.2.2]oct-3-yl]5-(5-methoxythiazol-2-yl)-thiophene-2-carboxamide; N-[(2S,3R)-2-methyl-1-azabicyclo[2.2.2]oct-3-yl]-5-(5-chlorothiazol-2-yl)-thiophene-2-carboxamide; N-[(2S,3R)-2-methyl-1-azabicyclo[2.2.2]oct-3-yl]-5-(thiazol-5-yl)-thiophene-2-carboxamide; N-[(2S,3R)-2-methyl-1-azabicyclo[2.2.2]oct-3-yl]-5-(2-methylthiazol-5-yl)-thiophene-2-carboxamide; N-[(2S,3R)-2-methyl-1-azabicyclo[2.2.2]oct-3-yl]-5-(2-methoxythiazol-5-yl)-thiophene-2-carboxamide; N-[(2S,3R)-2-methyl-1-azabicyclo[2.2.2]oct-3-yl]-5-(2-chlorothiazol-5-yl)-thiophene-2-carboxamide; N-[(2S,3R)-2-methyl-1-azabicyclo[2.2.2]oct-3-yl]-5-(4-methylthiazol-2-yl)-thiophene-2-carboxamide; N-[(2S,3R)-2-methyl-1-azabicyclo[2.2.2]oct-3-yl]-5-(4-methoxythiazol-2-yl)-thiophene-2-carboxamide; N-[(2S,3R)-2-methyl-1-azabicyclo[2.2.2]oct-3-yl]-5-(4-chlorothiazol-2-yl)-thiophene-2-carboxamide; N-[(2S,3R)-2-methyl-1-azabicyclo[2.2.2]oct-3-yl]-5-(4-methylo N-[(2S,3R)-2-methyl-1-azabicyclo[2.2.2]oct-3-yl]-5-(5-chlorothiophen-2-yloxy)-thiophene-2-carboxamide; N-[(2S,3R)-2-methyl-1-azabicyclo[2.2.2]oct-3-yl]-5-(furan-4-yloxy)-thiophene-2-carboxamide; N-[(2S,3R)-2-methyl-1-azabicyclo[2.2.2]oct-3-yl]-5-(5-methylfuran-2-yloxy)-thiophene-2-carboxamide; N-[(2S,3R)-2-methyl-1-azabicyclo[2.2.2]oct-3-yl]-5-(5-methoxyfuran-2-yloxy)-thiophene-2-carboxamide; N-[(2S,3R)-2-methyl-1-azabicyclo[2.2.2]oct-3-yl]-5-(5-chlorofuran-2-yloxy)-thiophene-2-carboxamide; N-[(2S,3R)-2-methyl-1-azabicyclo[2.2.2]oct-3-yl]-5-(oxazol-2-yloxy)-thiophene-2-carboxamide; N-[(2S,3R)-2-methyl-1-azabicyclo[2.2.2]oct-3-yl]-5-(5-methyloxazol-2-yloxy)-thiophene-2-carboxamide; N-[(2S,3R)-2-methyl-1-azabicyclo[2.2.2]oct-3-yl]-5-(5-methoxyoxazol-2-yloxy)-thiophene-2-carboxamide; N-[(2S,3R)-2-methyl-1-azabicyclo[2.2.2]oct-3-yl]-5-(5-chlorooxazol-2-yloxy)-thiophene-2-carboxamide; N-[(2S,3R)-2-methyl-1-azabicyclo[2.2.2]oct-3-yl]-5-(oxazol-5-yloxy)-thiophene-2-carboxamide; N-[(2S,3R)-2-methyl-1-azabicyclo[2.2.2]oct-3-yl]-5-(2-methyloxazol-5-yloxy)-thiophene-2-carboxamide; N-[(2S,3R)-2-methyl-1-azabicyclo[2.2.2]oct-3-yl]-5-(2-methoxyoxazol-5-yloxy)-thiophene-2-carboxamide; N-[(2S,3R)-2-methyl-1-azabicyclo[2.2.2]oct-3-yl]-5-(2-chlorooxazol-5-yloxy)-thiophene-2-carboxamide; N-[(2S,3R)-2-methyl-1-azabicyclo[2.2.2]oct-3-yl]-5-(thiazol-2-yloxy)-thiophene-2-carboxamide; N-[(2S,3R)-2-methyl-1-azabicyclo[2.2.2]oct-3-yl]-5-(5-methylthiazol-2-yloxy)-thiophene-2-carboxamide; N-[(2S,3R)-2-methyl-1-azabicyclo[2.2.2]oct-3-yl]-5-(5-methoxythiazol-2-yloxy)-thiophene-2-carboxamide; N-[(2S,3R)-2-methyl-1-azabicyclo[2.2.2]oct-3-yl]-5-(5-chlorothiazol-2-yloxy)-thiophene-2-carboxamide; N-[(2S,3R)-2-methyl-1-azabicyclo[2.2.2]oct-3-yl]-5-(thiazol-5-yloxy)-thiophene-2-carboxamide; N-[(2S,3R)-2-methyl-1-azabicyclo[2.2.2]oct-3-yl]-5-(2-methylthiazol-5-yloxy)-thiophene-2-carboxamide; N-[(2S,3R)-2-methyl-1-azabicyclo[2.2.2]oct-3-yl]-5-(2-methoxythiazol-5-yloxy)-thiophene-2-carboxamide; N-[(2S,3R)-2-methyl-1-azabicyclo[2.2.2]oct-3-yl]-5-(2-chlorothiazol-5-yloxy)-thiophene-2-carboxamide; N-[(2S,3R)-2-methyl-1-azabicyclo[2.2.2]oct-3-yl]-5-(4-methylthiazol-2-yloxy)-thiophene-2-carboxamide; N-[(2S,3R)-2-methyl-1-azabicyclo[2.2.2]oct-3-yl]-5-(4-methoxythiazol-2-yloxy)-thiophene-2-carboxamide; N-[(2S,3R)-2-methyl-1-azabicyclo[2.2.2]oct-3-yl]-5-(4-chlorothiazol-2-yloxy)-thiophene-2-carboxamide; N-[(2S,3R)-2-methyl-1-azabicyclo[2.2.2]oct-3-yl]-5-(4-methyloxazol-2-yloxy)-thiophene-2-carboxamide; N-[(2S,3R)-2-methyl-1-azabicyclo[2.2.2]oct-3-yl]-5-(4-methoxyoxazol-2-yloxy)-thiophene-2-carboxamide; N-[(2S,3R)-2-methyl-1-azabicyclo[2.2.2]oct-3-yl]-5-(4-chlorooxazol-2-yloxy)-thiophene-2-carboxamide; N-[(2S,3R)-2-methyl-1-azabicyclo[2.2.2]oct-3-yl]-5-([1,3,4]thiadiazol-2-yloxy)-thiophene-2-carboxamide; N-[(2S,3R)-2-methyl-1-azabicyclo[2.2.2]oct-3-yl]-5-(5-methyl[1,3,4]thiadiazol-2-yloxy)-thiophene-2-carboxamide; N-[(2S,3R)-2-methyl-1-azabicyclo[2.2.2]oct-3-yl]-5-(5-methoxy[1,3,4]thiadiazol-2-yloxy)-thiophene-2-carboxamide; N-[(2S,3R)-2-methyl-1-azabicyclo[2.2.2]oct-3-yl]-5-(5-chloro[1,3,4]thiadiazol-2-yloxy)-thiophene-2-carboxamide; N-[(2S,3R)-2-methyl-1-azabicyclo[2.2.2]oct-3-yl]-5-([1,3,4]oxadiazol-2-yloxy)-thiophene-2-carboxamide; N-[(2S,3R)-2-methyl-1-azabicyclo[2.2.2]oct-3-yl]-5-(5-methyl[1,3,4]oxadiazol-2-yloxy)-thiophene-2-carboxamide; N-[(2S,3R)-2-methyl-1-azabicyclo[2.2.2]oct-3-yl]-5-(5-methoxy 1,3,4]oxadiazol-2-yloxy)-thiophene-2-carboxamide; N-[(2S,3R)-2-methyl-1-azabicyclo[2.2.2]oct-3-yl]-5-(5-chloro[1,3,4]oxadiazol-2-yloxy)-thiophene-2-carboxamide; N-[(2S,3R)-2-methyl-1-azabicyclo[2.2.2]oct-3-yl]-5-(thiophene-4-ylsulfanyl)-thiophene-2-carboxamide; N-[(2S,3R)-2-methyl-1-azabicyclo[2.2.2]oct-3-yl-5-(oxazol-2-ylsulfanyl)-thiophene-2-carboxamide; N-[(2S,3R)-2-methyl-1-azabicyclo[2.2.2]oct-3-yl]-5-(5-methyloxazol-2-ylsulfanyl)-thiophene-2-carboxamide; N-[(2S,3R)-2-methyl-1-azabicyclo[2.2.2]oct-3-yl]-5-(5-methoxyoxazol-2-ylsulfanyl)-thiophene-2-carboxamide; N-[(2S,3R)-2-methyl-1-azabicyclo[2.2.2]oct-3-yl]-5-(5-chlorooxazol-2-ylsulfanyl)-thiophene-2-carboxamide; N-[(2S,3R)-2-methyl-1-azabicyclo[2.2.2]oct-3-yl]-5-(oxazol-5-ylsulfanyl)-thiophene-2-carboxamide; N-[(2S,3R)-2-methyl-1-azabicyclo[2.2.2]oct-3-yl]-5-(2-methyloxazol-5-ylsulfanyl)-thiophene-2-carboxamide; N-[(2S,3R)-2-methyl-1-azabicyclo[2.2.2]oct-3-yl]-5-(2-methoxyoxazol-5-ylsulfanyl)-thiophene-2-carboxamide; N-[(2S,3R)-2-methyl-1-azabicyclo[2.2.2]oct-3-yl]-5-(2-chlorooxazol-5-ylsulfanyl)-thiophene-2-carboxamide; N-[(2S,3R)-2-methyl-1-azabicyclo[2.2.2]oct-3-yl]-5-(thiazol-2-ylsulfanyl)-thiophene-2-carboxamide; N-[(2S,3R)-2-methyl-1-azabicyclo[2.2.2]oct-3-yl]-5-(5-methylthiazol-2-ylsulfanyl)-thiophene-2-carboxamide; N-[(2S,3R)-2-methyl-1-azabicyclo[2.2.2]oct-3-yl]-5-(5-methoxythiazol-2-ylsulfanyl)-thiophene-2-carboxamide; N-[(2S,3R)-2-methyl-1-azabicyclo[2.2.2]oct-3-yl]-5-(5-chlorothiazol-2-ylsulfanyl)-thiophene-2-carboxamide; N-[(2S,3R)-2-methyl-1-azabicyclo[2.2.2]oct-3-yl]-5-(thiazol-5- ylsulfanyl)-thiophene-2-carboxamide; N-[(2S,3R)-2-methyl-1-azabicyclo[2.2.2]oct-3-yl]-5-(2-methylthiazol-5-ylsulfanyl)-thiophene-2-carboxamide; N-[(2S,3R)-2-methyl-1-azabicyclo[2.2.2]oct-3-yl]-5-(2-methoxythiazol-5-ylsulfanyl)-thiophene-2-carboxamide; N-[(2S,3R)-2-methyl-1-azabicyclo[2.2.2]oct-3-yl]-5-(2-chlorothiazol-5-ylsulfanyl)-thiophene-2-carboxamide; N-[(2S,3R)-2-methyl-1-azabicyclo[2.2.2]oct-3-yl]-5-(4-methylthiazol-2-ylsulfanyl)-thiophene-2-carboxamide; N-[(2S,3R)-2-methyl-1-azabicyclo[2.2.2]oct-3-yl]-5-(4-methoxythiazol-2-ylsulfanyl)-thiophene-2-carboxamide; N-[(2S,3R)-2-methyl-1-azabicyclo[2.2.2]oct-3-yl]-5-(4-chlorothiazol-2-ylsulfanyl)-thiophene-2-carboxamide; N-[(2S,3R)-2-methyl-1-azabicyclo[2.2.2]oct-3-yl]-5-(4-methyloxazol-2-ylsulfanyl)-thiophene-2-carboxamide; N-[(2S,3R)-2-methyl-1-azabicyclo[2.2.2]oct-3-yl]-5-(4-methoxyoxazol-2-ylsulfanyl)-thiophene-2-carboxamide; N-[(2S,3R)-2-methyl-1-azabicyclo[2.2.2]oct-3-yl]-5-(4-chlorooxazol-2-ylsulfanyl)-thiophene-2-carboxamide; N-[(2S,3R)-2-methyl-1-azabicyclo[2.2.2]oct-3-yl]-5-([1,3,4]thiadiazol-2-ylsulfanyl)-thiophene-2-carboxamide; N-[(2S,3R)-2-methyl-1-azabicyclo[2.2.2]oct-3-yl]-5-(5-methyl[1,3,4]thiadiazol-2-ylsulfanyl)-thiophene-2-carboxamide; N-[(2S,3R)-2-methyl-1-azabicyclo[2.2.2]oct-3-yl]-5-(5-methoxy[1,3,4]thiadiazol-2-ylsulfanyl)-thiophene-2-carboxamide; N-[(2S,3R)-2-methyl-1-azabicyclo[2.2.2]oct-3-yl]-5-(5-chloro[1,3,4]thiadiazol-2-ylsulfanyl)-thiophene-2-carboxamide; N-[(2S,3R)-2-methyl-1-azabicyclo[2.2.2]oct-3-yl]-5-([1,3,4]oxadiazol-2-ylsulfanyl)-thiophene-2-carboxamide; N-[(2S,3R)-2-methyl-1-azabicyclo[2.2.2]oct-3-yl]-5-(5-methyl[1,3,4]oxadiazol-2-ylsulfanyl)-thiophene-2-carboxamide; N-[(2S,3R)-2-methyl-1-azabicyclo[2.2.2]oct-3-yl]-5-(5-methoxy[1,3,4]oxadiazol-2-ylsulfanyl)-thiophene-2-carboxamide; N-[(2S,3R)-2-methyl-1-azabicyclo[2.2.2]oct-3-yl]-5-(5-chloro[1,3,4]oxadiazol-2-ylsulfanyl)-thiophene-2-carboxamide; N-[(2S,3R)-2-methyl-1-azabicyclo[2.2.2]oct-3-yl]-5-(pyrrole-2-yl)-thiophene-2-carboxamide; N-[(2S,3R)-2-methyl-1-azabicyclo[2.2.2]oct-3-yl]-5-(isothiazol-3-yl)-thiophene-2-carboxamide; N-[(2S,3R)-2-methyl-1-azabicyclo[2.2.2]oct-3-yl]-5-(isoxazol-3-yl)-thiophene-2-carboxamide; N-[(2S,3R)-2-methyl-1-azabicyclo[2.2.2]oct-3-yl]-5-(3H-imidazolyl)-thiophene-2-carboxamide; N-[(2S,3R)-2-methyl-1-azabicyclo[2.2.2]oct-3-yl]-4-(4-hydroxyphenylsulfanyl)-thiophene-2-carboxamide; N-[(2S,3R)-2-methyl-1-azabicyclo[2.2.2]oct-3-yl]-4-(3-acetamidophenylsulfanyl)-thiophene-2-carboxamide; N-[(2S,3R)-2-methyl-1-azabicyclo[2.2.2]oct-3-yl]-4-(2-methanesulfonylaminophenyl)-thiophene-2-carboxamide; N-[(2S,3R)-2-methyl-1-azabicyclo[2.2.2]oct-3-yl]-4-(pyridin-2-yloxy)-thiophene-2-carboxamide; N-[(2S,3R)-2-methyl-1-azabicyclo[2.2.2]oct-3-yl]-4-(2-methylpyridin-4-yloxy)-thiophene-2-carboxamide; N-[(2S,3R)-2-methyl-1-azabicyclo[2.2.2]oct-3-yl]-4-(4-trifluoromethylphenyl)-thiophene-2-carboxamide; N-[(2S,3R)-2-methyl-1-azabicyclo[2.2.2]oct-3-yl]-4-(2-acetylphenyl)-thiophene-2-carboxamide; N-[(2S,3R)-2-methyl-1-azabicyclo[2.2.2]oct-3-yl]-4-chloro-5-phenyl-thiophene-2-carboxamide; N[(2S,3R)-2-methyl-1-azabicyclo[2.2.2]oct-3-yl]-4-methyl-5-phenyl-thiophene-2-carboxamide; N-[(2S,3R)-2-methyl-1-azabicyclo[2.2.2]oct-3-yl]-4-cyano-5-phenyl-thiophene-2-carboxamide; N-[(2S,3R)-2-methyl-1-azabicyclo[2.2.2]oct-3-yl]-4-methoxy-5-phenyl-thiophene-2-carboxamide; N-[(2S,3R)-2-methyl-1-azabicyclo[2.2.2]oct-3-yl]-5-chloro-4-phenyl-thiophene-2-carboxamide; N-[(2S,3R)-2-methyl-1-azabicyclo[2.2.2]oct-3-yl]-5-methyl-4-phenyl-thiophene-2-carboxamide; N-[(2S,3R)-2-methyl-1-azabicyclo[2.2.2]oct-3-yl]-5-cyano-4-phenyl-thiophene-2-carboxamide; N-[(2S,3R)-2-methyl-1-azabicyclo[2.2.2]oct-3-yl]-5-methoxy-4-phenyl-thiophene-2-carboxamide; N-[(2S,3R)-2-methyl-1-azabicyclo[2.2.2]oct-3-yl]-4-chloro-5-bromo-thiophene-2-carboxamide; N-[(2S,3R)-2-methyl-1-azabicyclo[2.2.2]oct-3-yl]-4-chloro-5-methylsulfanyl-thiophene-2-carboxamide; N-[(2S,3R)-2-methyl-1-azabicyclo[2.2.2]oct-3-yl]-4-chloro-5-methyl-thiophene-2-carboxamide; N-[(2S,3R)-2-methyl-1-azabicyclo[2.2.2]oct-3-yl]-4-chloro-5-cyano-thiophene-2-carboxamide; N-[(2S,3R)-2-methyl-1-azabicyclo[2.2.2]oct-3-yl]-5-chloro-4-bromo-thiophene-2-carboxamide; N-[(2S,3R)-2-methyl-1-azabicyclo[2.2.2]oct-3-yl]-5-chloro-4-methylsulfanyl-thiophene-2-carboxamide; N-[(2S,3R)-2-methyl-1-azabicyclo[2.2.2]oct-3-yl]-5-chloro-4-methyl-thiophene-2-carboxamide; N-[(2S,3R)-2-methyl-1-azabicyclo[2.2.2]oct-3-yl]-5-chloro-4-cyano-thiophene-2-carboxamide;

N-[(3R)-1-azabicyclo[2.2.2]oct-3-yl]-5-(2-bromophenyl)-furan-2-carboxamide; N-[(3R)-1-azabicyclo[2.2.2]oct-3-yl]-5-(3-bromophenyl)-furan-2-carboxamide; N-[(3R)-1-azabicyclo[2.2.2]oct-3-yl]-5-(2,3-dichlorophenyl)-furan-2-carboxamide; N-[(3R)-1-azabicyclo[2.2.2]oct-3-yl]-5-(2,4-dichlorophenyl)-furan-2-carboxamide; N-[(3R)-1-azabicyclo[2.2.2]oct-3-yl]-5-(2,5-dichlorophenyl)-furan-2-carboxamide; N-[(3R)-1-azabicyclo[2.2.2]oct-3-yl]-5-(2,6-dichlorophenyl)-furan-2-carboxamide; N-[(3R)-1-azabicyclo[2.2.2]oct-3-yl]-5-(3,4-dichlorophenyl)-furan-2-carboxamide; N-[(3R)-1-azabicyclo[2.2.2]oct-3-yl]-5-(3,5-dichlorophenyl)-furan-2-carboxamide; N-[(3R)-1-azabicyclo[2.2.2]oct-3-yl]-5-(4-amino-2-fluorophenyl)-furan-2-carboxamide; N-[(3R)-1-azabicyclo[2.2.2]oct-3-yl]-5-(3-amino-2-fluorophenyl)-furan-2-carboxamide; N-[(3R)-1-azabicyclo[2.2.2]oct-3-yl]-5-(4-amino-2-chlorophenyl)-furan-2-carboxamide; N-[(3R)-1-azabicyclo[2.2.2]oct-3-yl]-5-(3-amino-2-chlorophenyl)-furan-2-carboxamide; N-[(3R)-1-azabicyclo[2.2.2]oct-3-yl]-5-(3-aminophenyl)-furan-2-carboxamide; N-[(3R)-1-azabicyclo[2.2.2]oct-3-yl]-5-(2-cyanophenyl)-furan-2-carboxamide; N-[(3R)-1-azabicyclo[2.2.2]oct-3-yl]-5-(3-cyanophenyl)-furan-2-carboxamide; N-[(3R)-1-azabicyclo[2.2.2]oct-3-yl]-5-(2-hydroxyphenyl)-furan-2-carboxamide; N-[(3R)-1-azabicyclo[2.2.2]oct-3-yl]-5-(3-hydroxyphenyl)-furan-2-carboxamide; N-[(3R)-1-azabicyclo[2.2.2]oct-3-yl]-5-(4-hydroxyphenyl)-furan-2-carboxamide; N-[(3R)-1-azabicyclo[2.2.2]oct-3-yl]-5-(2-fluoro-4-methylphenyl)-furan-2-carboxamide; N-[(3R)-1-azabicyclo[2.2.2]oct-3-yl]-5-(2-fluoro-3-methoxyphenyl)-furan-2-carboxamide; N-[(3R)-1-azabicyclo[2.2.2]oct-3-yl]-5-(2-fluoro-4-methoxyphenyl)-furan-2-carboxamide; N-[(3R)-1-azabicyclo[2.2.2]oct-3-yl]-5-(2-[(methylsulfonyl)amino]phenyl)-furan-2-carboxamide; N-[(3R)-1-azabicyclo[2.2.2]oct-3-yl]-5-(3-[(methylsulfonyl)amino]phenyl)-furan-2-carboxamide; N-[(3R)-1-azabicyclo[2.2.2]oct-3-yl]-5-(4-[(methylsulfonyl)amino]phenyl)-furan-2-carboxamide; N-[(3R)-1-azabicyclo[2.2.2]oct-3-yl]-5-(2-([(trifluoromethyl)sulfonyl]amino)phenyl)-furan-2-carboxamide; N-[(3R)-1-azabicyclo[2.2.2]oct-3-yl]-5-(3-([(trifluoromethyl)sulfonyl]amino)phenyl)-furan-2-carboxamide; N-[(3R)-1-azabicyclo[2.2.2]oct-3-yl]-5-(4-([(trifluoromethyl)sulfonyl]amino)phenyl)-furan-2-carboxamide; N-[(3R)-1-azabicyclo[2.2.2]oct-3-yl]-5-2-[(phenylsulfonyl)amino]phenyl)-furan-2-carboxamide; N-[(3R)-1-azabicyclo[2.2.2]oct-3-yl]-5-(3-[(phenylsulfonyl)amino]phenyl)-furan-2-carboxamide; N-[(3R)-1-azabicyclo[2.2.2]oct-3-yl]-5-(4-

[(phenylsulfonyl)amino]phenyl)-furan-2-carboxamide; N-[(3R)-1-azabicyclo[2.2.2]oct-3-yl]-5-(2-[(methylamino)carbonyl]phenyl)-furan-2-carboxamide; N-[(3R)-1-azabicyclo[2.2.2]oct-3-yl]-5-(3-[(methylamino)carbonyl]phenyl)-furan-2-carboxamide; N-[(3R)-1-azabicyclo[2.2.2]oct-3-yl]-5-(4-[(methylamino)carbonyl]phenyl)-furan-2-carboxamide; N-[(3R)-1-azabicyclo[2.2.2]oct-3-yl]-5-(2-[(methylamino)sulfonyl]phenyl)-furan-2-carboxamide; N-[(3R)-1-azabicyclo[2.2.2]oct-3-yl]-5-(3-[(methylamino)sulfonyl]phenyl)-furan-2-carboxamide; N-[(3R)-1-azabicyclo[2.2.2]oct-3-yl]-5-(4-[(methylamino)sulfonyl]phenyl)-furan-2-carboxamide; N-[(3R)-1-azabicyclo[2.2.2]oct-3-yl]-5-[2-(methylamino)phenyl]-furan-2-carboxamide; N-[(3R)-1-azabicyclo[2.2.2]oct-3-yl]-5-[3-(methylamino)phenyl]-furan-2-carboxamide; N-[(3R)-1-azabicyclo[2.2.2]oct-3-yl]-5-[4-(methylamino)phenyl]-furan-2-carboxamide; N-[(3R)-1-azabicyclo[2.2.2]oct-3-yl]-5-[2-(ethylamino)phenyl]-furan-2-carboxamide; N-[(3R)-1-azabicyclo[2.2.2]oct-3-yl]-5-[3-(ethylamino)phenyl]-furan-2-carboxamide; N-[(3R)-1-azabicyclo[2.2.2]oct-3-yl]-5-[4-(ethylamino)phenyl]-furan-2-carboxamide; N-[(3R)-1-azabicyclo[2.2.2]oct-3-yl]-5-(2-acetylphenyl)-furan-2-carboxamide; N-[(3R)-1-azabicyclo[2.2.2]oct-3-yl]-5-(3-acetylphenyl)-furan-2-carboxamide; N-[(3R)-1-azabicyclo[2.2.2]oct-3-yl]-5-(4-acetylphenyl)-furan-2-carboxamide; N-[(3R)-1-azabicyclo[2.2.2]oct-3-yl]-5-[2-(methylthio)phenyl]-furan-2-carboxamide; N-[(3R)-1-azabicyclo[2.2.2]oct-3-yl]-5-[3-(methylthio)phenyl]-furan-2-carboxamide; N-[(3R)-1-azabicyclo[2.2.2]oct-3-yl]-5-[4-(methylthio)phenyl]-furan-2-carboxamide; N-[(3R)-1-azabicyclo[2.2.2]oct-3-yl]-5-[2-(phenylthio)phenyl]-furan-2-carboxamide; N-[(3R)-1-azabicyclo[2.2.2]oct-3-1-yl-5-[3-(phenylthio)phenyl]-furan-2-carboxamide; N-[(3R)-1-azabicyclo[2.2.2]oct-3-yl]-5-[4-(phenylthio)phenyl]-furan-2-carboxamide; N-[(3R)-1-azabicyclo[2.2.2]oct-3-yl]-5-(2-phenoxyphenyl)-furan-2-carboxamide; N-[(3R)-1-azabicyclo[2.2.2]oct-3-yl]-5-(3-phenoxyphenyl)-furan-2-carboxamide; N-[(3R)-1-azabicyclo[2.2.2]oct-3-yl]-5-(4-phenoxyphenyl)-furan-2-carboxamide; N-[(3R)-1-azabicyclo[2.2.2]oct-3-yl]-5-(2-anilinophenyl)-furan-2-carboxamide; N-[(3R)-1-azabicyclo[2.2.2]oct-3-yl]-5-(3-anilinophenyl)-furan-2-carboxamide; N-[(3R)-1-azabicyclo[2.2.2]oct-3-yl]-5-(4-anilinophenyl)-furan-2-carboxamide; N-[(3R)-1-azabicyclo[2.2.2]oct-3-yl]-5-(phenylthio)-furan-2-carboxamide; N-[(3R)-1-azabicyclo[2.2.2]oct-3-yl]-5-[(2-fluorophenyl)thio]-furan-2-carboxamide; N-[(3R)-1-azabicyclo[2.2.2]oct-3-yl]-5-[(3-fluorophenyl)thio]-furan-2-carboxamide; N-[(3R)-1-azabicyclo[2.2.2]oct-3-yl]-5-[(4-fluorophenyl)thio]-furan-2-carboxamide; N-[(3R)-1-azabicyclo[2.2.2]oct-3-yl]-5-[(2-chlorophenyl)thio]-furan-2-carboxamide; N-[(3R)-1-azabicyclo[2.2.2]oct-3-yl]-5-[(3-chlorophenyl)thio]-furan-2-carboxamide; N-[(3 R)-1-azabicyclo[2.2.2]oct-3-yl]-5-[(4-chlorophenyl)thio]-furan-2-carboxamide; N-[(3R)-1-azabicyclo[2.2.2]oct-3-yl]-5-(2-fluorophenoxy)-furan-2-carboxamide; N-[(3R)-1-azabicyclo[2.2.2]oct-3-yl]-5-(3-fluorophenoxy)-furan-2-carboxamide; N-[(3R)-1-azabicyclo[2.2.2]oct-3-yl]-5-(4-fluorophenoxy)-furan-2-carboxamide; N-[(3R)-1-azabicyclo[2.2.2]oct-3-yl]-5-(2-chlorophenoxy)-furan-2-carboxamide; N-[(3R)-1-azabicyclo[2.2.2]oct-3-yl]-5-(3-chlorophenoxy)-furan-2-carboxamide; N-[(3R)-1-azabicyclo[2.2.2]oct-3-yl]-5-(4-chlorophenoxy)-furan-2-carboxamide; N-[(3R)-1-azabicyclo[2.2.2]oct-3-yl]-5-pyridin-2-yl-furan-2-carboxamide; N-[(3R)-1-azabicyclo[2.2.2]oct-3-yl]-5-pyridin-3-yl-furan-2-carboxamide; N-[(3R)-1-azabicyclo[2.2.2]oct-3-yl]-5-pyridin-4-yl-furan-2-carboxamide; N-[(3R)-1-azabicyclo[2.2.2]oct-3-yl]-5-(3-fluoropyridin-2-yl)-furan-2-carboxamide; N-[(3R)-1-azabicyclo[2.2.2]oct-3-yl]-5-(4-fluoropyridin-2-yl)-furan-2-carboxamide; N-[(3R)-1-azabicyclo[2.2.2]oct-3-yl]-5-(4-fluoropyridin-2-yl)-furan-2-carboxamide; N-[(3R)-1-azabicyclo[2.2.2]oct-3-yl]-5-(2-fluoropyridin-yl)-furan-2-carboxamide; N-[(3R)-1-azabicyclo[2.2.2]oct-3-yl]-5-(2-fluoropyridin-3-yl)-furan-2-carboxamide; N-[(3R)-1-azabicyclo[2.2.2]oct-3-yl]-5-(4-fluoropyridin-3-yl)-furan-2-carboxamide; N-[(3R)-1-azabicyclo[2.2.2]oct-3-yl]-5-(6-fluoropyridin-3-yl)-furan-2-carboxamide; N-[(3R)-1-azabicyclo[2.2.2]oct-3-yl]-5-(2-fluoropyridin-3-yl)-furan-2-carboxamide; N-[(3R)-1-azabicyclo[2.2.2]oct-3-yl]-5-(2-fluoropyridin-4-yl)-furan-2-carboxamide; N-[(3R)-1-azabicyclo[2.2.2]oct-3-yl]-5-(3-flu N-[(3R)-1-azabicyclo[2.2.2]oct-3-yl]-5-(4-pyrrolidin-1-ylphenyl)-furan-2-carboxamide; N-[(3R)-1-azabicyclo[2.2.2]oct-3-yl]-5-[2-(1H-pyrrol-2-yl)phenyl]-furan-2-carboxamide; N-[(3R)-1-azabicyclo[2.2.2]oct-3-yl]-5-[3-(1H-pyrrol-2-yl)phenyl]-furan-2-carboxamide; N-[(3R)-1-azabicyclo[2.2.2]oct-3-yl]-5-[4-(1H-pyrrol-2-yl)phenyl]-furan-2-carboxamide; N-[(3R)-1-azabicyclo[2.2.2]oct-3-yl]-5-[2-(2-furyl)phenyl]-furan-2-carboxamide; N-[(3R)-1-azabicyclo[2.2.2]oct-3-yl]-5-[2-(3-(furyl)phenyl]-furan-2-carboxamide; N-[(3R)-1-azabicyclo[2.2.2]oct-3-yl]-5-[2-(5-methyl-2-furyl)phenyl]-furan-2-carboxamide; N-[(3R)-1-azabicyclo[2.2.2]oct-3-yl]-5-[3-(2-furyl)phenyl]-furan-2 carboxamide; N-[(3R)-1-azabicyclo[2.2.2]oct-3-yl]-5-[3-(3-furyl)phenyl]-furan-2-carboxamide; N-[(3R)1-azabicyclo[2.2.2]oct-3-yl]-5-[3-(5-methyl-2-furyl)phenyl]-furan-2-carboxamide; N-[(3R)-1-azabicyclo[2.2.2]oct-3-yl]-5-[4-(2-furyl)phenyl]-furan-2-carboxamide; N-[(3R)-1-azabicyclo[2.2.2]oct-3-yl]-5-[4-(3-furyl)phenyl]-furan-2-carboxamide; N-[(3R)-1-azabicyclo[2.2.2]oct-3-yl]-5-[4-(5-methyl-2-furyl)phenyl]-furan-2-carboxamide; N-[(3R)-1-azabicyclo[2.2.2]oct-3-yl]-5-[2-(1,3-thiazol-2-yl)phenyl]-furan-2-carboxamide; N-[(3R)-1-azabicyclo[2.2.2]oct-3-yl]-5-[3-(1,3-thiazol-2-yl)phenyl]furan-2-carboxamide; N-[(3R)-1-azabicyclo[2.2.2]oct-3-yl]-5-[4-(1,3-thiazol-2-yl)phenyl]-furan-2-carboxamide; N-[(3R)-1-azabicyclo[2.2.2]oct-3-yl]-5-[2-(1,3-oxazol-2-yl)phenyl]-furan-2-carboxamide; N-[(3R)-1-azabicyclo[2.2.2]oct-3-yl]-5-[3-(1,3-oxazol-2-yl) phenyl]-furan-2-carboxamide; N-[(3R)-1-azabicyclo[2.2.2]oct-3-yl]-5-[(1,3-oxazo-2-yl)phenyl]-furan-2-carboxamide; N-[(3R)-1-azabicyclo[2.2.2]oct-3-yl]-5-(2-isothiazol-5-ylphenyl)-furan-2-carboxamide; N-[(3R)-1-azabicyclo[2.2.2]oct-3-yl]-5-(3-isothiazo-5-ylphenyl)-furan-2-carboxamide; N-[(3R)-1-azabicyclo[2.2.2]oct-3-yl]-5-(4-isothiazo-5-ylphenyl)-furan-2-carboxamide; N-[(3R)-1-azabicyclo[2.2.2]oct-3-yl]-5-[4-(1H-indol-2-yl)phenyl]-furan-2-carboxamide; N-[(3R)-1-azabicyclo[2.2.2]oct-3-yl]-5-[4-(1H-indol-3-yl)phenyl]-furan-2-carboxamide; N-[(3R)-1-azabicyclo[2.2.2]oct-3-yl]-5-(1H-indol-5-yl)-furan-2-carboxamide; N-[(3R)-1-azabicyclo[2.2.2]oct-3-yl]-5-(1H-indol-6-yl)-furan-2-carboxamide;

N-[(2S,3R)-2-methyl-1-azabicyclo[2.2.2]oct-3-yl]-5-(2-bromophenyl)-furan-2-carboxamide; N-[(2S,3R)-2-methyl-1-azabicyclo[2.2.2]oct-3-yl]-5-(3-bromophenyl)-furan-2-carboxamide; N-[(2S,3R)-2-methyl-1-azabicyclo[2.2.2]oct-3-yl]-5-(2,3-dichlorophenyl)-furan-2-carboxamide; N-[(2S,3R)-2-methyl-1-azabicyclo[2.2.2]oct-3-yl]-5-(2,4-dichlorophenyl)-furan-2-carboxamide; N-[(2S,3R)-2-methyl-1-azabicyclo[2.2.2]oct-3-yl]-5-(2,5-dichlorophenyl)-furan-2-carboxamide; N-[(2S,3R)-2-methyl-1-azabicyclo[2.2.2]oct-3-yl]-5-(2,6-dichlorophenyl)-furan-2-carboxamide; N-[(2S,3R)-2-methyl-1-azabicyclo[2.2.2]oct-3-yl]-5-(3,4-dichlorophenyl)-furan-2-carboxamide; N-[(2S,3R)-2- methyl-1-azabicyclo[2.2.2]oct-3-yl]-5-(3,5-dichlorophenyl)-furan-2-carboxamide; N-[(2S,3R)-2-methyl-1-azabicyclo[2.2.2]oct-3-yl]-5-(4-amino-2-fluorophenyl)-furan-2-carboxamide; N-[(2S,3R)-2-methyl-1-azabicyclo[2.2.2]oct-3-yl]-5-(3-amino-2-fluorophenyl)-furan-2-carboxamide; N-[(2S,3R)-2-methyl-1-azabicyclo[2.2.2]oct-3-yl]-5-(4-amino-2-chlorophenyl)-furan-2-carboxamide; N-[(2S,3R)-2-methyl-1-azabicyclo[2.2.2]oct-3-yl]-5-(3-amino-2-chlorophenyl)-furan-2-carboxamide; N-[(2S,3R)-2-methyl-1-azabicyclo[2.2.2]oct-3-yl]-5-(3-aminophenyl)-furan-2-carboxamide; N-[(2S,3R)-2-methyl-1-azabicyclo[2.2.2]oct-3-yl]-5-(2-cyanophenyl)-furan-2-carboxamide; N-[(2S,3R)-2-methyl-1-azabicyclo[2.2.2]oct-3-yl]-5-(3-cyanophenyl)-furan-2-carboxamide; N-[(2S,3R)-2-methyl-1-azabicyclo[2.2.2]oct-3-yl]-5-(2-hydroxyphenyl)-furan-2-carboxamide; N-[(2S,3R)-2-methyl-1-azabicyclo[2.2.2]oct-3-yl]-5-(3-hydroxyphenyl)-furan-2-carboxamide; N-[(2S,3R)-2-methyl-1-azabicyclo[2.2.2]oct-3-yl]-5-(4-hydroxyphenyl)-furan-2-carboxamide; N-[(2S,3R)-2-methyl-1-azabicyclo[2.2.2]oct-3-yl]-5-(2-fluoro-4-methylphenyl)-furan-2-carboxamide; N-[(2S,3R)-2-methyl-1-azabicyclo[2.2.2]oct-3-yl]-5-(2-fluoro-3-methoxyphenyl)-furan-2-carboxamide; N-[(2S,3R)-2-methyl-1-azabicyclo[2.2.2]oct-3-yl]-5-(2-fluoro-4-methoxyphenyl)-furan-2-carboxamide; N-[(2S,3R)-2-methyl-1-azabicyclo[2.2.2]oct-3-yl]-5-(2-[(methylsulfonyl)amino]phenyl)-furan-2-carboxamide; N-[(2S,3R)-2-methyl-1-azabicyclo[2.2.2]oct-3-yl]-5-(3-[(methylsulfonyl)amino]phenyl)-furan-2-carboxamide; N-[(2S,3R)-2-methyl-1-azabicyclo[2.2.2]oct-3-yl]-5-(4-[(methylsulfonyl)amino]phenyl)-furan-2-carboxamide; N-[(2S,3R)-2-methyl-1-azabicyclo[2.2.2]oct-3-yl]-5-[2-([(trifluoromethyl)sulfonyl]amino)phenyl]-furan-2-carboxamide; N-[(2S,3R)-2-methyl-1-azabicyclo[2.2.2]oct-3-yl]-5-[3-([(trifluoromethyl)sulfonyl]amino)phenyl)-furan-2-carboxamide; N-[(2S,3R)-2-methyl-1-azabicyclo[2.2.2]oct-3-yl]-5-(4-([(trifluoromethyl)sulfonyl]amino)phenyl)-furan-2-carboxamide; N-[(2S,3R)-2-methyl-1-azabicyclo[2.2.2]oct-3-yl]-5-(2-[(phenylsulfonyl)amino]phenyl)-furan-2-carboxamide; N-[(2S,3R)-2-methyl-1-azabicyclo[2.2.2]oct-3-yl]-5-(3-[(phenylsulfonyl)amino]phenyl)-furan-2-carboxamide; N-[(2S,3R)-2-methyl-1-azabicyclo[2.2.2]oct-3-yl]-5-(4-[(phenylsulfonyl)amino]phenyl)-furan-2-carboxamide; N-[(2S,3R)-2-methyl-1-azabicyclo[2.2.2]oct-3-yl]-5-(2-[(methylamino)carbonyl]phenyl)-furan-2-carboxamide; N-[(2S,3R)-2-methyl-1-azabicyclo[2.2.2]oct-3-yl]-5-(3-[(methylamino)carbonyl]phenyl)-furan-2-carboxamide; N-[(2S,3R)-2-methyl-1-azabicyclo[2.2.2]oct-3-yl]-5-(4-[(methylamino)carbonyl]phenyl)-furan-2-carboxamide; N-[(2S,3R)-2-methyl-1-azabicyclo[2.2.2]oct-3-yl]-5-(2-[(methylamino)sulfonyl]phenyl)-furan-2-carboxamide; N-[(2S,3R)-2-methyl-1-azabicyclo[2.2.2]oct-3-yl]-5-(3-[(methylamino)sulfonyl]phenyl)-furan-2-carboxamide; N-[(2S,3R)-2-methyl-1-azabicyclo[2.2.2]oct-3-yl]-5-(4-1 (methylamino)sulfonyl]phenyl)-furan-2-carboxamide; N-[(2S,3R)-2-methyl-1-azabicyclo[2.2.2]oct-3-yl]-5-[2-(methylamino)phenyl]-furan-2-carboxamide; N-[(2S,3R)-2-methyl-1-azabicyclo[2.2.2]oct-3-yl]-5-[3-(methylamino)phenyl]-furan-2-carboxamide; N-[(2S,3R)-2-methyl-1-azabicyclo[2.2.2]oct-3-yl]-5-[4-(methylamino)phenyl]-furan-2-carboxamide; N-[(2S,3R)-2-methyl-1-azabicyclo[2.2.2]oct-3-yl]-5-[2-(ethylamino)phenyl]-furan-2-carboxamide; N-[(2S,3R)-2-methyl-1-azabicyclo[2.2.2]oct-3-yl]-5-[3-(ethylamino)phenyl]-furan-2-carboxamide; N-[(2S,3R)-2-methyl-1-azabicyclo[2.2.2]oct-3-yl]-5-[4-(ethylamino)phenyl]-furan-2-carboxamide; N-[(2S,3R)-2-methyl-1-azabicyclo[2.2.2]oct-3-yl]-5-(2-acetylphenyl)-furan-2-carboxamide; N-[(2S,3R)-2-methyl-1-azabicyclo[2.2.2]oct-3-yl]-5-(3-acetylphenyl)-furan-2-carboxamide; N-[(2S,3R)-2-methyl-1-azabicyclo[2.2.2]oct-3-yl]-5-(4-acetylphenyl)-furan-2-carboxamide; N-[(2S,3R)-2-methyl-1-azabicyclo[2.2.2]oct-3-yl]-5-[2-(methylthio)phenyl]-furan-2-carboxamide; N-[(2S,3R)-2-methyl-1-azabicyclo[2.2.2]oct-3-yl]-5-[3-(methylthio)phenyl]-furan-2-carboxamide; N-[(2S,3R)-2-methyl-1-azabicyclo[2.2.2]oct-3-yl]-5-[4-(methylthio)phenyl]-furan-2-carboxamide; N-[(2S,3R)-2-methyl-1-azabicyclo[2.2.2]oct-3-yl]-5-[2-(phenylthio)phenyl]-furan-2-carboxamide; N-[(2S,3R)-2-methyl-1-azabicyclo[2.2.2]oct-3-yl]-5-[3-(phenylthio)phenyl]-furan-2-carboxamide; N-[(2S,3R)-2-methyl-1-azabicyclo[2.2.2]oct-3-yl]-5-[4-(phenylthio)phenyl]-furan-2-carboxamide; N-[(2S,3R)-2-methyl-1-azabicyclo[2.2.2]oct-3-yl]-5-(2-phenoxyphenyl)-furan-2-carboxamide; N-[(2S,3R)-2-methyl-1-azabicyclo[2.2.2]oct-3-yl]-5-(3-phenoxyphenyl)-furan-2-carboxamide; N-[(2S,3R)-2-methyl-1-azabicyclo[2.2.2]oct-3-yl]-5-(4-phenoxyphenyl)-furan-2-carboxamide; N-[(2S,3R)-2-methyl-1-azabicyclo[2.2.2]oct-3-yl]-5-(2-anilinophenyl)-furan-2-carboxamide; N-[(2S,3R)-2-methyl-1-azabicyclo[2.2.2]oct-3-yl]-5-(3-anilinophenyl)-furan-2-carboxamide; N-[(2S,3R)-2-methyl-1-azabicyclo[2.2.2]oct-3-yl]-5-(4-anilinophenyl)-furan-2-carboxamide; N-[(2S,3R)-2-methyl-1-azabicyclo[2.2.2]oct-3-yl]-5-(phenylthio)-furan-2-carboxamide; N-[(2S,3R)-2-methyl-1-azabicyclo[2.2.2]oct-3-yl]-5-[(2-fluorophenyl)thio]-furan-2-carboxamide; N-[(2S,3R)-2-methyl-1-azabicyclo[2.2.2]oct-3-yl]-5-[(3-fluorophenyl)thio]-furan-2-carboxamide; N-[(2S,3R)-2-methyl-1-azabicyclo[2.2.2]oct-3-yl]-5-[(4-fluorophenyl)thiol-furan-2-carboxamide; N-[(2S,3R)-2-methyl-1-azabicyclo[2.2.2]oct-3-yl]-5-[(2-chlorophenyl)thio]-furan-2-carboxamide; N-[(2S,3R)-2-methyl-1-azabicyclo[2.2.2]oct-3-yl]-5-[(3-chlorophenyl)thio]-furan-2-carboxamide; N-[(2S,3R)-2-methyl-1-azabicyclo[2.2.2]oct-3-yl]-5-[(4-chlorophenyl)thio]-furan-2-carboxamide; N-[(2S,3R)-2-methyl-1-azabicyclo[2.2.2]oct-3-yl]-5-(2-fluorophenoxy)-furan-2-carboxamide; N-[(2S,3R)-2-methyl-1-azabicyclo[2.2.2]oct-3-yl]-5-(3-fluorophenoxy)-furan-2-carboxamide; N-[(2S,3R)-2-methyl-1-azabicyclo[2.2.2]oct-3-yl]-5-(4-fluorophenoxy)-furan-2-carboxamide; N-[(2S,3R)-2-methyl-1-azabicyclo[2.2.2]oct-3-yl]-5-(2-chlorophenoxy)-furan-2-carboxamide; N-[(2S,3R)-2-methyl-1-azabicyclo[2.2.2]oct-3-yl]-5-(3-chlorophenoxy)-furan-2-carboxamide; N-[(2S,3R)-2-methyl-1-azabicyclo[2.2.2]oct-3-yl]-5-(4-chlorophenoxy)-furan-2-carboxamide; N-[(2S,3R)-2-methyl-1-azabicyclo[2.2.2]oct-3-yl]-5-pyridin-2-yl-furan-2-carboxamide; N-[(2S,3R)-2-methyl-1-azabicyclo[2.2.2]oct-3-yl]-5-pyridin-3-yl-furan-2-carboxamide; N-[(2S,3R)-2-methyl-1-azabicyclo[2.2.2]oct-3-yl]-5-pyridin-4-yl-furan-2-carboxamide; N-[(2S,3R)-2-methyl-1-azabicyclo[2.2.2]oct-3-yl]-5-(3-fluoropyridin-2-yl)-furan-2-carboxamide; N-[(2S,3R)-2-methyl-1-azabicyclo[2.2.2]oct-3-yl]-5-(4-fluoropyridin-2-yl)-furan-2-carboxamide; N-[(2S,3R)-2-methyl-1-azabicyclo[2.2.2]oct-3-yl]-5-(5-fluoropyridin-2-yl)-furan-2-carboxamide; N-[(2S,3R)-2-methyl-1-azabicyclo[2.2.2]oct-3-yl]-5-(6-fluoropyridin-2-yl)-furan-2-carboxamide; N-[(2S,3R)-2-methyl-1-azabicyclo[2.2.2]oct-3-yl]-5-(2-fluoropyridin-3-yl)-furan-2-carboxamide; N-[(2S,3R)-2-methyl-1-azabicyclo[2.2.2]oct-3-yl]-5-(4-fluoropyridin-3-yl)-furan-2-carboxamide; N-[(2S,3R)-2-methyl-1-azabicyclo[2.2.2]oct-3-yl]-5-(5-fluoropyridin-3-yl)-furan-2-carboxamide; N-[(2S,3R)-2-methyl-1-azabicyclo[2.2.2]oct-3-yl]-5-(6-fluoropyridin-3-yl)-furan-2-carboxamide; N-[(2S,3R)-2-methyl-1-azabicyclo[2.2.2]oct-3-yl]-5-(2-fluoropyridin-4-yl)-furan-2-carboxamide;

N-[(2S,3R)-2-methyl-1-azabicyclo [2.2.2]oct-3-yl]-5-(3-fluoropyridin-4-yl)-furan-2-carboxamide; N-[(2S,3R)-2-methyl-1-azabicyclo[2.2.2]oct-3-yl]-5-(3-chloropyridin-2-yl)-furan-2-carboxamide; N-[(2S,3R)-2-methyl-1-azabicyclo[2.2.2]oct-3-yl]-5-(4-chloropyridin-2-yl)-furan-2-carboxamide; N-[(2S,3R)-2-methyl-1-azabicyclo[2.2.2]oct-3-yl]-5-(5-chloropyridin-2-yl)-furan-2-carboxamide; N-[(2S,3R)-2-methyl-1-azabicyclo[2.2.2]oct-3-yl-5-(6-chloropyridin-2-yl)-furan-2-carboxamide; N-[(2S,3R)-2-methyl-1-azabicyclo[2.2.2]oct-3-yl]-5-(2-chloropyridin-3-yl)-furan-2-carboxamide; N-[(2S,3R)-2-methyl-1-azabicyclo[2.2.2]oct-3-yl]-5-(4-chloropyridin-3-yl)-furan-2-carboxamide; N-[(2S,3R)-2-methyl-1-azabicyclo[2.2.2]oct-3-yl]-5-(5-chloropyridin-3-yl)-furan-2-carboxamide; N-[(2S,3R)-2-methyl-1-azabicyclo[2.2.2]oct-3-yl]-5-(6-chloropyridin-3-yl)-furan-2-carboxamide; N-[(2S,3R)-2-methyl-1-azabicyclo[2.2.2]oct-3-yl]-5-(2-chloropyridin-4-yl)-furan-2-carboxamide; N-[(2S,3R)-2-methyl-1-azabicyclo[2.2.2]oct-3-yl]-5-(3-chloropyridin-4-yl)-furan-2-carboxamide; N-[(2S,3R)-2-methyl-1-azabicyclo[2.2.2]oct-3-yl]-5-(2-piperidin-1-ylphenyl)-furan-2-carboxamide; N-[(2S,3R)-2-methyl-1-azabicyclo[2.2.2]oct-3-yl]-5-(3-piperidin-1-ylphenyl)-furan-2-carboxamide; N-[(2S,3R)-2-methyl-1-azabicyclo[2.2.2]oct-3-yl]-5-(4-piperidin-1-ylphenyl)-furan-2-carboxamide; N-[(2S,3R)-2-methyl-1-azabicyclo[2.2.2]oct-3-yl]-5-(2-morpholin-4-ylphenyl)-furan-2-carboxamide; N-[(2S,3R)-2-methyl-1-azabicyclo[2.2.2]oct-3-yl]-5-(3-morpholin-4-ylphenyl)-furan-2-carboxamide; N-[(2S,3R)-2-methyl-1-azabicyclo[2.2.2]oct-3-yl]-5-(4-morpholin-4-ylphenyl)-furan-2-carboxamide; N-[(2S,3R)-2-methyl-1-azabicyclo[2.2.2]oct-3-yl]-5-(2-pyrrolidin-1-ylphenyl)-furan-2-carboxamide; N-[(2S,3R)-2-methyl-1-azabicyclo[2.2.2]oct-3-yl]-5-(3-pyrrolidin-1-ylphenyl)-furan-2-carboxamide; N-[(2S,3R)-2-methyl-1-azabicyclo[2.2.2]oct-3-yl]-5-(4-pyrrolidin-1-ylphenyl)-furan-2-carboxamide; N-[(2S,3R)-2-methyl-1-azabicyclo[2.2.2]oct-3-yl]-5-[2-(1H-pyrrol-2-yl)phenyl-furan-2-carboxamide; N-[(2S,3R)-2-methyl-1-azabicyclo[2.2.2]oct-3-yl]-5-[3-(1H-pyrrol-2-yl)phenyl]-furan-2-carboxamide; N-[(2S,3R)-2-methyl-1-azabicyclo[2.2.2]oct-3-yl]-5-[4-(1H-pyrrol-2-yl)phenyl]-furan-2-carboxamide; N-[(2S,3R)-2-methyl-1-azabicyclo[2.2.2]oct-3-yl]-5-[2-(2-furyl)phenyl]-furan-2-carboxamide; N-[(2S,3R)-2-methyl-1-azabicyclo[2.2.2]oct-3-yl]-5-[2-(3-furyl)phenyl]-furan-2-carboxamide; N-[(2S,3R)-2-methyl-1-azabicyclo[2.2.2]oct-3-yl]-5-[2-(5-methyl-2-furyl)phenyl]-furan-2-carboxamide; N-[(2S,3R)-2-methyl-1-azabicyclo[2.2.2]oct-3-yl]-5-[3-(2-furyl)phenyl]-furan-2-carboxamide; N-[(2S,3R)-2-methyl-1-azabicyclo[2.2.2]oct-3-yl]-5-[3-(3-furyl)phenyl]-furan-2-carboxamide; N-[(2S,3R)-2-methyl-1-azabicyclo[2.2.2]oct-3-yl]-5-L3-(5-methyl-2-furyl)phenyl]-furan-2-carboxamide; N-[(2S,3R)-2-methyl-1-azabicyclo[2.2.2]oct-3-yl]-5-[4-(2-furyl)phenyl]-furan-2-carboxamide; N-[(2S,3R)-2-methyl-1

N-[(3R)-1-azabicyclo[2.2.2]oct-3-yl]-2-(2,3-difluorophenyl)-1,3-thiazole-5-carboxamide; N-[(3R)-1-azabicyclo[2.2.2]oct-3-yl]-2-(2,4-difluorophenyl)-1,3-thiazole-5-carboxamide; N-[(3R)-1-azabicyclo[2.2.2]oct-3-yl]-2-(2,5-difluorophenyl)-1,3-thiazole-5-carboxamide; N-[(3R)-1-azabicyclo[2.2.2]oct-3-yl]-2-(2,6-difluorophenyl)-1,3-thiazole-5-carboxamide; N-[(3R)-1-azabicyclo[2.2.2]oct-3-yl]-2-(3,4-difluorophenyl)-1,3-thiazole-5-carboxamide; N-[(3R)-1-azabicyclo[2.2.2]oct-3-yl]-2-(3,5-difluorophenyl)-1,3-thiazole-5-carboxamide; N-[(3R)-1-azabicyclo[2.2.2]oct-3-yl]-2-(2-chlorophenyl)-1,3-thiazole-5-carboxamide; N-[(3R)-1-azabicyclo[2.2.2]oct-3-yl]-2-(3-chlorophenyl)-1,3-thiazole-5-carboxamide; N-[(3R)-1-azabicyclo[2.2.2]oct-3-yl]-2-(4-chlorophenyl)-1,3-thiazole-5-carboxamide; N-[(3R)-1-azabicyclo[2.2.2]oct-3-yl]-2-(2-bromophenyl)-1,3-thiazole-5-carboxamide; N-[(3R)-1-azabicyclo[2.2.2]oct-3-yl]-2-(3-bromophenyl)-1,3-thiazole-5-carboxamide; N-[(3R)-1-azabicyclo[2.2.2]oct-3-yl]-2-(4-bromophenyl)-1,3-thiazole-5-carboxamide; N-[(3R)-1-azabicyclo[2.2.2]oct-3-yl]-2-(2-cyanophenyl)-1,3-thiazole-5-carboxamide; N-[(3R)-1-azabicyclo[2.2.2]oct-3-yl]-2-(3-cyanophenyl)-1,3-thiazole-5-carboxamide; N-[(3R)-1-azabicyclo[2.2.2]oct-3-yl]-2-(2-cytrophenyl)-1,3 thiazole-5-carboxamide; N-[(3R)-1-azabicyclo[2.2.2]oct-3-yl]-2-(4-nitrophenyl)-1,3-thiazole-5-carboxamide; N-[(3R)-1-azabicyclo[2.2.2]oct-3-yl]-2-(4-nitrophenyl)-1,3-thiazole-5-carboxamide; N-[(3R)-1-azabicyclo[2.2.2]oct-3-yl]-2-(2-nitrophenyl)-1,3-thiazole-5-carboxamide; N-[(3R)-1-azabicyclo[2.2.2]oct-3-yl]-2-(2-aminophenyl)-1,3-thiazole-5-carboxamide; N-[(3R)-1-azabicyclo[2.2.2]oct-3-yl]-2-(3-aminophenyl)-1,3-thiazole-5-carboxamide; N-[(3R)-1-azabicyclo[2.2.2]oct-3-yl]-2-(4-aminophenyl)-1,3-thiazole-5-carboxamide; N-[(3R)-1-azabicyclo[2.2.2]oct-3-yl]-2-(3-aminophenyl)-1,3-thiazole-5-carboxamide; N-[(3R)-1-azabicyclo[2.2.2]oct-3-yl]-2-(4-aminophenyl)-1,3-thiazole-5-carboxamide; N-[(3R)-1-azabicyclo[2.2.2]oct-3-yl]-2-[2-(methylamino)phenyl]-1,3-thiazole-5-carboxamide; N-[(3R)-1-azabicyclo[2.2.2]oct-3-yl]-2-[3-(methylamino)phenyl]-1,3-thiazole-5-carboxamide; N-[(3R)-1-azabicyclo[2.2.2]oct-3-yl]-2-[4-(methylamino)phenyl]-1,3-thiazole-5-carboxamide; N-[(3R)-1-azabicyclo[2.2.2]oct-3-yl]-2-[2-(acetylamino)phenyl]-1,3-thiazole-5-carboxamide; N-[(3R)-1-azabicyclo[2.2.2]oct-3-yl]-2-[3-(acetylamino)phenyl]-1,3-thiazole-5-carboxamide; N-[(3R)-1-azabicyclo[2.2.2]oct-3-yl]-2-[4-(acetylamino)phenyl]-1,3-thiazole-5-carboxamide; N-[(3R)-1-azabicyclo[2.2.2]oct-3-yl]-2-(2-[(trifluoroacetyl)amino]phenyl)-1,3-thiazole-5-carboxamide; N-[(3R)-1-azabicyclo[2.2.2]oct-3-yl]-2-(3-[(trifluoroacetyl)amino]phenyl)-1,3-thiazole-5-carboxamide; N-[(3R)-1-azabicyclo[2.2.2]oct-3-yl]-2-(4-[(trifluoroacetyl)amino]phenyl)-1,3-thiazole-5-carboxamide; N-[(3R)-1-azabicyclo[2.2.2]oct-3-yl]-2-(2-[(methylsulfonyl)amino]phenyl)-1,3-thiazole-5-carboxamide; N-[(3R)-1-azabicyclo[2.2.2]oct-3-yl]-2-(3-[(methylsulfonyl)amino]phenyl)-1,3-thiazole-5-carboxamide; N-[(3R)-1-azabicyclo[2.2.2]oct-3-yl]-2-(4-[(methylsulfonyl)amino]phenyl)-1,3-thiazole-5-carboxamide; N-[(3R)-1-azabicyclo[2.2.2]oct-3-yl]-2-(3-hydroxyphenyl)-1,3-thiazole-5-carboxamide; N-[(3R)-1-azabicyclo[2.2.2]oct-3-yl]-2-(4-hydroxyphenyl)-1,3-thiazole-5-carboxamide; N-[(3R)-1-azabicyclo[2.2.2]oct-3-yl]-2-(2-methoxyphenyl)-1,3-thiazole-5-carboxamide; N-[(3R)-1-azabicyclo[2.2.2]oct-3-yl]-2-(3-methoxyphenyl)-1,3-thiazole-5-carboxamide; N-[(3R)-1-azabicyclo[2.2.2]oct-3-yl]-2-(4-methoxyphenyl)-1,3-thiazole-5-carboxamide; N-[(3R)-1-azabicyclo[2.2.2]oct-3-yl]-2-[2-(trifluoromethoxy)phenyl]-1,3-thiazole-5-carboxamide; N-[(3R)-1-azabicyclo[2.2.2]oct-3-yl]-2-[3-(trifluoromethoxy)phenyl]-1,3-thiazole-5-carboxamide; N-[(3R)-1-azabicyclo[2.2.2]oct-3-yl]-2-[4-(trifluoromethoxy)phenyl]-1,3-thiazole-5-carboxamide; N-[(3R)-1-azabicyclo[2.2.2]oct-3-yl]-2-pyridin-2-yl-1,3-thiazole-5-carboxamide; N-[(3R)-1-azabicyclo[2.2.2]oct-3-yl]-2-pyridin-3-yl-1,3-thiazole-5-carboxamide; N-[(3R)-1-azabicyclo[2.2.2]oct-3-yl]-2-pyridin-4-yl-1,3-thiazole-5-carboxamide; N-[(3R)-1-azabicyclo[2.2.2]oct-3-yl]-2-(6-fluoropyridin-2-yl)-1,3-thiazole-5-carboxamide; N-[(3R)-1-azabicyclo[2.2.2]oct-3-yl ]-2-(5-fluoropyridin-2-yl)-1,3-thiazole-5-carboxamide; N-[(3R)-1-azabicyclo[2.2.2]oct-3-yl]-2-(4-fluoropyridin-2-yl)-1,3-thiazole-5-carboxamide;

N-[(3R)-1-azabicyclo[2.2.2]oct-3-yl]-2-(3-fluoropyridin-2-yl]-1,3-thiazole-5-carboxamide; N-[(3R)-1-azabicyclo[2.2.2]oct-3-yl]-2-(2-fluoropyridin-2-yl)-1,3-thiazole-5-carboxamide; N-[(3R)-1-azabicyclo[2.2.2]oct-3-yl]-2-(6-fluoropyridin-3-yl)-1,3-thiazole-5-carboxamide; N-[(3R)-1-azabicyclo[2.2.2]oct-3-yl-2-(5-fluoropyridin-3-y)-1,3-thiazole-5-carboxamide; N-[(3R)-1-azabicyclo[2.2.2]oct-3-yl]-2-(4-fluoropyridin-3-yl)-1,3-thiazole-5-carboxamide; N-[(3R)-1-azabicyclo[2.2.2]oct-3-yl]-2-(2-fluoropyridin-3-yl)-1,3-thiazole-5-carboxamide; N-[(3R)-1-azabicyclo[2.2.2]oct-3-yl]-2-(2-fluoropyridin)-yl)-1,3-thiazole-5-carboxamide; N-[(3R)-1-azabicyclo[2.2.2]oct-3-yl)-2-(3-fluoropyridin-4-yl)-1,3-thiazole-5-carboxamide;

N-[(3R)-1-azabicyclo[2.2.2]oct-3-yl]-5-(methylthio)-1,3-thiazole-2-carboxamide; N-[(3R)-1-azabicyclo[2.2.2]oct-3-yl]-5-chloro-1,3-thiazole-2-carboxamide; N-[(3R)-1-azabicyclo[2.2.2]oct-3-yl]-5-bromo-1,3-thiazole-2-carboxamide; N-[(3R)-1-azabicyclo[2.2.2]oct-3-yl]-5-(phenylthio)-1,3-thiazole-2-carboxamide; N-[(3R)-1-azabicyclo[2.2.2]oct-3-yl]-5-[(2-fluorophenyl)thio]-1,3-thiazole-2-carboxamide; N-[(3R)-1-azabicyclo[2.2.2]oct-3-yl]-5-[(3-fluorophenyl)thio]-1,3-thiazole-2-carboxamide; N-[(3R)-1-azabicyclo[2.2.2]oct-3-yl]-5-[(4-fluorophenyl)thio]-1,3-thiazole-2-carboxamide; N-[(3R)-1-azabicyclo[2.2.2]oct-3-yl]-5-[(2-chlorophenyl)thio]-1,3-thiazole-2-carboxamide; N-[(3R)-1-azabicyclo[2.2.2]oct-3-yl]-5-[(3-chlorophenyl)thio]-1,3-thiazole-2-carboxamide; N-[(3R)-1-azabicyclo[2.2.2]oct-3-yl]-5-[(4-chlorophenyl)thio]-1,3-thiazole-2-carboxamide; N-[(3R)-1-azabicyclo[2.2.2]oct-3-yl]-5-phenoxy-1,3-thiazole-2-carboxamide; N-[(3R)-1-azabicyclo[2.2.2]oct-3-yl]-5-(2-fluorophenoxy)-1,3-thiazole-2-carboxamide; N-[(3R)-1-azabicyclo[2.2.2]oct-3-yl]-5-(3-fluorophenoxy)-1,3-thiazole-2-carboxamide; N-[(3R)-1-azabicyclo[2.2.2]oct-3-yl]-5-(4-fluorophenoxy)-1,3-thiazole-2-carboxamide; N-[(3R)-1-azabicyclo[2.2.2]oct-3-yl]-5-(2-chlorophenoxy)-1,3-thiazole-2-carboxamide; N-[(3R)-1-azabicyclo[2.2.2]oct-3-yl]-5-(3-chlorophenoxy)-1,3-thiazole-2-carboxamide; N-[(3R)-1-azabicyclo[2.2.2]oct-3-yl]-5-(4-chlorophenoxy)-1,3-thiazole-2-carboxamide; N-[(3R)-1-azabicyclo[2.2.2]oct-3-yl)]-5-thien-3-yl-1,3-thiazole-2-carboxamide; N-[(3R)-1-azabicyclo[2.2.2]oct-3-yl]-5-(2,4-difluorophenyl)-1,3-thiazole-2-carboxamide; N-[(3R)-1-azabicyclo[2.2.2]oct-3-yl]-5-(3,5-difluorophenyl)-1,3-thiazole-2-carboxamide; N-[(3R)-1-azabicyclo[2.2.2]oct-3-yl]-5-(2,4-dichlorophenyl)-1,3-thiazole-2-carboxamide; N-[(3R)-1-azabicyclo[2.2.2]oct-3-yl]-5-(3,5-dichlorophenyl)-1,3-thiazole-2-carboxamide; N-[(3R)-1-azabicyclo[2.2.2]oct-3-yl]-5-(2-bromophenyl)-1,3-thiazole-2-carboxamide; N-[(3R)-1-azabicyclo[2.2.2]oct-3-yl]-5-(3-bromophenyl)-1,3-thiazole-2-carboxamide; N-[(3R)-1-azabicyclo[2.2.2]oct-3-yl]-5-(2-cyanophenyl)-1,3-thiazole-2-carboxamide; N-[(3R)-1-azabicyclo[2.2.2]oct-3-yl]-5-(3-cyanophenyl)-1,3-thiazole-2-carboxamide; N-[(3R)-1-azabicyclo[2.2.2]oct-3-yl]-5-(4-cyanophenyl)-1,3-thiazole-2-carboxamide; N-[(3R)-1-azabicyclo[2.2.2]oct-3-yl]-5-(2-hydroxyphenyl)-1,3-thiazole-2-carboxamide; N-[(3R)-1-azabicyclo[2.2.2]oct-3-yl]-5-(3-hydroxyphenyl)-1,3-thiazole-2-carboxamide; N-[(3R)-1-azabicyclo[2.2.2]oct-3-yl]-5-(4-hydroxyphenyl)-1,3-thiazole-2-carboxamide; N-[(3R)-1-azabicyclo[2.2.2]oct-3-yl]-5-(2-nitrophenyl)-1,3-thiazole-2-carboxamide; N-[(3R)-1-azabicyclo[2.2.2]oct-3-yl]-5-(4-nitrophenyl)-1,3-thiazole-2-carboxamide; N-[(3R)-1-azabicyclo[2.2.2]oct-3-yl]-5-(2-methylphenyl)-1,3-thiazole-2-carboxamide; N-[(3R)-1-azabicyclo[2.2.2]oct-3-yl]-5-(3-methylphenyl)-1,3-thiazole-2-carboxamide; N-[(3R)-1-azabicyclo[2.2.2]oct-3-yl]-5-(4-methylphenyl)-1,3-thiazole-2-carboxamide; N-[(3R)-1-azabicyclo[2.2.2]oct-3-yl]-5-(2-aminophenyl)-1,3-thiazole-2-carboxamide; N-[(3R)-1-azabicyclo[2.2.2]oct-3-yl]-5-(3-aminophenyl)-1,3-thiazole-2-carboxamide; N-[(3R)-1-azabicyclo[2.2.2]oct-3-yl]-5-(4-aminophenyl)-1,3-thiazole-2-carboxamide; N-[(3R)-1-azabicyclo[2.2.2]oct-3-yl]-5-[(2-(acetylamino)phenyl]-1,3-thiazole-2-carboxamide; N-[(3R)-1-azabicyclo[2.2.2]oct-3-yl]-5-[3-(acetylamino)phenyl]-1,3-thiazole-2-carboxamide; N-[(3R)-1-azabicyclo[2.2.2]oct-3-yl]-5-[4-(acetylamino)phenyl]-1,3-thiazole-2-carboxamide; N-[(3R)-1-azabicyclo[2.2.2]oct-3-yl]-5-(pyridin-2-yl)-1,3-thiazole-2-carboxamide; N-[(3R)-1-azabicyclo[2.2.2]oct-3-yl]-5-(pyridin-3-yl)-1,3-thiazole-2-carboxamide; N-[(3R)-1-azabicyclo[2.2.2]oct-3-yl]-5-(pyridin-4-yl)-1,3-thiazole-2-carboxamide; N-[(3R)-1-azabicyclo[2.2.2]oct-3-yl]-5-(3-fluoropyridin-2-yl)-1,3-thiazole-2-carboxamide; N-[(3R)-1-azabicyclo[2.2.2]oct-3-yl]-5-(4-fluoropyridin-2-yl)-1,3-thiazole-2-carboxamide; N-[(3R)-1-azabicyclo[2.2.2]oct-3-yl]-5-(5-fluoropyridin-2-y 1)-1,3-thiazole-2-carboxamide; N-[(3R)-1-azabicyclo[2.2.2]oct-3-yl]-5-(6-fluoropyridin-2-yl)-1,3-thiazole-2-carboxamide; N-[(3R)-1-azabicyclo[2.2.2]oct-3-yl]-5-(2-fluoropyridin-3-yl)-1,3-thiazole-2-carboxamide; N-[(3R)-1-azabicyclo[2.2.2]oct-3-yl]-5-(4-fluoropyridin-3-yl)-1,3-thiazole-2-carboxamide; N-[(3R)-1-azabicyclo[2.2.2]oct-3-yl]-5-(5-fluoropyridin-3-yl)-1,3-thiazole-2-carboxamide; N-[(3R)-1-azabicyclo[2.2.2]oct-3-yl]-5-(6-fluoropyridin-3-yl)-1,3-thiazole-2-carboxamide; N-[(3R)-1-azabicyclo[2.2.2]oct-3-yl]-5-(2-fluoropyridin-4-yl)-1,3-thiazole-2-carboxamide; N-[(3R)-1-azabicyclo[2.2.2]oct-3-yl]-5-[(2-methoxyphenyl)thio]-1,3-thiazole-2-carboxamide; N-[(3R)-1-azabicyclo[2.2.2]oct-3-yl]-5-[(3-methoxyphenyl)thio]-1,3-thiazole-2-carboxamide; N-[(3R)-1-azabicyclo[2.2.2]oct-3-yl]-5-[(4-methoxyphenyl)thio]-1,3-thiazole-2-carboxamide; N-[(3R)-1-azabicyclo[2.2.2]oct-3-yl]-5-[(2-methylphenyl)thio]-1,3-thiazole-2-carboxamide; N-[(3R)-1-azabicyclo[2.2.2]oct-3-yl]-5-[(3-methylphenyl)thiol-1,3-thiazole-2-carboxamide; N-[(3R)-1-azabicyclo[2.2.2]oct-3-yl]-5-1(4-methylphenyl)thio]-1,3-thiazole-2-carboxamide; N-[(3R)-1-azabicyclo[2.2.2]oct-3-yl]-5-([4-(acetylamino)phenyl]thio)-1,3-thiazole-2-carboxamide; N-[(3R)-1-azabicyclo[2.2.2]oct-3-yl]-5-[(4-aminophenyl)thio]-1,3-thiazole-2-carboxamide; N-[(3R)-1-azabicyclo[2.2.2]oct-3-yl]-5-[(4-hydroxyphenyl)thio]-1,3-thiazole-2-carboxamide; N-[(3R)-1-azabicyclo[2.2.2]oct-3-yl]-5-(2-methylphenoxy)-1,3-thiazole-2-carboxamide; N-[(3R)-1-azabicyclo[2.2.2]oct-3-yl]-5-(3-methylphenoxy)-1,3-thiazole-2-carboxamide; N-[(3R)-1-azabicyclo[2.2.2]oct-3-yl]-5-(4-methylphenoxy)-1,3-thiazole-2-carboxamide; N-[(3R)-1-azabicyclo[2.2.2]oct-3-yl]-5-(2-methoxyphenoxy)-1,3-thiazole-2-carboxamide; N-[(3R)-1-azabicyclo[2.2.2]oct-3-yl]-5-(3-methoxyphenoxy)-1,3-thiazole-2-carboxamide; N-[(3R)-1-azabicyclo[2.2.2]oct-3-yl]-5-(4-methoxyphenoxy)-1,3-thiazole-2-carboxamide; N-[(3R)-1-azabicyclo[2.2.2]oct-3-yl]-5-(4-hydroxyphenoxy)-1,3-thiazole-2-carboxamide; N-[(3R)-1-azabicyclo[2.2.2]oct-3-yl]-5-(4-aminophenoxy)-1,3-thiazole-2-carboxamide; N-[(3R)-1-azabicyclo[2.2.2]oct-3-yl]-5-[4-(acetylamino)phenoxy]-1,3-thiazole-2-carboxamide; N-[(3R)-1-azabicyclo[2.2.2]oct-3-yl]-5-(2-fluorophenyl)-4-methyl-1,3-thiazole-2-carboxamide; N-[(3R)-1-azabicyclo[2.2.2]oct-3-yl]-5-(3-fluorophenyl)-4-methyl-1,3-thiazole-2-carboxamide; N-[(3R)-1-azabicyclo[2.2.2]oct-3-yl]-5-(2-chlorophenyl)-4-methyl-1,3-thiazole-2-carboxamide; N-[(3R)-1-azabicyclo[2.2.2]oct-3-yl]-5-(3-chlorophenyl)-4-methyl-1,3-thiazole-2-carboxamide; N-[(3R)-1-azabicyclo[2.2.2]oct-3-yl]-5-(2-methoxyphenyl)-4-methyl-1,3-thiazole-2-carboxamide; N-[(3R)-1-azabicyclo[2.2.2]oct-3-yl]-5-(3- methoxyphenyl)-4-methyl-1,3-thiazole-2-carboxamide; N-[(3R)-1-azabicyclo[2.2.2]oct-3-yl]-4-methyl-5-thien-2-yl-1,3-thiazole-2-carboxamide, N-[(2S,3R)-2-methyl-1-azabicyclo[2.2.2]oct-3-yl]-2-(2,3-difluorophenyl)-1,3-thiazole-5-carboxamide; N-[(2S,3R)-2-methyl-1-azabicyclo[2.2.2]oct-3-yl]-2-(2,4-difluorophenyl)-1,3-thiazole-5-carboxamide; N-[(2S,3R)-2-methyl-1-azabicyclo[2.2.2]oct-3-yl]-2-(2,5-difluorophenyl)-1,3-thiazole-5-carboxamide; N-[(2S,3R)-2-methyl-1-azabicyclo[2.2.2]oct-3-yl]-2-(2,6-difluorophenyl)-1,3-thiazole-5-carboxamide; N-[(2S,3R)-2-methyl-1-azabicyclo[2.2.2]oct-3-yl]-2-(3,4-difluorophenyl)-1,3-thiazole-5-carboxamide; N-[(2S,3R)-2-methyl-1-azabicyclo[2.2.2]oct-3-yl]-2-(3,5-difluorophenyl)-1,3-thiazole-5-carboxamide; N-[(2S,3R)-2-methyl-1-azabicyclo[2.2.2]oct-3-yl]-2-(2-chlorophenyl)-1,3-thiazole-5-carboxamide; N-[(2S,3R)-2-methyl-1-azabicyclo[2.2.2]oct-3-yl]-2-(3-chlorophenyl)-1,3-thiazole-5-carboxamide; N-[(2S,3R)-2-methyl-1-azabicyclo[2.2.2]oct-3-yl]-2-(4-chlorophenyl)-1,3-thiazole-5-carboxamide; N-[(2S,3R)-2-methyl-1-azabicyclo[2.2.2]oct-3-yl]-2-(2-bromophenyl)-1,3-thiazole-5-carboxamide; N-[(2S,3R)-2-methyl-1-azabicyclo[2.2.2]oct-3-yl]-2-(3-bromophenyl)-1,3-thiazole-5-carboxamide; N-[(2S,3R)-2-methyl-1-azabicyclo[2.2.2]oct-3-yl]-2-(4-bromophenyl)-1,3-thiazole-5-carboxamide; N-[(2S,3R)-2-methyl-1-azabicyclo[2.2.2]oct-3-yl]-2-(2-cyanophenyl)-1,3-thiazole-5-carboxamide; N-[(2S,3R)-2-methyl-1-azabicyclo[2.2.2]oct-3-yl]-2-(3-cyanophenyl)-1,3-thiazole-5-carboxamide; N-[(2S,3R)-2-methyl-1-azabicyclo[2.2.2]oct-3-yl]-2-(4-cyanophenyl)-1,3-thiazole-5-carboxamide; N-[(2S,3R)-2-methyl-1-azabicyclo[2.2.2]oct-3-yl]-2-(2-nitrophenyl)-1,3-thiazole-5-carboxamide; N-[(2S,3R)-2-methyl-1-azabicyclo[2.2.2]oct-3-yl]-2-(3-nitrophenyl)-1,3-thiazole-5-carboxamide; N-[(2S,3R)-2-methyl-1-azabicyclo[2.2.2]oct-3-yl]-2-(4-nitrophenyl)-1,3-thiazole-5-carboxamide; N-[(2S,3R)-2-methyl-1-azabicyclo[2.2.2]oct-3-yl]-2-(2-methylphenyl)-1,3-thiazole-5-carboxamide; N-[(2S,3R)-2-methyl-1-azabicyclo[2.2.2]oct-3-yl]-2-(3-methylphenyl)-1,3-thiazole-5-carboxamide; N-[(2S,3R)-2-methyl-1-azabicyclo[2.2.2]oct-3-yl]-2-(2-aminophenyl)-1,3-thiazole-5-carboxamide; N-[(2S,3R)-2-methyl-1-azabicyclo[2.2.2]oct-3-yl]-2-(3-aminophenyl)-1,3-thiazole-5-carboxamide; N-[(2S,3R)-2-methyl-1-azabicyclo[2.2.2]ot-3-yl]-2-(4-aminophenyl)-1,3-thiazole-5-carboxamide; N-[(2S,3R)-2-methyl-1-azabicyclo[2.2.2]oct-3-yl]-2-[2-(methylamino)phenyl]-1,3-thiazole-5-carboxamide; N-[(2S,3R)-2-methyl-1-azabicyclo[2.2.2]oct-3-yl-2-[3-(methylamino)phenyl]-1,3-thiazole-5-carboxamide; N-[(2S,3R)-2-methyl-1-azabicyclo[2.2.2]oct-3-yl]-2-[4-(methylamino)phenyl]-1,3-thiazole-5-carboxamide; N-[(2S,3R)-2-methyl-1-azabicyclo[2.2.2]oct-3-yl]-2-[2-(acetylamino)phenyl]-1,3-thiazole-5-carboxamide; N-[(2S,3R)-2-methyl-1-azabicyclo[2.2.2]oct-3-yl]-2-[3-(acetylamino)phenyl]-1,3-thiazole-5-carboxamide; N-[(2S,3R)-2-methyl-1-azabicyclo[2.2.2]oct-3-yl]-2-[4-(acetylamino)phenyl]-1,3-thiazole-5-carboxamide; N-[(2S,3R)-2-methyl-1-azabicyclo[2.2.2]oct-3-yl]-2-(2-[(trifluoroacetyl)amino]phenyl)-1,3-thiazole-5-carboxamide; N-[(2S,3R)-2-methyl-1-azabicyclo[2.2.2]oct-3-yl]-2-(3-[(trifluoroacetyl)amino phenyl)-1,3-thiazole-5-carboxamide; N-[(2S,3R)-2-methyl-1-azabicyclo[2.2.2]oct-3-yl]-2-(4-[(trifluoroacetyl)amino]phenyl)-1,3-thiazole-5-carboxamide; N-[(2S,3R)-2-methyl-1-azabicyclo[2.2.2]oct-3-yl]-2-(2-[(methylsulfonyl)amino]phenyl)-1,3-thiazole-5-carboxamide; N-[(2S,3R)-2-methyl-1-azabicyclo[2.2.2]oct-3-yl]-2-(3-[(methylsulfonyl)amino]phenyl)-1,3-thiazole-5-carboxamide; N-[(2S,3R)-2-methyl-1-azabicyclo[2.2.2]oct-3-yl]-2-(4-[(methylsulfonyl)amino]phenyl)-1,3-thiazole-5-carboxamide; N-[(2S,3R)-2-methyl-1-azabicyclo[2.2.2]oct-3-yl]-2-(3-hydroxyphenyl)-1,3-thiazole-5-carboxamide; N-[(2S,3R)-2-methyl-1-azabicyclo[2.2.2]oct-3-yl]-2-(4-hydroxyphenyl)-1,3-thiazole-5-carboxamide; N-[(2S,3R)-2-methyl-1-azabicyclo[2.2.2]oct-3-yl]-2-(2-methoxyphenyl)-1,3-thiazole-5-carboxamide; N-[(2S,3R)-2-methyl-1-azabicyclo[2.2.2]oct-3-yl]-2-(3-methoxyphenyl)-1,3-thiazole-5-carboxamide; N-[(2S,3R)-2-methyl-1-azabicyclo[2.2.2]oct-3-yl]-2-(4-methoxyphenyl)-1,3-thiazole-5-carboxamide; N-[(2S,3R)-2-methyl-1-azabicyclo[2.2.2]oct-3-yl]-2-[2-(trifluoromethoxy)phenyl]-1,3-thiazole-5-carboxamide; N-[(2S,3R)-2-methyl-1-azabicyclo[2.2.2]oct-3-yl]-2-[3-(trifluoromethoxy)phenyl]-1,3-thiazole-5-carboxamide; N-[(2S,3R)-2-methyl-1-azabicyclo[2.2.2]oct-3-yl]-2-[4-(trifluoromethoxy)phenyl]-1,3-thiazole-5-carboxamide; N-[(2S,3R)-2-methyl-1-azabicyclo[2.2.2]oct-3-yl]-2-pyridin-2-yl-1,3-thiazole-5-carboxamide; N-[(2S,3R)-2-methyl-1-azabicyclo[2.2.2]oct-3-yl]-2-pyridin-3-yl-1,3-thiazole-5-carboxamide; N-[(2S,3R)-2-methyl-1-azabicyclo[2.2.2]oct-3-yl]-2-pyridin-4-yl-1,3-thiazole-5-carboxamide; N-[(2S,3R)-2-methyl-1-azabicyclo[2.2.2]oct-3-yl]-2-(6-fluoropyridin-2-yl)-1,3-thiazole-5-carboxamide; N-[(2S,3R)-2-methyl-1-azabicyclo[2.2.2]oct-3-yl]-2-(5-fluoropyridin-2-yl)-1,3-thiazole-5-carboxamide; N-[(2S,3R)-2-methyl-1-azabicyclo[2.2.2]oct-3-yl]-2-(4-fluoropyridin-2-yl)-1,3-thiazole-5-carboxamide; N-[(2S,3R)-2-methyl-1-azabicyclo[2.2.2]oct-3-yl]-2-(3-fluoropyridin-2-yl)-1,3-thiazole-5-carboxamide; N-[(2S,3R)-2-methyl-1-azabicyclo[2.2.2]oct-3-yl]-2-(2-fluoropyridin-2-yl)-1,3-thiazole-5-carboxamide; N-[(2S,3R)-2-methyl-1-azabicyclo[2.2.2]oct-3-yl)-2-(6-fluoropyridin-3-yl)-1,3-thiazole-5-carboxamide; N-[(2S,3R)-2-methyl-1-azabicyclo[2.2.2]oct-3-yl]-2-(5-fluoropyridin-3-yl)-1,3-thiazole-5-carboxamide; N-[(2S,3R)-2-methyl-1-azabicyclo[2.2.2]oct-3-yl]-2-(4-fluoropyridin-3-yl)-1,3-thiazole-5-carboxamide; N-[(2S,3R)-2-methyl-1-azabicyclo[2.2.2]oct-3-yl]-2-(2-fluoropyridin-3-yl)-1,3-thiazole-5-carboxamide; N-[(2S,3R)-2-methyl-1-azabicyclo[2.2.2]oct-3-yl]-2-(2-fluoropyridin-4-yl)-1,3-thiazole-5-carboxamide; N-[(2S,3R)-2-methyl-1-azabicyclo[2.2.2]oct-3-yl]-2-(3-fluoropyridin-4-yl)-1,3-thiazole-5-carboxamide;

N-[(2S,3R)-2-methyl-1-azabicyclo[2.2.2]oct-3-yl]-5-(methylthio)-1,3-thiazole-2-carboxamide; N-[(2S,3R)-2-methyl-1-azabicyclo[2.2.2]oct-3-yl]-5-chloro-1,3-thiazole-2-carboxamide; N-[(2S,3R)-2-methyl-1-azabicyclo[2.2.2]oct-3-yl]-5-bromo-1,3-thiazole-2-carboxamide, N-[(2S,3R)-2-methyl-1-azabicyclo[2.2.2]oct-3-yl]-5-(phenylthio)-1,3-thiazole-2-carboxamide; N-[(2S,3R)-2-methyl-1-azabicyclo[2.2.2]oct-3-yl]-5-[(2-fluorophenyl)thio]-1,3-thiazole-2-carboxamide; N-[(2S,3R)-2-methyl-1-azabicyclo[2.2.2]oct-3-yl]-5-[(3-fluorophenyl)thio]-1,3-thiazole-2-carboxamide; N-[(2S,3R)-2-methyl-1-azabicyclo[2.2.2]oct-3-yl]-5-[(4-fluorophenyl)thio]-1,3-thiazole-2-carboxamide; N-[(2S,3R)-2-methyl-1-azabicyclo[2.2.2]oct-3-yl]-5-[(2-chlorophenyl)thio]-1,3-thiazole-2-carboxamide; N-[(2S,3R)-2-methyl-1-azabicyclo[2.2.2]oct-3-yl]-5-[(3-chlorophenyl)thio]-1,3-thiazole-2-carboxamide; N-[(2S,3R)-2-methyl-1-azabicyclo[2.2.2]oct-3-yl]-5-[(4-chlorophenyl)thio]-1,3-thiazole-2-carboxamide; N-[(2S,3R)-2-methyl-1-azabicyclo[2.2.2]oct-3-yl]-5-phenoxy-1,3-thiazole-2-carboxamide; N-[(2S,3R)-2-methyl-1-azabicyclo[2.2.2]oct-3-yl]-5-(2-fluorophenoxy)-1,3-thiazole-2-carboxamide; N-[(2S,3R)-2-methyl-1-azabicyclo[2.2.2]oct-3-yl]-5-(3-fluorophenoxy)-1,3-thiazole-2-carboxamide; N-[(2S,3R)-2-methyl-1-azabicyclo[2.2.2]oct-3-yl]-5-(4- fluorophenoxy)-1,3-thiazole-2-carboxamide; N-[(2S,3R)-2-methyl-1-azabicyclo[2.2.2]oct-3-yl]-5-(2-chlorophenoxy)-1,3-thiazole-2-carboxamide; N-[(2S,3R)-2-methyl-1-azabicyclo[2.2.2]oct-3-yl]-5-(3-chlorophenoxy)-1,3-thiazole-2-carboxamide; N-[(2S,3R)-2-methyl-1-azabicyclo[2.2.2]oct-3-yl]-5-(4-chlorophenoxy)-1,3-thiazole-2-carboxamide; N-[(2S,3R)-2-methyl-1-azabicyclo[2.2.2]oct-3-yl]-5-thien-3-yl-1,3-thiazole-2-carboxamide; N-[(2S,3R)-2-methyl-1-azabicyclo[2.2.2]oct-3-yl]-5-(2,4-difluorophenyl)-1,3-thiazole-2-carboxamide; N-[(2S,3R)-2-methyl-1-azabicyclo[2.2.2]oct-3-yl]-5-(3,5-difluorophenyl)-1,3-thiazole-2-carboxamide; N-[(2S,3R)-2-methyl-1-azabicyclo[2.2.2]oct-3-yl]-5-(2,4-dichlorophenyl)-1,3-thiazole-2-carboxamide; N-[(2S,3R)-2-methyl-1-azabicyclo[2.2.2]oct-3-yl]-5-(3,5-dichlorophenyl)-1,3-thiazole-2-carboxamide; N-[(2S,3R)-2-methyl-1-azabicyclo[2.2.2]oct-3-yl]-5-(2-bromophenyl)-1,3-thiazole-2-carboxamide; N-[(2S,3R)-2-methyl-1-azabicyclo[2.2.2]oct-3-yl]-5-(3-bromophenyl)-1,3-thiazole-2-carboxamide; N-[(2S,3R)-2-methyl-1-azabicyclo[2.2.2]oct-3-yl]-5-(2-cyanophenyl)-1,3-thiazole-2-carboxamide; N-[(2S,3R)-2-methyl-1-azabicyclo[2.2.2]oct-3-yl]-5-(3-cyanophenyl)-1,3-thiazole-2-carboxamide; N-[(2S,3R)-2-methyl-1-azabicyclo[2.2.2]oct-3-yl]-5-(4-cyanophenyl)-1,3-thiazole-2-carboxamide; N-[(2S,3R)-2-methyl-1-azabicyclo[2.2.2]oct-3-yl]-5-(2-hydroxyphenyl)-1,3-thiazole-2-carboxamide; N-[(2S,3R)-2-methyl-1-azabicyclo[2.2.2]oct-3-yl]-5-(3-hydroxyphenyl)-1,3-thiazole-2-carboxamide; N-[(2S,3R)-2-methyl-1-azabicyclo[2.2.2]oct-3-yl]-5-(4-hydroxyphenyl)-1,3-thiazole-2-carboxamide; N-[(2S,3R)-2-methyl-1-azabicyclo[2.2.2]oct-3-yl]-5-(2-nitrophenyl)-1,3-thiazole-2-carboxamide; N-[(2S,3R)-2-methyl-1-azabicyclo[2.2.2]oct-3-yl]-5-(4-nitrophenyl)-1,3-thiazole-2-carboxamide; N-[(2S,3R)-2-methyl-1-azabicyclo[2.2.2]oct-3-yl]-5-(2-methylphenyl)-1,3-thiazole-2-carboxamide; N-1(2S,3R)-2-methyl-1-azabicyclo[2.2.2]oct-3-yl]-5-(3-methylphenyl)-1,3-thiazole-2-carboxamide; N-[(2S,3R)-2-methyl-1-azabicyclo[2.2.2]oct-3-yl]-5-(4-methylphenyl)-1,3-thiazole-2-carboxamide; N-[(2S,3R)-2-methyl-1-azabicyclo[2.2.2]oct-3-yl]-5-(2-aminophenyl)-1,3-thiazole-2-carboxamide; N-[(2S,3R)-2-methyl-1-azabicyclo[2.2.2]oct-3-yl]-5-(3-aminophenyl)-1,3-thiazole-2-carboxamide; N-[(2S,3R)-2-methyl-1-azabicyclo[2.2.2]oct-3-yl]-5-(4-aminophenyl)-1,3-thiazole-2-carboxamide; N-[(2S,3R)-2-methyl-1-azabicyclo[2.2.2]oct-3-yl]-5-[2-(acetylamino)phenyl]-1,3-thiazole-2-carboxamide; N-[(2S,3R)-2-methyl-1-azabicyclo[2.2.2]oct-3-yl]-5-[3-(acetylamino)phenyl]-1,3-thiazole-2-carboxamide; N-[(2S,3R)-2-methyl-1-azabicyclo[2.2.2]oct-3-yl]-5-[4-(acetylamino)phenyl]-1,3-thiazole-2-carboxamide; N-[(2S,3R)-2-methyl-1-azabicyclo[2.2.2]oct-3-yl]-5-(pyridin-2-yl)-1,3-thiazole-2-carboxamide; N-[(2S,3R)-2-methyl-1-azabicyclo[2.2.2]oct-3-yl]-5-(pyridin-3-yl)-1,3-thiazole-2-carboxamide; N-[(2S,3R)-2-methyl-1-azabicyclo[2.2.2]oct-3-yl]-5-(pyridin-4-yl)-1,3-thiazole-2-carboxamide; N-[(2S,3R)-2-methyl-1-azabicyclo[2.2.2]oct-3-yl]-5-(3-fluoropyridin-2-yl)-1,3-thiazole-2-carboxamide; N-[(2S,3R)-2-methyl-1-azabicyclo[2.2.2]oct-3-yl]-5-(4-fluoropyridin-2-yl)-1,3-thiazole-2-carboxamide; N-[(2S,3R)-2-methyl-1-azabicyclo[2.2.2]oct-3-yl]-5-(5-fluoropyridin-2-yl)-1,3-thiazole-2-carboxamide; N-[(2S,3R)-2-methyl-1-azabicyclo[2.2.2]oct-3-yl]-5-(6-fluoropyridin-2-yl)-1,3-thiazole-2-carboxamide; N-[(2S,3R)-2-methyl-1-azabicyclo[2.2.2]oct-3-yl]-5-(2-fluoropyridin-3-yl)-1,3-thiazole-2-carboxamide; N-[(2S,3R)-2-methyl-1-azabicyclo[2.2.2]oct-3-yl]-5-(4-fluoropyridin-3-yl)-1,3-thiazole-2-carboxamide; N-[(2S,3R)-2-methyl-1-azabicyclo[2.2.2]oct-3-yl]-5-(5-fluoropyridin-3-yl)-1,3-thiazole-2-carboxamide; N-[(2S,3R)-2-methyl-1-azabicyclo[2.2.2]oct-3-yl]-5-(6-fluoropyridin-3-yl)-1,3-thiazole-2-carboxamide; N-[(2S,3R)-2-methyl-1-azabicyclo[2.2.2]oct-3-yl]-5-(2-fluoropyridin-4-yl)-1,3-thiazole-2-carboxamide; N-[(2S,3R)-2-methyl-1-azabicyclo[2.2.2]oct-3-yl]-5-[(2-methoxyphenyl)thio]-1,3-thiazole-2-carboxamide; N-[(2S,3R)-2-methyl-1-azabicyclo[2.2.2]oct-3-yl]-5-[(3-methoxyphenyl)thio]-1,3-thiazole-2-carboxamide; N-[(2S,3R)-2-methyl-1-azabicyclo[2.2.2]oct-3-yl]-5-[(4-methoxyphenyl)thio]-1,3-thiazole-2-carboxamide; N-[(2S,3R)-2-methyl-1-azabicyclo[2.2.2]oct-3-yl]-5-[(2-methylphenyl)thio]-1,3-thiazole-2-carboxamide; N-[(2S,3R)-2-methyl-1-azabicyclo[2.2.2]oct-3-yl]-5-[(3-methylphenyl)thio]-1,3-thiazole-2-carboxamide; N-[(2S,3R)-2-methyl-1-azabicyclo[2.2.2]oct-3-yl]-5-[(4-methylphenyl)thio]-1,3-thiazole-2-carboxamide; N-[(2S,3R)-2-methyl-1-azabicyclo[2.2.2]oct-3-yl]-5-([4-(acetylamino)phenylthio)-1,3-thiazole-2-carboxamide; N-[(2S,3R)-2-methyl-1-azabicyclo[2.2.2]oct-3-yl]-5-[(4-aminophenyl)thio]-1,3-thiazole-2-carboxamide; N-[(2S,3R)-2-methyl-1-azabicyclo[2.2.2]oct-3-yl]-5-[(4-hydroxyphenyl)thio]-1,3-thiazole-2-carboxamide; N-[(2S,3R)-2-methyl-1-azabicyclo[2.2.2]oct-3-yl]-5-(2-methylphenoxy)-1,3-thiazole-2-carboxamide; N-[(2S,3R)-2-methyl-1-azabicyclo[2.2.2]oct-3-yl]-5-(3-methylphenoxy)-1,3-thiazole-2-carboxamide; N-[(2S,3R)-2-methyl-1-azabicyclo[2.2.2]oct-3-yl]-5-(4-methylphenoxy)-1,3-thiazole-2-carboxamide; N-[(2S,3R)-2-methyl-1-azabicyclo[2.2.2]oct-3-yl]-5-(2-methoxyphenoxy)-1,3-thiazole-2-carboxamide; N-[(2S,3R)-2-methyl-1-azabicyclo[2.2.2]oct-3-yl]-5-(3-methoxyphenoxy)-1,3-thiazole-2-carboxamide; N-[(2S,3R)-2-methyl-1-azabicyclo[2.2.2]oct-3-yl]-5-(4-methoxyphenoxy)-1,3-thiazole-2-carboxamide; N-1(2S,3R)-2-methyl-1-azabicyclo[2.2.2]oct-3-yl]-5-(4-hydroxyphenoxy)-1,3-thiazole-2-carboxamide; N-[(2S,3R)-2-methyl-1-azabicyclo[2.2.2]oct-3-yl]-5-(4-aminophenoxy)-1,3-thiazole-2-carboxamide; N-[(2S,3R)-2-methyl-1-azabicyclo[2.2.2]oct-3-yl]-5-[4-(acetylamino)phenoxy-1,3-thiazole-2-carboxamide; N-[(2S,3R)-2-methyl-1-azabicyclo[2.2.2]oct-3-yl]-5-(2-fluorophenyl)-4-methyl-1,3-thiazole-2-carboxamide; N-[(2S,3R)-2-methyl-1-azabicyclo[2.2.2]oct-3-yl]-5-(3-fluorophenyl)-4-methyl-1,3-thiazole-2-carboxamide; N-[(2S,3R)-2-methyl-1-azabicyclo[2.2.2]oct-3-yl]-5-(2-chlorophenyl)-4-methyl-1,3-thiazole-2-carboxamide; N-[(2S,3R)-2-methyl-1-azabicyclo[2.2.2]oct-3-yl]-5-(3-chlorophenyl)-4-methyl-1,3-thiazole-2-carboxamide; N-[(2S,3R)-2-methyl-1-azabicyclo[2.2.2]oct-3-yl]-5-(2-methoxyphenyl)-4-methyl-1,3-thiazole-2-carboxamide; N-[(2S,3R)-2-methyl-1-azabicyclo[2.2.2]oct-3-yl]-5-(3-methoxyphenyl)-4-methyl-1,3-thiazole-2-carboxamide;

N-[(2S,3R)-2-methyl-1-azabicyclo[2.2.2]oct-3-yl]-4-methyl-5-thien-2-yl-1,3-thiazole-2-carboxamide, N-[(2S,3R)-2-methyl-1-azabicyclo[2.2.2]oct-3-yl]-5-phenyl-1,3-thiazole-2-carboxamide; N-[(2S,3R)-2-methyl-1-azabicyclo[2.2.2]oct-3-yl]-5-phenyl-4-methyl-1,3-thiazole-2-carboxamide; N-[(2S,3R)-2-methyl-1-azabicyclo[2.2.2]oct-3-yl]-5-(2-fluorophenyl)-1,3-thiazole-2-carboxamide; N-[(2S,3R)-2-methyl-1-azabicyclo[2.2.2]oct-3-yl]-5-(3-fluorophenyl)-1,3-thiazole-2-carboxamide; N-[(2S,3R)-2-methyl-1-azabicyclo[2.2.2]oct-3-yl]-5-(4-fluorophenyl)-1,3-thiazole-2-carboxamide; N-[(2S,3R)-2-methyl-1-azabicyclo[2.2.2]oct-3-yl]-5-thien-2-yl-1,3-thiazole-2-carboxamide; N-[(2S,3R)-2-methyl-1-azabicyclo[2.2.2]oct- 3-yl]-5-(2-chlorophenyl)-1,3-thiazole-2-carboxamide; N-[(2S,3R)-2-methyl-1-azabicyclo[2.2.2]oct-3-yl]-5-(3-chlorophenyl)-1,3-thiazole-2-carboxamide; N-[(2S,3R)-2-methyl-1-azabicyclo[2.2.2]oct-3-yl]-5-(4-chlorophenyl)-1,3-thiazole-2-carboxamide; N-[(2S,3R)-2-methyl-1-azabicyclo[2.2.2]oct-3-yl]-5-(4-bromophenyl)-1,3-thiazole-2-carboxamide; N-[(2S,3R)-2-methyl-1-azabicyclo[2.2.2]oct-3-yl]-5-(3-nitrophenyl)-1,3-thiazole-2-carboxamide; N-[(2S,3R)-2-methyl-1-azabicyclo[2.2.2]oct-3-yl]-5-(2-methoxyphenyl)-1,3-thiazole-2-carboxamide; N-[(2S,3R)-2-methyl-1-azabicyclo[2.2.2]oct-3-yl]-5-(3-methoxyphenyl)-1,3-thiazole-2-carboxamide; N-[(2S,3R)-2-methyl-1-azabicyclo[2.2.2]oct-3-yl]-5-(4-methoxyphenyl)-1,3-thiazole-2-carboxamide; N-[(2S,3R)-2-methyl-1-azabicyclo[2.2.2]oct-3-yl]-2-(2-hydroxyphenyl)-1,3-thiazole-5-carboxamide; N-[(2S,3R)-2-methyl-1-azabicyclo[2.2.2]oct-3-yl]-2-(4-methylphenyl)-1,3-thiazole-5-carboxamide; N-[(2S,3R)-2-methyl-1-azabicyclo[2.2.2]oct-3-yl]-2-phenyl-1,3-thiazole-5-carboxamide; N-[(2S,3R)-2-methyl-1-azabicyclo[2.2.2]oct-3-yl]-2-(2-fluorophenyl)-1,3-thiazole-5-carboxamide; N-[(2S,3R)-2-methyl-1-azabicyclo[2.2.2]oct-3-yl]-2-(3-fluorophenyl)-1,3-thiazole-5-carboxamide; N-[-(2S,3R)-2-methyl-1-azabicyclo[2.2.2]oct-3-yl]-2-(4-fluorophenyl)-1,3-thiazole-5-carboxamide; N-[(3R)-1-azabicyclo[2.2.2]oct-3-yl]-5-phenylsulfanyl-1,3-oxazole-2-carboxamide; N-[(3R)-1-azabicyclo[2.2.2]oct-3-yl]-5-(2-fluorophenylsulfanyl)-1,3-oxazole-2-carboxamide; N-[(3R)-1-azabicyclo[2.2.2]oct-3-yl]-5-(3-fluorophenylsulfanyl)-1,3-oxazole-2-carboxamide; N-[(3R)-1-azabicyclo[2.2.2]oct-3-yl]-5-(4-fluorophenylsulfanyl)-1,3-oxazole-2-carboxamide; N-[(3R)-1-azabicyclo[2.2.2]oct-3-yl]-5-(3,4-difluorophenylsulfanyl)-1,3-oxazole-2-carboxamide; N-[(3R)-1-azabicyclo[2.2.2]oct-3-yl]-5-(2,4-difluorophenylsulfanyl)-1,3-oxazole-2-carboxamide; N-[(3R)-1-azabicyclo[2.2.2]oct-3-yl]-5-(3,5-difluorophenylsulfanyl)-1,3-oxazole-2-carboxamide; N-[(3R)-1-azabicyclo[2.2.2]oct-3-yl]-5-(2-chlorophenylsulfanyl)-1,3-oxazole-2-carboxamide; N-[(3R)-1-azabicyclo[2.2.2]oct-3-yl]-5-(3-chlorophenylsulfanyl)-1,3-oxazole-2-carboxamide; N-[(3R)-1-azabicyclo[2.2.2]oct-3-yl]-5-(4-chlorophenylsulfanyl)-1,3-oxazole-2-carboxamide; N-[(3R)-1-azabicyclo[2.2.2]oct-3-yl]-5-(3,4-dichlorophenylsulfanyl)-1,3-oxazole-2-carboxamide; N-[(3R)-1-azabicyclo[2.2.2]oct-3-yl]-5-(2,4-dichlorophenylsulfanyl)-1,3-oxazole-2-carboxamide; N-[(3R)-1-azabicyclo[2.2.2]oct-3-yl]-5-(3,5-dichlorophenylsulfanyl)-1,3-oxazole-2-carboxamide; N-[(3R)-1-azabicyclo[2.2.2]oct-3-yl]-5-(2-fluorophenyl)-1,3-oxazole-2-carboxamide; N-[(3R)-1-azabicyclo[2.2.2]oct-3-yl]-5-(3-fluorophenyl)-1,3-oxazole-2-carboxamide; N-[(3R)-1-azabicyclo[2.2.2]oct-3-yl]-5-(3,4-difluorophenyl)-1,3-oxazole-2-carboxamide; N-[(3R)-1-azabicyclo[2.2.2]oct-3-yl]-5-(2,4-difluorophenyl)-1,3-oxazole-2-carboxamide; N-[(3R)-1-azabicyclo[2.2.2]oct-3-yl]-5-(3,5-difluorophenyl)-1,3-oxazole-2-carboxamide; N-[(3R)-1-azabicyclo[2.2.2]oct-3-yl]-5-(4-chlorophenyl)-1,3-oxazole-2-carboxamide; N-[(3R)-1-azabicyclo[2.2.2]oct-3-yl]-5-(3,4-dichlorophenyl)-1,3-oxazole-2-carboxamide; N-[(3R)-1-azabicyclo[2.2.2]oct-3-yl]-5-(2,4-dichlorophenyl)-1,3-oxazole-2-carboxamide; N-[(3R)-1-azabicyclo[2.2.2]oct-3-yl]-5-(3,5-dichlorophenyl)-1,3-oxazole-2-carboxamide; N-[(3R)-1-azabicyclo[2.2.2]oct-3-yl]-5-(2-bromophenyl)-1,3-oxazole-2-carboxamide; N-[(3R)-1-azabicyclo[2.2.2]oct-3-yl]-5-(3-bromophenyl)-1,3-oxazole-2-carboxamide; N-[(3R)-1-azabicyclo[2.2.2]oct-3-yl]-5-(2-cyanophenyl)-1,3-oxazole-2-carboxamide; N-[(3R)-1-azabicyclo[2.2.2]oct-3-yl]-5-(4-cyanophenyl)-1,3-oxazole-2-carboxamide; N-[(3R)-1-azabicyclo[2.2.2]oct-3-yl]-5-(2-hydroxyphenyl)-1,3-oxazole-2-carboxamide; N-[(3R)-1-azabicyclo[2.2.2]oct-3-yl]-5-(3-hydroxyphenyl)-1,3-oxazole-2-carboxamide; N-[(3R)-1-azabicyclo[2.2.2]oct-3-yl]-5-(4-hydroxyphenyl)-1,3-oxazole-2-carboxamide; N-[(3R)-1-azabicyclo[2.2.2]oct-3-yl]-5-(4-nitrophenyl)-1,3-oxazole-2-carboxamide; N-[(3R)-1-azabicyclo[2.2.2]oct-3-yl]-5-(2-methylphenyl)-1,3-oxazole-2-carboxamide; N-[(3R)-1-azabicyclo[2.2.2]oct-3-yl]-5-(3-methylphenyl)-1,3-oxazole-2-carboxamide; N-[(3R)-1-azabicyclo[2.2.2]oct-3-yl]-5-(4-methylphenyl)-1,3-oxazole-2-carboxamide; N-[(3R)-1-azabicyclo[2.2.2]oct-3-yl]-5-(2-methylaminophenyl)-1,3-oxazole-2-carboxamide; N-[(3R)-1-azabicyclo[2.2.2]oct-3-yl]-5-(3-methylaminophenyl)-1,3-oxazole-2-carboxamide; N-[(3R)-1-azabicyclo[2.2.2]oct-3-yl]-5-(4-methylaminophenyl)-1,3-oxazole-2-carboxamide; N-[(3R)-1-azabicyclo[2.2.2]oct-3-yl]-5-(2-aminophenyl)-1,3-oxazole-2-carboxamide; N-[(3R)-1-azabicyclo[2.2.2]oct-3-yl]-5-(3-aminophenyl)-1,3-oxazole-2-carboxamide; N-[(3R)-1-azabicyclo[2.2.2]oct-3-yl]-5-(4-aminophenyl)-1,3-oxazole-2-carboxamide; N-[(3R)-1-azabicyclo[2.2.2]oct-3-yl]-5-[2-(acetylamino)phenyl]-1,3-oxazole-2-carboxamide; N-[(3R)-1-azabicyclo[2.2.2]oct-3-yl]-5-[3-(acetylamino)phenyl]-1,3-oxazole-2-carboxamide; N-[(3R)-1-azabicyclo[2.2.2]oct-3-yl]-5-[4-(acetylamino)phenyl-1,3-oxazole-2-carboxamide; N-[(3R)-1-azabicyclo[2.2.2]oct-3-yl]-5-(pyridin-2-yl)-1,3-oxazole-2-carboxamide; N-[(3R)-1-azabicyclo[2.2.2]oct-3-yl]-5-(pyridin-3-yl)-1,3-oxazole-2-carboxamide; N-[(3R)-1-azabicyclo[2.2.2]oct-3-yl]-5-(pyridin-4-yl)-1,3-oxazole-2-carboxamide; N-[(3R)-1-azabicyclo[2.2.2]oct-3-yl]-5-(3-fluoropyridin-2-yl)-1,3-oxazole-2-N-[(3R)-1-azabicyclo[2.2.2]oct-3-yl-(3-5(4-fluoropyridin-2-yl-1,3-oxazole-2-carboxamide; N-[(3R)-1-azabicyclo[2.2.2]oct-3-yl]5-(5-fluoropyridin-2-yl)-1,3-oxazole-2-carboxamide; N-[(3R)-1-azabicyclo[2.2.2]oct-3-yl]-5-(6-fluoropyridin-2-yl)-1,3-oxazole-2-carboxamide; N-[(3R)-1-azabicyclo[2.2.2]oct-3-yl]-5-(2-fluoropyridin-3-yl)-1,3-oxazole-2-carboxamide; N-[(3R)-1-azabicyclo[2.2.2]oct-3-yl]-5-(4-fluoropyridin-3-yl)-1,3-oxazole-2-carboxamide; N-1(3R)-1-azabicyclo[2.2.2]oct-3-yl]-5-(5-fluoropyridin-3-yl)-1,3-oxazole-2-carboxamide; N-[(3R)-1-azabicyclo[2.2.2]oct-3-yl]-5-(6-fluoropyridin-3-yl)-1,3-oxazole-2-carboxamide; N-[(3R)-1-azabicyclo[2.2.2]oct-3-yl]-5-(2-fluoropyridin-4-yl)-1,3-oxazole-2-carboxamide; N-[(3R)-1-azabicyclo[2.2.2]oct-3-yl]-5-(2-fluoropyridin-3-yl)-1,3-oxazole-2-carboxamide; N-[(3R)-1-azabicyclo[2.2.2]oct-3-yl]-5-phenoxy-1,3-oxazole-2-carboxamide; N-[(3R)-1-azabicyclo[2.2.2]oct-3-yl]-5-(2-fluorophenoxy)-1,3-oxazole-2-carboxamide; N-[(3R)-1-azabicyclo[2.2.2]oct-3-yl]-5-(3-fluorophenoxy)-1,3-oxazole-2-carboxamide; N-[(3R)-1-azabicyclo[2.2.2]oct-3-yl]-5-(4-fluorophenoxy)-1,3-oxazole-2-carboxamide; N-[(3R)-1-azabicyclo[2.2.2]oct-3-yl]-5-(3,4-difluorophenoxy)-1,3-oxazole-2-carboxamide; N-[(3R)-1-azabicyclo[2.2.2]oct-3-yl]-5-(2,4-difluorophenoxy)-1,3-oxazole-2-carboxamide; N-[(3R)-1-azabicyclo[2.2.2]oct-3-yl]-5-(3,5-difluorophenoxy)-1,3-oxazole-2-carboxamide; N-[(3R)-1-azabicyclo[2.2.2]oct-3-yl]-5-(2-chlorophenoxy)-1,3-oxazole-2-carboxamide; N-[(3R)-1-azabicyclo[2.2.2]oct-3-yl]-5-(3-chlorophenoxy)-1,3-oxazole-2-carboxamide; N-[(3R)-1-azabicyclo[2.2.2]oct-3-yl]-5-(4-chlorophenoxy)-1,3-oxazole-2-carboxamide; N-[(3R)-1 azabicyclo[2.2.2]oct-3-yl]-5-(3,4-dichlorophenoxy)-1,3-oxazole-2-carboxamide; N-[(3R)-1-azabicyclo[2.2.2]oct-3-yl]-5-(2,4-dichlorophenoxy)-1,3- oxazole-2-carboxamide; N-[(3R)-1-azabicyclo[2.2.2]oct-3-yl]-5-(3,5-dichlorophenoxy)-1,3-oxazole-2-carboxamide;

N-[(2S,3R)-2-methyl-1-azabicyclo[2.2.2]oct-3-yl]-5-phenylsulfanyl-1,3-oxazole-2-carboxamide; N-[(2S,3R)-2-methyl-1-azabicyclo[2.2.2]oct-3-yl]-5-(2-fluorophenylsulfanyl)-1,3-oxazole-2-carboxamide; N-[(2S,3R)-2-methyl-1-azabicyclo[2.2.2]oct-3-yl]-5-(3-fluorophenylsulfanyl)-1,3-oxazole-2-carboxamide; N-[(2S,3R)-2-methyl-1-azabicyclo[2.2.2]oct-3-yl-5-(4-fluorophenylsulfanyl)-1,3-oxazole-2-carboxamide; N-[(2S,3R)-2-methyl-1-azabicyclo[2.2.2]oct-3-yl]-5-(3,4-difluorophenylsulfanyl)-1,3-oxazole-2-carboxamide; N-[(2S,3R)-2-methyl-1-azabicyclo[2.2.2]oct-3-yl]-5-(2,4-difluorophenylsulfanyl)-1,3-oxazole-2-carboxamide; N-[(2S,3R)-2-methyl-1-azabicyclo[2.2.2]oct-3-yl]-5-(3,5-difluorophenylsulfanyl)-1,3-oxazole-2-carboxamide; N-[(2S,3R)-2-methyl-1-azabicyclo[2.2.2]oct-3-yl]-5-(2-chlorophenylsulfanyl)-1,3-oxazole-2-carboxamide; N-[(2S,3R)-2-methyl-1-azabicyclo[2.2.2]oct-3-yl-5-(3-chlorophenylsulfanyl)-1,3-oxazole-2-carboxamide; N-[(2S,3R)-2-methyl-1-azabicyclo[2.2.2]oct-3-yl]-5-(4-chlorophenylsulfanyl)-1,3-oxazole-2-carboxamide; N-[(2S,3R)-2-methyl-1-azabicyclo[2.2.2]oct-3-yl]-5-(3,4-dichlorophenylsulfanyl)-1,3-oxazole-2-carboxamide; N-[(2S,3R)-2-methyl-1-azabicyclo[2.2.2]oct-3-yl]-5-(2,4-dichlorophenylsulfanyl)-1,3-oxazole-2-carboxamide; N-[(2S,3R)-2-methyl-1-azabicyclo[2.2.2]oct-3-yl]-5-(3,5-dichlorophenylsulfanyl)-1,3-oxazole-2-carboxamide; N-[(2S,3R)-2-methyl-1-azabicyclo[2.2.2]oct-3-yl]-5-(2-fluorophenyl)-1,3-oxazole-2-carboxamide; N-[(2S,3R)-2-methyl-1-azabicyclo[2.2.2]oct-3-yl]-5-(3-fluorophenyl)-1,3-oxazole-2-carboxamide; N-[(2S,3R)-2-methyl-1-azabicyclo[2.2.2]oct-3-yl]-5-(3,4-difluorophenyl)-1,3-oxazole-2-carboxamide; N-[(2S,3R)-2-methyl-1-azabicyclo[2.2.2]oct-3-yl]-5-(2,4-difluorophenyl)-1,3-oxazole-2-carboxamide; N-[(2S,3R)-2-methyl-1-azabicyclo[2.2.2]oct-3-yl]-5-(3,5-difluorophenyl)-1,3-oxazole-2-carboxamide; N-[(2S,3R)-2-methyl-1-azabicyclo[2.2.2]oct-3-yl]-5-(4-chlorophenyl)-1,3-oxazole-2-carboxamide; N-[(2S,3R)-2-methyl-1-azabicyclo[2.2.2]oct-3-yl]-5-(3,4-dichlorophenyl)-1,3-oxazole-2-carboxamide; N-[(2S,3R)-2-methyl-1-azabicyclo[2.2.2]oct-3-yl]-5-(2,4-dichlorophenyl)-1,3-oxazole-2-carboxamide; N-[(2S,3R)-2-methyl-1-azabicyclo[2.2.2]oct-3-yl]-5-(3,5-dichlorophenyl)-1,3-oxazole-2-carboxamide; N-[(2S,3R)-2-methyl-1-azabicyclo[2.2.2]oct-3-yl]-5-(2-bromophenyl)-1,3-oxazole-2-carboxamide; N-[(2S,3R)-2-methyl-1-azabicyclo[2.2.2]oct-3-yl]-5-(3-bromophenyl)-1,3-oxazole-2-carboxamide; N-[(2S,3R)-2-methyl-1-azabicyclo[2.2.2]oct-3-yl]-5-(2-cyanophenyl)-1,3-oxazole-2-carboxamide; N-1(2S,3R)-2-methyl-1-azabicyclo[2.2.2]oct-3-yl]-5-(4-cyanophenyl)-1,3-oxazole-2-carboxamide; N-[(2S,3R)-2-methyl-1-azabicyclo[2.2.2]oct-3-yl]-5-(2-hydroxyphenyl)-1,3-oxazole-2-carboxamide; N-[(2S,3R)-2-methyl-1-azabicyclo[2.2.2]oct-3-yl]-5-(3-hydroxyphenyl)-1,3-oxazole-2-carboxamide; N-[(2S,3R)-2-methyl-1-azabicyclo[2.2.2]oct-3-yl]-5-(4-hydroxyphenyl)-1,3-oxazole-2-carboxamide; N-[(2S,3R)-2-methyl-1-azabicyclo[2.2.2]oct-3-yl]-5-(4-nitrophenyl)-1,3-oxazole-2-carboxamide; N-[(2S,3R)-2-methyl-1-azabicyclo[2.2.2]oct-3-yl]-5-(2-methylphenyl)-1,3-oxazole-2-carboxamide; N-[(2S,3R)-2-methyl-1-azabicyclo[2.2.2]oct-3-yl]-5-(3-methylphenyl)-1,3-oxazole-2-carboxamide; N-[(2S,3R)-2-methyl-1-azabicyclo[2.2.2]oct-3-yl]-5-(4-methylphenyl)-1,3-oxazole-2-carboxamide; N-[(2S,3R)-2-methyl-1-azabicyclo[2.2.2]oct-3-yl]-5-(2-methylaminophenyl)-1,3-oxazole-2-carboxamide; N-[(2S,3R)-2-methyl-1-azabicyclo[2.2.2]oct-3-yl]-5-(3-methylaminophenyl)-1,3-oxazole-2-carboxamide; N-[(2S,3R)-2-methyl-1-azabicyclo[2.2.2]oct-3-yl]-5-(4-methylaminophenyl)-1,3-oxazole-2-carboxamide; N-[(2S,3R)-2-methyl-1-azabicyclo[2.2.2]oct-3-yl]-5-(2-aminophenyl)-1,3-oxazole-2-carboxamide; N-[(2S,3R)-2-methyl-1-azabicyclo[2.2.2]oct-3-yl]-5-(3-aminophenyl)-1,3-oxazole-2-carboxamide; N-[(2S,3R)-2-methyl-1-azabicyclo[2.2.2]oct-3-yl]-5-(4-aminophenyl)-1,3-oxazole-2-carboxamide; N-[(2S,3R)-2-methyl-1-azabicyclo[2.2.2]oct-3-yl]-5-[2-(acetylamino)phenyl]-1,3-oxazole-2-carboxamide; N-[(2S,3R)-2-methyl-1-azabicyclo[2.2.2]oct-3-yl]-5-13-(acetylamino)phenyl]-1,3-oxazole-2-carboxamide; N-[(2S,3R)-2-methyl-1-azabicyclo[2.2.2]oct-3-yl]-5-[4-(acetylamino)phenyl]-1,3-oxazole-2-carboxamide; N-[(2S,3R)-2-methyl-1-azabicyclo[2.2.2]oct-3-yl]-5-(pyridin-2-yl)-1,3-oxazole-2-carboxamide; N-[(2S,3R)-2-methyl-1-azabicyclo[2.2.2]oct-3-yl]-5-(pyridin-3-yl)-1,3-oxazole-2-carboxamide; N-[(2S,3R)-2-methyl-1-azabicyclo[2.2.2]oct-3-yl]-5-(pyridin-4-yl)-1,3-oxazole-2-carboxamide; N-[(2S,3R)-2-methyl-1-azabicyclo[2.2.2]oct-3-yl]-5-(3-fluoropyridin-2-yl)-1,3-oxazole-2-carboxamide; N-[(2S,3R)-2-methyl-1-azabicyclo[2.2.2]oct-3-yl]-5-(4-fluoropyridin-2-yl)-1,3-oxazole-2-carboxamide; N-[(2S,3R)-2-methyl-1-azabicyclo[2.2.2]oct-3-yl]-5-(5-fluoropyridin-2-yl)-1,3-oxazole-2-carboxamide; N-[(2S,3R)-2-methyl-1-azabicyclo[2.2.2]oct-3-yl]-5-(6-fluoropyridin-2-yl)-1,3-oxazole-2-carboxamide; N-[(2S,3R)-2-methyl-1-azabicyclo[2.2.2]oct-3-yl]-5-(2-fluoropyridin-3-yl)-1,3-oxazole-2-carboxamide; N-[(2S,3R)-2-methyl-1-azabicyclo[2.2.2]oct-3-yl]-5-(4-fluoropyridin-3-yl)—,3-oxazole-2-carboxamide; N-[(2S,3R)-2-methyl-1-azabicyclo[2.2.2]oct-3-yl]-5-(5-fluoropyridin-3-yl)-1,3-oxazole-2-carboxamide; N-[(2S,3R)-2-methyl-1-azabicyclo[2.2.2]oct-3-yl]-5-(6-fluoropyridin-3-yl)-1,3-oxazole-2-carboxamide; N-[(2S,3R)-2-methyl-1-azabicyclo[2.2.2]oct-3-yl]-5-(2-fluoropyridinyl)-1,3-oxazole-2-carboxamide; N-[(2S,3R)-2-methyl-1-azabicyclo[2.2.2]oct-3-yl]-5-(2-fluoropyridin-3-yl)-1,3-oxazole-2-carboxamide; N-[(2S,3R)-2-methyl-1-azabicyclo[2.2.2]oct-3-yl]-5-phenoxy-1,3-oxazole-2-carboxamide; N-[(2S,3R)-2-methyl-1-azabicyclo[2.2.2]oct-3-yl]-5-(2-fluorophenoxy)-1,3-oxazole-2-carboxamide; N-[(2S,3R)-2-methyl-1-azabicyclo[2.2.2]oct-3-yl]-5-(3-fluorophenoxy)-1,3-oxazole-2-carboxamide; N-[(2S,3R)-2-methyl-azabicyclo[2.2.2]oct-3-yl]-5-(4-fluorophenoxy)-1,3-oxazole-2-carboxamide; N-[(2S,3R)-2-methyl-1-azabicyclo[2.2.2]oct-3-yl]-5-(3,4-difluorophenoxy)-1,3-oxazole-2-carboxamide; N-[(2S,3R)-2-methyl-1-azabicyclo[2.2.2]oct-3-yl]-5-(2,4-difluorophenoxy)-1,3-oxazole-2-carboxamide; N-[(2S,3R)-2-methyl-1-azabicyclo[2.2.2]oct-3-yl]-5-(3,5-difluorophenoxy)-1,3-oxazole-2-carboxamide; N-[(2S,3R)-2-methyl-1-azabicyclo[2.2.2]oct-3-yl]-5-(2-chlorophenoxy)-1,3-oxazole-2-carboxamide; N-[(2S,3R)-2-methyl-1-azabicyclo[2.2.2]oct-3-yl]-5-(3-chlorophenoxy)-1,3-oxazole-2-carboxamide; N-[(2S,3R)-2-methyl-1-azabicyclo[2.2.2]oct-3-yl]-5-(4-chlorophenoxy)-1,3-oxazole-2-carboxamide; N-[(2S,3R)-2-methyl-1-azabicyclo[2.2.2]oct-3-yl]-5-(3,4-dichlorophenoxy)-1,3-oxazole-2-carboxamide; N-[(2S,3R)-2-methyl-1-azabicyclo[2.2.2]oct-3-yl]-5-(2,4-dichlorophenoxy)-1,3-oxazole-2-carboxamide; N-[(2S,3R)-2-methyl-1-azabicyclo[2.2.2]oct-3-yl]-5-(3,5-dichlorophenoxy)-1,3-oxazole-2-carboxamide;

N-[(3R)-1-azabicyclo[2.2.2]oct-3-yl]-5-bromo-1-methyl-1H-pyrrole-2-carboxamide; N-[(3R)-1-azabicyclo[2.2.2]oct-3-yl]-5-[2-(methylthio)phenyl]-1-methyl-1H-pyrrole-2-carboxamide; N-[(3R)-1-azabicyclo[2.2.2]oct-3-yl]-5-[4-(methylthio)phenyl]-1-methyl-1H-pyrrole-2-carboxamide;

N-[(3R)-1-azabicyclo[2.2.2]oct-3-yl]-5-phenyl-1H-pyrrole-2-carboxamide; N-[(3R)-1-azabicyclo[2.2.2]oct-3-yl]-5-(2-fluorophenyl)-1-methyl-1H-pyrrole-2-carboxamide; N-[(3R)-1-azabicyclo[2.2.2]oct-3-yl]-5-(3-fluorophenyl)-1-methyl-1H-pyrrole-2-carboxamide; N-[(3R)-1-azabicyclo[2.2.2]oct-3-yl]-5-(4-fluorophenyl)-1-methyl-1H-pyrrole-2-carboxamide; N-[(3R)-1-azabicyclo[2.2.2]oct-3-yl]-5-(2,3-difluorophenyl)-1-methyl-1H-pyrrole-2-carboxamide; N-[(3R)-1-azabicyclo[2.2.2]oct-3-yl]-5-(2,4-difluorophenyl)-1-methyl-1H-pyrrole-2-carboxamide; N-[(3R)-1-azabicyclo[2.2.2]oct-3-yl]-5-(2,6-difluorophenyl)-1-methyl-1H-pyrrole-2-carboxamide; N-[(3R)-1-azabicyclo[2.2.2]oct-3-yl]-5-(3,4-difluorophenyl)-1-methyl-1H-pyrrole-2-carboxamide; N-[(3R)-1-azabicyclo[2.2.2]oct-3-yl]-5-(3,5-difluorophenyl)-1-methyl-1H-pyrrole-2-carboxamide; N-[(3R)-1-azabicyclo[2.2.2]oct-3-yl]-5-(2,4,6-trifluorophenyl)-1-methyl-1H-pyrrole-2-carboxamide; N-[(3R)-1-azabicyclo[2.2.2]oct-3-yl]-5-(2-chlorophenyl)-1-methyl-1H-pyrrole-2-carboxamide; N-[(3R)-1-azabicyclo[2.2.2]oct-3-yl]-5-(3-chlorophenyl)-1-methyl-1H-pyrrole-2-carboxamide; N-[(3R)-1-azabicyclo[2.2.2]oct-3-yl]-5-(4-chlorophenyl)-1-methyl-1H-pyrrole-2-carboxamide; N-[(3R)-1-azabicyclo[2.2.2]oct-3-yl]-5-(2,4-dichlorophenyl)-1-methyl-1H-pyrrole-2-carboxamide; N-[(3R)-1-azabicyclo[2.2.2]oct-3-yl]-5-(3,4-dichlorophenyl)-1-methyl-1H-pyrrole-2-carboxamide; N-[(3R)-1-azabicyclo[2.2.2]oct-3-yl]-5-(3,5-dichlorophenyl)-1-methyl-1H-pyrrole-2-carboxamide; N-[(3R)-1-azabicyclo[2.2.2]oct-3-yl]-5-(2-bromophenyl)-1-methyl-1H-pyrrole-2-carboxamide; N-[(3R)-1-azabicyclo[2.2.2]oct-3-yl]-5-(3-bromophenyl)-1-methyl-1H-pyrrole-2-carboxamide; N-[(3R)-1-azabicyclo[2.2.2]oct-3-yl]-5-(4-bromophenyl)-1-methyl-1H-pyrrole-2-carboxamide; N-[(3R)-1-azabicyclo[2.2.2]oct-3-yl]-5-(2-hydroxyphenyl)-1-methyl-1H-pyrrole-2-carboxamide; N-[(3R)-1-azabicyclo[2.2.2]oct-3-yl]-5-(3-hydroxyphenyl)-1-methyl-1H-pyrrole-2-carboxamide; N-[(3R)-1-azabicyclo[2.2.2]oct-3-yl]-5-(4-hydroxyphenyl)-1-methyl-1H-pyrrole-2-carboxamide; N-[(3R)-1-azabicyclo[2.2.2]oct-3-yl]-5-(2-methoxyphenyl)-1-methyl-1H-pyrrole-2-carboxamide; N-[(3R)-1-azabicyclo[2.2.2]oct-3-yl]-5-(3-methoxyphenyl)-1-methyl-1H-pyrrole-2-carboxamide; N-[(3R)-1-azabicyclo[2.2.2]oct-3-yl]-5-(4-methoxyphenyl)-1-methyl-1H-pyrrole-2-carboxamide; N-[(3R)-1-azabicyclo[2.2.2]oct-3-yl]-5-(2-methylphenyl)-1-methyl-1H-pyrrole-2-carboxamide; N-[(3R)-1-azabicyclo[2.2.2]oct-3-yl]-5-(3-methylphenyl)-1-methyl-1H-pyrrole-2-carboxamide; N-[(3R)-1-azabicyclo[2.2.2]oct-3-yl]-5-(4-methylphenyl)-1-methyl-1H-pyrrole-2-carboxamide; N-[(3R)-1-azabicyclo[2.2.2]oct-3-yl]-5-(2-methylaminophenyl)-1-methyl-1H-pyrrole-2-carboxamide; N-[(3R)-1-azabicyclo[2.2.2]oct-3-yl]-5-(3-methylaminophenyl)-1-methyl-1H-pyrrole-2-carboxamide; N-[(3R)-1-azabicyclo[2.2.2]oct-3-yl]-5-(4-methylaminophenyl)-1-methyl-1H-pyrrole-2-carboxamide; N-[(3R)-1-azabicyclo[2.2.2]oct-3-yl]-5-(2-nitrophenyl)-1-methyl-1H-pyrrole-2-carboxamide; N-[(3R)-1-azabicyclo[2.2.2]oct-3-yl]-5-(3-nitrophenyl)-1-methyl-1H-pyrrole-2-carboxamide; N-[(3R)-1-azabicyclo[2.2.2]oct-3-yl]-5-(4-nitrophenyl)-1-methyl-1H-pyrrole-2-carboxamide; N-[(3R)-1-azabicyclo[2.2.2]oct-3-yl]-5-(2-aminophenyl)-1-methyl-1H-pyrrole-2-carboxamide; N-[(3R)-1-azabicyclo[2.2.2]oct-3-yl]-5-(3-aminophenyl)-1-methyl-1H-pyrrole-2-carboxamide; N-[(3R)-1-azabicyclo[2.2.2]oct-3-yl]-5-(4-aminophenyl)-1-methyl-1H-pyrrole-2-carboxamide; N-[(3R)-1-azabicyclo[2.2.2]oct-3-yl]-5-[2-(acetylamino)phenyl]-1-methyl-1H-pyrrole-2-carboxamide; N-[(3R)-1-azabicyclo[2.2.2]oct-3-yl]-5-[3-(acetylamino)phenyl]-1-methyl-1H-pyrrole-2-carboxamide; N-[(3R)-1-azabicyclo[2.2.2]oct-3-yl]-5-[4-(acetylamino)phenyl]-1-methyl-1H-pyrrole-2-carboxamide; N-[(3R)-1-azabicyclo[2.2.2]oct-3-yl]-5-(pyrid-2-yl)-1-methyl-1H-pyrrole-2-carboxamide; N-[(3R)-1-azabicyclo[2.2.2]oct-3-yl]-5-(pyrid-3-yl)-1-methyl-1H-pyrrole-2-carboxamide; N-[(3R)-1-azabicyclo[2.2.2]oct-3-yl]-5-(pyridin-4-yl)-1-methyl-1H-pyrrole-2-carboxamide; N-[(3R)-1-azabicyclo[2.2.2]oct-3-yl]-5-(3-fluoropyrid-2-yl)-1-methyl-1H-pyrrole-2-carboxamide; N-[(3R)-1-azabicyclo[2.2.2]oct-3-yl]-5-(4-fluoropyrid-2-yl)-1-methyl-1H-pyrrole-2-carboxamide; N-[(3R)-1-azabicyclo[2.2.2]oct-3-yl]-5-(5-fluoropyrid-2-yl)-1-methyl-1H-pyrrole-2-carboxamide; N-[(3R)-1-azabicyclo[2.2.2]oct-3-yl]-5-(6-fluoropyrid-2-yl)-1-methyl-1H-pyrrole-2-carboxamide; N-[(3R)-1-azabicyclo[2.2.2]oct-3-yl]-5-(2-fluoropyrid-3-yl)-1-methyl-1H-pyrrole-2-carboxamide; N-[(3R)-1-azabicyclo[2.2.2]oct-3-yl]-5-(4-fluoropyrid-3-yl)-1-methyl-1H-pyrrole-2-carboxamide; N-[(3R)-1-azabicyclo[2.2.2]oct-3-yl]-5-(5-fluoropyrid-3-yl)-1-methyl-1H-pyrrole-2-carboxamide; N-[(3R)-1-azabicyclo[2.2.2]oct-3-yl]-5-(6-fluoropyrid-3-yl)-1-methyl-1H-pyrrole-2-carboxamide; N-[(3R)-1-azabicyclo[2.2.2]oct-3-yl]-5-(2-fluoropyrid-4-yl)-1-methyl-1H-pyrrole-2-carboxamide; N-[(3R)-1-azabicyclo[2.2.2]oct-3-yl]-5-(3-fluoropyrid-4-yl)-1-methyl-1H-pyrrole-2-carboxamide; N-[(3R)-1-azabicyclo[2.2.2]oct-3-yl]-5-(2-cyanophenyl)-1-methyl-1H-pyrrole-2-carboxamide; N-[(3R)-1-azabicyclo[2.2.2]oct-3-yl]-5-(3-cyanophenyl)-1-methyl-1H-pyrrole-2-carboxamide; N-[(3R)-1-azabicyclo[2.2.2]oct-3-yl]-5-(4-cyanophenyl)-1-methyl-1H-pyrrole-2-carboxamide; N-[(3R)-1-azabicyclo[2.2.2]oct-3-yl]-5-(2-fluorophenyl)-1H-pyrrole-2-carboxamide; N-[(3R)-1-azabicyclo[2.2.2]oct-3-yl]-5-(3-fluorophenyl)-1H-pyrrole-2-carboxamide; N-[(3R)-1-azabicyclo[2.2.2]oct-3-yl]-5-(4-fluorophenyl)-1H-pyrrole-2-carboxamide; N-[(3R)-1-azabicyclo[2.2.2]oct-3-yl]-5-(3,5-difluorophenyl)-1H-pyrrole-2-carboxamide; N-[(3R)-1-azabicyclo[2.2.2]oct-3-yl]-5-(3,4-difluorophenyl)-1H-pyrrole-2-carboxamide; N-[(3R)-1-azabicyclo[2.2.2]oct-3-yl]-5-(2,4-difluorophenyl)-1H-pyrrole-2-carboxamide; N-[(3R)-1-azabicyclo[2.2.2]oct-3-yl]-5-(2-chlorophenyl)-1H-pyrrole-2-carboxamide; N-[(3R)-1-azabicyclo[2.2.2]oct-3-yl]-5-(3-chlorophenyl)-1H-pyrrole-2-carboxamide; N-[(3R)-1-azabicyclo[2.2.2]oct-3-yl]-5-(4-chlorophenyl)-1H-pyrrole-2-carboxamide; N-[(3R)-1-azabicyclo[2.2.2]oct-3-yl]-5-(3,5-chlorophenyl)-1H-pyrrole-2-carboxamide; N-[(3R)-1-azabicyclo[2.2.2]oct-3-yl]-5-(3,4-dichlorophenyl)-1H-pyrrole-2-carboxamide; N-[(3R)-1-azabicyclo[2.2.2]oct-3-yl]-5-(2,4-dichlorophenyl)-1H-pyrrole-2-carboxamide; N-[(3R)-1-azabicyclo[2.2.2]oct-3-yl]-5-(2-bromophenyl)-1H-pyrrole-2-carboxamide; N-[(3R)-1-azabicyclo[2.2.2]oct-3-yl]-5-(3-bromophenyl)-1H-pyrrole-2-carboxamide; N-[(3R)-1-azabicyclo[2.2.2]oct-3-yl]-5-(4-bromophenyl)-1H-pyrrole-2-carboxamide; N-[(3R)-1-azabicyclo[2.2.2]oct-3-yl]-5-(2-hydroxyphenyl)-1H-pyrrole-2-carboxamide; N-[(3R)-1-azabicyclo[2.2.2]oct-3-yl]-5-(3-hydroxyphenyl)-1H-pyrrole-2-carboxamide; N-[(3R)-1-azabicyclo[2.2.2]oct-3-yl]-5-(4-hydroxyphenyl)-1H-pyrrole-2-carboxamide; N-[(3R)-1-azabicyclo[2.2.2]oct-3-yl]-5-(2-methoxyphenyl)-1H-pyrrole-2-carboxamide; N-[(3R)-1-azabicyclo[2.2.2]oct-3-yl]-5-(3-methoxyphenyl)-1H-pyrrole-2-carboxamide; N-[(3R)-1-azabicyclo[2.2.2]oct-3-yl]-5-(4-methoxyphenyl)-1H-pyrrole-2-carboxamide; N-[(3R)-1-azabicyclo[2.2.2]oct-3-yl]-5-(2-methylphenyl)-1H-pyrrole-2-carboxamide; N-[(3R)-1-azabicyclo[2.2.2]

oct-3-yl]-5-(3-methylphenyl)-1H-pyrrole-2-carboxamide; N-[(3R)-1-azabicyclo[2.2.2]oct-3-yl]-5-(4-methylphenyl)-1H-pyrrole-2-carboxamide; N-[(3R)-1-azabicyclo[2.2.2]oct-3-yl]-5-(2-methylaminophenyl)-1H-pyrrole-2-carboxamide; N-[(3R)-1-azabicyclo[2.2.2]oct-3-yl]-5-(3-methylaminophenyl)-1H-pyrrole-2-carboxamide; N-[(3R)-1-azabicyclo[2.2.2]oct-3-yl]-5-(4-methylaminophenyl)-1H-pyrrole-2-carboxamide; N-[(3R)-1-azabicyclo[2.2.2]oct-3-yl]-5-(2-nitrophenyl)-1H-pyrrole-2-carboxamide; N-[(3R)-1-azabicyclo[2.2.2]oct-3-yl]-5-(3-nitrophenyl)-1H-pyrrole-2-carboxamide; N-[(3R)-1-azabicyclo[2.2.2]oct-3-yl]-5-(4-nitrophenyl)-1H-pyrrole-2-carboxamide; N-[(3R)-1-azabicyclo[2.2.2]oct-3-yl]-5-(2-aminophenyl)-1H-pyrrole-2-carboxamide; N-[(3R)-1-azabicyclo[2.2.2]oct-3-yl]-5-(3-aminophenyl)-1H-pyrrole-2-carboxamide; N-[(3R)-1-azabicyclo[2.2.2]oct-3-yl]-5-(4-aminophenyl)-1H-pyrrole-2-carboxamide; N-[(3R)-1-azabicyclo[2.2.2]oct-3-yl]-5-[2-(acetylamino)phenyl]-1H-pyrrole-2-carboxamide; N-[(3R)-1-azabicyclo[2.2.2]oct-3-yl]-5-[3-(acetylamino)phenyl]-1H-pyrrole-2-carboxamide; N-[(3R)-1-azabicyclo[2.2.2]oct-3-yl]-5-[4-(acetylamino)phenyl]-1H-pyrrole-2-carboxamide; N-[(3R)-1-azabicyclo[2.2.2]oct-3-yl]-5-(pyrid-2-yl)-1H-pyrrole-2-carboxamide; N-[(3R)-1-azabicyclo[2.2.2]oct-3-yl]-5-(pyrid-3-yl)-1H-pyrrole-2-carboxamide; N-[(3R)-1-azabicyclo[2.2.2]oct-3-yl]-5-(pyrid-4-yl)-1H-pyrrole-2-carboxamide; N-[(3R)-1-azabicyclo[2.2.2]oct-3-yl]-5-(3-fluoropyrid-2-yl)-1H-pyrrole-2-carboxamide; N-[(3R)-1-azabicyclo[2.2.2]oct-3-yl]-5-(4-fluoropyrid-2-yl)-1H-pyrrole-2-carboxamide; N-[(3R)-1-azabicyclo[2.2.2]oct-3-yl]-5-(5-fluoropyrid-2-yl)-1H-pyrrole-2-carboxamide; N-[(3R)-1-azabicyclo[2.2.2]oct-3-yl]-5-(6-fluoropyrid-2-yl)-1H-pyrrole-2-carboxamide; N-[(3R)-1-azabicyclo[2.2.2]oct-3-yl]-5-(2-fluoropyrid-3-yl)-1H-pyrrole-2-carboxamide; N-[(3R)-1-azabicyclo[2.2.2]oct-3-yl]-5-(4-fluoropyrid-3-yl)-1H-pyrrole-2-carboxamide; N-[(3R)-1-azabicyclo[2.2.2]oct-3-yl]-5-(5-fluoropyrid-3-yl)-1H-pyrrole-2-carboxamide; N-[(3R)-1-azabicyclo[2.2.2]oct-3-yl]-5-(6-fluoropyrid-3-yl)-1H-pyrrole-2-carboxamide; N-[(3R)-1-azabicyclo[2.2.2]oct-3-yl]-5-(2-fluoropyrid-4-yl)-1H-pyrrole-2-carboxamide; N-[(3R)-1-azabicyclo[2.2.2]oct-3-yl]-5-(3-fluoropyrid-4-yl)-1H-pyrrole-2-carboxamide; N-[(3R)-1-azabicyclo[2.2.2]oct-3-yl]-5-(2-cyanophenyl)-1H-pyrrole-2-carboxamide; N-[(3R)-1-azabicyclo[2.2.2]oct-3-yl]-5-(3-cyanophenyl)-1H-pyrrole-2-carboxamide; N-[(3R)-1-azabicyclo[2.2.2]oct-3-yl]-5-(4-cyanophenyl)-1H-pyrrole-2-carboxamide;

N-[(2S,3R)-2-methyl-1-azabicyclo[2.2.2]oct-3-yl]-5-bromo-1-methyl-1H-pyrrole-2-carboxamide; N-[(2S,3R)-2-methyl-1-azabicyclo[2.2.2]oct-3-yl]-5-[2-(methylthio)phenyl]-1-methyl-1H-pyrrole-2-carboxamide; N-[(2S,3R)-2-methyl-1-azabicyclo[2.2.2]oct-3-yl]-5-[4-(methylthio)phenyl]-1-methyl-1H-pyrrole-2-carboxamide; N-[(2S,3R)-2-methyl-1-azabicyclo[2.2.2]oct-3-yl]-5-phenyl-1H-pyrrole-2-carboxamide; N-[(2S,3R)-2-methyl-1-azabicyclo[2.2.2]oct-3-yl]-5-(2-fluorophenyl)-1-methyl-1H-pyrrole-2-carboxamide; N-[(2S,3R)-2-methyl-1-azabicyclo[2.2.2]oct-3-yl]-5-(3-fluorophenyl)-1-methyl-1H-pyrrole-2-carboxamide; N-[(2S,3R)-2-methyl-1-azabicyclo[2.2.2]oct-3-yl]-5-(4-fluorophenyl)-1-methyl-1H-pyrrole-2-carboxamide; N-[(2S,3R)-2-methyl-1-azabicyclo[2.2.2]oct-3-yl]-5-(2,3-difluorophenyl)-1-methyl-1H-pyrrole-2-carboxamide; N-[(2S,3R)-2-methyl-1-azabicyclo[2.2.2]oct-3-yl]-5-(2,4-difluorophenyl)-1-methyl-1H-pyrrole-2-carboxamide; N-[(2S,3R)-2-methyl-1-azabicyclo[2.2.2]oct-3-yl]-5-(2,6-difluorophenyl)-1-methyl-1H-pyrrole-2-carboxamide; N-[(2S,3R)-2-methyl-1-azabicyclo[2.2.2]oct-3-yl]-5-(3,4-difluorophenyl)-1-methyl-1H-pyrrole-2-carboxamide; N-[(2S,3R)-2-methyl-1-azabicyclo[2.2.2]oct-3-yl]-5-(3,5-difluorophenyl)-1-methyl-1H-pyrrole-2-carboxamide; N-[(2S,3R)-2-methyl-1-azabicyclo[2.2.2]oct-3-yl]-5-(2,4,6-trifluorophenyl)-1-methyl-1H-pyrrole-2-carboxamide; N-[(2S,3R)-2-methyl-1-azabicyclo[2.2.2]oct-3-yl]-5-(2-chlorophenyl)-1-methyl-1H-pyrrole-2-carboxamide; N-[(2S,3R)-2-methyl-1-azabicyclo[2.2.2]oct-3-yl]-5-(3-chlorophenyl)-1-methyl-1H-pyrrole-2-carboxamide; N-[(2S,3R)-2-methyl-1-azabicyclo[2.2.2]oct-3-yl]-5-(4-chlorophenyl)-1-methyl-1H-pyrrole-2-carboxamide; N-[(2S,3R)-2-methyl-1-azabicyclo[2.2.2]oct-3-yl]-5-(2,4-dichlorophenyl)-1-methyl-1H-pyrrole-2-carboxamide; N-[(2S,3R)-2-methyl-1-azabicyclo[2.2.2]oct-3-yl]-5-(3,4-dichlorophenyl)-1-methyl-1H-pyrrole-2-carboxamide; N-[(2S,3R)-2-methyl-1-azabicyclo[2.2.2]oct-3-yl]-5-(3,5-dichlorophenyl)-1-methyl-1H-pyrrole-2-carboxamide; N-[(2S,3R)-2-methyl-1-azabicyclo[2.2.2]oct-3-yl]-5-(2-bromophenyl)-1-methyl-1H-pyrrole-2-carboxamide; N-[(2S,3R)-2-methyl-1-azabicyclo[2.2.2]oct-3-yl]-5-(3-bromophenyl)-1-methyl-1H-pyrrole-2-carboxamide; N-[(2S,3R)-2-methyl-1-azabicyclo[2.2.2]oct-3-yl]-5-(4-bromophenyl)-1-methyl-1H-pyrrole-2-carboxamide; N-[(2S,3R)-2-methyl-1-azabicyclo[2.2.2]oct-3-yl]-5-(2-hydroxyphenyl)-1-methyl-1H-pyrrole-2-carboxamide; N-[(2S,3R)-2-methyl-1-azabicyclo[2.2.2]oct-3-yl]-5-(3-hydroxyphenyl)-1-methyl-1H-pyrrole-2-carboxamide; N-[(2S,3R)-2-methyl-1-azabicyclo[2.2.2]oct-3-yl]-5-(4-hydroxyphenyl)-1-methyl-1H-pyrrole-2-carboxamide; N-[(2S,3R)-2-methyl-1-azabicyclo[2.2.2]oct-3-yl]-5-(2-methoxyphenyl)-1-methyl-1H-pyrrole-2-carboxamide; N-[(2S,3R)-2-methyl-1-azabicyclo[2.2.2]oct-3-yl]-5-(3-methoxyphenyl)-1-methyl-1H-pyrrole-2-carboxamide; N-[(2S,3R)-2-methyl-1-azabicyclo[2.2.2]oct-3-yl]-5-(4-methoxyphenyl)-1-methyl-1H-pyrrole-2-carboxamide; N-[(2S,3R)-2-methyl-1-azabicyclo[2.2.2]oct-3-yl]-5-(2-methylphenyl)-1-methyl-1H-pyrrole-2-carboxamide; N-[(2S,3R)-2-methyl-1-azabicyclo[2.2.2]oct-3-yl]-5-(3-methylphenyl)-1-methyl-1H-pyrrole-2-carboxamide; N-[(2S,3R)-2-methyl 1-azabicyclo[2.2.2]oct-3-yl]-5-(4-methylphenyl)-1-methyl-1H-pyrrole-2-carboxamide; N-[(2S,3R)-2-methyl-1-azabicyclo[2.2.2]oct-3-yl]-5-(2-methyaminophenyl)-1-methyl-1H-pyrrole-2-carboxamide; N-[(2S,3R)-2-methyl-1-azabicyclo[2.2.2]oct-3-yl]-5-(3-methylaminophenyl)-1-methyl-1H-pyrrole-2-carboxamide; N-[(2S,3R)-2-methyl-1-azabicyclo[2.2.2]oct-3-yl]-5-(4-methylaminophenyl)-1-methyl-1H-pyrrole-2-carboxamide; N-[(2S,3R)-2-methyl-1-azabicyclo[2.2.2]oct-3-yl]-5-(2-nitrophenyl)-1-methyl-1H-pyrrole-2-carboxamide; N-[(2S,3R)-2-methyl-1-azabicyclo[2.2.2]oct-3-yl]-5-(3-nitrophenyl)-1-methyl-1H-pyrrole-2-carboxamide; N-[(2S,3R)-2-methyl-1-azabicyclo[2.2.2]oct-3-yl]-5-(4-nitrophenyl)-1-methyl-1H-pyrrole-2-carboxamide; N-[(2S,3R)-2-methyl-1-azabicyclo[2.2.2]oct-3-yl]-5-(2-aminophenyl)-1-methyl-1H-pyrrole-2-carboxamide; N-[(2S,3R)-2-methyl-1-azabicyclo[2.2.2]oct-3-yl]-5-(3-aminophenyl)-1-methyl-1H-pyrrole-2-carboxamide; N-[(2S,3R)-2-methyl-1-azabicyclo[2.2.2]oct-3-yl]-5-(4-aminophenyl)-1-methyl-1H-pyrrole-2-carboxamide; N-[(2S,3R)-2-methyl-1-azabicyclo[2.2.2]oct-3-yl]-5-[2-(acetylamino)phenyl]-1-methyl-1H-pyrrole-2-carboxamide; N-[(2S,3R)-2-methyl-1-azabicyclo[2.2.2]oct-3-yl]-5-[3-(acetylamino)phenyl]-1-methyl-1H-pyrrole-2-carboxamide; N-[(2S,3R)-2-methyl-1-azabicyclo[2.2.2]oct-3-yl]-5-[4-(acetylamino)phenyl]-1-methyl-1H-pyrrole-2-carboxamide; N-[(2S,3R)-2-methyl-1-azabicyclo[2.2.2]oct-3-yl]-5-(pyrid-2-yl)-1-methyl-1H-pyrrole-2-carboxamide;

N-[(2S,3R)-2-methyl-1-azabicyclo[2.2.2]oct-3-yl]-5-(pyrid-3-yl)-1-methyl-1H-pyrrole-2-carboxamide; N-[(2S,3R)-2-methyl-1-azabicyclo[2.2.2]oct-3-yl]-5-pyridin-4-yl-1-methyl-1H-pyrrole-2-carboxamide; N-[(2S,3R)-2-methyl-1-azabicyclo[2.2.2]oct-3-yl]-5-(3-fluoropyrid-2-yl)-1-methyl-1H-pyrrole-2-carboxamide; N-[(2S,3R)-2-methyl-1-azabicyclo[2.2.2]oct-3-yl]-5-(4-fluoropyrid-2-yl)-1-methyl-1H-pyrrole-2-carboxamide; N-[(2S,3R)-2-methyl-1-azabicyclo[2.2.2]oct-3-yl]-5-(5-fluoropyrid-2-yl)-1-methyl-1H-pyrrole-2-carboxamide; N-[(2S,3R)-2-methyl-1-azabicyclo[2.2.2]oct-3-yl]-5-(6-fluoropyrid-2-yl)-1-methyl-1H-pyrrole-2-carboxamide; N-[(2S,3R)-2-methyl-1-azabicyclo[2.2.2]oct-3-yl]-5-(2-fluoropyrid-3-yl)-1-methyl-1H-pyrrole-2-carboxamide; N-[(2S,3R)-2-methyl-1-azabicyclo[2.2.2]oct-3-yl]-5-(4-fluoropyrid-3-yl)-1-methyl-1H-pyrrole-2-carboxamide; N-[(2S,3R)-2-methyl-1-azabicyclo[2.2.2]oct-3-yl]-5-(5-fluoropyrid-3-yl)-1-methyl-1H-pyrrole-2-carboxamide; N-[(2S,3R)-2-methyl-1-azabicyclo[2.2.2]oct-3-yl]-5-(6-fluoropyrid-3-yl)-1-methyl-1H-pyrrole-2-carboxamide; N-[(2S,3R)-2-methyl-1-azabicyclo[2.2.2]oct-3-yl]-5-(2-fluoropyrid-4-yl)-1-methyl-1H-pyrrole-2-carboxamide; N-[(2S,3R)-2-methyl-1-azabicyclo[2.2.2]oct-3-yl]-5-(3-fluoropyrid-4-yl)-1-methyl-1H-pyrrole-2-carboxamide; N-[(2S,3R)-2-methyl-1-azabicyclo[2.2.2]oct-3-yl]-5-(2-cyanophenyl)-1-methyl-1H-pyrrole-2-carboxamide; N-[(2S,3R)-2-methyl-1-azabicyclo[2.2.2]oct-3-yl]-5-(3-cyanophenyl)-1-methyl-1H-pyrrole-2-carboxamide; N-[(2S,3R)-2-methyl-1-azabicyclo[2.2.2]oct-3-yl]-5-(4-cyanophenyl)-1-methyl-1H-pyrrole-2-carboxamide; N-[(2S,3R)-2-methyl-1-azabicyclo[2.2.2]oct-3-yl]-5-(2-fluorophenyl)-1H-pyrrole-2-carboxamide; N-[(2S,3R)-2-methyl-1-azabicyclo[2.2.2]oct-3-yl]-5-(3-fluorophenyl)-1H-pyrrole-2-carboxamide; N-[(2S,3R)-2-methyl-1-azabicyclo[2.2.2]oct-3-yl]-5-(4-fluorophenyl)-1H-pyrrole-2-carboxamide; N-[(2S,3R)-2-methyl-1-azabicyclo[2.2.2]oct-3-yl]-5-(3,5-difluorophenyl)-1H-pyrrole-2-carboxamide; N-[(2S,3R)-2-methyl-1-azabicyclo[2.2.2]oct-3-yl]-5-(3,4-difluorophenyl)-1H-pyrrole-2-carboxamide; N-[(2S,3R)-2-methyl-1-azabicyclo[2.2.2]oct-3-yl]-5-(2,4-difluorophenyl)-1H-pyrrole-2-carboxamide; N-[(2S,3R)-2-methyl-1-azabicyclo[2.2.2]oct-3-yl]-5-(2-chlorophenyl)-1H-pyrrole-2-carboxamide; N-[(2S,3R)-2-methyl-1-azabicyclo[2.2.2]oct-3-yl]-5-(3-chlorophenyl)-1H-pyrrole-2-carboxamide; N-[(2S,3R)-2-methyl-1-azabicyclo[2.2.2]oct-3-yl]-5-(4-chlorophenyl)-1H-pyrrole-2-carboxamide; N-[(2S,3R)-2-methyl-1-azabicyclo[2.2.2]oct-3-yl]-5-(3,5-dichlorophenyl)-1H-pyrrole-2-carboxamide; N-[(2S,3R)-2-methyl-1-azabicyclo[2.2.2]oct-3-yl]-5-(3,4-dichlorophenyl)-1H-pyrrole-2-carboxamide; N-[(2S,3R)-2-methyl-1-azabicyclo[2.2.2]oct-3-yl]-5-(2,4-dichlorophenyl)-1H-pyrrole-2-carboxamide; N-[(2S,3R)-2-methyl-1-azabicyclo[2.2.2]oct-3-yl]-5-(2-bromophenyl)-1H-pyrrole-2-carboxamide; N-[(2S,3R)-2-methyl-1-azabicyclo[2.2.2]oct-3-yl]-5-(3-bromophenyl)-1H-pyrrole-2-carboxamide; N-[(2S,3R)-2-methyl-1-azabicyclo[2.2.2]oct-3-yl]-5-(4-bromophenyl)-1H-pyrrole-2-carboxamide; N-[(2S,3R)-2-methyl-1-azabicyclo[2.2.2]oct-3-yl]-5-(2-hydroxyphenyl)-1H-pyrrole-2-carboxamide; N-[(2S,3R)-2-methyl-1-azabicyclo[2.2.2]oct-3-yl]-5-(3-hydroxyphenyl)-1H-pyrrole-2-carboxamide; N-[(2S,3R)-2-methyl-1-azabicyclo[2.2.2]oct-3-yl]-5-(4-hydroxyphenyl)-1H-pyrrole-2-carboxamide; N-[(2S,3R)-2-methyl-1-azabicyclo[2.2.2]oct-3-yl]-5-(2-methoxyphenyl)-1H-pyrrole-2-carboxamide; N-[(2S,3R)-2-methyl-1-azabicyclo[2.2.2]oct-3-yl]-5-(3-methoxyphenyl)-1H-pyrrole-2-carboxamide; N-[(2S,3R)-2-methyl-1-azabicyclo[2.2.2]oct-3-yl]-5-(4-methoxyphenyl)-1H-pyrrole-2-carboxamide; N-[(2S,3R)-2-methyl-1-azabicyclo[2.2.2]oct-3-yl]-5-(2-methylphenyl)-1H-pyrrole-2-carboxamide; N-[(2S,3R)-2-methyl-1-azabicyclo[2.2.2]oct-3-yl]-5-(3-methylphenyl)-1H-pyrrole-2-carboxamide; N-[(2S,3R)-2-methyl-1-azabicyclo[2.2.2]oct-3-yl]-5-(4-methylphenyl)-5H-pyrrole-2-carboxamide; N-[(2S,3R)-2-methyl-1-azabicyclo[2.2.2]oct-3-yl]-5-(2-methyaminophenyl)-1H-pyrrole-2-carboxamide; N-[(2S,3R)-2-methyl-1-azabicyclo[2.2.2]oct-3-yl]-5-(3-methylaminophenyl)-1H-pyrrole-2-carboxamide; N-[(2S,3R)-2-methyl-1-azabicyclo[2.2.2]oct-3-yl]-5-(4-methylaminophenyl)-1H-pyrrole-2-carboxamide; N-[(2S,3R)-2-methyl-1-azabicyclo[2.2.2]oct-3-yl]-5-(2-nitrophenyl)-1H-pyrrole-2-carboxamide; N-[(2S,3R)-2-methyl-1-azabicyclo[2.2.2]oct-3-yl]-5-(3-nitrophenyl)-1H-pyrrole-2-carboxamide; N-[(2S,3R)-2-methyl-1-azabicyclo[2.2.2]oct-3-yl]-5-(4-nitrophenyl)-1H-pyrrole-2-carboxamide; N-[(2S,3R)-2-methyl-1-azabicyclo[2.2.2]oct-3-yl]-5-(2-aminophenyl)-1H-pyrrole-2-carboxamide; N-[(2S,3R)-2-methyl-1-azabicyclo[2.2.2]oct-3-yl]-5-(3-aminophenyl)-1H-pyrrole-2-carboxamide; N-[(2S,3R)-2-methyl-1-azabicyclo[2.2.2]oct-3-yl]-5-(4-aminophenyl)-1H-pyrrole-2-carboxamide; N-[(2S,3R)-2-methyl-1-azabicyclo[2.2.2]oct-3-yl]-5-[2-(acetylamino)phenyl]-1H-pyrrole-2-carboxamide; N-[(2S,3R)-2-methyl-1-azabicyclo[2.2.2]oct-3-yl]-5-[3-(acetylamino)phenyl]-1H-pyrrole-2-carboxamide; N-[(2S,3R)-2-methyl-1-azabicyclo[2.2.2]oct-3-yl]-5-[4-(acetylamino)phenyl]-1H-pyrrole-2-carboxamide; N-[(2S,3R)-2-methyl-1-azabicyclo[2.2.2]oct-3-yl]-5-(pyrid-2-yl)-1H-pyrrole-2-carboxamide; N-[(2S,3R)-2-methyl-1-azabicyclo[2.2.2]oct-3-yl]-5-(pyrid-3-yl)-1H-pyrrole-2-carboxamide; N-[(2S,3R)-2-methyl-1-azabicyclo[2.2.2]oct-3-yl]-5-(pyrid-4-yl)-1H-pyrrole-2-carboxamide; N-[(2S,3R)-2-methyl-1-azabicyclo[2.2.2]oct-3-yl]-5-(3-fluoropyrid-2-yl)-1H-pyrrole-2-carboxamide; N-[(2S,3R)-2-methyl-1-azabicyclo[2.2.2]oct-3-yl]-5-(4-fluoropyrid-2-yl)-1H-pyrrole-2-carboxamide; N-[(2S,3R)-2-methyl-1-azabicyclo[2.2.2]oct-3-yl]-5-(5-fluoropyrid-2-yl)-1H-pyrrole-2-carboxamide; N-[(2S,3R)-2-methyl-1-azabicyclo[2.2.2]oct-3-yl]-5-(6-fluoropyrid-2-yl)-1H-pyrrole-2-carboxamide; N-[(2S,3R)-2-methyl-1-azabicyclo[2.2.2]oct-3-yl]-5-(2-fluoropyrid-3-yl)-1H-pyrrole-2-carboxamide; N-[(2S,3R)-2-methyl-1-azabicyclo[2.2.2]oct-3-yl]-5-(4-fluoropyrid-3-yl)-1H-pyrrole-2-carboxamide; N-[(2S,3R)-2-methyl-1-azabicyclo[2.2.2]oct-3-yl]-5-(5-fluoropyrid-3-yl)-1H-pyrrole-2-carboxamide; N-[(2S,3R)-2-methyl-1-azabicyclo[2.2.2]oct-3-yl]-5-(6-fluoropyrid-3-yl)-1H-pyrrole-2-carboxamide; N-[(2S,3R)-2-methyl-1-azabicyclo[2.2.2]oct-3-yl]-5-(2-fluoropyrid-4-yl)-1H-pyrrole-2-carboxamide; N-[(2S,3R)-2-methyl-1-azabicyclo[2.2.2]oct-3-yl]-5-(3-fluoropyrid-4-yl)-1H-pyrrole-2-carboxamide; N-[(2S,3R)-2-methyl-1-azabicyclo[2.2.2]oct-3-yl]-5-(2-cyanophenyl)-1H-pyrrole-2-carboxamide; N-[(2S,3R)-2-methyl-1-azabicyclo[2.2.2]oct-3-yl]-5-(3-cyanophenyl)-1H-pyrrole-2-carboxamide; or N-[(2S,3R)-2-methyl-1-azabicyclo[2.2.2]oct-3-yl]-5-(4-cyanophenyl)-1H-pyrrole-2-carboxamide.

Materials and Methods for Identifying Binding Constants:

Membrane Preparation. Male Sprague-Dawley rats (300–350 g) are sacrificed by decapitation and the brains (whole brain minus cerebellum) are dissected quickly, weighed and homogenized in 9 volumes/g wet weight of ice-cold 0.32 M sucrose using a rotating pestle on setting 50 (10 up and down strokes). The homogenate is centrifuged at 1,000× g for 10 minutes at 4° C. The supernatant is collected and centrifuged at 20,000× g for 20 minutes at 4° C. The resulting pellet is resuspended to a protein concentration of 1–8 mg/mL. Aliquots of 5 mL homogenate are frozen at −80° C. until needed for the assay. On the day of the assay, aliquots are thawed at room temperature and diluted with Kreb's-20 mM Hepes buffer pH 7.0 (at room temperature) containing 4.16 mM $NaHCO_3$, 0.44 mM $KH_2PO_4$, 127 mM NaCl, 5.36 mM KCl, 1.26 mM $CaCl_2$, and 0.98 mM $MgCl_2$, so that 25–150 μg protein are added per test tube. Proteins are determined by the Bradford method (Bradford, M. M., *Anal. Biochem.*, 72, 248–254, 1976) using bovine serum albumin as the standard.

Binding Assay. For saturation studies, 0.4 mL homogenate are added to test tubes containing buffer and various concentrations of radioligand, and are incubated in a final volume of 0.5 mL for 1 hour at 25° C. Nonspecific binding was determined in tissues incubated in parallel in the presence of 0.05 ml MLA for a final concentration of 1 μM MLA, added before the radioligand. In competition studies, drugs are added in increasing concentrations to the test tubes before addition of 0.05 ml [3H]-MLA for a final concentration of 3.0 to 4.0 nM [3H]-MLA. The incubations are terminated by rapid vacuum filtration through Whatman GF/B glass filter paper mounted on a 48 well Brandel cell harvester. Filters are pre-soaked in 50 MM Tris HCl pH 7.0–0.05% polyethylenimine. The filters are rapidly washed two times with 5 mL aliquots of cold 0.9% saline and then counted for radioactivity by liquid scintillation spectrometry.

Data Analysis. In competition binding studies, the inhibition constant (Ki) was calculated from the concentration dependent inhibition of [$^3$H]-MLA binding obtained from non-linear regression fitting program according to the Cheng-Prusoff equation (Cheng, Y. C. and Prussoff, W. H., *Biochem. Pharmacol.*, 22, p. 3099–3108, 1973). Hill coefficients were obtained using non-linear regression (GraphPad Prism sigmoidal dose-response with variable slope).

The aforementioned examples have the provided Ki values:

| Example # | Ki (nM) |
|---|---|
| 1 | 13–33 |
| 2 | 110 |
| 3 | 95–157 |
| 4 | 60–73 |
| 5 | 9–15 |
| 6 | 5–10 |
| 7 | 25–30 |
| 8 | 46 |
| 9 | 540–570 |
| 12 | 45–75 |
| 14 | 12–16 |
| 15 | 40–90 |
| 16 | 3–8 |
| 17 | 260–385 |
| 18 | 240–290 |
| 19 | 2–4 |
| 20 | 3–5 |
| 21 | 1–2 |
| 22 | 1–6 |
| 23 | 6–10 |
| 25 | 10–15 |
| 26 | 5–20 |
| 27 | 35–160 |
| 33 | 27 |
| 34 | 30–39 |
| 35 | 30–50 |
| 36 | 110–115 |
| 40 | 12–16 |
| 41 | 3–4 |

-continued

| Example # | Ki (nM) |
|---|---|
| 43 | 3–5 |
| 50 | 68–564 |
| 52 | 340–480 |
| 53 | 1900–1970 |
| 55 | 60–70 |
| 58 | 920–1005 |
| 79 | 20–75 |
| 80 | 50–60 |
| 81 | 55–175 |
| 82 | 115–125 |
| 83 | 2–3 |
| 84 | 1100–1490 |
| 85 | 30–40 |
| 86 | 30–40 |
| 87 | 130–150 |
| 88 | 65–80 |
| 89 | 310–400 |
| 90 | 80–150 |
| 92 | 190–375 |
| 93 | 40–45 |
| 94 | 125 |
| 95 | 1085 |
| 96 | 95–110 |
| 98 | 50–80 |
| 99 | 310–325 |
| 103 | 17–50 |
| 104 | 20–130 |
| 104 | 75 |
| 105 | 90 |
| 106 | 15–190 |
| 106 | 22–110 |
| 108 | 415–560 |
| 109 | 1.5–6 |
| 110 | 4–190 |
| 112 | 5–24 |
| 113 | 90–125 |
| 114 | 135 |
| 117 | 1860 |
| 118 | 45–69 |
| 119 | 415–560 |
| 120 | 1050 |
| 128 | 6–7 |
| 130 | 420–565 |
| 130 | 330–410 |
| 132 | 875–2085 |
| 133 | 30–70 |
| 134 | 60–100 |
| 135 | 16–45 |
| 136 | 15–20 |
| 138 | 525–590 |
| 140 | 35–65 |
| 141 | 260–275 |
| 146 | 35–140 |
| 147 | 2–3 |
| 150 | 290–330 |
| 151 | 225–835 |
| 152 | 20–65 |
| 153 | 1555 |
| 154 | >1000 |
| 155 | 1380 |
| 158 | 12–20 |

What is claimed:

1. A method for treating a disease or condition in a mammal in need thereof, wherein the α7 nicotinic acetylcholine receptor is implicated, wherein the disease or condition is cognitive and attention deficit symptoms of Alzheimer's, neurodegeneration associated with diseases such as Alzheimer's disease, pre-senile dementia (mild cognitive impairment), or senile dementia comprising administering to a mammal a therapeutically effective amount of a compound of Formula I:

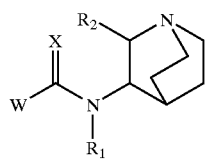

Formula I or a pharmaceutically acceptable salt thereof,
wherein $R_1$ is selected from —H, alkyl, cycloalkyl, halogenated alkyl, or aryl;

Alkyl is both straight and branched-chain moieties having from 1–6 carbon atoms;

Halogenated alkyl is an alkyl moiety having from 1–6 carbon atoms and having 1 to (2n+1) substituent(s) independently selected from —F, —Cl, —Br, or —I where n is the maximum number of carbon atoms in the moiety;

Cycloalkyl is a cyclic alkyl moiety having from 3–6 carbon atoms;

Aryl is phenyl, substituted phenyl, naphthyl, or substituted naphthyl;

Substituted phenyl is a phenyl either having 1–4 substituents independently selected from —F, —Cl, —Br, or —I, or having 1 substituent selected from —$R_{12}$ and 0–3 substituents independently selected from —F, —Cl, —Br, or —I;

Substituted naphthyl is a naphthalene moiety either having 1–4 substituents independently selected from —F, —Cl, —Br, or —I, or having 1 substituent selected from —$R_{12}$ and 0–3 substituents independently selected from —F, —Cl, —Br, or —I, where the substitution can be independently on either the same ring or different rings of said napthalene moiety;

$R_2$ is —H, alkyl, halogenated alkyl, substituted alkyl, cycloalkyl, benzyl, substituted benzyl, or aryl;

Substituted alkyl is an alkyl moiety having from 1–6 carbon atoms and having 0–3 substituents independently selected from —F, —Cl, —Br, or —I, and further having 1 substituent selected from —$R_7$, —$R_9$, —$OR_{10}$, —$SR_{10}$, —$NR_{10}R_{10}$, —$C(O)R_{10}$, —$NO_2$, —$C(O)NR_{10}R_{10}$, —CN, —$NR_{10}C(O)R_{10}$, —$S(O)_2NR_{10}R_{10}$, —$NR_{10}S(O)_2R_{10}$, phenyl, or substituted phenyl;

Substituted benzyl is a benzyl either having 1–4 substituents independently selected from —F, —Cl, —Br, or —I, or having 1 substituent selected from —$R_{12}$ and 0–3 substituents independently selected from —F, —Cl, —Br, or —I;

X is O or S;

W is a cyclic heteroaromatic moiety where the heteroatoms can be from 1–3 atoms selected from oxygen, sulfur, or nitrogen of the following structures:

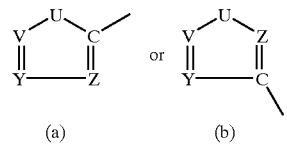

(a)  (b)

wherein U is —O—, —S—, or —$N(R_3)$—;
V and Y are independently selected from =N—, or =$C(R_5)$—;

Z is =N—, or =CH—, provided that when both V and Y are =$C(R_5)$— and Z is =CH—, only one =$C(R_5)$— can be —CH—, and further provided that when U is —O—, Y is =$C(R_5)$— and Z is =C(H)—, V cannot be =N—;

$R_3$ is —H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, or aryl, and provided that when W is (b) and Z is =N— and U is $N(R_3)$, $R_3$ cannot be phenyl, substituted phenyl, or benzyl substituted with methyl on the phenyl ring of the benzyl;

Alkenyl is straight and branched-chain moieties having from 2–6 carbon atoms and having at least one carbon—carbon double bond;

Halogenated alkenyl is an unsaturated alkenyl moiety having from 2–6 carbon atoms and having 1 to (2n–1) substituent(s) independently selected from —F, —Cl, —Br, or —I where n is the maximum number of carbon atoms in the moiety;

Substituted alkenyl is an unsaturated alkenyl moiety having from 2–6 carbon atoms and having 0–3 substituents independently selected from —F, or —Cl, and further having 1 substituent selected from —$R_7$, —$R_9$, —$OR_{10}$, —$SR_{10}$, —$NR_{10}R_{10}$, —$C(O)R_{10}$, —$C(O)NR_{10}R_{10}$, —CN, —$NR_{10}C(O)R_{10}$, —$S(O)_2NR_{10}R_{10}$, —$NR_{10}S(O)_2R_{10}$, phenyl, or substituted phenyl;

Alkynyl is straight and branched-chain moieties having from 2–6 carbon atoms and having at least one carbon—carbon triple bond;

Halogenated alkynyl is an unsaturated alkynyl moiety having from 3–6 carbon atoms and having 1 to (2n–3) substituent(s) independently selected from —F, —Cl, —Br, or —I where n is the maximum number of carbon atoms in the moiety;

Substituted alkynyl is an unsaturated alkynyl moiety having from 3–6 carbon atoms and having 0–3 substituents independently selected from —F, or —Cl, and further having 1 substituent selected from —$R_7$, —$R_9$, —$OR_{10}$, —$SR_{10}$, —$NR_{10}R_{10}$, —$C(O)R_{10}$, —CN, —$C(O)NR_{10}R_{10}$, —$NR_{10}C(O)R_{10}$, —$S(O)_2NR_{10}R_{10}$, —$NR_{10}S(O)_2R_{10}$, phenyl, or substituted phenyl;

Halogenated cycloalkyl is a cyclic moiety having from 3–6 carbon atoms and having 1–4 substituents independently selected from —F, or —Cl;

Substituted cycloalkyl is a cyclic moiety having from 3–6 carbon atoms and having 0–3 substituents independently selected from —F, or —Cl, and further having 1 substituent selected from —$OR_{10}$, —$SR_{10}$, —$NR_{10}R_{10}$, —$C(O)R_{10}$, —$C(O)NR_{10}R_{10}$, —CN, —$NR_{10}C(O)R_{10}$, —$S(O)_2NR_{10}R_{10}$, —$NR_{10}S(O)_2R_{10}$, —$NO_2$, phenyl, or substituted phenyl;

Heterocycloalkyl is a cyclic moiety having 4–7 atoms with 1–2 atoms within the ring being —S—, —$N(R_3)$—, or —O—;

Halogenated heterocycloalkyl is a cyclic moiety having from 4–7 atoms with 1–2 atoms within the ring being —S—, —$N(R_3)$—, or —O—, and having 1–4 substituents independently selected from —F, or —Cl;

Substituted heterocycloalkyl is a cyclic moiety having from 4–7 atoms with 1–2 atoms within the ring being —S—, —$N(R_3)$—, or —O—and having 0–3 substituents independently selected from —F, or —Cl, and further having 1 substituent selected from —$OR_{10}$, —$SR_{10}$, —$NR_{10}R_{10}$, —$C(O)R_{10}$, —$C(O)NR_{10}R_{10}$, —CN, —$NR_{10}C(O)R_{10}$, —$NO_2$, —$S(O)_2NR_{10}R_{10}$, —$NR_{10}S(O)_2R_{10}$, phenyl, or substituted phenyl;

$R_5$ is independently selected from the group consisting of —H, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, aryl, —$OR_8$, —$SR_8$, —F, —Cl, —Br, —I, —$NR_8R_8$, —$C(O)R_8$, —$C(O)NR_8R_8$, —CN, —$NR_8C(O)R_{11}$, —$S(O)_2NR_8R_8$, —$OS(O)_2R_{11}$, —$S(O)_2R_8$, —$NR_8S(O)_2R_8$, —$N(H)C(O)N(H)R_8$, —$NO_2$, —$R_7$, and —$R_9$;

$R_7$ is 5-membered heteroaromatic mono-cyclic moieties containing within the ring 1–3 heteroatoms independently selected from the group consisting of —O—, =N—, —$N(R_3)$—, and —S—, and having 0–1 substituent selected from —$R_{12}$ and 0–3 substituents independently selected from —F, —Cl, —Br, or —I, or $R_7$ is a 9-membered fused-ring moiety having a 6-membered ring fused to a 5-membered ring and having the formula

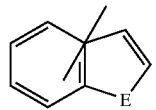

wherein E is O, S, or $NR_3$,

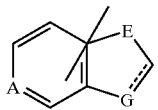

wherein E and G are independently selected from $CR_{18}$, O, S, or $NR_3$, and A is $CR_{18}$ or N, or

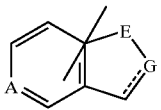

wherein E and C are independently selected from $CR_{18}$, O, S, or $NR_3$, and A is $CR_{18}$ or N, each 9-membered fused-ring moiety having 0–1 substituent selected from —$R_{12}$ and 0–3 substituent(s) independently selected from —F, —Cl, —Br, or —I, and having a bond directly or indirectly attached to the core molecule where valency allows in either the 6-membered or the 5-membered ring of the fused-ring moiety;

Each $R_8$ is independently selected from —H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, —$R_7$, —$R_9$, phenyl, or substituted phenyl;

$R_9$ is 6-membered heteroaromatic mono-cyclic moieties containing within the ring 1–3 heteroatoms selected from =N— and having 0–1 substituent selected from —$R_{12}$ and 0–3 substituent(s) independently selected from —F, —Cl, —Br, or —I, or 10-membered heteroaromatic bi-cyclic moieties containing within one or both rings 1–3 heteroatoms selected from N—, including quinolinyl or isoquinolinyl, each 10-membered fused-ring moiety having 0–1 substituent selected from —$R_{12}$ and 0–3 substituent(s) independently selected from —F, —Cl, —Br, or —I and having a bond directly or indirectly attached to the core molecule where valency allows;

Each $R_{10}$ is independently selected from —H, alkyl, cycloalkyl, heterocycloalkyl, alkyl substituted with 1 substituent selected from $R_{13}$, cycloalkyl substituted with 1 substituent selected from $R_{13}$, heterocycloalkyl substituted with 1 substituent selected from $R_{13}$, halogenated alkyl, halogenated cycloalkyl, halogenated heterocycloalkyl, phenyl, substituted phenyl, —$R_7$, or —$R_9$;

Each $R_{11}$ is independently selected from —H, alkyl, cycloalkyl, heterocycloalkyl, halogenated alkyl, halogenated cycloalkyl, or halogenated heterocycloalkyl;

$R_{12}$ is selected from —$OR_{11}$, —$SR_{11}$, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, or —$NR_{11}S(O)_2R_{11}$;

$R_{13}$ is selected from —$OR_{11}$, —$SR_{11}$, —$NR_{11}R_{11}$, —$C(O)R_{11}$, —$C(O)NR_{11}R_{11}$, —CN, —$NR_{11}C(O)R_{11}$, —$S(O)_2NR_{11}R_{11}$, —$NR_{11}S(O)_2R_{11}$, —$CF_3$, or —$NO_2$;

$R_{14}$ is independently selected from —H, alkyl, halogenated alkyl, limited substituted alkyl, cycloalkyl, halogenated cycloalkyl, substituted cycloalkyl, heterocycloalkyl, halogenated heterocycloalkyl, substituted heterocycloalkyl;

Each $R_{18}$ is independently selected from —H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, or —$NR_{11}S(O)_2R_{11}$, —F, —Cl, —Br, or —I, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, or —$NR_{11}S(O)_2R_{11}$, and further provided that the fused-ring moiety has 0–3 substituent(s) selected from —F, —Cl, —Br, or —I;

Limited substituted alkyl is a substituted alkyl having from 1–6 carbon atoms and having 0–3 substituents independently selected from —F, —Cl, —Br, or —I, and further having 1 substituent on either only the ω carbon and selected from —$OR_{11}$, —$SR_{11}$, —$NR_{11}R_{11}$, —$C(O)R_{11}$, —$NO_2$, —$C(O)NR_{11}R_{11}$, —CN, —$NR_{10}C(O)R_{11}$, —$S(O)_2NR_{10}R_{10}$, or —$NR_{10}S(O)_2R_{10}$, or on any carbon with sufficient valency but not on the ω carbon and selected from —$R_7$, —$R_9$, —$OR_{10}$, —$SR_{10}$, —$NR_{10}R_{10}$, —$C(O)R_{10}$, —$NO_2$, —$C(O)NR_{10}R_{10}$, —CN, —$NR_{10}C(O)R_{10}$, —$S(O)_2NR_{10}R_{10}$, —$NR_{10}S(O)_2R_{10}$, phenyl, or substituted phenyl;

Limited substituted alkenyl is a substituted alkenyl having from 1–6 carbon atoms and having 0–3 substituents independently selected from —F, —Cl, —Br, or —I, and further having 1 substituent on either only the ω carbon and selected from —OR$_{11}$, —SR$_{11}$, —NR$_{11}$R$_{11}$, —C(O)R$_{11}$, —NO$_2$, —C(O)NR$_{11}$R$_{11}$, —CN, —NR$_{10}$C(O)R$_{11}$, —S(O)$_2$NR$_{10}$R$_{10}$, or —NR$_{10}$S(O)$_2$R$_{10}$, or on any carbon with sufficient valency but not on the ω carbon and selected from —R$_7$, —R$_9$, —OR$_{10}$, —SR$_{10}$, —NR$_{10}$R$_{10}$, —C(O)R$_{10}$, —NO$_2$, —C(O)NR$_{10}$R$_{10}$, —CN, —NR$_{10}$C(O)R$_{10}$, —S(O)$_2$NR$_{10}$R$_{10}$, —NR$_{10}$S(O)$_2$R$_{10}$, phenyl, or substituted phenyl;

Limited substituted alkynyl is a substituted alkynyl having from 1–6 carbon atoms and having 0–3 substituents independently selected from —F, —Cl, —Br, or —I, and further having 1 substituent on either only the ω carbon and selected from —OR$_{11}$, —SR$_{11}$, —NR$_{11}$R$_{11}$, —C(O)R$_{11}$, —NO$_2$, —C(O)NR$_{11}$R$_{11}$, —CN, —NR$_{10}$C(O)R$_{11}$, or —NR$_{10}$S(O)$_2$R$_{10}$, or on any carbon with sufficient valency but not on the ω carbon and selected from —R$_7$, —R$_9$, —OR$_{10}$, —SR$_{10}$, —NR$_{10}$R$_{10}$, —C(O)R$_{10}$, —NO$_2$, —C(O)NR$_{10}$R$_{10}$, —CN, —NR$_{10}$C(O)R$_{10}$, —S(O)$_2$NR$_{10}$R$_{10}$, —NR$_{10}$S(O)$_2$R$_{10}$, phenyl, or substituted phenyl.

2. The method according to claim 1, wherein said compound(s) is(are) administered rectally, topically, orally, sublingually, or parenterally.

3. The method according to claim 1, wherein said compound(s) is(are) administered from about 0.001 to about 100 mg/kg of body weight of said mammal per day.

4. The method according to claim 1, wherein said compound(s) is(are) administered from about 0.1 to about 50 mg/kg of body weight of said mammal per day.

5. The method according to claim 1, wherein X is O; R$_1$ and R$_2$ are each H; and R$_5$ is independently selected from the group consisting of —H, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, limited substituted alkyl, limited substituted alkenyl, limited substituted alkynyl, substituted cycloalkyl, substituted heterocycloalkyl, —OR$_{14}$, —SR$_{14}$, —F, —Cl, —Br, —I, —NR$_{14}$R$_{14}$, —C(O)R$_{14}$, —C(O)NR$_{14}$R$_{14}$, —CN, —NR$_8$C(O)R$_{11}$, —S(O)$_2$NR$_8$R$_8$, —OS(O)$_2$R$_{11}$, —S(O)$_2$R$_{14}$, —NR$_8$S(O)$_2$R$_8$, —N(H)C(O)N(H)R$_8$, and —NO$_2$.

6. The method according to claim 5, wherein said compound(s) is(are) administered rectally, topically, orally, sublingually or parenterally.

7. The method according to claim 5, wherein said compound(s) is(are) administered from about 0.001 to about 100 mg/kg of body weight of said mammal per day.

8. The method according to claim 5, wherein said compound(s) is(are) administered from about 0.1 to about 50 mg/kg of body weight of said mammal per day.

9. The method according to claim 5, wherein R$_3$ is —H, alkyl, cycloalkyl, heterocycloalkyl, halogenated alkyl, halogenated cycloalkyl, halogenated heterocycloalkyl, limited substituted alkyl, substituted cycloalkyl, or substituted heterocycloalkyl.

10. The method according to claim 9, wherein said compound(s) is(are) administered rectally, topically, orally, sublingually, or parenterally.

11. The method according to claim 9, wherein said compound(s) is(are) administered from about 0.001 to about 100 mg/kg of body weight of said mammal per day.

12. The method according to claim 9, wherein said compound(s) is(are) administered from about 0.1 to about 50 mg/kg of body weight of said mammal per day.

13. The method according to claim 1, wherein the compound is the R steroisomer at the C3 position of the quinuclidine of Formula I:

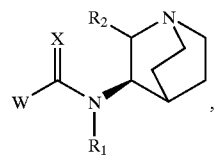

or a pharmaceutically acceptable salt thereof.

14. The method according to claim 13, wherein said compound(s) is(are) administered rectally, topically, orally, sublingually or parenterally.

15. The method according to claim 13, wherein said compound(s) is(are) administered from about 0.001 to about 100 mg/kg of body weight of said mammal per day.

16. The method according to claim 13, wherein said compound(s) is(are) administered from about 0.1 to about 50 mg/kg of body weight of said mammal per day.

17. The method according to claim 13 where X of Formula I is O.

18. The method according to claim 17, wherein said compound(s) is(are) administered rectally, topically, orally, sublingually, or parenterally.

19. The method according to claim 17, wherein said compound(s) is(are) administered from about 0.001 to about 100 mg/kg of body weight of said mammal per day.

20. The method according to claim 17, wherein said compound(s) is(are) administered from about 0.1 to about 50 mg/kg of body weight of said mammal per day.

21. The method according to claim 17, wherein R$_2$ of Formula I is alkyl, halogenated alkyl, substituted alkyl, cycloalkyl, benzyl, substituted benzyl, or aryl.

22. The method according to claim 21, wherein said compound(s) is(are) administered rectally, topically, orally, sublingually, or parenterally.

23. The method according to claim 21, wherein said compound(s) is(are) administered from about 0.001 to about 100 mg/kg of body weight of said mammal per day.

24. The method according to claim 21, wherein said compound(s) is(are) administered from about 0.1 to about 50 mg/kg of body weight of said mammal per day.

25. The method according to claim 21, wherein R$_2$ is alkyl, cycloalkyl, or aryl.

26. The method according to claim 25, wherein said compound(s) is(are) administered rectally, topically, orally, sublingually, or parenterally.

27. The method according to claim 25, wherein said compound(s) is(are) administered from about 0.001 to about 100 mg/kg of body weight of said mammal per day.

28. The method according to claim 25, wherein said compound(s) is(are) administered from about 0.1 to about 50 mg/kg of body weight of said mammal per day.

29. The method according to claim 17, wherein for Formula I R$_1$ and R$_2$ are both H.

30. The method according to claim 29, wherein said compound(s) is(are) administered rectally, topically, orally, sublingually, or parenterally.

31. The method according to claim 29, wherein said compound(s) is(are) administered from about 0.001 to about 100 mg/kg of body weight of said mammal per day.

32. The method according to claim 29, wherein said compound(s) is(are) administered from about 0.1 to about 50 mg/kg of body weight of said mammal per day.

33. The method according to claim 29 wherein W of Formula I is selected from the following:

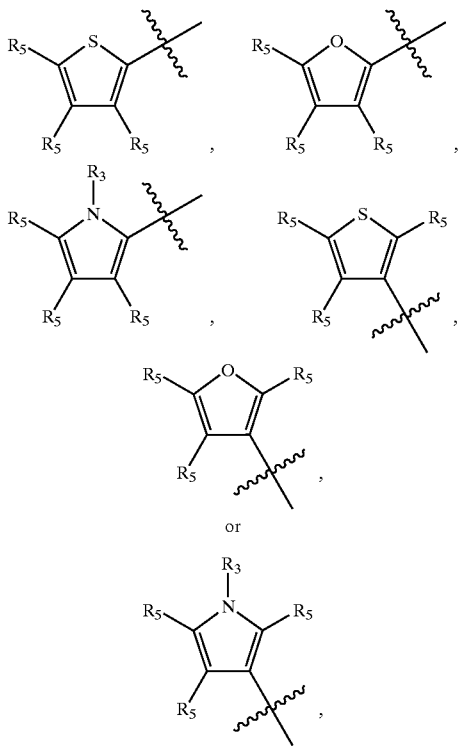

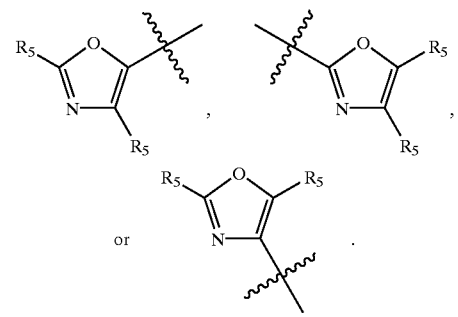

provided that at least one R$_5$ is not H.

34. The method according to claim 33, wherein said compound(s) is(are) administered rectally, topically, orally, sublingually, or parenterally.

35. The method according to claim 33, wherein said compound(s) is(are) administered from about 0.001 to about 100 mg/kg of body weight of said mammal per day.

36. The method according to claim 33, wherein said compound(s) is(are) administered from about 0.1 to about 50 mg/kg of body weight of said mammal per day.

37. The method according to claim 33 wherein W of Formula I is selected from the following:

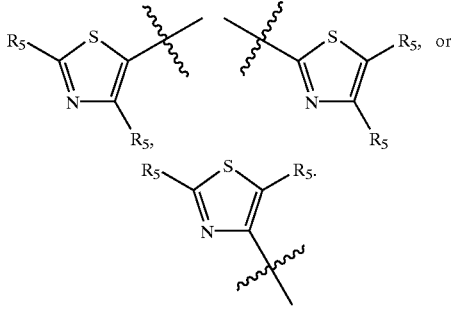

38. The method according to claim 37, wherein said compound(s) is(are) administered rectally, topically, orally, sublingually, or parenterally.

39. The method according to claim 37, wherein said compound(s) is(are) administered from about 0.001 to about 100 mg/kg of body weight of said mammal per day.

40. The method according to claim 37 wherein said compound(s) is(are) administered from about 0.1 to about 50 mg/kg of body weight of said mammal per day.

41. The method according to claim 29, wherein W of Formula I is selected from the following:

42. The method according to claim 41, wherein said compound(s) is(are) administered rectally, topically, orally, sublingually, or parenterally.

43. The method according to claim 41, wherein said compound(s) is(are) administered from about 0.001 to about 100 mg/kg of body weight of said mammal per day.

44. The method according to claim 41, wherein said compound(s) is(are) administered from about 0.1 to about 50 mg/kg of body weight of said mammal per day.

45. The method according to claim 13, wherein the compound of Formula I is selected from the group consisting of:

N-[(3R)-1-azabicyclo[2.2.2]oct-3-yl]-5-phenyl-thiophene-2-carboxamide;

N-[(3R)-1-azabicyclo[2.2.2]oct-3-yl]-5-(4-chlorophenyl)-thiophene-2-carboxamide;

N-[(3R)-1-azabicyclo[2.2.2]oct-3-yl]-5-(3-chlorophenyl)-thiophene-2-carboxamide;

N-[(3R)-1-azabicyclo[2.2.2]oct-3-yl]-5-(2-chlorophenyl)-thiophene-2-carboxamide;

N-[(3R)-1-azabicyclo[2.2.2]oct-3-yl]-2,3'-bithiophene-5-carboxamide;

N-[(3R)-1-azabicyclo[2.2.2]oct-3-yl]-5-(2-nitrophenyl)-thiophene-2-carboxamide;

N-[(3R)-1-azabicyclo[2.2.2]oct-3-yl]-5-(3-nitrophenyl)-thiophene-2-carboxamide;

N-[(3R)-1-azabicyclo[2.2.2]oct-3-yl]-4-phenyl-thiophene-2-carboxamide;

N-[(3R)-1-azabicyclo[2.2.2]oct-3-yl]-5-(3-benzyloxyphenyl)thiophene-2-carboxamide;

N-[(3R)-1-azabicyclo[2.2.2]oct-3-yl]-5-(4-benzyloxyphenyl)-thiophene-2-carboxamide;

N-[(3R)-1-azabicyclo[2.2.2]oct-3-yl]-5-(3-fluoro-4-benzyloxyphenyl) thiophene-2-carboxamide;

5-(2-aminophenyl)-N-[(3R)-1-azabicyclo[2.2.2]oct-3-yl]-thiophene-2-carboxamide;

N-[(3R)-1-azabicyclo[2.2.2]oct-3-yl]-5-pyridin-3-yl-thiophene-2-carboxamide;

N-[(3R)-1-azabicyclo[2.2.2]oct-3-yl]-5'-methyl-2,2'-bithiophene-5-carboxamide;

N-[(3R)-1-azabicyclo[2.2.2]oct-3-yl]-5'-chloro-2,2'-bithiophene-5-carboxamide;

N-[(3R)-1-azabicyclo[2.2.2]oct-3-yl]-5-nitro-thiophene-2-carboxamide;

5-(aminomethyl)-N-[(3R)-1-azabicyclo[2.2.2]oct-3-yl]-thiophene-2-carboxamide;

N-[(3R)-1-azabicyclo[2.2.2]oct-3-yl]-5-cyano-thiophene-2-carboxamide;

N-[(3R)-1-azabicyclo[2.2.2]oct-3-yl]-5-methoxy-thiophene-2-carboxamide;

N-[(3R)-1-azabicyclo[2.2.2]oct-3-yl]-5-(pyridin-2-yl)-thiophene-2-carboxamide;
N-[(3R)-1-azabicyclo[2.2.2]oct-3-yl]-[2,2']bithiophenyl-5-carboxamide;
N-[(3R)-1-azabicyclo[2.2.2]oct-3-yl]-5-(methylsulfanyl)-thiophene-2-carboxamide;
N-[(3R)-1-azabicyclo[2.2.2]oct-3-yl]-5-chloro-thiophene-2-carboxamide;
N-[(3R)-1-azabicyclo[2.2.2]oct-3-yl]-5-acetyl-thiophene-2-carboxamide;
N-[(3R)-1-azabicyclo[2.2.2]oct-3-yl]-5-methyl-thiophene-2-carboxamide;
N-[(3R)-1-azabicyclo[2.2.2]oct-3-yl]-5-bromo-thiophene-2-carboxamide;
N-[(3R)-1-azabicyclo[2.2.2]oct-3-yl]-5-(phenylsulfanyl)-thiophene-2-carboxamide;
N-[(3R)-1-azabicyclo[2.2.2]oct-3-yl]-5-(acetylamino)-furan-2-carboxamide;
N-[(3R)-1-azabicyclo[2.2.2]oct-3-yl]-5-trifluoromethyl-furan-2-carboxamide;
N-[(3R)-1-azabicyclo[2.2.2]oct-3-yl]-5-(2-methyl-5-trifluoromethyl-2H-pyrazole-3-yl)-thiophene-2-carboxamide;
N-[(3R)-1-azabicyclo[2.2.2]oct-3-yl]-5-(2-methylthiazol-4-yl)-thiophene-2-carboxamide;
N-[(3R)-1-azabicyclo[2.2.2]oct-3-yl]-5-[2-(3-chlorophenyl)-vinyl]-thiophene 2-carboxamide;
N-[(3R)-1-azabicyclo[2.2.2]oct-3-yl]-5-(4-chlorophenylsulfanyl)-thiophene-2-carboxamide;
N-[(3R)-1-azabicyclo[2.2.2]oct-3-yl]-5-(2,4-difluorophenyl-sulfanyl)-thiophene-2-carboxamide;
N-[(3R)-1-azabicyclo[2.2.2]oct-3-yl]-5-(3-chlorophenyl-sulfanyl)-thiophene-2-carboxamide;
N-[(3R)-1-azabicyclo[2.2.2]oct-3-yl]-5-(3-chloro-4-fluoro-phenylsulfanyl)-thiophene-2-carboxamide;
N-[(3R)-1-azabicyclo[2.2.2]oct-3-yl]-5-(2,3-dichlorophenyl-sulfanyl)-thiophene-2-carboxamide;
N-[(3R)-1-azabicyclo[2.2.2]oct-3-yl]-5-(2,4,5-trichlorophenyl-sulfanyl)-thiophene-2-carboxamide;
N-[(3R)-1-azabicyclo[2.2.2]oct-3-yl]-5-(3,4-dichlorophenyl-sulfanyl)-thiophene-2-carboxamide;
N-[(3R)-1-azabicyclo[2.2.2]oct-3-yl]-5-phenoxy-thiophene-2-carboxamide;
N-[(3R)-1-azabicyclo[2.2.2]oct-3-yl]-5-(2-hydroxyphenyl)-thiophene-2-carboxamide;
N-[(3R)-1-azabicyclo[2.2.2]oct-3-yl]-5-(3-hydroxyphenyl)-thiophene-2-carboxamide;
N-[(3R)-1-azabicyclo[2.2.2]oct-3-yl]-5-(3-fluoro-4-hydroxyphenyl)-thiophene-2-carboxamide;
N-[(3R)-1-azabicyclo[2.2.2]oct-3-yl]-2-(phenylsulfanyl)-1,3-thiazole-5-carboxamide;
N-[(3R)-1-azabicyclo[2.2.2]oct-3-yl]-2-[(4-chlorophenyl)-sulfanyl]-1,3-thiazole-5-carboxamide;
N-[(3R)-1-azabicyclo[2.2.2]oct-3-yl]-2-phenoxy-1,3-thiazole-5-carboxamide;
N-[(3R)-1-azabicyclo[2.2.2]oct-3-yl]-2-[(4-fluorophenyl)-sulfanyl]-1,3-thiazole-5-carboxamide;
N-[(3R)-1-azabicyclo[2.2.2]oct-3-yl]-2-(methylsulfanyl)-1,3-thiazole-5-carboxamide;
N-[(3R)-1-azabicyclo[2.2.2]oct-3-yl]-2-(4-chlorophenoxy)-1,3-thiazole-5-carboxamide;
N-[(3R)-1-azabicyclo[2.2.2]oct-3-yl]-2-phenyl-1,3-thiazole-5-carboxamide;
N-[(3R)-1-azabicyclo[2.2.2]oct-3-yl]-2,4-dimethyl-1,3-thiazole-5-carboxamide;
N-[(3R)-1-azabicyclo[2.2.2]oct-3-yl]-2-(2-fluorophenyl)-1,3-thiazole-5-carboxamide;
N-[(3R)-1-azabicyclo[2.2.2]oct-3-yl]-2-(3-fluorophenyl)-1,3-thiazole-5-carboxamide;
N-[(3R)-1-azabicyclo[2.2.2]oct-3-yl]-2-(4-fluorophenyl)-1,3-thiazole-5-carboxamide;
N-[(3R)-1-azabicyclo[2.2.2]oct-3-yl]-2-(2-hydroxyphenyl)-1,3-thiazole-5-carboxamide;
N-[(3R)-1-azabicyclo[2.2.2]oct-3-yl]-2-(4-methylphenyl)-1,3-thiazole-5-carboxamide;
N-[(3R)-1-azabicyclo[2.2.2]oct-3-yl]-2-[4-(benzyloxy)phenyl]-1,3-thiazole-5-carboxamide;
N-[(3R)-1-azabicyclo[2.2.2]oct-3-yl]-2-pyridin-3-yl-1,3-thiazole-4-carboxamide;
N-[(3R)-1-azabicyclo[2.2.2]oct-3-yl]-4-methyl-2-phenyl-1,3-thiazole-5-carboxamide;
N-[(3R)-1-azabicyclo[2.2.2]oct-3-yl]-2-(4-chlorophenyl)-4-methyl-1,3-thiazole-5-carboxamide;
N-[(3R)-1-azabicyclo[2.2.2]oct-3-yl]-4-methyl-2-pyridin-2-yl-1,3-thiazole-5-carboxamide;
N-[(3R)-1-azabicyclo[2.2.2]oct-3-yl]-4-methyl-2-pyridin-4-yl-1,3-thiazole-5-carboxamide;
N-[(3R)-1-azabicyclo[2.2.2]oct-3-yl]-2-(methylamino)-1,3-thiazole-5-carboxamide;
N-[(3R)-1-azabicyclo[2.2.2]oct-3-yl]-5-(phenylsulfanyl)-1,3,4-thiadiazole-2-carboxamide;
N-[(3R)-1-azabicyclo[2.2.2]oct-3-yl]-5-phenoxy-1,3,4-thiadiazole-2-carboxamide;
N-[(3R)-1-azabicyclo[2.2.2]oct-3-yl]-5-[(4-chlorophenyl)-sulfanyl]-1,3,4-thiadiazole-2-carboxamide;
N-[(3R)-1-azabicyclo[2.2.2]oct-3-yl]-5-(4-fluorophenoxy)-1,3,4-thiadiazole-2-carboxamide;
N-[(3R)-1-azabicyclo[2.2.2]oct-3-yl]-5-(4-chlorophenoxy)-1,3,4-thiadiazole-2-carboxamide;
N-[(3R)-1-azabicyclo[2.2.2]oct-3-yl]-5-[(3-fluorophenyl)-sulfanyl]-1,3,4-thiadiazole-2-carboxamide;
N-[(3R)-1-azabicyclo[2.2.2]oct-3-yl]-5-[(2-chlorophenyl)-sulfanyl]-1,3,4-thiadiazole-2-carboxamide;
N-[(3R)-1-azabicyclo[2.2.2]oct-3-yl]-5-[(4-fluorophenyl)-sulfanyl]-1,3,4-thiadiazole-2-carboxamide;
N-[(3R)-1-azabicyclo[2.2.2]oct-3-yl]-5-[(3-chlorophenyl)-sulfanyl]-1,3,4-thiadiazole-2-carboxamide;
N-[(3R)-1-azabicyclo[2.2.2]oct-3-yl]-5-phenyl-1H-1,2,4-triazole-3-carboxamide;
N-[(3R)-1-azabicyclo[2.2.2]oct-3-yl]-5-phenyl-1,3,4-oxadiazole-2-carboxamide;
N-[(3R)-1-azabicyclo[2.2.2]oct-3-yl]-5-(methylthio)-1,3,4-oxadiazole-2-carboxamide;
N-[(3R)-1-azabicyclo[2.2.2]oct-3-yl]-5-(3-chlorophenyl)-1,3-oxazole-2-carboxamide;
N-[(3R)-1-azabicyclo[2.2.2]oct-3-yl]-5-(3-methoxyphenyl)-1,3-oxazole-2-carboxamide;
N-[(3R)-1-azabicyclo[2.2.2]oct-3-yl]-5-(3-nitrophenyl)-1,3-oxazole-2-carboxamide;
N-[(3R)-1-azabicyclo[2.2.2]oct-3-yl]-5-(4-methoxyphenyl)-1,3-oxazole-2-carboxamide;

N-[(3R)-1-azabicyclo[2.2.2]oct-3-yl]-5-(2-nitrophenyl)-1,3-oxazole-2-carboxamide;
N-[(3R)-1-azabicyclo[2.2.2]oct-3-yl]-5-(2-methoxyphenyl)-1,3-oxazole-2-carboxamide;
N-[(3R)-1-azabicyclo[2.2.2]oct-3-yl]-5-(4-fluorophenyl)-1,3-oxazole-2-carboxamide;
N-[(3R)-1-azabicyclo[2.2.2]oct-3-yl]-5-(2-chlorophenyl)-1,3-oxazole-2-carboxamide;
N-[(3R)-1-azabicyclo[2.2.2]oct-3-yl]-5-(3-cyanophenyl)-1,3-oxazole-2-carboxamide;
N-[(3R)-1-azabicyclo[2.2.2]oct-3-yl]-5-(4-bromophenyl)-1,3-oxazole-2-carboxamide;
N-[(3R)-1-azabicyclo[2.2.2]oct-3-yl]-4-methyl-5-phenyl-1,3-thiazole-2-carboxamide;
N-[(3R)-1-azabicyclo[2.2.2]oct-3-yl]-5-phenyl-1,3-thiazole-2-carboxamide;
N-[(3R)-1-azabicyclo[2.2.2]oct-3-yl]-5-(4-bromophenyl)-1,3-thiazole-2-carboxamide;
N-[(3R)-1-azabicyclo[2.2.2]oct-3-yl]-5-(3-nitrophenyl)-1,3-thiazole-2-carboxamide;
N-[(3R)-1-azabicyclo[2.2.2]oct-3-yl]-5-(3-methoxyphenyl)-1,3-thiazole-2-carboxamide;
N-[(3R)-1-azabicyclo[2.2.2]oct-3-yl]-5-(2-chlorophenyl)-1,3-thiazole-2-carboxamide;
N-[(3R)-1-azabicyclo[2.2.2]oct-3-yl]-5-(4-fluorophenyl)-1,3-thiazole-2-carboxamide;
N-[(3R)-1-azabicyclo[2.2.2]oct-3-yl]-5-(2-methoxyphenyl)-1,3-thiazole-2-carboxamide;
N-[(3R)-1-azabicyclo[2.2.2]oct-3-yl]-5-(4-chlorophenyl)-1,3-thiazole-2-carboxamide;
N-[(3R)-1-azabicyclo[2.2.2]oct-3-yl]-5-methyl-1,3-thiazole-2-carboxamide;
N-[(3R)-1-azabicyclo[2.2.2]oct-3-yl]-5-(3-chlorophenyl)-1,3-thiazole-2-carboxamide;
N-[(3R)-1-azabicyclo[2.2.2]oct-3-yl]-5-(2-fluorophenyl)-1,3-thiazole-2-carboxamide;
N-[(3R)-1-azabicyclo[2.2.2]oct-3-yl]-5-(3-fluorophenyl)-1,3-thiazole-2-carboxamide;
N-[(3R)-1-azabicyclo[2.2.2]oct-3-yl]-5-thien-2-yl-1,3-thiazole-2-carboxamide;
N-[(3R)-1-azabicyclo[2.2.2]oct-3-yl]-5-phenyl-furan-2-carboxamide;
N-[(3R)-1-azabicyclo[2.2.2]oct-3-yl]-5-(2-chlorophenyl)-furan-2-carboxamide;
N-[(3R)-1-azabicyclo[2.2.2]oct-3-yl]-5-(3-chlorophenyl)-furan-2-carboxamide;
N-[(3R)-1-azabicyclo[2.2.2]oct-3-yl]-5-(4-chlorophenyl)-furan-2-carboxamide;
N-[(3R)-1-azabicyclo[2.2.2]oct-3-yl]-5-(4-bromophenyl)-furan-2-carboxamide;
N-[(3R)-1-azabicyclo[2.2.2]oct-3-yl]-5-[2-(trifluoromethyl)phenyl]-furan-2-carboxamide;
N-[(3R)-1-azabicyclo[2.2.2]oct-3-yl]-5-[3-(trifluoromethyl)-phenyl]furan-2-carboxamide;
N-[(3R)-1-azabicyclo[2.2.2]oct-3-yl]-5-(2-nitrophenyl)-furan-2-carboxamide;
N-[(3R)-1-azabicyclo[2.2.2]oct-3-yl]-5-(3-nitrophenyl)-furan-2-carboxamide;
N-[(3R)-1-azabicyclo[2.2.2]oct-3-yl]-5-(4-nitrophenyl)-furan-2-carboxamide;
N-[(3R)-1-azabicyclo[2.2.2]oct-3-yl]-5-(2-fluorophenyl)-furan-2-carboxamide;
N-[(3R)-1-azabicyclo[2.2.2]oct-3-yl]-5-(3-fluorophenyl)-furan-2-carboxamide;
N-[(3R)-1-azabicyclo[2.2.2]oct-3-yl]-5-(4-fluorophenyl)-furan-2-carboxamide;
N-[(3R)-1-azabicyclo[2.2.2]oct-3-yl]-5-(2,4-difluorophenyl)-furan-2-carboxamide;
N-[(3R)-1-azabicyclo[2.2.2]oct-3-yl]-5-(2,5-difluorophenyl)-furan-2-carboxamide;
N-[(3R)-1-azabicyclo[2.2.2]oct-3-yl]-5-(2-methoxyphenyl)-furan-2-carboxamide;
N-[(3R)-1-azabicyclo[2.2.2]oct-3-yl]-5-(3-methoxyphenyl)-furan-2-carboxamide;
N-[(3R)-1-azabicyclo[2.2.2]oct-3-yl]-5-[3-(trifluoromethoxy)phenyl]-furan-2-carboxamide;
N-[(3R)-1-azabicyclo[2.2.2]oct-3-yl]-5-[2-chloro-5-(trifluoromethyl)phenyl]-furan-2-carboxamide;
N-[(3R)-1-azabicyclo[2.2.2]oct-3-yl]-5-(4-fluoro-3-methylphenyl)-furan-2-carboxamide;
N-[(3R)-1-azabicyclo[2.2.2]oct-3-yl]-5-(4-cyanophenyl)-furan-2-carboxamide;
N-[(3R)-1-azabicyclo[2.2.2]oct-3-yl]-5-thien-2-yl-furan-2-carboxamide;
N-[(3R)-1-azabicyclo[2.2.2]oct-3-yl]-5-thien-3-yl-furan-2-carboxamide;
N-[(3R)-1-azabicyclo[2.2.2]oct-3-yl]-5-bromo-furan-2-carboxamide;
N-[(3R)-1-azabicyclo[2.2.2]oct-3-yl]-5-nitro-furan-2-carboxamide;
N-[(3R)-1-azabicyclo[2.2.2]oct-3-yl]-4,5-dimethyl-furan-2-carboxamide;
N-[(3R)-1-azabicyclo[2.2.2]oct-3-yl]-5-(4-chloro-2-nitrophenyl)-furan-2-carboxamide;
N-[(3R)-1-azabicyclo[2.2.2]oct-3-yl]-5-(4-methyl-2-nitrophenyl)-furan-2-carboxamide;
N-[(3R)-1-azabicyclo[2.2.2]oct-3-yl]-5-(2,3-difluorophenyl)-furan-2-carboxamide;
N-[(3R)-1-azabicyclo[2.2.2]oct-3-yl]-5-(3,4-difluorophenyl)-furan-2-carboxamide;
N-[(3R)-1-azabicyclo[2.2.2]oct-3-yl]-5-(3,5-difluorophenyl)-furan-2-carboxamide;
N-[(3R)-1-azabicyclo[2.2.2]oct-3-yl]-5-(4-methoxyphenyl)-furan-2-carboxamide;
N-[(3R)-1-azabicyclo[2.2.2]oct-3-yl]-5-(2-methylphenyl)-furan-2-carboxamide;
N-[(3R)-1-azabicyclo[2.2.2]oct-3-yl]-5-(3-methylphenyl)-furan-2-carboxamide;
N-[(3R)-1-azabicyclo[2.2.2]oct-3-yl]-5-(4-methylphenyl)-furan-2-carboxamide;
N-[(3R)-1-azabicyclo[2.2.2]oct-3-yl]-5-[2-(trifluoromethoxy)phenyl]-furan-2-carboxamide;
N-[(3R)-1-azabicyclo[2.2.2]oct-3-yl]-5-[4-(trifluoromethoxy)phenyl]-furan-2-carboxamide;
N-[(3R)-1-azabicyclo[2.2.2]oct-3-yl]-5-(4-tert-butylphenyl)-furan-2-carboxamide;
N-[(3R)-1-azabicyclo[2.2.2]oct-3-yl]-5-(1-benzothien-2-yl)-furan-2-carboxamide;
N-[(3R)-1-azabicyclo[2.2.2]oct-3-yl]-5-quinolin-3-yl-furan-2-carboxamide;
N-[(3R)-1-azabicyclo[2.2.2]oct-3-yl]-5-(4-ethylphenyl)-furan-2-carboxamide;
N-[(3R)-1-azabicyclo[2.2.2]oct-3-yl]-5-(4-isopropylphenyl)-furan-2-carboxamide;

N-[(3R)-1-azabicyclo[2.2.2]oct-3-yl]-5-(3-fluoro-4-methoxyphenyl)-furan-2-carboxamide;
N-[(3R)-1-azabicyclo[2.2.2]oct-3-yl]-5-(1-benzofuran-2-yl)-furan-2-carboxamide;
5-(2-aminophenyl)-N-[(3R)-1-azabicyclo[2.2.2]oct-3-yl]-furan-2-carboxamide;
5-(4-aminophenyl)-N-[(3R)-1-azabicyclo[2.2.2]oct-3-yl]-furan-2-carboxamide;
5-(2-amino-4-methylphenyl)-N-[(3R)-1-azabicyclo[2.2.2]oct-3-yl]-furan-2-carboxamide;
N-[(3R)-1-azabicyclo[2.2.2]oct-3-yl]-5-(phenylethynyl)-furan-2-carboxamide;
N-[(3R)-1-azabicyclo[2.2.2]oct-3-yl]-5-phenoxy-furan-2-carboxamide;
N-[(3R)-1-azabicyclo[2.2.2]oct-3-yl]-1-methyl-5-phenyl-1H-pyrrole-2-carboxamide;
N-[(3R)-1-azabicyclo[2.2.2]oct-3-yl]-5-phenyl-1,3-oxazole-2-carboxamide;
N-[(3R)-1-azabicyclo[2.2.2]oct-3-yl]-3-phenyl-1,2,4-oxadiazole-5-carboxamide;
N-[(3R)-1-azabicyclo[2.2.2]oct-3-yl]-2-phenyl-1,3-oxazole-5-carboxamide;
N-[(3R)-1-azabicyclo[2.2.2]oct-3-yl]-2-phenyl-1,3-oxazole-4-carboxamide;
N-[(3R)-1-azabicyclo[2.2.2]oct-3-yl]-5-phenylisoxazole-3-carboxamide;
5-bromo-N-(2-methyl-1-azabicyclo[2.2.2]oct-3-yl)-thiophene-2-carboxamide;
N-[(3R)-1-azabicyclo[2.2.2]oct-3-yl]-5-phenyl-thiophene-2-carbothioamide; and
pharmaceutically acceptable salts thereof.

46. The method according to claim 45, wherein said compound(s) is(are) administered rectally, topically, orally, sublingually, or parenterally.

47. The method according to claim 45, wherein said compound(s) is(are) administered from about 0.001 to about 100 mg/kg of body weight of said mammal per day.

48. The method according to claim 45, wherein said compound(s) is(are) administered from about 0.1 to about 50 mg/kg of body weight of said mammal per day.

49. The method according to claim 13, wherein the compound of Formula I is anyone of or combination of the compounds including:

N-[(2S,3R)-2-methyl-1-azabicyclo[2.2.2]oct-3-yl]-5-phenyl-thiophene-2-carboxamide; N-[(2S,3R)-2-methyl-1-azabicyclo[2.2.2]oct-3-yl]-5-(4-chlorophenyl)-thiophene-2-carboxamide; N-[(2S,3R)-2-methyl-1-azabicyclo[2.2.2]oct-3-yl]-5-(3-chlorophenyl)-thiophene-2-carboxamide; N-[(2S,3R)-2-methyl-1-azabicyclo[2.2.2]oct-3-yl]-5-(2-chlorophenyl)-thiophene-2-carboxamide; N-[(2S,3R)-2-methyl-1-azabicyclo[2.2.2]oct-3-yl]-2,3'-bithiophene-5-carboxamide; N-[(2S,3R)-2-methyl-1-azabicyclo[2.2.2]oct-3-yl]-5-(2-nitrophenyl)-thiophene-2-carboxamide; N-[(2S,3R)-2-methyl-1-azabicyclo[2.2.2]oct-3-yl]-5-(3-nitrophenyl)-thiophene-2-carboxamide; N-[(2S,3R)-2-methyl-1-azabicyclo[2.2.2]oct-3-yl]-4-phenyl-thiophene-2-carboxamide; N-[(2S,3R)-2-methyl-1-azabicyclo[2.2.2]oct-3-yl]-5-(3-benzyloxyphenyl)-thiophene-2-carboxamide; N-[(2S,3R)-2-methyl-1-azabicyclo[2.2.2]oct-3-yl]-5-(4-benzyloxyphenyl)-thiophene-2-carboxamide; N-[(2S,3R)-2-methyl-1-azabicyclo[2.2.2]oct-3-yl]-5-(3-fluoro-4-benzyloxyphenyl)-thiophene-2-carboxamide; 5-(2-aminophenyl)-N-[(2S,3R)-2-methyl-1-azabicyclo[2.2.2]oct-3-yl]-thiophene-2-carboxamide; N-[(2S,3R)-2-methyl-1-azabicyclo[2.2.2]oct-3-yl]-5-pyridin-3-yl-thiophene-2-carboxamide; N-[(2S,3R)-2-methyl-1-azabicyclo[2.2.2]oct-3-yl]-5'-methyl-2,2'-bithiophene-5-carboxamide; N-[(2S,3R)-2-methyl-1-azabicyclo[2.2.2]oct-3-yl]-5'-chloro-2,2'-bithiophene-5-carboxamide; N-[(2S,3R)-2-methyl-1-azabicyclo[2.2.2]oct-3-yl]-5-nitro-thiophene-2-carboxamide; 5-(aminomethyl)-N-[(2S,3R)-2-methyl-1-azabicyclo[2.2.2]oct-3-yl]-thiophene-2-carboxamide; N-[(2S,3R)-2-methyl-1-azabicyclo[2.2.2]oct-3-yl]-5-cyano-thiophene-2-carboxamide; N-[(2S,3R)-2-methyl-1-azabicyclo[2.2.2]oct-3-yl]-5-methoxy-thiophene-2-carboxamide; N-[(2S,3R)-2-methyl-1-azabicyclo[2.2.2]oct-3-yl]-5-(pyridin-2-yl)-thiophene-2-carboxamide; N-[(2S,3R)-2-methyl-1-azabicyclo[2.2.2]oct-3-yl]-[2,2']bithiophenyl-5-carboxamide; N-[(2S,3R)-2-methyl-1-azabicyclo[2.2.2]oct-3-yl]-5-(methylsulfanyl)-thiophene-2-carboxamide; N-[(2S,3R)-2-methyl-1-azabicyclo[2.2.2]oct-3-yl]-5-chloro-thiophene-2-carboxamide; N-[(2S,3R)-2-methyl-1-azabicyclo[2.2.2]oct-3-yl]-5-acetyl-thiophene-2-carboxamide; N-[(2S,3R)-2-methyl-1-azabicyclo[2.2.2]oct-3-yl]-5-methyl-thiophene-2-carboxamide; N-[(2S,3R)-2-methyl-1-azabicyclo[2.2.2]oct-3-yl]-5-bromo-thiophene-2-carboxamide; N-[(2S,3R)-2-methyl-1-azabicyclo[2.2.2]oct-3-yl]-5-(phenylsulfanyl)-thiophene-2-carboxamide; N-[(2S,3R)-2-methyl-1-azabicyclo[2.2.2]oct-3-yl]-5-(acetylamino)-furan-2-carboxamide; N-[(2S,3R)-2-methyl-1-azabicyclo[2.2.2]oct-3-yl]-5-trifluoromethyl-furan-2-carboxamide; N-[(2S,3R)-2-methyl-1-azabicyclo[2.2.2]oct-3-yl]-5-(2-methyl-5-trifluoromethyl-2H-pyrazole-3-yl)-thiophene-2-carboxamide; N-[(2S,3R)-2-methyl-1-azabicyclo[2.2.2]oct-3-yl]-5-(2-methylthiazol-4-yl)-thiophene-2-carboxamide; N-[(2S,3R)-2-methyl-1-azabicyclo[2.2.2]oct-3-yl]-5-[2-(3-chlorophenyl)-vinyl]-thiophene-2-carboxamide; N-[(2S,3R)-2-methyl-1-azabicyclo[2.2.2]oct-3-yl]-5-(4-chlorophenylsulfanyl)-thiophene-2-carboxamide; N-[(2S,3R)-2-methyl-1-azabicyclo[2.2.2]oct-3-yl]-5-(2,4-difluorophenyl-sulfanyl)-thiophene-2-carboxamide; N-[(2S,3R)-2-methyl-1-azabicyclo[2.2.2]oct-3-yl]-5-(3-chlorophenylsulfanyl)-thiophene-2-carboxamide; N-[(2S,3R)-2-methyl-1-azabicyclo[2.2.2]oct-3-yl]-5-(3-chloro-4-fluoro-phenylsulfanyl)-thiophene-2-carboxamide; N-[(2S,3R)-2-methyl 1-azabicyclo[2.2.2]oct-3-yl]-5-(2,3-dichlorophenyl-sulfanyl)-thiophene-2-carboxamide; N-[(2S,3R)-2-methyl-1-azabicyclo[2.2.2]oct-3-yl]-5-(2,4,5-trichlorophenyl-sulfanyl)-thiophene-2-carboxamide; N-[(2S,3R)-2-methyl-1-azabicyclo[2.2.2]oct-3-yl]-5-(3,4-dichlorophenyl-sulfanyl)thiophene-2-carboxamide; N-[(2S,3R)-2-methyl-1-azabicyclo[2.2.2]oct-3-yl]-5-phenoxy-thiophene-2-carboxamide; N-[(2S,3R)-2-methyl-1-azabicyclo[2.2.2]oct-3-yl]-5-(2-hydroxyphenyl)-thiophene-2-carboxamide; N-[(2S,3R)-2-methyl-1-azabicyclo[2.2.2]oct-3-yl]-5-(3-hydroxyphenyl)thiophene-2-carboxamide; N-[(2S,3R)-2-methyl-1-azabicyclo[2.2.2]oct-3-yl]-5-(3-fluoro-4-hydroxyphenyl)-thiophene-2-carboxamide; N-[(2S,3R)-2-methyl-1-azabicyclo[2.2.2]oct-3-yl]-2-(phenylsulfanyl)-1,3-thiazole-5-carboxamide; N-[(2S,3R)-2-methyl-1-azabicyclo[2.2.2]oct-3-yl]-2-[(4- chlorophenyl)-sulfanyl]-1,3-thiazole-5-carboxamide; N-[(2S,3R)-2-methyl-1-azabicyclo[2.2.2]oct-3-yl]-2-phenoxy-1,3-thiazole-5-carboxamide; N-[(2S,3R)-2-methyl-1-azabicyclo[2.2.2]oct-3-yl]-2-[(4-fluorophenyl)-sulfanyl]-1,3-thiazole-5-carboxamide; N-[(2S,3R)-2-methyl-1-azabicyclo[2.2.2]oct-3-yl]-2-(methylsulfanyl)-1,3-thiazole-5-carboxamide; N-[(2S,3R)-2-methyl-1-azabicyclo[2.2.2]oct-3-yl]-2-(4-chlorophenoxy)-1,3-thiazole-5-carboxamide; N-[(2S,3R)-2-methyl-1-azabicyclo[2.2.2]oct-3-yl]-2-phenyl-1,3-thiazole-5-carboxamide; N-[(2S,3R)-2-methyl-1-azabicyclo[2.2.2]oct-3-yl]-2,4-dimethyl-1,3-thiazole-5-carboxamide; N-[(2S,3R)-2-methyl-1-azabicyclo[2.2.2]oct-3-yl]-2-(2-fluorophenyl)-1,3-thiazole-5-carboxamide; N-[(2S,3R)-2-methyl-1-azabicyclo[2.2.2]oct-3-yl]-2-(3-fluorophenyl)-1,3-thiazole-5-carboxamide; N-[(2S,3R)-2-methyl-1-azabicyclo[2.2.2]oct-3-yl]-2-(4-fluorophenyl)-1,3-thiazole-5-carboxamide; N-[(2S,3R)-2-methyl-1-azabicyclo[2.2.2]oct-3-yl]-2-(2-hydroxyphenyl)-1,3-thiazole-5-carboxamide; N-[(2S,3R)-2-methyl-1-azabicyclo[2.2.2]oct-3-yl]-2-(4-methylphenyl)-1,3-thiazole-5-carboxamide; N-([(2S,3R)-2-methyl-1-azabicyclo[2.2.2]oct-3-yl]-2-[4-(benzyloxy)phenyl]-1,3-thiazole-5-carboxamide; N-[(2S,3R)-2-methyl-1-azabicyclo[2.2.2]oct-3-yl]-2-pyridin-3-yl-1,3-thiazole-4-carboxamide; N-[(2S,3R)-2-methyl-1-azabicyclo[2.2.2]oct-3-yl]-4-methyl-2-phenyl-1,3-thiazole-5-carboxamide; N-[(2S,3R)-2-methyl-1-azabicyclo[2.2.2]oct-3-yl]-2-(4-chlorophenyl)-4-methyl-1,3-thiazole-5-carboxamide; N-[(2S,3R)-2-methyl-1-azabicyclo[2.2.2]oct-3-yl]-4-methyl-2-pyridin-2-yl-1,3-thiazole-5-carboxamide; N-[(2S,3R)-2-methyl-1-azabicyclo[2.2.2]oct-3-yl]-4-methyl-2-pyridin-4-yl-1,3-thiazole-5-carboxamide; N-[(2S,3R)-2-methyl-1-azabicyclo[2.2.2]oct-3-yl]-2-(methylamino)-1,3-thiazole-5-carboxamide; N-[(2S,3R)-2-methyl-1-azabicyclo[2.2.2]oct-3-yl]-5-(phenylsulfanyl)-1,3,4-thiadiazole-2-carboxamide; N-[(2S,3R)-2-methyl-1-azabicyclo[2.2.2]oct-3-yl]-5-phenoxy-1,3,4-thiadiazole-2-carboxamide; N-[(2S,3R)-2-methyl-1-azabicyclo[2.2.2]oct-3-yl]-5-[(4-chlorophenyl)-sulfanyl]-1,3,4-thiadiazole-2-carboxamide; N-[(2S,3R)-2-methyl-1-azabicyclo[2.2.2]oct-3-yl]-5-(4-fluorophenoxy)-1,3,4-thiadiazole-2-carboxamide; N-[(2S,3R)-2-methyl-1-azabicyclo[2.2.2]oct-3-yl]-5-(4-chlorophenoxy)-1,3,4-thiadiazole-2-carboxamide; N-[(2S,3R)-2-methyl-1-azabicyclo[2.2.2]oct-3-yl]-5-[(3-fluorophenyl)-sulfanyl]-1,3,4-thiadiazole-2-carboxamide; N-[(2S,3R)-2-methyl-1-azabicyclo[2.2.2]oct-3-yl]-5-[(2-chlorophenyl)-sulfanyl]-1,3,4-thiadiazole-2-carboxamide; N-[(2S,3R)-2-methyl-1-azabicyclo[2.2.2]oct-3-yl]-5-[(4-fluorophenyl)-sulfanyl]-1,3,4-thiadiazole-2-carboxamide; N-[(2S,3R)-2-methyl-1-azabicyclo[2.2.2]oct-3-yl]-5-[(3-chlorophenyl)-sulfanyl]-1,3,4-thiadiazole-2-carboxamide; N-[(2S,3R)-2-methyl-1-azabicyclo[2.2.2]oct-3-yl]-5-phenyl-1H-1,2,4-triazole-3-carboxamide; N-[(2S,3R)-2-methyl-1-azabicyclo[2.2.2]oct-3-yl]-5-phenyl-1,3,4-oxadiazole-2-carboxamide; N-[(2S,3R)-2-methyl-1-azabicyclo[2.2.2]oct-3-yl]-5-(methylthio)-1,3,4-oxadiazole-2-carboxamide; N-[(2S,3R)-2-methyl-1-azabicyclo[2.2.2]oct-3-yl]-5-(3-chlorophenyl)-1,3-oxazole-2-carboxamide; N-[(2S,3R)-2-methyl-1-azabicyclo[2.2.2]oct-3-yl]-5-(3-methoxyphenyl)-1,3-oxazole-2-carboxamide; N-[(2S,3R)-2-methyl-1-azabicyclo[2.2.2]oct-3-yl]-5-(3-nitrophenyl)-1,3-oxazole-2-carboxamide; N-[(2S,3R)-2-methyl N-[(2S,3R)-2-methyl-1-azabicyclo[2.2.2]oct-3-yl]-5-(4-bromophenyl)-1,3-thiazole-2-carboxamide; N-[(2S,3R)-2-methyl-1-azabicyclo[2.2.2]oct-3-yl]-5-(3-nitrophenyl)-1,3-thiazole-2-carboxamide; N-[(2S,3R)-2-methyl-1-azabicyclo[2.2.2]oct-3-yl]-5-(3-methoxyphenyl)-1,3-thiazole-2-carboxamide; N-[(2S,3R)-2-methyl-1-azabicyclo[2.2.2]oct-3-yl]-5-(2-chlorophenyl)-1,3-thiazole-2-carboxamide; N-[(2S,3R)-2-methyl-1-azabicyclo[2.2.2]oct-3-yl]-5-(4-fluorophenyl)-1,3-thiazole-2-carboxamide; N-[(2S,3R)-2-methyl-1-azabicyclo[2.2.2]oct-3-yl]-5-(2-methoxyphenyl)-1,3-thiazole-2-carboxamide; N-[(2S,3R)-2-methyl-1-azabicyclo[2.2.2]oct-3-yl]-5-(4-chlorophenyl)-1,3-thiazole-2-carboxamide; N-[(2S,3R)-2-methyl-1-azabicyclo[2.2.2]oct-3-yl]-5-methyl-1,3-thiazole-2-carboxamide; N-[(2S,3R)-2-methyl-1-azabicyclo[2.2.2]oct-3-yl]-5-(3-chlorophenyl)-1,3-thiazole-2-carboxamide; N-[(2S,3R)-2-methyl-1-azabicyclo[2.2.2]oct-3-yl]-5-(2-fluorophenyl)-1,3-thiazole-2-carboxamide; N-[(2S,3R)-2-methyl-1-azabicyclo[2.2.2]oct-3-yl]-5-(3-fluorophenyl)-1,3-thiazole-2-carboxamide; N-[(2S,3R)-2-methyl-1-azabicyclo[2.2.2]oct-3-yl]-5-thien-2-yl-1,3-thiazole-2-carboxamide; N-[(2S,3R)-2-methyl-1-azabicyclo[2.2.2]oct-3-yl]-5-phenyl-furan-2-carboxamide; N-[(2S,3R)-2-methyl-1-azabicyclo[2.2.2]oct-3-yl]-5-(2-chlorophenyl)-furan-2-carboxamide; N-[(2S,3R)-2-methyl-1-azabicyclo[2.2.2]oct-3-yl]-5-(3-chlorophenyl)-furan-2-carboxamide; N-[(2S,3R)-2-methyl-1-azabicyclo[2.2.2]oct-3-yl]-5-(4-chlorophenyl)-furan-2-carboxamide; N-[(2S,3R)-2-methyl-1-azabicyclo[2.2.2]oct-3-yl]-5-(4-bromophenyl)-furan-2-carboxamide; N-[(2S,3R)-2-methyl-1-azabicyclo[2.2.2]oct-3-yl]-5-[2-(trifluoromethyl)-phenyl]-furan-2-carboxamide; N-[(2S,3R)-2-methyl-1-azabicyclo[2.2.2]oct-3-yl]-5-[3-(trifluoromethyl)-phenyl]-furan-2-carboxamide; N-[(2S,3R)-2-methyl-1-azabicyclo[2.2.2]oct-3-yl]-5-(2-nitrophenyl)-furan-2-carboxamide; N-[(2S,3R)-2-methyl-1-azabicyclo[2.2.2]oct-3-yl]-5-(3-nitrophenyl)-furan-2-carboxamide; N-[(2S,3R)-2-methyl-1-azabicyclo[2.2.2]oct-3-yl]-5-(4-nitrophenyl)-furan-2-carboxamide; N-[(2S,3R)-2-methyl-1-azabicyclo[2.2.2]oct-3-yl]-5-(2-fluorophenyl)-furan-2-carboxamide; N-[(2S,3R)-2-methyl-1-azabicyclo[2.2.2]oct-3-yl]-5-(3-fluorophenyl)-furan-2-carboxamide; N-[(2S,3R)-2-methyl-1-azabicyclo[2.2.2]oct-3-yl]-5-(4-fluorophenyl)-furan-2-carboxamide; N-[(2S,3R)-2-methyl-1-azabicyclo[2.2.2]oct-3-yl]-5-(2,4-difluorophenyl)-furan-2-carboxamide; N-[(2S,3R)-2-methyl-1-azabicyclo[2.2.2]oct-3-yl]-5-(2,5-difluorophenyl)-furan-2-carboxamide; N-[(2S,3R)-2-methyl-1-azabicyclo[2.2.2]oct-3-yl]-5-(2-methoxyphenyl)-furan-2-carboxamide; N-[(2S,3R)-2-methyl-1-azabicyclo[2.2.2]oct-3-yl]-5-(3-methoxyphenyl)-furan-2-carboxamide; N-[(2S,3R)-2-methyl-1-azabicyclo[2.2.2]oct-3-yl]-5-[3(trifluoromethoxy)phenyl]-furan-2-carboxamide; N-[(2S,3R)-2-methyl-1-azabicyclo[2.2.2]oct-3-yl]-5-[2-chloro-5-(trifluoromethyl)phenyl]-furan-2-carboxamide; N-[(2S,3R)-2-methyl-1-azabicyclo[2.2.2]oct-3-yl]-5-(4-fluoro-3-methylphenyl)-furan-2-carboxamide; N-[(2S,3R)-2-methyl-1-azabicyclo[2.2.2]oct-3-yl]-5-(4-cyanophenyl)-furan-2-carboxamide; N-[(2S,3R)-2- methyl-1-azabicyclo[2.2.2]oct-3-yl]-5-thien-2-yl-furan-2-carboxamide; N-[(2S,3R)-2-methyl-1-azabicyclo[2.2.2]oct-3-yl]-5-thien-3-yl-furan-2-carboxamide; N-[(2S,3R)-2-methyl-1-azabicyclo[2.2.2]oct-3-yl]-5-bromo-furan-2-carboxamide; N-[(2S,3R)-2-methyl-1-azabicyclo[2.2.2]oct-3-yl]-5-nitro-furan-2-carboxamide; N-[(2S,3R)-2-methyl-1-azabicyclo[2.2.2]oct-3-yl]-4,5-dimethyl-furan-2-carboxamide; N-[(2S,3R)-2-methyl-1-azabicyclo[2.2.2]oct-3-yl]-5-(4-chloro-2-nitrophenyl)-furan-2-carboxamide; N-[(2S,3R)-2-methyl-1-azabicyclo[2.2.2]oct-3-yl]-5-(4-methyl-2-nitrophenyl)-furan-2-carboxamide; N-[(2S,3R)-2-methyl-1-azabicyclo[2.2.2]oct-3-yl]-5-(2,3-difluorophenyl)-furan-2-carboxamide; N-[(2S,3R)-2-methyl-1-azabicyclo[2.2.2]oct-3-yl]-5-(3,4-difluorophenyl)-furan-2-carboxamide; N-[(2S,3R)-2-methyl-1-azabicyclo[2.2.2]oct-3-yl]-5-(3,5-difluorophenyl)-furan-2-carboxamide; N-[(2S,3R)-2-methyl-1-azabicyclo[2.2.2]oct-3-yl]-5-(4-methoxy-phenyl)-furan-2-carboxamide; N-[(2S,3R)-2-methyl-1-azabicyclo[2.2.2]oct-3-yl]-5-(2-methylphenyl)-furan-2-carboxamide; N-[(2S,3R)-2-methyl-1-azabicyclo[2.2.2]oct-3-yl]-5-(3-methylphenyl)-furan-2-carboxamide; N-[(2S,3R)-2-methyl-1-azabicyclo[2.2.2]oct-3-yl]-5-(4-methylphenyl)-furan-2-carboxamide; N-[(2S,3R)-2-methyl-1-azabicyclo[2.2.2]oct-3-yl]-5-[2-(trifluoromethoxy)phenyl]-furan-2-carboxamide; N-[(2S,3R)-2-methyl-1-azabicyclo[2.2.2]oct-3-yl]-5-[4-(trifluoromethoxy)phenyl]furan-2-carboxamide; N-[(2S,3R)-2-methyl-1-azabicyclo[2.2.2]oct-3-yl]-5-(4-tert-butylphenyl)-furan-2-carboxamide; N-[(2S,3R)-2-methyl-1-azabicyclo[2.2.2]oct-3-yl]-5-(1-benzothien-2-yl)-furan-2-carboxamide; N-[(2S,3R)-2-methyl-1-azabicyclo[2.2.2]oct-3-yl]-5-quinolin-3-yl-furan-2-carboxamide; N-[(2S,3R)-2-methyl-1-azabicyclo[2.2.2]oct-3-yl]-5-(4-ethylphenyl)-furan-2-carboxamide; N-[(2S,3R)-2-methyl-1-azabicyclo[2.2.2]oct-3-yl]-5-(4-isopropylphenyl)-furan-2-carboxamide; N-[(2S,3R)-2-methyl-1-azabicyclo[2.2.2]oct-3-yl]-5-(3-fluoro-4-methoxyphenyl)-furan-2-carboxamide; N-[(2S,3R)-2-methyl-1-azabicyclo[2.2.2]oct-3-yl]-5-(1-benzofuran-2-yl)-furan-2-carboxamide; 5-(2-aminophenyl)-N-[(2S,3R)-2-methyl-1-azabicyclo[2.2.2]oct-3-yl]-furan-2-carboxamide; 5-(4-aminophenyl)-N-[(2S,3R)-2-methyl-1-azabicyclo[2.2.2]oct-3-yl]-furan-2-carboxamide; 5-(2-amino-4-methylphenyl)-N[(2S,3R)-2-methyl-1-azabicyclo[2.2.2]oct-3-yl]-furan-2-carboxamide; N-[(2S,3R)-2-methyl-1-azabicyclo[2.2.2]oct-3-yl]-5-(phenylethynyl)-furan-2-carboxamide; N-[(2S,3R)-2-methyl-1-azabicyclo[2.2.2]oct-3-yl]-5-phenoxy-furan-2-carboxamide; N-[(2S,3R)-2-methyl-1-azabicyclo[2.2.2]oct-3-yl-]-1-methyl-5-phenyl-1H-pyrrole-2-carboxamide; N-[(2S,3R)-2-methyl-1-azabicyclo[2.2.2]oct-3-yl]-5-phenyl-1,3-oxazole-2-carboxamide; N-[(2S,3R)-2-methyl-1-azabicyclo[2.2.2]oct-3-yl]-3-phenyl-1,2,4-oxadiazole-5-carboxamide; N-[(2S,3R)-2-methyl-1-azabicyclo[2.2.2]oct-3-yl]-2-phenyl-1,3-oxazole-5-carboxamide; N-[(2S,3R)-2-methyl-1-azabicyclo[2.2.2]oct-3-yl]-2-phenyl-1,3-oxazole-4-carboxamide; N-[(2S,3R)-2-methyl-1-azabicyclo[2.2.2]oct-3-yl]-5-phenylisoxazole-3-carboxamide; 5-bromo-N-[(2S,3R)-2-methyl-1-azabicyclo[2.2.2]oct-3-yl]-thiophene-2-carboxamide; N-[(2S,3R)-2-methyl-1-azabicyclo[2.2.2]oct-3-yl]-5-phenyl-thiophene-2-carbothioamide;

N-[(3R)-1-azabicyclo[2.2.2]oct-3-yl]-5-(2-acetamidophenyl)-thiophene-2-carboxamide; N-[(3R)-1-azabicyclo[2.2.2]oct-3-yl]-5-(3-acetamidophenyl)-thiophene-2-carboxamide; N-[(3R)-1-azabicyclo[2.2.2]oct-3-yl]-5-(4-acetamidophenyl)-thiophene-2-carboxamide; N-[(3R)-1-azabicyclo[2.2.2]oct-3-yl]-5-(2-trifluoroacetamidophenyl)-thiophene-2-carboxamide; N-[(3R)-1-azabicyclo[2.2.2]oct-3-yl]-5-(3-trifluoroacetamidophenyl)-thiophene-2-carboxamide; N-[(3R)-1-azabicyclo[2.2.2]oct-3-yl]-5-(4-trifluoroacetamidophenyl)-thiophene-2-carboxamide; N-[(3R)-1-azabicyclo[2.2.2]oct-3-yl]-5-(2-methanesulfonylaminophenyl)-thiophene-2-carboxamide; N-[(3R)-1-azabicyclo[2.2.2]oct-3-yl]-5-(3-methanesulfonylaminophenyl)-thiophene-2-carboxamide; N-[(3R)-1-azabicyclo[2.2.2]oct-3-yl]-5-(4-methanesulfonylaminophenyl)-thiophene-2-carboxamide; N-[(3R)-1-azabicyclo[2.2.2]oct-3-yl]-5-(2-trifluoromethanesulfonylaminophenyl)-thiophene-2-carboxamide; N-[(3R)-1-azabicyclo[2.2.2]oct-3-yl]-5-(3-tifluoromethanesulfonylaminophenyl)-thiophene-2-carboxamide; N-[(3R)-1-azabicyclo[2.2.2]oct-3-yl]-5-(4-trifluoromethanesulfonylaminophenyl)-thiophene-2-carboxamide; N-[(3R)-1-azabicyclo[2.2.2]oct-3-yl]-5-(2-difluoroacetamidophenyl)-thiophene-2-carboxamide; N-[(3R)-1-azabicyclo[2.2.2]oct-3-yl]-5-(3-difluoroacetamidophenyl)-thiophene-2-carboxamide; N-[(3R)-1-azabicyclo[2.2.2]oct-3-yl]-5-(4-difluoroacetamidophenyl)-thiophene-2-carboxamide; N-[(3R)-1-azabicyclo[2.2.2]oct-3-yl]-5-(2-carbamoylphenyl)-thiophene-2-carboxamide; N-[(3R)-1-azabicyclo[2.2.2]oct-3-yl]-5-(3-carbamoylphenyl)-thiophene-2-carboxamide; N-[(3R)-1-azabicyclo[2.2.2]oct-3-yl]-5-(4-carbamoylphenyl)-thiophene-2-carboxamide; N-[(3R)-1-azabicyclo[2.2.2]oct-3-yl]-5-(2-sulfamoylphenyl)-thiophene-2-carboxamide; N-[(3R)-1-azabicyclo[2.2.2]oct-3-yl]-5-(3-sulfamoylphenyl)-thiophene-2-carboxamide; N-[(3R)-1-azabicyclo[2.2.2]oct-3-yl]-5-(4-sulfamoylphenyl)-thiophene-2-carboxamide; N-[(3R)-1-azabicyclo[2.2.2]oct-3-yl]-5-(2-acetamidophenylsulfanyl)-thiophene-2-carboxamide; N-[(3R)-1-azabicyclo[2.2.2]oct-3-yl]-5-(3-acetamidophenylsulfanyl)-thiophene-2-carboxamide; N-[(3R)-1-azabicyclo[2.2.2]oct-3-yl]-5-(4-acetamidophenylsulfanyl)-thiophene-2-carboxamide; N-[(3R)-1-azabicyclo[2.2.2]oct-3-yl]-5-(2-trifluoroacetamidophenylsulfanyl)-thiophene-2-carboxamide; N-[(3R)-1-azabicyclo[2.2.2]oct-3-yl]-5-(3-trifluoroacetamidophenylsulfanyl)thiophene-2-carboxamide; N-[(3R)-1-azabicyclo[2.2.2]oct-3-yl]-5-(4-trifluoroacetamidophenylsulfanyl)-thiophene-2-carboxamide; N-[(3R)-1-azabicyclo[2.2.2]oct-3-yl]-5-(2-methanesulfonylaminophenylsulfanyl)-thiophene-2-carboxamide; N-[(3R)-1-azabicyclo[2.2.2]oct-3-yl]-5-(3-methanesulfonylaminophenylsulfanyl)-thiophene-2-carboxamide; N-[(3R)-1-azabicyclo[2.2.2]oct-3-yl]-5-(4-methanesulfonylaminophenylsulfanyl)-thiophene-2-carboxamide; N-[(3R)-1-azabicyclo[2.2.2]oct-3-yl]-5-(2-trifluoromethanesulfonylaminophenylsulfanyl)-thiophene-2-carboxamide; N-[(3R)-1-azabicyclo[2.2.2]oct-3-yl]-5-(3-trifluoromethanesulfonylaminophenylsulfanyl)-thiophene-2-carboxamide; N-[(3R)-1-azabicyclo[2.2.2]oct-3-yl]-5-(4- trifluoromethanesulfonylaminophenylsulfanyl)-thiophene-2-carboxamide; N-[(3R)-1-azabicyclo[2.2.2]oct-3-yl]-5-(2-difluoroacetamidophenylsulfanyl)-thiophene-2-carboxamide; N-[(3R)-1-azabicyclo[2.2.2]oct-3-yl]-5-(3-difluoroacetamidophenylsulfanyl)-thiophene-2-carboxamide; N-[(3R)-1-azabicyclo[2.2.2]oct-3-yl]-5-(4-difluoroacetamidophenylsulfanyl)-thiophene-2-carboxamide; N-[(3R)-1-azabicyclo[2.2.2]oct-3-yl]-5-(2-carbamoylphenylsulfanyl)-thiophene-2-carboxamide; N-[(3R)-1-azabicyclo[2.2.2]oct-3-yl]-5-(3-carbamoylphenylsulfanyl)-thiophene-2-carboxamide; N-[(3R)-1-azabicyclo[2.2.2]oct-3-yl]-5-(4-carbamoylphenylsulfanyl)-thiophene-2-carboxamide; N-[(3R)-1-azabicyclo[2.2.2]oct-3-yl]-5-(2-sulfamoylphenylsulfanyl)-thiophene-2-carboxamide; N-[(3R)-1-azabicyclo[2.2.2]oct-3-yl]-5-(3-sulfamoylphenylsulfanyl)-thiophene-2-carboxamide; N-[(3R)-1-azabicyclo[2.2.2]oct-3-yl]-5-(4-sulfamoylphenylsulfanyl)-thiophene-2-carboxamide; N-[(3R)-1-azabicyclo[2.2.2]oct-3-yl]-5-(2-hydroxyphenylsulfanyl)-thiophene-2-carboxamide; N-[(3R)-1-azabicyclo[2.2.2]oct-3-yl]-5-(3-hydroxyphenylsulfanyl)-thiophene-2-carboxamide; N-[(3R)-1-azabicyclo[2.2.2]oct-3-yl]-5-(4-hydroxyphenylsulfanyl)-thiophene-2-carboxamide; N-[(3R)-1-azabicyclo[2.2.2]oct-3-yl]-5-(2-aminophenylsulfanyl)-thiophene-2-carboxamide; N-[(3R)-1-azabicyclo[2.2.2]oct-3-yl]-5-(3-aminophenylsulfanyl)-thiophene-2-carboxamide; N-[(3R)-1-azabicyclo[2.2.2]oct-3-yl]-5-(4-aminophenylsulfanyl)-thiophene-2-carboxamide; N-[(3R)-1-azabicyclo[2.2.2]oct-3-yl]-5-(2-acetamidophenoxy)-thiophene-2-carboxamide; N-[(3R)-1-azabicyclo[2.2.2]oct-3-yl]-5-(3-acetamidophenoxy)-thiophene-2-carboxamide; N-[(3R)-1-azabicyclo[2.2.2]oct-3-yl]-5-(4-acetamidophenoxy)-thiophene-2-carboxamide; N-[(3R)-1-azabicyclo[2.2.2]oct-3-yl]-5-(2-trifluoroacetamidophenoxy)-thiophene-2-carboxamide; N-[(3R)-1-azabicyclo[2.2.2]oct-3-yl]-5-(3-trifluoroacetamidophenoxy)-thiophene-2-carboxamide; N-[(3R)-1-azabicyclo[2.2.2]oct-3-yl]-5-(4-trifluoroacetamidophenoxy)-thiophene-2-carboxamide; N-[(3R)-1-azabicyclo[2.2.2]oct-3-yl]-5-(2-methanesulfonylaminophenoxy)-thiophene-2-carboxamide; N-[(3R)-1-azabicyclo[2.2.2]oct-3-yl]-5-(3-methanesulfonylaminophenoxy)-thiophene-2-carboxamide; N-[(3R)-1-azabicyclo[2.2.2]oct-3-yl]-5-(4-methanesulfonylaminophenoxy)-thiophene-2-carboxamide; N-[(3R)-1-azabicyclo[2.2.2]oct-3-yl]-5-(2-trifluoromethanesulfonylaminophenoxy)-thiophene-2-carboxamide; N-[(3R)-1-azabicyclo[2.2.2]oct-3-yl]-5-(3-trifluoromethanesulfonylaminophenoxy)-thiophene-2-carboxamide; N-[(3R)-1-azabicyclo[2.2.2]oct-3-yl]-5-(4-trifluoromethanesulfonylaminophenoxy)-thiophene-2-carboxamide; N-[(3R)-1-azabicyclo[2.2.2]oct-3-yl]-5-(2-difluoroacetamidophenoxy)-thiophene-2-carboxamide; N-[(3R)-1-azabicyclo[2.2.2]oct-3-yl]-5-(3-difluoroacetamidophenoxy)-thiophene-2-carboxamide; N-[(3R)-1-azabicyclo[2.2.2]oct-3-yl]-5-(4-difluoroacetamidophenoxy)-thiophene-2-carboxamide; N-[(3R)-1-azabicyclo[2.2.2]oct-3-yl]-5-(2-carbamoylphenoxy)-thiophene-2-carboxamide; N-[(3R)-1-azabicyclo[2.2.2]oct-3-yl]-5-(3-carbamoylphenoxy)-thiophene-2-carboxamide; N-[(3R)-1-azabicyclo[2.2.2]oct-3-yl]-5-(4-carbamoylphenoxy)-thiophene-2-carboxamide; N-[(3R)-1-azabicyclo[2.2.2]oct-3-yl]-5-(2-sulfamoylphenoxy)-thiophene-2-carboxamide; N-[(3R)-1-azabicyclo[2.2.2]oct-3-yl]-5-(3-sulfamoylphenoxy)-thiophene-2-carboxamide; N-[(3R)-1-azabicyclo[2.2.2]oct-3-yl]-5-(4-sulfamoylphenoxy)-thiophene-2-carboxamide; N-[(3R)-1-azabicyclo[2.2.2]oct-3-yl]-5-(2-hydroxyphenoxy)-thiophene-2-carboxamide; N-[(3R)-1-azabicyclo[2.2.2]oct-3-yl]-5-(3-hydroxyphenoxy)-thiophene-2-carboxamide; N-[(3R)-1-azabicyclo[2.2.2]oct-3-yl]-5-(4-hydroxyphenoxy)-thiophene-2-carboxamide; N-[(3R)-1-azabicyclo[2.2.2]oct-3-yl]-5-(2-aminophenoxy)-thiophene-2-carboxamide; N-[(3R)-1-azabicyclo[2.2.2]oct-3-yl]-5-(3-aminophenoxy)-thiophene-2-carboxamide; N-[(3R)-1-azabicyclo[2.2.2]oct-3-yl]-5-(4-aminophenoxy)-thiophene-2-carboxamide; N-[(3R)-1-azabicyclo[2.2.2]oct-3-yl]-5-(2-chlorophenoxy)-thiophene-2-carboxamide; N-[(3R)-1-azabicyclo[2.2.2]oct-3-yl]-5-(3-chlorophenyoxy)-thiophene-2-carboxamide; N-[(3R)-1-azabicyclo[2.2.2]oct-3-yl]-5-(4-chlorophenoxy)-thiophene-2-carboxamide; N-[(3R)-1-azabicyclo[2.2.2]oct-3-yl]-5-(2-cyanophenoxy)-thiophene-2-carboxamide; N-[(3R)-1-azabicyclo[2.2.2]oct-3-yl]-5-(3-cyanophenoxy)-thiophene-2-carboxamide; N-[(3R)-1-azabicyclo[2.2.2]oct-3-yl]-5-(4-cyanophenoxy)-thiophene-2-carboxamide; N-[(3R)-1-azabicyclo[2.2.2]oct-3-yl]-5-(2-methoxyphenyl)-thiophene-2-carboxamide; N-[(3R)-1-azabicyclo[2.2.2]oct-3-yl]-5-(3-methoxyphenyl)-thiophene-2-carboxamide; N-[(3R)-1-azabicyclo[2.2.2]oct-3-yl]-5-(4-methoxyphenyl)-thiophene-2-carboxamide; N-[(3R)-1-azabicyclo[2.2.2]oct-3-yl]-5-(2-methylphenyl)-thiophene-2-carboxamide; N-[(3R)-1-azabicyclo[2.2.2]oct-3-yl]-5-(3-methylphenyl)-thiophene-2-carboxamide; N-[(3R)-1-azabicyclo[2.2.2]oct-3-yl]-5-(4-methylphenyl)-thiophene-2-carboxamide; N-[(3R)-1-azabicyclo[2.2.2]oct-3-yl]-5-(2-trifluoromethylphenyl)-thiophene-2-carboxamide; N-[(3R)-1-azabicyclo[2.2.2]oct-3-yl]-5-(3-trifluoromethylphenyl)-thiophene-2-carboxamide; N-[(3R)-1-azabicyclo[2.2.2]oct-3-yl]-5-(4-trifluoromethylphenyl)-thiophene-2-carboxamide; N-[(3R)-1-azabicyclo[2.2.2]oct-3-yl]-5-(2-acetylphenyl)-thiophene-2-carboxamide; N-[(3R)-1-azabicyclo[2.2.2]oct-3-yl]-5-(3-acetylphenyl)-thiophene-2-carboxamide; N-[(3R)-1-azabicyclo[2.2.2]oct-3-yl]-5-(4-acetylphenyl)-thiophene-2-carboxamide; N-[(3R)-1-azabicyclo[2.2.2]oct-3-yl]-5-(2-cyanophenyl)-thiophene-2-carboxamide; N-[(3R)-1-azabicyclo[2.2.2]oct-3-yl]-5-(3-cyanophenyl)-thiophene-2-carboxamide; N-[(3R)-1-azabicyclo[2.2.2]oct-3-yl]-5-(4-cyanophenyl)-thiophene-2-carboxamide; N-[(3R)-1-azabicyclo[2.2.2]oct-3-yl]-5-(2-morpholin-4-yl-phenyl)-thiophene-2-carboxamide; N-[(3R)-1-azabicyclo[2.2.2]oct-3-yl]-5-(3-morpholin-4-yl-phenyl)-thiophene-2-carboxamide; N-[(3R)-1-azabicyclo[2.2.2]oct-3-yl]-5-(4-morpholin-4-yl-phenyl)-thiophene-2-carboxamide; N-[(3R)-1-azabicyclo[2.2.2]oct-3-yl]-5-(2-methoxyphenoxy)-thiophene-2-carboxamide; N-[(3R)-1-azabicyclo[2.2.2]oct-3-yl]-5-(3-methoxyphenoxy)-thiophene-2-carboxamide; N-[(3R)-1-azabicyclo[2.2.2]oct-3-yl]-5-(4-methoxyphenoxy)-thiophene-2-carboxamide; N-[(3R)-1-1-azabicyclo[2.2.2]oct-3-yl]-5-(2- methylphenoxy)-thiophene-2-carboxamide; N-[(3R)-1-azabicyclo[2.2.2]oct-3-yl]-5-(3-methylphenoxy)-thiophene-2-carboxamide; N-[(3R)-1-azabicyclo[2.2.2]oct-3-yl]-5-(4-methylphenoxy)-thiophene-2-carboxamide; N-[(3R)-1-azabicyclo[2.2.2]oct-3-yl]-5-(2-trifluoromethylphenoxy)-thiophene-2-carboxamide; N-[(3R)-1-azabicyclo[2.2.2]oct-3-yl]-5-(3-trifluoromethylphenoxy)-thiophene-2-carboxamide; N-[(3R)-1-azabicyclo[2.2.2]oct-3-yl]-5-(4-trifluoromethylphenoxy)-thiophene-2-carboxamide; N-[(3R)-1-azabicyclo[2.2.2]oct-3-yl]-5-(2-acetylphenoxy)-thiophene-2-carboxamide; N-[(3R)-1-azabicyclo[2.2.2]oct-3-yl]-5-(3-acetylphenoxy)-thiophene-2-carboxamide; N-[(3R)-1-azabicyclo[2.2.2]oct-3-yl]-5-(4-acetylphenoxy)-thiophene-2-carboxamide; N-[(3R)-1-azabicyclo[2.2.2]oct-3-yl]-5-(2-cyanophenoxy)-thiophene-2-carboxamide; N-[(3R)-1-azabicyclo[2.2.2]oct-3-yl]-5-(3-cyanophenoxy)-thiophene-2-carboxamide; N-[(3R)-1-azabicyclo[2.2.2]oct-3-yl]-5-(4-cyanophenoxy)-thiophene-2-carboxamide; N-[(3R)-1-azabicyclo[2.2.2]oct-3-yl]-5-(2-morpholin-4-yl-phenoxy)-thiophene-2-carboxamide; N-[(3R)-1-azabicyclo[2.2.2]oct-3-yl]-5-(3-morpholin-4-yl-phenoxy)-thiophene-2-carboxamide; N-[(3R)-1-azabicyclo[2.2.2]oct-3-yl]-5-(4-morpholin-4-yl-phenoxy)-thiophene-2-carboxamide; N-[(3R)-1-azabicyclo[2.2.2]oct-3-yl]-5-(2-methoxyphenylsulfanyl)-thiophene-2-carboxamide; N-[(3R)-1-azabicyclo[2.2.2]oct-3-yl]-5-(3-ethoxyphenylsulfanyl)-thiophene-2-carboxamide; N-[(3R)-1-azabicyclo[2.2.2]oct-3-yl]-5-(4-methoxyphenylsulfanyl)-thiophene-2-carboxamide; N-[(3R)-1-azabicyclo[2.2.2]oct-3-yl]-5-(2-methylphenylsulfanyl)-thiophene-2-carboxamide; N-[(3R)-1-azabicyclo[2.2.2]oct-3-yl]-5-(3-methylphenylsulfanyl)-thiophene-2-2-carboxamide; N-[(3R)-1-azabicyclo[2.2.2]oct-3-yl]5-5(4-methylphenylsulfanyl)-thiophene-2-carboxamide; N-[(3R)-1-azabicyclo[2.2.2]oct-3-yl]-5-(2-trifluoromethylphenylsulfanyl)-thiophene-2-carboxamide; N-[(3R)-1-azabicyclo[2.2.2]oct-3-yl]-5-(3-trifluoromethylphenylsulfanyl)-thiophene-2-carboxamide; N-[(3R)-1-azabicyclo[2.2.2]oct-3-yl]-5-(4-trifluoromethylphenylsulfanyl)-thiophene-2-carboxamide; N-[(3R)-1-azabicyclo[2.2.2]oct-3-yl]-5-(2-acetylphenylsulfanyl)-thiophene-2-carboxamide; N-[(3R)-1-azabicyclo[2.2.2]oct-3-yl]-5-(3-acetylphenylsulfanyl)-thiophene-2-carboxamide; N-[(3R)-1-azabicyclo[2.2.2]oct-3-yl]-5-(4-acetylphenylsulfanyl)-thiophene-2-carboxamide; N-[(3R)-1-azabicyclo[2.2.2]oct-3-yl]-5-(2-cyanophenylsulfanyl)-thiophene-2-carboxamide; N-[(3R)-1-azabicyclo[2.2.2]oct-3-yl]-5-(3-cyanophenylsulfanyl)-thiophene-2-carboxamide; N-[(3R)-1-azabicyclo[2.2.2]oct-3-yl]-5-(4-cyanophenylsulfanyl)-thiophene-2-carboxamide; N-[(3R)-1-azabicyclo[2.2.2]oct-3-yl]-5-(2-morpholin-4-yl-phenylsulfanyl)thiophene-2-carboxamide; N-[(3R)-1-azabicyclo[2.2.2]oct-3-yl]-5-(3-morpholin-4-yl-phenylsulfanyl)-thiophene-2-carboxamide; N-[(3R)-1-azabicyclo[2.2.2]oct-3-yl]-5-(4-morpholin-4-yl-phenylsulfanyl)-thiophene-2-carboxamide-; N-[(3R)-1-azabicyclo[2.2.2]oct-3-yl]-5-(pyridin-4-yl)-thiophene-2-carboxamide; N-[(3R)-1-azabicyclo[2.2.2]oct-3-yl]-5-(2-methylpyridin-4-yl)-thiophene-2-carboxamide; N-[(3R)-1-azabicyclo[2.2.2]oct-3-yl]-5-(6-methylpyridin-3-yl)-thiophene-2-carboxamide; N-[(3R)-1-azabicyclo[2.2.2]oct-3-yl]-5-(5-methylpyridin-2-yl)-thiophene-2-carboxamide; N-[(3R)-1-azabicyclo[2.2.2]oct-3-yl]-5-(2-methoxypyridin-4-yl)-thiophene-2-carboxamide; N-[(3R)-1-azabicyclo[2.2.2]oct-3-yl]-5-(6-methoxypyridin-3-yl)-thiophene-2-carboxamide; N-[(3R)-1-azabicyclo[2.2.2]oct-3-yl]-5-(5-methoxypyridin-2-yl)-thiophene-2-carboxamide; N-[(3R)-1-azabicyclo[2.2.2]oct-3-yl]-5-(2-chloropyridin-4-yl)-thiophene-2-carboxamide; N-[(3R)-1-azabicyclo[2.2.2]oct-3-yl]-5-(6-chloropyridin-3-yl)-thiophene-2-carboxamide; N-[(3R)-1-azabicyclo[2.2.2]oct-3-yl]-5-(5-chloropyridin-2-yl)-thiophene-2-carboxamide; N-[(3R)-1-azabicyclo[2.2.2]oct-3-yl]-5-(5-chloropyridin-3-yl)-thiophene-2-carboxamide; N-[(3R)-1-azabicyclo[2.2.2]oct-3-yl]-5-(6-chloropyridin-2-yl)-thiophene-2-carboxamide; N-[(3R)-1-azabicyclo[2.2.2]oct-3-yl]-5-(4-chloropyridin-2-yl)-thiophene-2-carboxamide; N-[(3R)-1-azabicyclo[2.2.2]oct-3-yl]-5-(pyridin-4-yloxy)-thiophene-2-carboxamide; N-[(3R)-1-azabicyclo[2.2.2]oct-3-yl]-5-(pyridin-3-yloxy)-thiophene-2-carboxamide; N-[(3R)-1-azabicyclo[2.2.2]oct-3-yl]-5-(pyridin-2-yloxy)-thiophene-2-carboxamide; N-[(3R)-1-azabicyclo[2.2.2]oct-3-yl]-5-(2-methylpyridin-4-yloxy)-thiophene-2-carboxamide; N-[(3R)-1-azabicyclo[2.2.2]oct-3-yl]-5-(6-methylpyridin-3-yloxy)-thiophene-2-carboxamide; N-[(3R)-1-azabicyclo[2.2.2]oct-3-yl]-5-(5-methylpyridin-2-yloxy)-thiophene-2-carboxamide; N-[(3R)-1-azabicyclo[2.2.2]oct-3-yl]-5-(2-methoxypyridin-4-yloxy)-thiophene-2-carboxamide; N-[(3R)-1-azabicyclo[2.2.2]oct-3-yl]-5-(6-methoxypyridin-3-yloxy)-thiophene-2-carboxamide; N-[(3R)-1-azabicyclo[2.2.2]oct-3-yl]-5-(5-methoxypyridin-2-yloxy)-thiophene-2-carboxamide; N-[(3R)-1-azabicyclo[2.2.2]oct-3-yl]-5-(2-chloropyridin-4-yloxy)-thiophene-2-carboxamide; N-[(3R)-1-azabicyclo[2.2.2]oct-3-yl]-5-(6-chloropyridin-3-yloxy)-thiophene-2-carboxamide; N-[(3R)-1-azabicyclo[2.2.2]oct-3-yl]-5-(5-chloropyridin-2-yloxy)-thiophene-2-carboxamide; N-[(3R)-1-azabicyclo[2.2.2]oct-3-yl]-5-(2-chloropyridin-4-yloxy)-thiophene-2-carboxamide; N-[(3R)-1-azabicyclo[2.2.2]oct-3-yl]-5-(6-chloropyridin-3-yloxy)-thiophene-2-carboxamide; N-[(3R)-1-azabicyclo[2.2.2]oct-3-yl]-5-(5-chloropyridin-2-yloxy)-thiophene-2-carboxamide; N-[(3R)-1-azabicyclo[2.2.2]oct-3-yl]-5-(5-chloropyridin-3-yloxy)-thiophene-2-carboxamide; N-[(3R)-1-azabicyclo[2.2.2]oct-3-yl]-5-(6-chloropyridin-2-yloxy)-thiophene-2-carboxamide; N-[(3R)-1-azabicyclo[2.2.2]oct-3-yl]-5-(4-chloropyridin-2-yloxy)-thiophene-2-carboxamide; N-[(3R)-1-azabicyclo[2.2.2]oct-3-yl]-5-(pyridin-4-ylsulfanyl)-thiophene-2-carboxamide; N-[(3R)-1-azabicyclo[2.2.2]oct-3-yl]-5-(pyridin-3-ylsulfanyl)-thiophene-2-carboxamide; N-[(3R)-1-azabicyclo[2.2.2]oct-3-yl]-5-(pyridin-2-ylsulfanyl)-thiophene-2-carboxamide; N-[(3R)-1-azabicyclo[2.2.2]oct-2-yl]-5-(2-methylpyridin-4-ylsulfanyl)-thiophene-2-carboxamide; N-[(3R)-1-azabicyclo[2.2.2]oct-3-yl]-5-(6-methylpyridin-3-ylsulfanyl)-thiophene-2-carboxamide; N-[(3R)-1-azabicyclo[2.2.2]oct-3-yl]-5-(5-methylpyridin-2-ylsulfanyl)-thiophene-2-carboxamide; N-[(3R)-1-azabicyclo[2.2.2]oct-3-yl]-5-

(2-methoxypyridin-4-ylsulfanyl)-thiophene-2-carboxamide; N-[(3R)-1-azabicyclo[2.2.2]oct-3-yl]-5-(6-methoxypyridin-3-ylsulfanyl)-thiophene-2-carboxamide; N-[(3R)-1-azabicyclo[2.2.2]oct-3-yl]-5-(5-methoxypyridin-2-ylsulfanyl)-thiophene-2-carboxamide; N-[(3R)-1-azabicyclo[2.2.2]oct-3-yl]-5-(2-chloropyridin-4-ylsulfanyl)-thiophene-2-carboxamide; N-[(3R)-1-azabicyclo[2.2.2]oct-3-yl]-5-(6-chloropyridin-3-ylsulfanyl)-thiophene-2-carboxamide; N-[(3R)-1-azabicyclo[2.2.2]oct-3-yl]-5-(5-chloropyridin-2-ylsulfanyl)-thiophene-2-carboxamide; N-[(3R)-1-azabicyclo[2.2.2]oct-3-yl]-5-(2-chloropyridin-4-ylsulfanyl)-thiophene-2-carboxamide; N-[(3R)-1-azabicyclo[2.2.2]oct-3-yl]-5-(6-chloropyridin-3-ylsulfanyl)-thiophene-2-carboxamide; N-[(3R)-1-azabicyclo[2.2.2]oct-3-yl]-5-(5-chloropyridin-2-ylsulfanyl)-thiophene-2-carboxamide; N-[(3R)-1-azabicyclo[2.2.2]oct-3-yl]5-5(5-chloropyridin-2-ylsulfanyl)-thiophene-2-carboxamide; N-[(3R)-1-azabicyclo[2.2.2]oct-3-yl]-5-(6-chloropyridin-2-ylsulfanyl)-thiophene-2-carboxamide; N-[(3R)-1-azabicyclo[2.2.2]oct-3-yl]-5-(4-chloropyridin-2-ylsulfanyl)-thiophene-2-carboxamide; N-[(3R)-1-azabicyclo[2.2.2]oct-3-yl]-5-(thiophen-4-yl)-thiophene-2-carboxamide; N-[(3R)-1-azabicyclo[2.2.2]oct-3-yl]-5-(5-methylthiophen-2-yl)-thiophene-2-carboxamide; N-[(3R)-1-azabicyclo[2.2.2]oct-3-yl]-5-(5-methoxythiophen-2-yl)-thiophene-2-carboxamide; N-[(3R)-1-azabicyclo[2.2.2]oct-3-yl]-5-(5-chlorothiophen-2-yl)-thiophene-2-carboxamide; N-[(3R)-1-azabicyclo[2.2.2]oct-3-yl]-5-(furan-4-yl)-thiophene-2-carboxamide; N-[(3R)-1-azabicyclo[2.2.2]oct-3-yl]-5-(5-methylfuran-2-yl)-thiophene-2-carboxamide; N-[(3R)-1-azabicyclo[2.2.2]oct-3-yl]-5-(5-methoxyfuran-2-yl)thiophene-2-carboxamide; N-[(3R)-1-azabicyclo[2.2.2]oct-3-yl]-5-(5-chlorofuran-2-yl)-thiophene-2-carboxamide; N-[(3R)-1-azabicyclo[2.2.2]oct-3-yl]-5-(oxazol-2-yl)-thiophene-2-carboxamide; N-[(3R)-1-azabicyclo[2.2.2]oct-3-yl]-5-(5-methyloxazol-2-yl)-thiophene-2-carboxamide; N-[(3R)-1-azabicyclo[2.2.2]oct-3-yl]-5-(5-methoxyoxazol-2-yl)-thiophene-2-carboxamide; N-[(3R)-1-azabicyclo[2.2.2]oct-3-yl]-5-(5-chlorooxazol-2-yl)-thiophene-2-carboxamide; N-[(3R)-1-azabicyclo[2.2.2]oct-3-yl]-5-(oxazol-5-yl)-thiophene-2-carboxamide; N-[(3R)-1-azabicyclo[2.2.2]oct-3-yl]-5-(2-methyloxazol-5-yl)-thiophene-2-carboxamide; N-[(3R)-1-azabicyclo[2.2.2]oct-3-yl]-5-(2-methoxyoxazol-5-yl)-thiophene-2-carboxamide; N-[(3R)-1-azabicyclo[2.2.2]oct-3-yl]-5-(2-chlorooxazol-5-yl)-thiophene-2-carboxamide; N-[(3R)-1-azabicyclo[2.2.2]oct-3-yl]-5-(thiazol-2-yl)-thiophene-2-carboxamide; N-[(3R)-1-azabicyclo[2.2.2]oct-3-yl]-5-(5-methylthiazol-2-yl)-thiophene-2-carboxamide; N-[(3R)-1-azabicyclo[2.2.2]oct-3-yl]-5-(5-methoxythiazol-2-yl)-thiophene-2-carboxamide; N-[(3R)-1-azabicyclo[2.2.2]oct-3-yl]-5-(5-chlorothiazol-2-yl)-thiophene-2-carboxamide; N-[(3R)-1-azabicyclo[2.2.2]oct-3-yl]-5-(thiazol-5-yl)-thiophene-2-carboxamide; N-[(3R)-1-azabicyclo[2.2.2]oct-3-yl]-5-(2-methylthiazol-5-yl)-thiophene-2-carboxamide; N-[(3R)-1-azabicyclo[2.2.2]oct-3-yl]-5-(2-methoxythiazol-5-yl)-thiophene-2-carboxamide; N-[(3R)-1-azabicyclo[2.2.2]oct-3-yl]-5-(2-chlorothiazol-5-yl)-thiophene-2-carboxamide; N-[(3R)-1-azabicyclo[2.2.2]oct-3-yl]-5-(4-methylthiazol-2-yl)-thiophene-2-carboxamide; N-[(3R)-1-azabicyclo[2.2.2]oct-3-yl]-5-(4-methoxythiazol-2-yl)-thiophene-2-carboxamide; N-[(3R)-1-azabicyclo[2.2.2]oct-3-yl]-5-(4-chlorothiazol-2-yl)-thiophene-2-carboxamide; N-[(3R)-1-azabicyclo[2.2.2]oct-3-yl]-5-(4-methyloxazol-2-yl)-thiophene-2-carboxamide; N-[(3R)-1-azabicyclo[2.2.2]oct-3-yl]-5-(4-methoxyoxazol-2-yl)-thiophene-2-carboxamide; N-[(3R)-1-azabicyclo[2.2.2]oct-3-yl]-5-(4-chlorooxazol-2-yl)-thiophene-2-carboxamide; N-[(3R)-1-azabicyclo[2.2.2]oct-3-yl]-5-([1,3,4]thiadiazol-2-yl)-thiophene-2-carboxamide; N-[(3R)-1-azabicyclo[2.2.2]oct-3-yl]-5-(5-methyl[1,3,4]thiadiazol-2-yl)-thiophene-2-carboxamide; N-[(3R)-1-azabicyclo[2.2.2]oct-3-yl]-5-(5-methoxy[1,3,4]thiadiazol-2-yl)-thiophene-2-carboxamide; N-[(3R)-1-azabicyclo[2.2.2]oct-3-yl]-5-(5-chloro[1,3,4]thiadiazol-2-yl)-thiophene-2-carboxamide; N-[(3R)-1-azabicyclo[2.2.2]oct-3-yl]-5-([1,3,4]oxadiazol-2-yl)-thiophene-2-carboxamide; N-[(3R)-1-azabicyclo[2.2.2]oct-3-yl]-5-(5-methyl [1,3,4]oxadiazol-2-yl)-thiophene-2-carboxamide; N-[(3R)-1-azabicyclo[2.2.2]oct-3-yl]-5-(5-methoxy[1,3,4]oxadiazol-2-yl)-thiophene-2-carboxamide; N-[(3R)-1-azabicyclo[2.2.2]oct-3-yl]-5-(5-chloro[1,3,4]oxadiazol-2-yl)-thiophene-2-carboxamide; N-[(3R)-1-azabicyclo[2.2.2]oct-3-yl]-5-(thiophen-4-yloxy)-thiophene-2-carboxamide; N-[(3R)-1-azabicyclo[2.2.2]oct-3-yl]-5-(5-meth N-[(3R)-1-azabicyclo[2.2.2]oct-3-yl]-5-(5-methoxythiophen-2-yloxy)-thiophene-2-carboxamide; N-[(3R)-1-azabicyclo[2.2.2]oct-3-yl]-5-(5-chlorothiophen-2-yloxy)-thiophene-2-carboxamide; N-[(3R)-1-azabicyclo[2.2.2]oct-3-yl]-5-(furan-4-yloxy)-thiophene-2-carboxamide; N-[(3R)-1-azabicyclo[2.2.2]oct-3-yl]-5-(5-methylfuran-2-yloxy)-thiophene-2-carboxamide; N-[(3R)-1-azabicyclo[2.2.2]oct-3-yl]-5-(5-methoxyfuran-2-yloxy)-thiophene-2-carboxamide; N-[(3R)-1-azabicyclo[2.2.2]oct-3-yl]-5-(5-chlorofuran-2-yloxy)-thiophene-2-carboxamide; N-[(3R)-1-azabicyclo[2.2.2]oct-3-yl]-5-(oxazol-2-yloxy)-thiophene-2-carboxamide; N-[(3R)-1-azabicyclo[2.2.2]oct-3-yl]-5-(5-methyloxazol-2-yloxy)-thiophene-2-carboxamide; N-[(3R)-1-azabicyclo[2.2.2]oct-3-yl]-5-(5-methoxyoxazol-2-yloxy)-thiophene-2-carboxamide; N-[(3R)-1-azabicyclo[2.2.2]oct-3-yl]-5-(5-chlorooxazol-2-yloxy)-thiophene-2-carboxamide; N-[(3R)-1-azabicyclo[2.2.2]oct-3-yl]-5-(oxazol-5-yloxy)-thiophene-2-carboxamide; N-[(3R)-1-azabicyclo[2.2.2]oct-3-yl]-5-(2-methyloxazol-5-yloxy)-thiophene-2-carboxamide; N-[(3R)-1-azabicyclo[2.2.2]oct-3-yl]-5-(2-methoxyoxazol-5-yloxy)-thiophene-2-carboxamide; N-[(3R)-1-azabicyclo[2.2.2]oct-3-yl]-5-(2-chlorooxazol-5-yloxy)-thiophene-2-carboxamide; N-[(3R)-1-azabicyclo[2.2.2]oct-3-yl]-5-(thiazol-2-yloxy)-thiophene-2-carboxamide; N-[(3R)-1-azabicyclo[2.2.2]oct-3-yl]-5-(5-methylthiazol-2-yloxy)-thiophene-2-carboxamide; N-[(3R)-1-azabicyclo[2.2.2]oct-3-yl]-5-(5-methoxythiazol-2-yloxy)-thiophene-2-carboxamide; N-[(3R)-1-azabicyclo[2.2.2]oct-3-yl]-5-(5-chlorothiazol-2-yloxy)-thiophene-2-carboxamide; N-[(3R)-1-azabicyclo[2.2.2]oct-3-yl]-5-(thiazol-5-yloxy)-thiophene-2-carboxamide; N-[(3R)-1-azabicyclo[2.2.2]oct-3-yl]-5-(2-methylthiazol-5-yloxy)-thiophene-2-carboxamide; N-[(3R)-1-azabicyclo[2.2.2]oct-3-yl]-5-(2- methoxythiazol-5-yloxy)-thiophene-2-carboxamide; N-[(3R)-1-azabicyclo[2.2.2]oct-3-yl]-5-(2-chlorothiazol-5-yloxy)-thiophene-2-carboxamide; N-[(3R)-1-azabicyclo[2.2.2]oct-3-yl]-5-(4-methylthiazol-2-yloxy)-thiophene-2-carboxamide; N-[(3R)-1-azabicyclo[2.2.2]oct-3-yl]-5-(4-methoxythiazol-2-yloxy)-thiophene-2-carboxamide; N-[(3R)-1-azabicyclo[2.2.2]oct-3-yl]-5-(4-chlorothiazol-2-yloxy)-thiophene-2-carboxamide; N-[(3R)-1-azabicyclo[2.2.2]oct-3-yl]-5-(4-methyloxazol-2-yloxy)-thiophene-2-carboxamide; N-[(3R)-1-azabicyclo[2.2.2]oct-3-yl]-5-(4-methoxyoxazol-2-yloxy)-thiophene-2-carboxamide; N-[(3R)-1-azabicyclo[2.2.2]oct-3-yl]-5-(4-chlorooxazol-2-yloxy)-thiophene-2-carboxamide; N-[(3R)-1-azabicyclo[2.2.2]oct-3-yl]-5-([1,3,4]thiadiazol-2-yloxy)-thiophene-2-carboxamide; N-[(3R)-1-azabicyclo[2.2.2]oct-3-yl]-5-(5-methyl[1,3,4]thiadiazol-2-yloxy)-thiophene-2-carboxamide; N-[(3R)-1-azabicyclo[2.2.2]oct-3-yl]-5-(5-methoxy[1,3,4]thiadiazol-2-yloxy)-thiophene-2-carboxamide; N-[(3R)-1-azabicyclo[2.2.2]oct-3-yl]-5-(5-chloro[1,3,4]thiadiazol-2-yloxy)-thiophene-2-carboxamide; N-[(3R)-1-azabicyclo[2.2.2]oct-3-yl]-5-([1,3,4]oxadiazol-2-yloxy)-thiophene-2-carboxamide; N-[(3R)-1-azabicyclo[2.2.2]oct-3-yl]-5-(5-methyl[1,3,4]oxadiazol-2-yloxy)-thiophene-2-carboxamide; N-[(3R)-1-azabicyclo[2.2.2]oct-3-yl]-5-(5-methoxy[1,3,4]oxadiazol-2-yloxy)-thiophene-2-carboxamide; N-[(3R)-1-azabicyclo[2.2.2]oct-3-yl]-5-(5-chloro[1,3,4]oxadiazol-2-yloxy)-thiophene-2-carboxamide; N-[(3R)-1-azabicyclo[2.2.2]oct-3-yl]-5-(thiophen-4-ylsulfanyl)-thiophene-2-carboxamide; N-[(3R)-1-azabicyclo[2.2.2]oct-3-yl]-5-(5-methylthiophen-2-ylsulfanyl)-thiophene-2-carboxamide; N-[(3R)-1-azabicyclo[2.2.2]oct-3-yl]-5-(5-methoxythiophen-2-ylsulfanyl)-thiophene-2-carboxamide; N-[(3R)-1-azabicyclo[2.2.2]oct-3-yl]-5-(5-chlorothiophen-2-ylsulfanyl)-thiophene-2-carboxamide; N-[(3R)-1-azabicyclo[2.2.2]oct-3-yl]-5-(furan-4-ylsulfanyl)-thiophene-2-carboxamide; N-[(3R)-1-azabicyclo[2.2.2]oct-3-yl]-5-(5-methylfuran-2-ylsulfanyl)-thiophene-2-carboxamide; N-[(3R)-1-azabicyclo[2.2.2]oct-3-yl]-5-(5-methoxyfuran-2-ylsulfanyl)-thiophene-2-carboxamide; N-[(3R)-1-azabicyclo[2.2.2]oct-3-yl]-5-(5-chlorofuran-2-ylsulfanyl)-thiophene-2-carboxamide; N-[(3R)-1-azabicyclo[2.2.2]oct-3-yl]-5-(oxazol-2-ylsulfanyl)-thiophene-2-carboxamide; N-[(3R)-1-azabicyclo[2.2.2]oct-3-yl]-5-(5-methyloxazol-2-ylsulfanyl)-thiophene-2-carboxamide; N-[(3R)-1-azabicyclo[2.2.2]oct-3-yl]-5-(5-methoxyoxazol-2-ylsulfanyl)-thiophene-2-carboxamide; N-[(3R)-1-azabicyclo[2.2.2]oct-3-yl]-5-(5-chlorooxazol-2-ylsulfanyl)-thiophene-2-carboxamide; N-[(3R)-1-azabicyclo[2.2.2]oct-3-yl]-5-(oxazol-5-ylsulfanyl)-thiophene-2-carboxamide; N-[(3R)-1-azabicyclo[2.2.2]oct-3-yl]-5-(2-methyloxazol-5-ylsulfanyl)-thiophene-2-carboxamide; N-[(3R)-1-azabicyclo[2.2.2]oct-3-yl]-5-(2-methoxyoxazol-5-ylsulfanyl)-thiophene-2-carboxamide; N-[(3R)-1-azabicyclo[2.2.2]oct-3-yl]-5-(2-chlorooxazol-5-ylsulfanyl)-thiophene-2-carboxamide; N-[(3R)-1-azabicyclo[2.2.2]oct-3-yl]-5-(thiazol-2-ylsulfanyl)-thiophene-2-carboxamide; N-[(3R)-1-azabicyclo[2.2.2]oct-3-yl]-5-(5-methylthiazol-2-ylsulfanyl)-thiophene-2-carboxamide; N-[(3R)-1-azabicyclo[2.2.2]oct-3-yl]-5-(5-methoxythiazol-2-ylsulfanyl)-thiophene-2-carboxamide; N-[(3R)-1-azabicyclo[2.2.2]oct-3-yl]-5-(5-chlorothiazol-2-ylsulfanyl)-thiophene-2-carboxamide; N-[(3R)-1-azabicyclo[2.2.2]oct-3-yl]-5-(thiazol-5-ylsulfanyl)-thiophene-2-carboxamide; N-[(3R)-1-azabicyclo[2.2.2]oct-3-yl]-5-(2-methylthiazol-5-ylsulfanyl)-thiophene-2-carboxamide; N-[(3R)-1-azabicyclo[2.2.2]oct-3-yl]-5-(2-methoxythiazol-5-ylsulfanyl)-thiophene-2-carboxamide; N-[(3R)-1-azabicyclo[2.2.2]oct-3-yl]-5-(2-chlorothiazol-5-ylsulfanyl)thiophene-2-carboxamide; N-[(3R)-1-azabicyclo[2.2.2]oct-3-yl]-5-(4-methylthiazol-2-ylsulfanyl)-thiophene-2-carboxamide; N-[(3R)-1-azabicyclo[2.2.2]oct-3-yl]-5-(4-methoxythiazol-2-ylsulfanyl)-thiophene-2-carboxamide; N-[(3R)-1-azabicyclo[2.2.2]oct-3-yl]-5-(4-chlorothiazol-2-ylsulfanyl)-thiophene-2-carboxamide-N-[(3R)-1-azabicyclo[2.2.2]oct-3-yl]-5-(4-methyloxazol-2-ylsulfanyl)-thiophene-2-carboxamide; N-[(3R)-1-azabicyclo[2.2.2]oct-3-yl]-5-(4-methoxyoxazol-2-ylsulfanyl)-thiophene-2-carboxamide; N-[(3R)-1-azabicyclo[2.2.2]oct-3-yl]-5-(4-chlorooxazol-2-ylsulfanyl)-thiophene-2-carboxamide; N-[(3R)-1-azabicyclo[2.2.2]oct-3-yl]-5-([1,3,4]thiadiazol-2-ylsulfanyl)-thiophene-2-carboxamide; N-[(3R)-1-azabicyclo[2.2.2]oct-3-yl]-5-(5-methyl[1,3,4]thiadiazol-2-ylsulfanyl)-thiophene-2-carboxamide; N-[(3R)-1-azabicyclo[2.2.2]oct-3-yl]-5-(5-methoxy[1,3,4]thiadiazol-2-ylsulfanyl)-thiophene-2-carboxamide; N-[(3R)-1-azabicyclo[2.2.2]oct-3-yl]-5-(5-chloro[1,3,4]thiadiazol-2-ylsulfanyl)-thiophene-2-carboxamide; N-[(3R)-1-azabicyclo[2.2.2]oct-3-yl]-5-([1,3,4]oxadiazol-2-ylsulfanyl)-thiophene-2-carboxamide; N-[(3R)-1-azabicyclo[2.2.2]oct-3-yl]-5-(5-methyl[1,3,4]oxadiazol-2-ylsulfanyl)-thiophene-2-carboxamide; N-[(3R)-1-azabicyclo[2.2.2]oct-3-yl]-5-(5-methoxy[1,3,4]oxadiazol-2-ylsulfanyl)-thiophene-2-carboxamide; N-[(3R)-1-azabicyclo[2.2.2]oct-3-yl]-5-(5-chloro[1,3,4]oxadiazol-2-ylsulfanyl)-thiophene-2-carboxamide; N-[(3R)-1-azabicyclo[2.2.2]oct-3-yl]-5-(pyrrole-2-yl)-thiophene-2-carboxamide; N-[(3R)-1-azabicyclo[2.2.2]oct-3-yl]-5-(isothiazol-3-yl)-thiophene-2-carboxamide; N-[(3R)-1-azabicyclo[2.2.2]oct-3-yl]-5-(isoxazol-3-yl)-thiophene-2-carboxamide; N-[(3R)-1-azabicyclo[2.2.2]oct-3-yl]-5-(3H-imidazol-4-yl)-thiophene-2-carboxamide; N-[(3R)-1-azabicyclo[2.2.2]oct-3-yl]-4-(4-hydroxyphenylsulfanyl)-thiophene-2-carboxamide; N-[(3R)-1-azabicyclo[2.2.2]oct-3-yl]-4-(3-acetamidophenylsulfanyl)-thiophene-2-carboxamide; N-[(3R)-1-azabicyclo[2.2.2]oct-3-yl]-4-(2-methanesulfonylaminophenyl)-thiophene-2-carboxamide; N-[(3R)-1-azabicyclo[2.2.2]oct-3-yl]-4-(pyridin-2-yloxy)-thiophene-2-carboxamide; N-[(3R)-1-azabicyclo[2.2.2]oct-3-yl]-4-(2-methylpyridin-4-yloxy)-thiophene-2-carboxamide; N-[(3R)-1-azabicyclo[2.2.2]oct-3-yl]-4-(4-trifluoromethylphenyl)-thiophene-2-carboxamide; N-[(3R)-1-azabicyclo[2.2.2]oct-3-yl]-4-(2-acetylphenyl)-thiophene-2-carboxamide; N-[(3R)-1-azabicyclo[2.2.2]oct-3-yl]-4-chloro-5-phenyl-thiophene-2-carboxamide; N-[(3R)-1-azabicyclo[2.2.2]oct-3-yl]-4-methyl-5-phenyl-thiophene-2-carboxamide; N-[(3R)-1-azabicyclo[2.2.2]oct-3-yl]-4-cyano-5-phenyl-thiophene-2-carboxamide; N-[(3R)-1-azabicyclo[2.2.2]oct-3-yl]-4-methoxy-5-phenyl-thiophene-2-carboxamide; N-[(3R)-1-azabicyclo

[2.2.2]oct-3-yl]-5-chloro-4-phenyl-thiophene-2-carboxamide; N-[(3R)-1-azabicyclo[2.2.2]oct-3-yl]-5-methyl-4-phenyl-thiophene-2-carboxamide; N-[(3R)-1-azabicyclo[2.2.2]oct-3-yl]-5-cyano-4-phenyl-thiophene-2-carboxamide; N-[(3R)-1-azabicyclo[2.2.2]oct-3-yl]-5-methoxy-4-phenyl-thiophene-2-carboxamide; N-[(3R)-1-azabicyclo[2.2.2]oct-3-yl]-4-chloro-5-bromo-thiophene-2-carboxamide; N-[(3R)-1-azabicyclo[2.2.2]oct-3-yl]-4-chloro-5-methylsulfanyl-thiophene-2-carboxamide; N-[(3R)-1-azabicyclo[2.2.2]oct-3-yl]-4-chloro-5-methyl-thiophene-2-carboxamide; N-[(3R)-1-azabicyclo[2.2.2]oct-3-yl]-4-chloro-5-cyano-thiophene-2-carboxamide; N-[(3R)-1-azabicyclo[2.2.2]oct-3-yl]-5-chloro-4-bromo-thiophene-2-carboxamide; N-[(3R)-1-azabicyclo[2.2.2]oct-3-yl]-5-chloro-4-methylsulfanyl-thiophene-2-carboxamide; N-[(3R)-1-azabicyclo[2.2.2]oct-3-yl]-5-chloro-4-methyl-thiophene-2-carboxamide; N-[(3R)-1-azabicyclo[2.2.2]oct-3-yl]-5-chloro-4-cyano-thiophene-2-carboxamide;

N-[(2S,3R)-2-methyl-1-azabicyclo[2.2.2]oct-3-yl]-5-(2-acetamidophenyl)-thiophene-2-carboxamide; N-[(2S,3R)-2-methyl-1-azabicyclo[2.2.2]oct-3-yl]-5-(3-acetamidophenyl)-thiophene-2-carboxamide; N-[(2S,3R)-2-methyl-1-azabicyclo[2.2.2]oct-3-yl]-5-(4-acetamidophenyl)-thiophene-2-carboxamide; N-[(2S,3R)-2-methyl-1-azabicyclo[2.2.2]oct-3-yl]-5-(2-trifluoroacetamidophenyl)-thiophene-2-carboxamide; N-[(2S,3R)-2-methyl-1-azabicyclo[2.2.2]oct-3-yl]-5-(3-trifluoroacetamidophenyl)-thiophene-2-carboxamide; N-[(2S,3R)-2-methyl-1-azabicyclo[2.2.2]oct-3-yl]-5-(4-trifluoroacetamidophenyl)-thiophene-2-carboxamide; N-[(2S,3R)-2-methyl-1-azabicyclo[2.2.2]oct-3-yl]-5-(2-methanesulfonylaminophenyl)-thiophene-2-carboxamide; N-[(2S,3R)-2-methyl-1-azabicyclo[2.2.2]oct-3-yl]-5-(3-methanesulfonylaminophenyl)-thiophene-2-carboxamide; N-[(2S,3R)-2-methyl-1-azabicyclo[2.2.2]oct-3-yl]-5-(4-methanesulfonylaminophenyl)-thiophene-2-carboxamide; N-[(2S,3R)-2-methyl-1-azabicyclo[2.2.2]oct-3-yl]-5-(2-trifluoromethanesulfonylaminophenyl)-thiophene-2-carboxamide; N-[(2S,3R)-2-methyl-1-azabicyclo[2.2.2]oct-3-yl]-5-(3-tifluoromethanesulfonylaminophenyl)-thiophene-2-carboxamide; N-[(2S,3R)-2-methyl-1-azabicyclo[2.2.2]oct-3-yl]-5-(4-trifluoromethanesulfonylaminophenyl)-thiophene-2-carboxamide; N-[(2S,3R)-2-methyl-1-azabicyclo[2.2.2]oct-3-yl]-5-(2-difluoroacetamidophenyl)-thiophene-2-carboxamide; N-[(2S,3R)-2-methyl-1-azabicyclo[2.2.2]oct-3-yl]-5-(3-difluoroacetamidophenyl)-thiophene-2-carboxamide; N-[(2S,3R)-2-methyl-1-azabicyclo[2.2.2]oct-3-yl]-5-(4-difluoroacetamidophenyl)-thiophene-2-carboxamide; N-[(2S,3R)-2-methyl-1-azabicyclo[2.2.2]oct-3-yl]-5-(2-carbamoylphenyl)-thiophene-2-carboxamide; N-[(2S,3R)-2-methyl-1-azabicyclo[2.2.2]oct-3-yl]-5-(3-carbamoylphenyl)-thiophene-2-carboxamide; N-[(2S,3R)-2-methyl-1-azabicyclo[2.2.2]oct-3-yl]-5-(4-carbamoylphenyl)-thiophene-2-carboxamide; N-[(2S,3R)-2-methyl-1-azabicyclo[2.2.2]oct-3-yl]-5-(2-sulfamoylphenyl)-thiophene-2-carboxamide; N-[(2S,3R)-2-methyl-1-azabicyclo[2.2.2]oct-3-yl]-5-(3-sulfamoylphenyl)-thiophene-2-carboxamide; N-[(2S,3R)-2-methyl-1-azabicyclo[2.2.2]oct-3-yl]-5-(4-sulfamoylphenyl)-thiophene-2-carboxamide; N-[(2S,3R)-2-methyl-1-azabicyclo[2.2.2]oct-3-yl]-5-(2-acetamidophenylsulfanyl)-thiophene-2-carboxamide; N-[(2S,3R)-2-methyl-1-azabicyclo[2.2.2]oct-3-yl]-5-(3-acetamidophenylsulfanyl)-thiophene-2-carboxamide; N-[(2S,3R)-2-methyl-1-azabicyclo[2.2.2]oct-3-yl]-5-(4-acetamidophenylsulfanyl)-thiophene-2-carboxamide; N-[(2S,3R)-2-methyl-1-azabicyclo[2.2.2]oct-3-yl]-5-(2-trifluoroacetamidophenylsulfanyl)-thiophene-2-carboxamide; N-[(2S,3R)-2-methyl-1-azabicyclo[2.2.2]oct-3-yl]-5-(3-trifluoroacetamidophenylsulfanyl)-thiophene-2-carboxamide; N-[(2S,3R)-2-methyl-1-azabicyclo[2.2.2]oct-3-yl]-5-(4-trifluoroacetamidophenylsulfanyl)-thiophene-2-carboxamide; N-[(2S,3R)-2-methyl-1-azabicyclo[2.2.2]oct-3-yl]-5-(2-methanesulfonylaminophenylsulfanyl)-thiophene-2-carboxamide; N-[(2S,3R)-2-methyl-1-azabicyclo[2.2.2]oct-3-yl]-5-(3-methanesulfonylaminophenylsulfanyl)-thiophene-2-carboxamide; N-[(2S,3R)-2-methyl-1-azabicyclo[2.2.2]oct-3-yl]-5-(4-methanesulfonylaminophenylsulfanyl)-thiophene-2-carboxamide; N-[(2S,3R)-2-methyl-1-azabicyclo[2.2.2]oct-3-yl]-5-(2-trifluoromethanesulfonylaminophenylsulfanyl)-thiophene-2-carboxamide; N-[(2S,3R)-2-methyl-1-azabicyclo[2.2.2]oct-3-yl]-5-(3-trifluoromethanesulfonylaminophenylsulfanyl)-thiophene-2-carboxamide; N-[(2S,3R)-2-methyl-1-azabicyclo[2.2.2]oct-3-yl]-5-(4-trifluoromethanesulfonylaminophenylsulfanyl)-thiophene-2-carboxamide; N-[(2S,3R)-2-methyl-1-azabicyclo[2.2.2]oct-3-yl]-5-(2-difluoroacetamidophenylsulfanyl)-thiophene-2-carboxamide; N-[(2S,3R)-2-methyl-1-azabicyclo[2.2.2]oct-3-yl]-5-(3-difluoroacetamidophenylsulfanyl)-thiophene-2-carboxamide; N-[(2S,3R)-2-methyl-1-azabicyclo[2.2.2]oct-3-yl]-5-(4-difluoroacetamidophenylsulfanyl)-thiophene-2-carboxamide; N-[(2S,3R)-2-methyl-1-azabicyclo[2.2.2]oct-3-yl]-5-(2-carbamoylphenylsulfanyl)-thiophene-2-carboxamide; N-[(2S,3R)-2-methyl-1-azabicyclo[2.2.2]oct-3-yl]-5-(3-carbamoylphenylsulfanyl)-thiophene-2-carboxamide; N-[(2S,3R)-2-methyl-1-azabicyclo[2.2.2]oct-3-yl]-5-(4-carbamoylphenylsulfanyl)-thiophene-2-carboxamide; N-[(2S,3R)-2-methyl-1-azabicyclo[2.2.2]oct-3-yl]-5-(2-sulfamoylphenylsulfanyl)-thiophene-2-carboxamide; N-[(2S,3R)-2-methyl-1-azabicyclo[2.2.2]oct-3-yl]-5-(3-sulfamoylphenylsulfanyl)-thiophene-2-carboxamide; N-[(2S,3R)-2-methyl-1-azabicyclo[2.2.2]oct-3-yl]-5-(4-sulfamoylphenylsulfanyl)-thiophene-2-carboxamide; N-[(2S,3R)-2-methyl-1-azabicyclo[2.2.2]oct-3-yl]-5-(2-hydroxyphenylsulfanyl)-thiophene-2-carboxamide; N-[(2S,3R)-2-methyl-1-azabicyclo[2.2.2]oct-3-yl]-5-(3-hydroxyphenylsulfanyl)-thiophene-2-carboxamide; N-[(2S,3R)-2-methyl-1-azabicyclo[2.2.2]oct-3-yl]-5-(4-hydroxyphenylsulfanyl)-thiophene-2-carboxamide; N-[(2S,3R)-2-methyl-1-azabicyclo[2.2.2]oct-3-yl]-5-(2-aminophenylsulfanyl)-thiophene-2-carboxamide;

N-[(2S,3R)-2-methyl-1-azabicyclo[2.2.2]oct-3-yl]-5-(3-aminophenylsulfanyl)-thiophene-2-carboxamide; N-[(2S,3R)-2-methyl-1-azabicyclo[2.2.2]oct-3-yl]-5-(4-aminophenylsulfanyl)-thiophene-2-carboxamide; N-[(2S,3R)-2-methyl-1-azabicyclo[2.2.2]oct-3-yl]-5-(2-acetamidophenoxy)-thiophene-2-carboxamide; N-[(2S,3R)-2-methyl-1-azabicyclo[2.2.2]oct-3-yl]-5-(3-acetamidophenoxy)-thiophene-2-carboxamide; N-[(2S,3R)-2-methyl-1-azabicyclo[2.2.2]oct-3-yl]-5-(4-acetamidophenoxy)-thiophene-2-carboxamide; N-[(2S,3R)-2-methyl-1-azabicyclo[2.2.2]oct-3-yl]-5-(2-trifluoroacetamidophenoxy)-thiophene-2-carboxamide; N-[(2S,3R)-2-methyl-1-azabicyclo[2.2.2]oct-3-yl]-5-(3-trifluoroacetamidophenoxy)-thiophene-2-carboxamide; N-[(2S,3R)-2-methyl-1-azabicyclo[2.2.2]oct-3-yl]-5-(4-trifluoroacetamidophenoxy)-thiophene-2-carboxamide; N-[(2S,3R)-2-methyl-1-azabicyclo[2.2.2]oct-3-yl]-5-(2-methanesulfonylaminophenoxy)-thiophene-2-carboxamide; N-[(2S,3R)-2-methyl-1-azabicyclo[2.2.2]oct-3-yl]-5-(3-methanesulfonylaminophenoxy)-thiophene-2-carboxamide; N-[(2S,3R)-2-methyl-1-azabicyclo[2.2.2]oct-3-yl]-5-(4-methanesulfonylaminophenoxy)-thiophene-2-carboxamide; N-[(2S,3R)-2-methyl-1-azabicyclo[2.2.2]oct-3-yl]-5-(2-trifluoromethanesulfonylaminophenoxy)-thiophene-2-carboxamide; N-[(2S,3R)-2-methyl-1-azabicyclo[2.2.2]oct-3-yl]-5-(3-trifluoromethanesulfonylaminophenoxy)-thiophene-2-carboxamide; N-[(2S,3R)-2-methyl-1-azabicyclo[2.2.2]oct-3-yl]-5-(4-trifluoromethanesulfonylaminophenoxy)-thiophene-2-carboxamide; N-[(2S,3R)-2-methyl-1-azabicyclo[2.2.2]oct-3-yl]-5-(2-difluoroacetamidophenoxy)-thiophene-2-carboxamide; N-[(2S,3R)-2-methyl-1-azabicyclo[2.2.2]oct-3-yl]-5-(3-difluoroacetamidophenoxy)-thiophene-2-carboxamide; N-[(2S,3R)-2-methyl-1-azabicyclo[2.2.2]oct-3-yl]-5-(4-difluoroacetamidophenoxy)-thiophene-2-carboxamide; N-[(2S,3R)-2-methyl-1-azabicyclo[2.2.2]oct-3-yl]-5-(2-carbamoylphenoxy)-thiophene-2-carboxamide; N-[(2S,3R)-2-methyl-1-azabicyclo[2.2.2]oct-3-yl]-5-(3-carbamoylphenoxy)-thiophene-2-carboxamide; N-[(2S,3R)-2-methyl-1-azabicyclo[2.2.2]oct-3-yl]-5-(4-carbamoylphenoxy)-thiophene-2-carboxamide; N-[(2S,3R)-2-methyl-1-azabicyclo[2.2.2]oct-3-yl]-5-(2-sulfamoylphenoxy)-thiophene-2-carboxamide; N-[(2S,3R)-2-methyl-1-azabicyclo[2.2.2]oct-3-yl]-5-(3-sulfamoylphenoxy)-thiophene-2-carboxamide; N-[(2S,3R)-2-methyl-1-azabicyclo[2.2.2]oct-3-yl]-5-(4-sulfamoylphenoxy)-thiophene-2-carboxamide; N-[(2S,3R)-2-methyl-1-azabicyclo[2.2.2]oct-3-yl]-5-(2-hydroxyphenoxy)-thiophene-2-carboxamide; N-[(2S,3R)-2-methyl-1-azabicyclo[2.2.2]oct-3-yl]-5-(3-hydroxyphenoxy)-thiophene-2-carboxamide; N-[(2S,3R)-2-methyl-1-azabicyclo[2.2.2]oct-3-yl]-5-(4-hydroxyphenoxy)-thiophene-2-carboxamide; N-[(2S,3R)-2-methyl-1-azabicyclo[2.2.2]oct-3-yl]-5-(2-aminophenoxy)-thiophene-2-carboxamide; N-[(2S,3R)-2-methyl-1-azabicyclo[2.2.2]oct-3-yl]-5-(3-aminophenoxy)-thiophene-2-carboxamide; N-[(2S,3R)-2-methyl-1-azabicyclo[2.2.2]oct-3-yl]-5-(4-aminophenoxy)-thiophene-2-carboxamide; N-[(2S,3R)-2-methyl-1-azabicyclo[2.2.2]oct-3-yl]-5-(2-chlorophenoxy)-thiophene-2-carboxamide; N-[(2S,3R)-2-methyl-1-azabicyclo[2.2.2]oct-3-yl]-5- N-[(2S,3R)-2-methyl-1-azabicyclo[2.2.2]oct-3-yl]-5-(2-cyanophenyl)-thiophene-2-carboxamide; N-[(2S,3R)-2-methyl-1-azabicyclo[2.2.2]oct-3-yl]-5-(3-cyanophenyl)-thiophene-2-carboxamide; N-[(2S,3R)-2-methyl-1-azabicyclo[2.2.2]oct-3-yl]-5-(4-cyanophenyl)-thiophene-2-carboxamide; N-[(2S,3R)-2-methyl-1-azabicyclo[2.2.2]oct-3-yl]-5-(2-morpholin-4-yl-phenyl)-thiophene-2-carboxamide; N-[(2S,3R)-2-methyl-1-azabicyclo[2.2.2]oct-3-yl]-5-(3-morpholin-4-yl-phenyl)-thiophene-2-carboxamide; N-[(2S,3R)-2-methyl-1-azabicyclo[2.2.2]oct-3-yl]-5-(4-morpholin-4-yl-phenyl)-thiophene-2-carboxamide; N-[(2S,3R)-2-methyl-1-azabicyclo[2.2.2]oct-3-yl]-5-(2-methoxyphenoxy)-thiophene-2-carboxamide; N-[(2S,3R)-2-methyl-1-azabicyclo[2.2.2]oct-3-yl]-5-(3-methoxyphenoxy)-thiophene-2-carboxamide; N-[(2S,3R)-2-methyl-1-azabicyclo[2.2.2]oct-3-yl]-5-(4-methoxyphenoxy)-thiophene-2-carboxamide; N-[(2S,3R)-2-methyl-1-azabicyclo[2.2.2]oct-3-yl]-5-(2-methylphenoxy)-thiophene-2-carboxamide; N-[(2S,3R)-2-methyl-1-azabicyclo[2.2.2]oct-3-yl]-5-(3-methylphenoxy-thiophene-2-carboxamide; N-[(2S,3R)-2-methyl-1-azabicyclo[2.2.2]oct-3-yl]-5-(4-methylphenoxy)-thiophene-2-carboxamide; N-[(2S,3R)-2-methyl-1-azabicyclo[2.2.2]oct-3-yl]-5-(2-trifluoromethylphenoxy)-thiophene-2-carboxamide; N-[(2S,3R)-2-methyl-1-azabicyclo[2.2.2]oct-3-yl]-5-(3-trifluoromethylphenoxy)-thiophene-2-carboxamide; N-[(2S,3R)-2-methyl-1-azabicyclo[2.2.2]oct-3-yl]-5-(4-trifluoromethylphenoxy)-thiophene-2-carboxamide; N-[(2S,3R)-2-methyl-1-azabicyclo[2.2.2]oct-3-yl]-5-(2-acetylphenoxy)-thiophene-2-carboxamide; N-[(2S,3R)-2-methyl-1-azabicyclo[2.2.2]oct-3-yl]-5-(3-acetylphenoxy)-thiophene-2-carboxamide; N-[(2S,3R)-2-methyl-1-azabicyclo[2.2.2]oct-3-yl]-5-(4-acetylphenoxy)-thiophene-2-carboxamide; N-[(2S,3R)-2-methyl-1-azabicyclo[2.2.2]oct-3-yl]-5-(2-cyanophenoxy)-thiophene-2-carboxamide; N-[(2S,3R)-2-methyl-1-azabicyclo[2.2.2]oct-3-yl]-5-(3-cyanophenoxy)-thiophene-2-carboxamide; N-[(2S,3R)-2-methyl-1-azabicyclo[2.2.2]oct-3-yl]-5-(4-cyanophenoxy)-thiophene-2-carboxamide; N-[(2S,3R)-2-methyl-1-azabicyclo[2.2.2]oct-3-yl]-5-(2-morpholin-4-yl-phenoxy)-thiophene-2-carboxamide; N-[(2S,3R)-2-methyl-1-azabicyclo[2.2.2]oct-3-yl]-5-(3-morpholin-4-yl-phenoxy)-thiophene-2-carboxamide; N-[(2S,3R)-2-methyl-1-azabicyclo[2.2.2]oct-3-yl]-5-(4-morpholin-4-yl-phenoxy)-thiophene-2-carboxamide; N-[(2S,3R)-2-methyl-1-azabicyclo[2.2.2]oct-3-yl]-5-(2-methoxyphenylsulfanyl)-thiophene-2-carboxamide; N-[(2S,3R)-2-methyl-1-azabicyclo[2.2.2]oct-3-yl]-5-(3-methoxyphenylsulfanyl)-thiophene-2-carboxamide; N-[(2S,3R)-2-methyl-1-azabicyclo[2.2.2]oct-3-yl]-5-(4-methoxyphenylsulfanyl)-thiophene-2-carboxamide; N-[(2S,3R)-2-methyl-1-azabicyclo[2.2.2]oct-3-yl]-5-(2-methylphenylsulfanyl)-thiophene-2-carboxamide; N-[(2S,3R)-2-methyl-1-azabicyclo[2.2.2]oct-3-yl]-5-(3-methylphenylsulfanyl)-thiophene-2-carboxamide; N-[(2S,3R)-2-methyl-1-azabicyclo[2.2.2]oct-3-yl]-5-(4-methylphenylsulfanyl)-thiophene-2-carboxamide; N-[(2S,3R)-2-methyl-1-azabicyclo[2.2.2]oct-3-yl]-5-(2-trifluoromethylphenylsulfanyl)-thiophene-2-carboxamide; N-[(2S,3R)-2-methyl-1-azabicyclo[2.2.2]oct-3-yl]-5-(3-trifluoromethylphenylsulfanyl)-thiophene-2-carboxamide; N-[(2S,3R)-2-methyl-1- azabicyclo[2.2.2]oct-3-yl]-5-(4-trifluoromethylphenylsulfanyl)-thiophene-2-carboxamide; N-[(2S,3R)-2-methyl-1-azabicyclo[2.2.2]oct-3-yl]-5-(2-acetylphenylsulfanyl)-thiophene-2-carboxamide; N-[(2S,3R)-2-methyl-1-azabicyclo[2.2.2]oct-3-yl]-5-(3-acetylphenylsulfanyl)-thiophene-2-carboxamide; N-[(2S,3R)-2-methyl-1-azabicyclo[2.2.2]oct-3-yl]-5-(4-acetylphenylsulfanyl)-thiophene-2-carboxamide; N-[(2S,3R)-2-methyl-1-azabicyclo[2.2.2]oct-3-yl]-5-(2-cyanophenylsulfanyl)-thiophene-2-carboxamide; N-[(2S,3R)-2-methyl-1-azabicyclo[2.2.2]oct-3-yl]-5-(3-cyanophenylsulfanyl)-thiophene-2-carboxamide; N-[(2S,3R)-2-methyl-1-azabicyclo[2.2.2]oct-3-yl]-5-(4-cyanophenylsulfanyl)-thiophene-2-carboxamide; N-[(2S,3R)-2-methyl-1-azabicyclo[2.2.2]oct-3-yl]-5-(2-morpholin-4-yl-phenylsulfanyl)-thiophene-2-carboxamide; N-[(2S,3R)-2-methyl-1-azabicyclo[2.2.2]oct-3-yl]-5-(3-morpholin-4-yl-phenylsulfanyl)-thiophene-2-carboxamide; N-[(2S,3R)-2-methyl-1-azabicyclo[2.2.2]oct-3-yl]-5-(4-morpholin-4-yl-phenylsulfanyl)-thiophene-2-carboxamide; N-[(2S,3R)-2-methyl-1-azabicyclo[2.2.2]oct-3-yl]-5-(pyridin-4-yl)-thiophene-2-carboxamide; N-[(2S,3R)-2-methyl-1-azabicyclo[2.2.2]oct-3-yl]-5-(2-methylpyridin-4-yl)-thiophene-2-carboxamide; N-[(2S,3R)-2-methyl-1-azabicyclo[2.2.2]oct-3-yl]-5-(6-methylpyridin-3-yl)-thiophene-2-carboxamide; N-[(2S,3R)-2-methyl-1-azabicyclo[2.2.2]oct-3-yl]-5-(5-methylpyridin-2-yl)-thiophene-2-carboxamide; N-[(2S,3R)-2-methyl-1-azabicyclo[2.2.2]oct-3-yl]-5-(2-methoxypyridin-4-yl)-thiophene-2-carboxamide; N-[(2S,3R)-2-methyl-1-azabicyclo[2.2.2]oct-3-yl]-5-(6-methoxypyridin-3-yl)-thiophene-2-carboxamide; N-[(2S,3R)-2-methyl-1-azabicyclo[2.2.2]oct-3-yl]-5-(5-methoxypyridin-2-yl)-thiophene-2-carboxamide; N-[(2S,3R)-2-methyl-1-azabicyclo[2.2.2]oct-3-yl]-5-(2-chloropyridin-4-yl)-thiophene-2-carboxamide; N-[(2S,3R)-2-methyl-1-azabicyclo[2.2.2]oct-3-yl]-5-(6-chloropyridin-3-yl)-thiophene-2-carboxamide; N-[(2S,3R)-2-methyl-1-azabicyclo[2.2.2]oct-3-yl]-5-(5-chloropyridin-2-yl)-thiophene-2-carboxamide; N-[(2S,3R)-2-methyl-1-azabicyclo[2.2.2]oct-3-yl]-5-(5-chloropyridin-3-yl)-thiophene-2-carboxamide; N-[(2S,3R)-2-methyl-1-azabicyclo[2.2.2]oct-3-yl]-5-(6-chloropyridin-2-yl)-thiophene-2-carboxamide; N-[(2S,3R)-2-methyl-1-azabicyclo[2.2.2]oct-3-yl]-5-(4-chloropyridin-2-yl)-thiophene-2-carboxamide; N-[(2S,3R)-2-methyl-1-azabicyclo[2.2.2]oct-3-yl]-5-(pyridin-4-yloxy)-thiophene-2-carboxamide; N-[(2S,3R)-2-methyl-1-azabicyclo[2.2.2]oct-3-yl]-5-(pyridin-3-yloxy)-thiophene-2-carboxamide; N-[(2S,3R)-2-methyl-1-azabicyclo[2.2.2]oct-3-yl]-5-(pyridin-2-yloxy)-thiophene-2-carboxamide; N-[(2S,3R)-2-methyl-1-azabicyclo[2.2.2]oct-3-yl]-5-(2-methylpyridin-4-yloxy)-thiophene-2-carboxamide; N-[(2S,3R)-2-methyl-1-azabicyclo[2.2.2]oct-3-yl]-5-(6-methylpyridin-3-yloxy)-thiophene-2-carboxamide; N-[(2S,3R)-2-methyl-1-azabicyclo[2.2.2]oct-3-yl]-5-(5-methylpyridin-2-yloxy)-thiophene-2-carboxamide; N-[(2S,3R)-2-methyl-1-azabicyclo[2.2.2]oct-3-yl]-5-(2-methoxypy N-[(2S,3R)-2-methyl-1-azabicyclo[2.2.2]oct-3-yl]-5-(2-chloropyridin-4-yloxy)-thiophene-2-carboxamide; N-[(2S,3R)-2-methyl-1-azabicyclo[2.2.2]oct-3-yl]-5-(6-chloropyridin-3-yloxy)-thiophene-2-carboxamide; N-[(2S,3R)-2-methyl-1-azabicyclo[2.2.2]oct-3-yl]-5-(5-chloropyridin-2-yloxy)-thiophene-2-carboxamide; N-[(2S,3R)-2-methyl-1-azabicyclo[2.2.2]oct-3-yl]-5-(2-chloropyridin-4-yloxy)-thiophene-2-carboxamide; N-[(2S,3R)-2-methyl-1-azabicyclo[2.2.2]oct-3-yl]-5-(6-chloropyridin-3-yloxy)-thiophene-2-carboxamide; N-[(2S,3R)-2-methyl-1-azabicyclo[2.2.2]oct-3-yl]-5-(5-chloropyridin-2-yloxy)-thiophene-2-carboxamide; N-[(2S,3R)-2-methyl-1-azabicyclo[2.2.2]oct-3-yl]-5-(5-chloropyridin-3-yloxy)-thiophene-2-carboxamide; N-[(2S,3R)-2-methyl-1-azabicyclo[2.2.2]oct-3-yl]-5-(6-chloropyridin-2-yloxy)-thiophene-2-carboxamide; N-[(2S,3R)-2-methyl-1-azabicyclo[2.2.2]oct-3-yl]-5-(4-chloropyridin-2-yloxy)-thiophene-2-carboxamide; N-[(2S,3R)-2-methyl-1-azabicyclo[2.2.2]oct-3-yl]-5-(pyridin-4-ylsulfanyl)-thiophene-2-carboxamide; N-[(2S,3R)-2-methyl-1-azabicyclo[2.2.2]oct-3-yl]-5-(pyridin-3-ylsulfanyl)-thiophene-2-carboxamide; N-[(2S,3R)-2-methyl-1-azabicyclo[2.2.2]oct-3-yl]-5-(pyridin-2-ylsulfanyl)-thiophene-2-carboxamide; N-[(2S,3R)-2-methyl-1-azabicyclo[2.2.2]oct-3-yl]-5-(2-methylpyridin-4-ylsulfanyl)-thiophene-2-carboxamide; N-[(2S,3R)-2-methyl-1-azabicyclo[2.2.2]oct-3-yl]-5-(6-methylpyridin-3-ylsulfanyl)-thiophene-2-carboxamide; N-[(2S,3R)-2-methyl-1-azabicyclo[2.2.2]oct-3-yl]-5-(5-methylpyridin-2-ylsulfanyl)-thiophene-2-carboxamide; N-[(2S,3R)-2-methyl-1-azabicyclo[2.2.2]oct-3-yl]-5-(2-methoxypyridin-4-ylsulfanyl)-thiophene-2-carboxamide; N-[(2S,3R)-2-methyl-1-azabicyclo[2.2.2]oct-3-yl]-5-(6-methoxypyridin-3-ylsulfanyl)-thiophene-2-carboxamide; N-[(2S,3R)-2-methyl-1-azabicyclo[2.2.2]oct-3-yl]-5-(5-methoxypyridin-2-ylsulfanyl)-thiophene-2-carboxamide; N-[(2S,3R)-2-methyl-1-azabicyclo[2.2.2]oct-3-yl]-5-(2-chloropyridin-4-ylsulfanyl)-thiophene-2-carboxamide; N-[(2S,3R)-2-methyl-1-azabicyclo[2.2.2]oct-3-yl]-5-(6-chloropyridin-3-ylsulfanyl)-thiophene-2-carboxamide; N-[(2S,3R)-2-methyl-1-azabicyclo[2.2.2]oct-3-yl]-5-(5-chloropyridin-2-ylsulfanyl)-thiophene-2-carboxamide; N-[(2S,3R)-2-methyl-1-azabicyclo[2.2.2]oct-3-yl]-5-(2-chloropyridin-4-ylsulfanyl)-thiophene-2-carboxamide; N-[(2S,3R)-2-methyl-1-azabicyclo[2.2.2]oct-3-yl]-5-(6-chloropyridin-3-ylsulfanyl)-thiophene-2-carboxamide; N-[(2S,3R)-2-methyl-1-azabicyclo[2.2.2]oct-3-yl]-5-(5-chloropyridin-2-ylsulfanyl)-thiophene-2-carboxamide; N-[(2S,3R)-2-methyl-1-azabicyclo[2.2.2]oct-3-yl]-5-(5-chloropyridin-3-ylsulfanyl)-thiophene-2-carboxamide; N-[(2S,3R)-2-methyl-1-azabicyclo[2.2.2]oct-3-yl]-5-(6-chloropyridin-2-ylsulfanyl)-thiophene-2-carboxamide; N-[(2S,3R)-2-methyl-1-azabicyclo[2.2.2]oct-3-yl]-5-(4-chloropyridin-2-ylsulfanyl)-thiophene-2-carboxamide; N-[(2S,3R)-2-methyl-1-azabicyclo[2.2.2]oct-3-yl]-5-(thiophen-4-yl)-thiophene-2-carboxamide; N-[(2S,3R)-2-methyl-1-azabicyclo[2.2.2]oct-3-yl]-5-(5-methyl-thiophen-2-yl)-thiophene-2-carboxamide; N-[(2S,3R)-2-methyl-1-azabicyclo[2.2.2]oct-3-yl]-5-(5-methoxythiophen-2-yl)-thiophene-2-carboxamide; N-[(2S,3R)-2-methyl-1-azabicyclo[2.2.2]oct-3-yl]-5-(5-chlorothiophen-2-yl)-thiophene-2-carboxamide; N-[(2S,3R)-2-methyl-1-azabicyclo[2.2.2]oct-3-yl]-5-(furan-4-yl)-thiophene-2-carboxamide; N-[(2S,3R)-2-methyl-1-azabicyclo[2.2.2]oct-3-yl]-5-(5-methylfuran-2-yl)-thiophene-2-carboxamide; N-[(2S,3R)-2-methyl-1-azabicyclo[2.2.2]oct-3-yl]-5-(5-methoxyfuran-2-yl)-thiophene-2-carboxamide; N-[(2S,3R)-2-methyl-1- azabicyclo[2.2.2]oct-3-yl]-5-(5-chlorofuran-2-yl)-thiophene-2-carboxamide; N-[(2S,3R)-2-methyl-1-azabicyclo[2.2.2]oct-3-yl]-5-(oxazol-2-yl)-thiophene-2-carboxamide; N-[(2S,3R)-2-methyl-1-azabicyclo[2.2.2]oct-3-yl]-5-(5-methyloxazol-2-yl)-thiophene-2-carboxamide; N-[(2S,3R)-2-methyl-1-azabicyclo[2.2.2]oct-3-yl]-5-(5-methoxyoxazol-2-yl)-thiophene-2-carboxamide; N-[(2S,3R)-2-methyl-1-azabicyclo[2.2.2]oct-3-yl]-5-(5-chlorooxazol-2-yl)-thiophene-2-carboxamide; N-[(2S,3R)-2-methyl-1-azabicyclo[2.2.2]oct-3-yl]-5-(oxazol-5-yl)-thiophene-2-carboxamide; N-[(2S,3R)-2-methyl-1-azabicyclo[2.2.2]oct-3-yl]-5-(2-methyloxazol-5-yl)-thiophene-2-carboxamide; N-[(2S,3R)-2-methyl-1-azabicyclo[2.2.2]oct-3-yl]-5-(2-methoxyoxazol-5-yl)-thiophene-2-carboxamide; N-[(2S,3R)-2-methyl-1-azabicyclo[2.2.2]oct-3-yl]-5-(2-chlorooxazol-5-yl)-thiophene-2-carboxamide; N-[(2S,3R)-2-methyl-1-azabicyclo[2.2.2]oct-3-yl]-5-(thiazol-2-yl)-thiophene-2-carboxamide; N-[(2S,3R)-2-methyl-1-azabicyclo[2.2.2]oct-3-yl]-5-(5-methylthiazol-2-yl)-thiophene-2-carboxamide; N-[(2S,3R)-2-methyl-1-azabicyclo[2.2.2]oct-3-yl]-5-(5-methoxythiazol-2-yl)-thiophene-2-carboxamide; N-[(2S,3R)-2-methyl-1-azabicyclo[2.2.2]oct-3-yl]-5-(5-chlorothiazol-2-yl)-thiophene-2-carboxamide; N-[(2S,3R)-2-methyl-1-azabicyclo[2.2.2]oct-3-yl]-5-(thiazol-5-yl)-thiophene-2-carboxamide; N-[(2S,3R)-2-methyl-1-azabicyclo[2.2.2]oct-3-yl]-5-(2-methylthiazol-5-yl)-thiophene-2-carboxamide; N-[(2S,3R)-2-methyl-1-azabicyclo[2.2.2]oct-3-yl]-5-(2-methoxythiazol-5-yl)-thio N-[(2S,3R)-2-methyl-1-azabicyclo[2.2.2]oct-3-yl]-5-(5-chlorothiophen-2-yloxy)-thiophene-2-carboxamide; N-[(2S,3R)-2-methyl-1-azabicyclo[2.2.2]oct-3-yl]-5-(furan-4-yloxy)-thiophene-2-carboxamide; N-[(2S,3R)-2-methyl-1-azabicyclo[2.2.2]oct-3-yl]-5-(5-methylfuran-2-yloxy)-thiophene-2-carboxamide; N-[(2S,3R)-2-methyl-1-azabicyclo[2.2.2]oct-3-yl]-5-(5-methoxyfuran-2-yloxy)-thiophene-2-carboxamide; N-[(2S,3R)-2-methyl-1-azabicyclo[2.2.2]oct-3-yl]-5-(5-chlorofuran-2-yloxy)-thiophene-2-carboxamide; N-[(2S,3R)-2-methyl-1-azabicyclo[2.2.2]oct-3-yl]-5-(oxazol-2-yloxy)-thiophene-2-carboxamide; N-[(2S,3R)-2-methyl-1-azabicyclo[2.2.2]oct-3-yl]-5-(5-methyloxazol-2-yloxy)-thiophene-2-carboxamide; N-[(2S,3R)-2-methyl-1-azabicyclo[2.2.2]oct-3-yl]-5-(5-methoxyoxazol-2-yloxy)-thiophene-2-carboxamide; N-[(2S,3R)-2-methyl-1-azabicyclo[2.2.2]oct-3-yl]-5-(5-chlorooxazol-2-yloxy)-thiophene-2-carboxamide; N-[(2S,3R)-2-methyl-1-azabicyclo[2.2.2]oct-3-yl]-5-(oxazol-5-yloxy)-thiophene-2-carboxamide; N-[(2S,3R)-2-methyl-1-azabicyclo[2.2.2]oct-3-yl]-5-(2-methyloxazol-(5-yloxy)-thiophene-2-carboxamide; N-[(2S,3R)-2-methyl-1-azabicyclo[2.2.2]oct-3-yl]-5-(2-methoxyoxazol-5-yloxy)-thiophene-2-carboxamide; N-[(2S,3R)-2-methyl-1-azabicyclo[2.2.2]oct-3-yl]-5-(2-chlorooxazol-5-yloxy)-thiophene-2-carboxamide; N-[(2S,3R)-2-methyl-1-azabicyclo[2.2.2]oct-3-yl]-5-(thiazol-2-yloxy)-thiophene-2-carboxamide; N-[(2S,3R)-2-methyl-1-azabicyclo[2.2.2]oct-3-yl]-5-(5-methylthiazol-2-yloxy)-thiophene-2-carboxamide; N-[(2S,3R)-2-methyl-1-azabicyclo[2.2.2]oct-3-yl]-5-(5-methoxythiazol-2-yloxy)-thiophene-2-carboxamide; N-[(2S,3R)-2-methyl-1-azabicyclo[2.2.2]oct-3-yl]-5-(5-chlorothiazol-2-yloxy)-thiophene-2-carboxamide; N-[(2S,3R)-2-methyl-1-azabicyclo[2.2.2]oct-3-yl]-5-(thiazol-5-yloxy)-thiophene-2-carboxamide; N-[(2S,3R)-2-methyl-1-azabicyclo[2.2.2]oct-3-yl]-5-(2-methylthiazol-5-yloxy)-thiophene-2-carboxamide; N-[(2S,3R)-2-methyl-1-azabicyclo[2.2.2]oct-3-yl]-5-(2-methoxythiazol-5-yloxy)-thiophene-2-carboxamide; N-[(2S,3R)-2-methyl-1-azabicyclo[2.2.2]oct-3-yl]-5-(2-chlorothiazol-5-yloxy)-thiophene-2-carboxamide; N-[(2S,3R)-2-methyl-1-azabicyclo[2.2.2]oct-3-yl]-5-(4-methylthiazol-2-yloxy)-thiophene-2-carboxamide; N-[(2S,3R)-2-methyl-1-azabicyclo[2.2.2]oct-3-yl]-5-(4-methoxythiazol-2-yloxy)-thiophene-2-carboxamide; N-[(2S,3R)-2-methyl-1-azabicyclo[2.2.2]oct-3-yl]-5-(4-chlorothiazol-2-yloxy)-thiophene-2-carboxamide; N-[(2S,3R)-2-methyl-1-azabicyclo[2.2.2]oct-3-yl]-5-(4-methyloxazol-2-yloxy)-thiophene-2-carboxamide; N-[(2S,3R)-2-methyl-1-azabicyclo[2.2.2]oct-3-yl]-5-(4-methoxyoxazol-2-yloxy)-thiophene-2-carboxamide; N-[(2S,3R)-2-methyl-1-azabicyclo[2.2.2]oct-3-yl]-5-(4-chlorooxazol-2-yloxy)-thiophene-2-carboxamide; N-[(2S,3R)-2-methyl-1-azabicyclo[2.2.2]oct-3-yl]-5-([1,3,4]thiadiazol-2-yloxy)-thiophene-2-carboxamide; N-[(2S,3R)-2-methyl-1-azabicyclo[2.2.2]oct-3-yl]-5-(5-methyl[1,3,4]thiadiazol-2-yloxy)-thiophene-2-carboxamide; N-[(2S,3R)-2-methyl-1-azabicyclo[2.2.2]oct-3-yl]-5-(5-methoxy[1,3,4]thiadiazol-2-yloxy)-thiophene-2-carboxamide; N-[(2S,3R)-2-methyl-1-azabicyclo[2.2.2]oct-3-yl]-5-(5-chloro[1,3,4]thiadiazol-2-yloxy)-thiophene-2-carboxamide; N-[(2S,3R)-2-methyl-1-azabicyclo[2.2.2]oct-3-yl]-5-([1,3,4]oxadiazol-2-yloxy)-thiophene-2-carboxamide; N-[(2S,3R)-2-methyl-1-azabicyclo[2.2.2]oct-3-yl]-5-(5-methyl[1,3,4]oxadiazol-2-yloxy)-thiophene-2-carboxamide; N-[(2S,3R)-2-methyl-1-azabicyclo[2.2.2]oct-3-yl]-5-(5-methoxy[1,3,4]oxadiazol-2-yloxy)-thiophene-2-carboxamide; N-[(2S,3R)-2-methyl-1-azabicyclo[2.2.2]oct-3-yl]-5-(5-chloro[1,3,4]oxadiazol-2-yloxy)-thiophene-2-carboxamide; N-[(2S,3R)-2-methyl-1-azabicyclo[2.2.2]oct-3-yl]-5-(thiophen-4-ylsulfanyl)-thiophene-2-carboxamide N-[(2S,3R)-2-methyl-1-azabicyclo[2.2.2]oct-3-yl]-5-(oxazol-2-ylsulfanyl)-thiophene-2-carboxamide; N-[(2S,3R)-2-methyl-1-azabicyclo[2.2.2]oct-3-yl]-5-(5-methyloxazol-2-ylsulfanyl)-thiophene-2-carboxamide; N-[(2S,3R)-2-methyl-1-azabicyclo[2.2.2]oct-3-yl]-5-(5-methoxyoxazol-2-ylsulfanyl)-thiophene-2-carboxamide; N-[(2S,3R)-2-methyl-1-azabicyclo[2.2.2]oct-3-yl]-5-(5-chlorooxazol-2-ylsulfanyl)-thiophene-2-carboxamide; N-[(2S,3R)-2-methyl-1-azabicyclo[2.2.2]oct-3-yl]-5-(oxazol-5-ylsulfanyl)-thiophene-2-carboxamide; N-[(2S,3R)-2-methyl-1-azabicyclo[2.2.2]oct-3-yl]-5-(2-methyloxazol-5-ylsulfanyl)-thiophene-2-carboxamide; N-[(2S,3R)-2-methyl-1-azabicyclo[2.2.2]oct-3-yl]-5-(2-methoxyoxazol-5-ylsulfanyl)-thiophene-2-carboxamide; N-[(2S,3R)-2-methyl-1-azabicyclo[2.2.2]oct-3-yl]-5-(2-chlorooxazol-5-ylsulfanyl)-thiophene-2-carboxamide; N-[(2S,3R)-2-methyl-1-azabicyclo[2.2.2]oct-3-yl]-5-(thiazol-2-ylsulfanyl)-thiophene-2-carboxamide; N-[(2S,3R)-2-methyl-1-azabicyclo[2.2.2]oct-3-yl]-5-(5-methylthiazol-2-ylsulfanyl)-thiophene-2-carboxamide; N-[(2S,3R)-2-methyl-1-azabicyclo[2.2.2]oct-3-yl]-5-(5-methoxythiazol-2-ylsulfanyl)-thiophene-2-carboxamide; N-[(2S,3R)-2-methyl-1-azabicyclo[2.2.2]oct-3-yl]-5-(5-chlorothiazol-2-ylsulfanyl)-thiophene-2-carboxamide; N-[(2S,3R)-2-methyl-1- azabicyclo[2.2.2]oct-3-yl]-5-(thiazol-5-ylsulfanyl)-thiophene-2-carboxamide; N-[(2S,3R)-2-methyl-1-azabicyclo[2.2.2]oct-3-yl]-5-(2-methylthiazol-5-ylsulfanyl)-thiophene-2-carboxamide; N-[(2S,3R)-2-methyl-1-azabicyclo[2.2.2]oct-3-yl]-5-(2-methoxythiazol-5-ylsulfanyl)-thiophene-2-carboxamide; N-[(2S,3R)-2-methyl-1-azabicyclo[2.2.2]oct-3-yl]-5-(2-chlorothiazol-5-ylsulfanyl)-thiophene-2-carboxamide; N-[(2S,3R)-2-methyl-1-azabicyclo[2.2.2]oct-3-yl]-5-(4-methylthiazol-2-ylsulfanyl)-thiophene-2-carboxamide; N-[(2S,3R)-2-methyl-1-azabicyclo[2.2.2]oct-3-yl]-5-(4-methoxythiazol-2-ylsulfanyl)-thiophene-2-carboxamide; N-[(2S,3R)-2-methyl-1-azabicyclo[2.2.2]oct-3-yl]-5-(4-chlorothiazol-2-ylsulfanyl)-thiophene-2-carboxamide; N-[(2S,3R)-2-methyl-1-azabicyclo[2.2.2]oct-3-yl]-5-(4-methyloxazol-2-ylsulfanyl)-thiophene-2-carboxamide; N-[(2S,3R)-2-methyl-1-azabicyclo[2.2.2]oct-3-yl]-5-(4-methoxyoxazol-2-ylsulfanyl)-thiophene-2-carboxamide; N-[(2S,3R)-2-methyl-1-azabicyclo[2.2.2]oct-3-yl]-5-(4-chlorooxazol-2-ylsulfanyl)-thiophene-2-carboxamide; N-[(2S,3R)-2-methyl-1-azabicyclo[2.2.2]oct-3-yl]-5-([1,3,4]thiadiazol-2-ylsulfanyl)-thiophene-2-carboxamide; N-[(2S,3R)-2-methyl-1-azabicyclo[2.2.2]oct-3-yl]-5-(5-methyl[1,3,4]thiadiazol-2-ylsulfanyl)-thiophene-2-carboxamide; N-[(2S,3R)-2-methyl-1-azabicyclo[2.2.2]oct-3-yl]-5-(5-methoxy[1,3,4]thiadiazol-2-ylsulfanyl)-thiophene-2-carboxamide; N-[(2S,3R)-2-methyl-1-azabicyclo[2.2.2]oct-3-yl]-5-(5-chloro[1,3,4]thiadiazol-2-ylsulfanyl)-thiophene-2-carboxamide; N-[(2S,3R)-2-methyl-1-azabicyclo[2.2.2]oct-3-yl]-5-([1,3,4]oxadiazol-2-ylsulfanyl)-thiophene-2-carboxamide; N-[(2S,3R)-2-methyl-1-azabicyclo[2.2.2]oct-3-yl]-5-(5-methyl [1,3,4]oxadiazol-2-ylsulfanyl)-thiophene-2-carboxamide; N-[(2S,3R)-2-methyl-1-azabicyclo[2.2.2]oct-3-yl]-5-(5-methoxy[1,3,4]oxadiazol-2-ylsulfanyl)-thiophene-2-carboxamide; N-[(2S,3R)-2-methyl-1-azabicyclo[2.2.2]oct-3-yl]-5-(5-chloro[1,3,4]oxadiazol-2-ylsulfanyl)-thiophene-2-carboxamide; N-[(2S,3R)-2-methyl-1-azabicyclo[2.2.2]oct-3-yl]-5-(pyrrole-2-yl)-thiophene-2-carboxamide; N-[(2S,3R)-2-methyl-1-azabicyclo[2.2.2]oct-3-yl]-5-(isothiazol-3-yl)-thiophene-2-carboxamide; N-[(2S,3R)-2-methyl-1-azabicyclo[2.2.2]oct-3-yl]-5-(isoxazol-3-yl)-thiophene-2-carboxamide; N-[(2S,3R)-2-methyl-1-azabicyclo[2.2.2]oct-3-yl]-5-(3H-imidazol-4-yl)-thiophene-2-carboxamide; N-[(2S,3R)-2-methyl-1-azabicyclo[2.2.2]oct-3-yl]-4-(4-hydroxyphenylsulfanyl)-thiophene-2-carboxamide; N-[(2S,3R)-2-methyl-1-azabicyclo[2.2.2]oct-3-yl]-4-(3-acetamidophenylsulfanyl)-thiophene-2-carboxamide; N-[(2S,3R)-2-methyl-1-azabicyclo[2.2.2]oct-3-yl]-4-(2-methanesulfonylaminophenyl)-thiophene-2-carboxamide; N-[(2S,3R)-2-methyl-1-azabicyclo[2.2.2]oct-3-yl]-4-(pyridin-2-yloxy)-thiophene-2-carboxamide; N-[(2S,3R)-2-methyl-1-azabicyclo[2.2.2]oct-3-yl]-4-(2-methylpyridin-4-yloxy)-thiophene-2-carboxamide; N-[(2S,3R)-2-methyl-1-azabicyclo[2.2.2]oct-3-yl]-4-(4-trifluoromethylphenyl)-thiophene-2-carboxamide; N-[(2S,3R)-2-methyl-1-azabicyclo[2.2.2]oct-3-yl]-4-(2-acetylphenyl)-thiophene-2-carboxamide; N-[(2S,3R)-2-methyl-1-azabicyclo[2.2.2]oct-3-yl]-4-chloro-5-phenyl-thiophene-2-carboxamide; N-[(2S,3R)-2-methyl-1-azabicyclo[2.2.2]oct-3-yl]-4-methyl-5-phenyl-thiophene-2-carboxamide; N-[(2S,3R)-2-methyl-1-azabicyclo[2.2.2]oct-3-yl]-4-cyano-5-phenyl-thiophene-2-carboxamide; N-[(2S,3R)-2-methyl-1-azabicyclo[2.2.2]oct-3-yl]-4-methoxy-5-phenyl-thiophene-2-carboxamide; N-[(2S,3R)-2-methyl-1-azabicyclo[2.2.2]oct-3-yl]-5-chloro-4-phenyl-thiophene-2-carboxamide; N-[(2S,3R)-2-methyl-1-azabicyclo[2.2.2]oct-3-yl]-5-methyl-4-phenyl-thiophene-2-carboxamide; N-[(2S,3R)-2-methyl-1-azabicyclo[2.2.2]oct-3-yl]-5-cyano-4-phenyl-thiophene-2-carboxamide; N-[(2S,3R)-2-methyl-1-azabicyclo[2.2.2]oct-3-yl]-5-methoxy-4-phenyl-thiophene-2-carboxamide; N-[(2S,3R)-2-methyl-1-azabicyclo[2.2.2]oct-3-yl]-4-chloro-5-bromo-thiophene-2-carboxamide; N-[(2S,3R)-2-methyl-1-azabicyclo[2.2.2]oct-3-yl]-4-chloro-5-methylsulfanyl-thiophene-2-carboxamide; N-[(2S,3R)-2-methyl-1-azabicyclo[2.2.2]oct-3-yl]-4-chloro-5-methyl-thiophene-2-carboxamide; N-[(2S,3R)-2-methyl-1-azabicyclo[2.2.2]oct-3-yl]-4-chloro-5-cyano-thiophene-2-carboxamide; N-[(2S,3R)-2-methyl-1-azabicyclo[2.2.2]oct-3-yl]-5-chloro-4-bromo-thiophene-2-carboxamide; N-[(2S,3R)-2-methyl-1-azabicyclo[2.2.2]oct-3-yl]-5-chloro-4-methylsulfanyl-thiophene-2-carboxamide; N-[(2S,3R)-2-methyl-1-azabicyclo[2.2.2]oct-3-yl]-5-chloro-4-methyl-thiophene-2-carboxamide; N-[(2S,3R)-2-methyl-1-azabicyclo[2.2.2]oct-3-yl]-5-chloro-4-cyano-thiophene-2-carboxamide;

N-[(3R)-1-azabicyclo[2.2.2]oct-3-yl]-5-(2-bromophenyl)-furan-2-carboxamide; N-[(3R)-1-azabicyclo[2.2.2]oct-3-yl]-5-(3-bromophenyl)-furan-2-carboxamide; N-[(3R)-1-azabicyclo[2.2.2]oct-3-yl]-5-(2,3-dichlorophenyl)-furan-2-carboxamide; N-[(3R)-1-azabicyclo[2.2.2]oct-3-yl]-5-(2,4-dichlorophenyl)-furan-2-carboxamide; N-[(3R)-1-azabicyclo[2.2.2]oct-3-yl]-5-(2,5-dichlorophenyl)-furan-2-carboxamide; N-[(3R)-1-azabicyclo[2.2.2]oct-3-yl]-5-(2,6-dichlorophenyl)-furan-2-carboxamide; N-[(3R)-1-azabicyclo[2.2.2]oct-3-yl]-5-(3,4-dichlorophenyl)-furan-2-carboxamide; N-[(3R)-1-azabicyclo[2.2.2]oct-3-yl]-5-(3,5-dichlorophenyl)-furan-2-carboxamide; N-[(3R)-1-azabicyclo[2.2.2]oct-3-yl]-5-(4-amino-2-fluorophenyl)-furan-2-carboxamide; N-[(3R)-1-azabicyclo[2.2.2]oct-3-yl]-5-(3-amino-2-fluorophenyl)-furan-2-carboxamide; N-[(3R)-1-azabicyclo[2.2.2]oct-3-yl]-5-(4-amino-2-chlorophenyl)-furan-2-carboxamide; N-[(3R)-1-azabicyclo[2.2.2]oct-3-yl]-5-(3-amino-2-chlorophenyl)-furan-2-carboxamide; N-[(3R)-1-azabicyclo[2.2.2]oct-3-yl]-5-(3-aminophenyl)-furan-2-carboxamide; N-[(3R)-1-azabicyclo[2.2.2]oct-3-yl]-5-(2-cyanophenyl)-furan-2-carboxamide; N-[(3R)-1-azabicyclo[2.2.2]oct-3-yl]-5-(3-cyanophenyl)-furan-2-carboxamide; N-[(3R)-1-azabicyclo[2.2.2]oct-3-yl]-5-(2-hydroxyphenyl)-furan-2-carboxamide; N-[(3R)-1-azabicyclo[2.2.2]oct-3-yl]-5-(3-hydroxyphenyl)-furan-2-carboxamide; N-[(3R)-1-azabicyclo[2.2.2]oct-3-yl]-5-(4-hydroxyphenyl)-furan-2-carboxamide; N-[(3R)-1-azabicyclo[2.2.2]oct-3-yl]-5-(2-fluoro-4-methylphenyl)-furan-2-carboxamide; N-[(3R)-1-azabicyclo[2.2.2]oct-3-yl]-5-(2-fluoro-3-methoxyphenyl)-furan-2-carboxamide; N-[(3R)-1-azabicyclo[2.2.2]oct-3-yl]-5-(2-fluoro-4-methoxyphenyl)-furan-2-carboxamide; N-[(3R)-1-azabicyclo[2.2.2]oct-3-yl]-5-(2-[(methylsulfonyl)amino]phenyl)-furan-2-carboxamide; N-[(3R)-1- azabicyclo[2.2.2]oct-3-yl]-5-(3-[(methylsulfonyl) amino]phenyl)-furan-2-carboxamide; N-[(3R)-1-azabicyclo[2.2.2]oct-3-yl]-5-(4-[(methylsulfonyl) amino]phenyl)-furan-2-carboxamide; N-[(3R)-1-azabicyclo[2.2.2]oct-3-yl]-5-(2-([(trifluoromethyl) sulfonyl]amino)phenyl)-furan-2-carboxamide; N-[(3R)-1-azabicyclo[2.2.2]oct-3-yl]-5-(3-([(trifluoromethyl)sulfonyl]amino)phenyl)-furan-2-carboxamide; N-[(3R)-1-azabicyclo[2.2.2]oct-3-yl]-5-(4-([(trifluoromethyl)sulfonyl]amino)phenyl)-furan-2-carboxamide; N-[(3R)-1-azabicyclo[2.2.2]oct-3-yl]-5-(2-[(phenylsulfonyl)amino]phenyl)-furan-2-carboxamide; N-[(3R)-1-azabicyclo[2.2.2]oct-3-yl]-5-(3-[(phenylsulfonyl)amino]phenyl)-furan-2-carboxamide; N-[(3R)-1-azabicyclo[2.2.2]oct-3-yl]-5-(4-[(phenylsulfonyl)amino]phenyl)-furan-2-carboxamide; N-[(3R)-1-azabicyclo[2.2.2]oct-3-yl]-5-(2-[(methylamino)carbonyl]phenyl)-furan-2-carboxamide; N-[(3R)-1-azabicyclo[2.2.2]oct-3-yl]-5-(3-[(methylamino)carbonyl]phenyl)-furan-2-carboxamide; N-[(3R)-1-azabicyclo[2.2.2]oct-3-yl]-5-(4-[(methylamino)carbonyl]phenyl)-furan-2-carboxamide; N-[(3R)-1-azabicyclo[2.2.2]oct-3-yl]-5-(2-[(methylamino)sulfonyl]phenyl)-furan-2-carboxamide; N-[(3R)-1-azabicyclo[2.2.2]oct-3-yl]-5-(3-[(methylamino)sulfonyl]phenyl)-furan-2-carboxamide; N-[(3R)-1-azabicyclo[2.2.2]oct-3-yl]-5-(4-[(methylamino)sulfonyl]phenyl)-furan-2-carboxamide; N-[(3R)-1-azabicyclo[2.2.2]oct-3-yl]-5-[2-(methylamino)phenyl]-furan-2-carboxamide; N-[(3R)-1-azabicyclo[2.2.2]oct-3-yl]-5-[3-(methylamino)phenyl]-furan-2-carboxamide; N-[(3R)-1-azabicyclo[2.2.2]oct-3-yl]-5-[4-(methylamino)phenyl]-furan-2-carboxamide; N-[(3R)-1-azabicyclo[2.2.2]oct-3-yl]-5-[2-(ethylamino)phenyl]-furan-2-carboxamide; N-[(3R)-1-azabicyclo[2.2.2]oct-3-yl]-5-[3-(ethylamino)phenyl]-furan-2-carboxamide; N-[(3R)-1-azabicyclo[2.2.2]oct-3-yl]-5-[4-(ethylamino)phenyl]-furan-2-carboxamide; N-[(3R)-1-azabicyclo[2.2.2]oct-3-yl]-5-(2-acetylphenyl)-furan-2-carboxamide; N-[(3R)-1-azabicyclo[2.2.2]oct-3-yl]-5-(3-acetylphenyl)-furan-2-carboxamide; N-[(3R)-1-azabicyclo[2.2.2]oct-3-yl]-5-(4-acetylphenyl)-furan-2-carboxamide; N-[(3R)-1-azabicyclo[2.2.2]oct-3-yl]-5-[2-(methylthio)phenyl]-furan-2-carboxamide; N-[(3R)-1-azabicyclo[2.2.2]oct-3-yl]-5-[3-(methylthio)phenyl]-furan-2-carboxamide; N-[(3R)-1-azabicyclo[2.2.2]oct-3-yl]-5-[4-(methylthio)phenyl]-furan-2-carboxamide; N-[(3R)-1-azabicyclo[2.2.2]oct-3-yl]-5-[2-(phenylthio)phenyl]-furan-2-carboxamide; N-[(3R)-1-azabicyclo[2.2.2]oct-3-yl]-5-[3-(phenylthio)phenyl]-furan-2-carboxamide; N-[(3R)-1-azabicyclo[2.2.2]oct-3-yl]-5-[4-(phenylthio)phenyl]-furan-2-carboxamide; N-[(3R)-1-azabicyclo[2.2.2]oct-3-yl]-5-(2-phenoxyphenyl)-furan-2-carboxamide; N-[(3R)-1-azabicyclo[2.2.2]oct-3-yl]-5-(3-phenoxyphenyl)-furan-2-carboxamide; N-[(3R)-1-azabicyclo[2.2.2]oct-3-yl]-5-(4-phenoxyphenyl)-furan-2-carboxamide; N-[(3R)-1-azabicyclo[2.2.2]oct-3-yl]-5-(2-anilinophenyl)-furan-2-carboxamide; N-[(3R)-1-azabicyclo[2.2.2]oct-3-yl]-5-(3-anilinophenyl)-furan-2-carboxamide; N-[(3R)-1-azabicyclo[2.2.2]oct-3-yl]-5-(4-anilinophenyl)-furan-2-carboxamide; N-[(3R)-1-azabicyclo[2.2.2]oct-3-yl]-5-(phenylthio)-furan-2-carboxamide; N-[(3R)-1-azabicyclo[2.2.2]oct-3-yl]-5-[(2-fluorophenyl)thio]-furan-2-carboxamide; N-[(3R)-1-azabicyclo[2.2.2]oct-3-yl]-5-[(3-fluorophenyl)thio]-furan-2-carboxamide; N-[(3R)-1-azabicyclo[2.2.2]oct-3-yl]-5-[(4-fluorophenyl)thio]-furan-2-carboxamide; N-[(3R)-1-azabicyclo[2.2.2]oct-3-yl]-5-[(2-chlorophenyl)thio]-furan-2-carboxamide; N-[(3R)-1-azabicyclo[2.2.2]oct-3-yl]-5-[(3-chlorophenyl)thio]-furan-2-carboxamide; N-[(3R)-1-azabicyclo[2.2.2]oct-3-yl]-5-[(4-chlorophenyl)thio]-furan-2-carboxamide; N-[(3R)-1-azabicyclo[2.2.2]oct-3-yl]-5-(2-fluorophenoxy)-furan-2-carboxamide; N-[(3R)-1-azabicyclo[2.2.2]oct-3-yl]-5-(3-fluorophenoxy)-furan-2-carboxamide; N-[(3R)-1-azabicyclo[2.2.2]oct-3-yl]-5-(4-fluorophenoxy)-furan-2-carboxamide; N-[(3R)-1-azabicyclo[2.2.2]oct-3-yl]-5-(2-chlorophenoxy)-furan-2-carboxamide; N-[(3R)-1-azabicyclo[2.2.2]oct-3-yl]-5-(3-chlorophenoxy)-furan-2-carboxamide; N-[(3R)-1-azabicyclo[2.2.2]oct-3-yl]-5-(4-chlorophenoxy)-furan-2-carboxamide; N-[(3R)-1-azabicyclo[2.2.2]oct-3-yl]-5-pyridin-2-yl-furan-2-carboxamide; N-[(3R)-1-azabicyclo[2.2.2]oct-3-yl]-5-pyridin-3-yl-furan-2-carboxamide; N-[(3R)-1-azabicyclo[2.2.2]oct-3-yl]-5-pyridin-4-yl-furan-2-carboxamide; N-[(3R)-1-azabicyclo[2.2.2]oct-3-yl]-5-(3-fluoropyridin-2-yl)-furan-2-carboxamide; N-[(3R)-1-azabicyclo[2.2.2]oct-3-yl]-5-(4-fluoropyridin-2-yl)-furan-2-carboxamide; N-[(3R)-1-azabicyclo[2.2.2]oct-3-yl]-5-(5-fluoropyridin-2-yl)-furan-2-carboxamide; N-[(3R)-1-azabicyclo[2.2.2]oct-3-yl]-5-(6-fluoropyridin-2-yl)-furan-2-carboxamide; N-[(3R)-1-azabicyclo[2.2.2]oct-3-yl]-5-(2-fluoropyridin-3-yl)-furan-2-carboxamide; N-[(3R)-1-azabicyclo[2.2.2]oct-3-yl]-5-(4-fluoropyridin-3-yl)-furan-2-carboxamide; N-[(3R)-1-azabicyclo[2.2.2]oct-3-yl]-5-(5-fluoropyridin-3-yl)-furan-2-carboxamide; N-[(3R)-1-azabicyclo[2.2.2]oct-3-yl]-5-(6-fluoropyridin-3-yl)-furan-2-carboxamide; N-[(3R)-1-azabicyclo[2.2.2]oct-3-yl]-5-(2-fluoropyridin-4-yl)-furan-2-carboxamide; N-[(3R)-1-azabicyclo[2.2.2]oct-3-yl]-5-(3 N-[(3R)-1-azabicyclo[2.2.2]oct-3-yl]-5-(4-pyrrolidin-1-ylphenyl)-furan-2-carboxamide; N-[(3R)-1-azabicyclo[2.2.2]oct-3-yl]-5-[2-(1H-pyrrol-2-yl)phenyl]-furan-2-carboxamide; N-[(3R)-1-azabicyclo[2.2.2]oct-3-yl]-5-[3-(1H-pyrrol-2-yl)phenyl]-furan-2-carboxamide; N-[(3R)-1-azabicyclo[2.2.2]oct-3-yl]-5-[4-(1H-pyrrol-2-yl)phenyl]-furan-2-carboxamide; N-[(3R)-1-azabicyclo[2.2.2]oct-3-yl]-5-[2-(2-furyl)phenyl]-furan-2-carboxamide; N-[(3R)-1-azabicyclo[2.2.2]oct-3-yl]-5-[2-(3-furyl)phenyl]-furan-2-carboxamide; N-[(3R)-1-azabicyclo[2.2.2]oct-3-yl]-5-[2-(5-methyl-2-furyl)phenyl]-furan-2-carboxamide; N-[(3R)-1-azabicyclo[2.2.2]oct-3-yl]-5-[3-(2-furyl)phenyl]-furan-2-carboxamide; N-[(3R)-1-azabicyclo[2.2.2]oct-3-yl]-5-[3-(3-furyl)phenyl]-furan-2-carboxamide; N-[(3R)-1-azabicyclo[2.2.2]oct-3-yl]-5-[3-(5-methyl-2-furyl)phenyl]-furan-2-carboxamide; N-[(3R)-1-azabicyclo[2.2.2]oct-3-yl]-5-[4-(2-furyl)phenyl]-furan-2-carboxamide; N-[(3R)-1-azabicyclo[2.2.2]oct-3-yl]-5-[4-(3-furyl)phenyl]-furan-2-carboxamide; N-[(3R)-1-azabicyclo[2.2.2]oct-3-yl]-5-[4-(5-methyl-2-furyl)phenyl]-furan-2-carboxamide; N-[(3R)-1-azabicyclo[2.2.2]oct-3-yl]-5-[2-(1,3-thiazol-2-yl)phenyl]-furan-2-carboxamide; N-[(3R)-1-azabicyclo[2.2.2]oct-3-yl]-5-[3-(1,3-thiazol-2-yl)phenyl]-furan-2-carboxamide; N-[(3R)-1-azabicyclo[2.2.2]oct-3-yl]-5-[4-(1,3-thiazol-2-yl)phenyl]-furan-2-carboxamide; N-[(3R)-1-azabicyclo[2.2.2]oct-3-yl]-5-[2-(1,3-oxazol-2-yl)phenyl]-furan-2-carboxamide; N-[(3R)-1-azabicyclo[2.2.2]oct-3-yl]-5-[3-(1,3-oxazol-2-yl)

phenyl]-furan-2-carboxamide; N-[(3R)-1-azabicyclo[2.2.2]oct-3-yl]-5-[4-(1,3-oxazol-2-yl)phenyl]-furan-2-carboxamide; N-[(3R)-1-azabicyclo[2.2.2]oct-3-yl]-5-(2-isothiazol-5-ylphenyl)-furan-2-carboxamide; N-[(3R)-1-azabicyclo[2.2.2]oct-3-yl]-5-(3-isothiazol-5-ylphenyl)-furan-2-carboxamide; N-[(3R)-1-azabicyclo[2.2.2]oct-3-yl]-5-(4-isothiazol-5-ylphenyl)-furan-2-carboxamide; N-[(3R)-1-azabicyclo[2.2.2]oct-3-yl]-5-[4-(1H-indol-2-yl)phenyl]-furan-2-carboxamide; N-[(3R)-1-azabicyclo[2.2.2]oct-3-yl]-5-[4-(1H-indol-3-yl)phenyl]-furan-2-carboxamide; N-[(3R)-1-azabicyclo[2.2.2]oct-3-yl]-5-(1H-indol-5-yl)-furan-2-carboxamide; N-[(3R)-1-azabicyclo[2.2.2]oct-3-yl]-5-(1H-indol-6-yl)-furan-2-carboxamide; N-[(2S,3R)-2-methyl-1-azabicyclo[2.2.2]oct-3-yl]-5-(2-bromophenyl)-furan-2-carboxamide; N-[(2S,3R)-2-methyl-1-azabicyclo[2.2.2]oct-3-yl]-5-(3-bromophenyl)-furan-2-carboxamide; N-[(2S,3R)-2-methyl-1-azabicyclo[2.2.2]oct-3-yl]-5-(2,3-dichlorophenyl)-furan-2-carboxamide; N-[(2S,3R)-2-methyl-1-azabicyclo[2.2.2]oct-3-yl]-5-(2,4-dichlorophenyl)-furan-2-carboxamide; N-[(2S,3R)-2-methyl-1-azabicyclo[2.2.2]oct-3-yl]-5-(2,5-dichlorophenyl)-furan-2-carboxamide; N-[(2S,3R)-2-methyl-1-azabicyclo[2.2.2]oct-3-yl]-5-(2,6-dichlorophenyl)-furan-2-carboxamide; N-[(2S,3R)-2-methyl-1-azabicyclo[2.2.2]oct-3-yl]-5-(3,4-dichlorophenyl)-furan-2-carboxamide; N-[(2S,3R)-2-methyl-1-azabicyclo[2.2.2]oct-3-yl]-5-(3,5-dichlorophenyl)-furan-2-carboxamide; N-[(2S,3R)-2-methyl-1-azabicyclo[2.2.2]oct-3-yl]-5-(4-amino-2-fluorophenyl)-furan-2-carboxamide; N-[(2S,3R)-2-methyl-1-azabicyclo[2.2.2]oct-3-yl]-5-(3-amino-2-fluorophenyl)-furan-2-carboxamide; N-[(2S,3R)-2-methyl-1-azabicyclo[2.2.2]oct-3-yl]-5-(4-amino-2-chlorophenyl)-furan-2-carboxamide; N-[(2S,3R)-2-methyl-1-azabicyclo[2.2.2]oct-3-yl]-5-(3-amino-2-chlorophenyl)-furan-2-carboxamide; N-[(2S,3R)-2-methyl-1-azabicyclo[2.2.2]oct-3-yl]-5-(3-aminophenyl)-furan-2-carboxamide; N-[(2S,3R)-2-methyl-1-azabicyclo[2.2.2]oct-3-yl]-5-(2-cyanophenyl)-furan-2-carboxamide; N-[(2S,3R)-2-methyl-1-azabicyclo[2.2.2]oct-3-yl]-5-(3-cyanophenyl)-furan-2-carboxamide; N-[(2S,3R)-2-methyl-1-azabicyclo[2.2.2]oct-3-yl]-5-(2-hydroxyphenyl)-furan-2-carboxamide; N-[(2S,3R)-2-methyl-1-azabicyclo[2.2.2]oct-3-yl]-5-(3-hydroxyphenyl)-furan-2-carboxamide; N-[(2S,3R)-2-methyl-1-azabicyclo[2.2.2]oct-3-yl]-5-(4-hydroxyphenyl)-furan-2-carboxamide; N-[(2S,3R)-2-methyl-1-azabicyclo[2.2.2]oct-3-yl]-5-(2-fluoro-4-methylphenyl)-furan-2-carboxamide; N-[(2S,3R)-2-methyl-1-azabicyclo[2.2.2]oct-3-yl]-5-(2-fluoro-3-methoxyphenyl)-furan-2-carboxamide; N-[(2S,3R)-2-methyl-1-azabicyclo[2.2.2]oct-3-yl]-5-(2-fluoro-4-methoxyphenyl)-furan-2-carboxamide; N-[(2S,3R)-2-methyl-1-azabicyclo[2.2.2]oct-3-yl]-5-(2-[(methylsulfonyl)amino]phenyl)-furan-2-carboxamide; N-[(2S,3R)-2-methyl-1-azabicyclo[2.2.2]oct-3-yl]-5-(3-[(methylsulfonyl)amino]phenyl)-furan-2-carboxamide; N-[(2S,3R)-2-methyl-1-azabicyclo[2.2.2]oct-3-yl]-5-(4-[(methylsulfonyl)amino]phenyl)-furan-2-carboxamide; N-[(2S,3R)-2-methyl-1-azabicyclo[2.2.2]oct-3-yl]-5-[2-([(trifluoromethyl)sulfonyl]amino)phenyl]-furan-2-carboxamide; N-[(2S,3R)-2-methyl-1-azabicyclo[2.2.2]oct-3-yl]-5-[3-([(trifluoromethyl)sulfonyl]amino)phenyl]-furan-2-carboxamide; N-[(2S,3R)-2-methyl-1-azabicyclo[2.2.2]oct-3-yl]-5-([(trifluoromethyl)sulfonyl]amino)phenyl)-furan-2-carboxamide; N-[(2S,3R)-2-methyl-1-azabicyclo[2.2.2]oct-3-yl]-5-(2-[(phenylsulfonyl)amino]phenyl)-furan-2-carboxamide; N-[(2S,3R)-2-methyl-1-azabicyclo[2.2.2]oct-3-yl]-5-(3-[(phenylsulfonyl)amino]phenyl)-furan-2-carboxamide; N-[(2S,3R)-2-methyl-1-azabicyclo[2.2.2]oct-3-yl]-5-(4-[(phenylsulfonyl)amino]phenyl)-furan-2-carboxamide; N-[(2S,3R)-2-methyl-1-azabicyclo[2.2.2]oct-3-yl]-5-(2-[(methylamino)carbonyl]phenyl)-furan-2-carboxamide; N-[(2S,3R)-2-methyl-1-azabicyclo[2.2.2]oct-3-yl]-5-(3-[(methylamino)carbonyl]phenyl)-furan-2-carboxamide; N-[(2S,3R)-2-methyl-1-azabicyclo[2.2.2]oct-3-yl]-5-(4-[(methylamino)carbonyl]phenyl)-furan-2-carboxamide; N-[(2S,3R)-2-methyl-1-azabicyclo[2.2.2]oct-3-yl]-5-(2-[(methylamino)sulfonyl]phenyl)-furan-2-carboxamide; N-[(2S,3R)-2-methyl-1-azabicyclo[2.2.2]oct-3-yl]-5-(3-[(methylamino)sulfonyl]phenyl)-furan-2-carboxamide; N-[(2S,3R)-2-methyl-1-azabicyclo[2.2.2]oct-3-yl]-5-(4-[(methylamino)sulfonyl]phenyl)-furan-2-carboxamide; N-[(2S,3R)-2-methyl-1-azabicyclo[2.2.2]oct-3-yl]-5-[2-(methylamino)phenyl]-furan-2-carboxamide; N-[(2S,3R)-2-methyl-1-azabicyclo[2.2.2]oct-3-yl]-5-[3-(methylamino)phenyl]-furan-2-carboxamide; N-[(2S,3R)-2-methyl-1-azabicyclo[2.2.2]oct-3-yl]-5-[4-(methylamino)phenyl]-furan-2-carboxamide; N-[(2S,3R)-2-methyl-1-azabicyclo[2.2.2]oct-3-yl]-5-[2-(ethylamino)phenyl]furan-2-carboxamide; N-[(2S,3R)-2-methyl-1-azabicyclo[2.2.2]oct-3-yl]-5-[3-(ethylamino)phenyl]-furan-2-carboxamide; N-[(2S,3R)-2-methyl-1-azabicyclo[2.2.2]oct-3-yl]-5-[4-(ethylamino)phenyl]-furan-2-carboxamide; N-[(2S,3R)-2-methyl-1-azabicyclo[2.2.2]oct-3-yl]-5-(2-acetylphenyl)-furan-2-carboxamide; N-[(2S,3R)-2-methyl-1-azabicyclo[2.2.2]oct-3-yl]-5-(3-acetylphenyl)-furan-2-carboxamide; N-[(2S,3R)-2-methyl-1-azabicyclo[2.2.2]oct-3-yl]-5-(4-acetylphenyl)-furan-2-carboxamide; N-[(2S,3R)-2-methyl-1-azabicyclo[2.2.2]oct-3-yl]-5-[2-(methylthio)phenyl]-furan-2-carboxamide; N-[(2S,3R)-2-methyl-1-azabicyclo[2.2.2]oct-3-yl]-5-[3-(methylthio)phenyl]-furan-2-carboxamide; N-[(2S,3R)-2-methyl-1-azabicyclo[2.2.2]oct-3-yl]-5-[4-(methylthio)phenyl]-furan-2-carboxamide; N-[(2S,3R)-2-methyl-1-azabicyclo[2.2.2]oct-3-yl]-5-[2-(phenylthio)phenyl]-furan-2-carboxamide; N-[(2S,3R)-2-methyl-1-azabicyclo[2.2.2]oct-3-yl]-5-[3-(phenylthio)phenyl]-furan-2-carboxamide; N-[(2S,3R)-2-methyl-1-azabicyclo[2.2.2]oct-3-yl]-5-[4-(phenylthio)phenyl]-furan-2-carboxamide; N-[(2S,3R)-2-methyl-1-azabicyclo[2.2.2]oct-3-yl]-5-(2-phenoxyphenyl)-furan-2-carboxamide; N-[(2S,3R)-2-methyl-1-azabicyclo[2.2.2]oct-3-yl]-5-(3-phenoxyphenyl)-furan-2-carboxamide; N-[(2S,3R)-2-methyl-1-azabicyclo[2.2.2]oct-3-yl]-5-(4-phenoxyphenyl)-furan-2-carboxamide; N-[(2S,3R)-2-methyl-1-azabicyclo[2.2.2]oct-3-yl]-5-(2-anilinophenyl)-furan-2-carboxamide; N-[(2S,3R)-2-methyl-1-azabicyclo[2.2.2]oct-3-yl]-5-(3-anilinophenyl)-furan-2-carboxamide; N-[(2S,3R)-2-methyl-1-azabicyclo[2.2.2]oct-3-yl]-5-(4-anilinophenyl)-furan-2-carboxamide; N-[(2S,3R)-2-methyl-1-azabicyclo[2.2.2]oct-3-yl]-5-(phenylthio)-furan-2-carboxamide; N-[(2S,3R)-2-methyl-1-azabicyclo[2.2.2]oct-3-yl]-5-

[(2-fluorophenyl)thio]-furan-2-carboxamide; N-[(2S,3R)-2-methyl-1-azabicyclo[2.2.2]oct-3-yl]-5-[(3-fluorophenyl)thio]-furan-2-carboxamide; N-[(2S,3R)-2-methyl-1-azabicyclo[2.2.2]oct-3-yl]-5-[(4-fluorophenyl)thio]-furan-2-carboxamide; N-[(2S,3R)-2-methyl-1-azabicyclo[2.2.2]oct-3-yl]-5-[(2-chlorophenyl)thio]-furan-2-carboxamide; N-[(2S,3R)-2-methyl-1-azabicyclo[2.2.2]oct-3-yl]-5-[(3-chlorophenyl)thio]-furan-2-carboxamide; N-[(2S,3R)-2-methyl-1-azabicyclo[2.2.2]oct-3-yl]-5-[(4-chlorophenyl)thio]-furan-2-carboxamide; N-[(2S,3R)-2-methyl-1-azabicyclo[2.2.2]oct-3-yl]-5-(2-fluorophenoxy)-furan-2-carboxamide; N-[(2S,3R)-2-methyl-1-azabicyclo[2.2.2]oct-3-yl]-5-(3-fluorophenoxy)-furan-2-carboxamide; N-[(2S,3R)-2-methyl-1-azabicyclo[2.2.2]oct-3-yl]-5-(4-fluorophenoxy)-furan-2-carboxamide; N-[(2S,3R)-2-methyl-1-azabicyclo[2.2.2]oct-3-yl]-5-(2-chlorophenoxy)-furan-2-carboxamide; N-[(2S,3R)-2-methyl-1-azabicyclo[2.2.2]oct-3-yl]-5-(3-chlorophenoxy)-furan-2-carboxamide; N-[(2S,3R)-2-methyl-1-azabicyclo[2.2.2]oct-3-yl]-5-(4-chlorophenoxy)-furan-2-carboxamide; N-[(2S,3R)-2-methyl-1-azabicyclo[2.2.2]oct-3-yl]-5-pyridin-2-yl-furan-2-carboxamide; N-[(2S,3R)-2-methyl-1-azabicyclo[2.2.2]oct-3-yl]-5-pyridin-3-yl-furan-2-carboxamide; N-[(2S,3R)-2-methyl-1-azabicyclo[2.2.2]oct-3-yl]-5-pyridin-4-yl-furan-2-carboxamide; N-[(2S,3R)-2-methyl-1-azabicyclo[2.2.2]oct-3-yl]-5-(3-fluoropyridin-2-yl)-furan-2-carboxamide; N-[(2S,3R)-2-methyl-1-azabicyclo[2.2.2]oct-3-yl]-5-(4-fluoropyridin-2-yl)-furan-2-carboxamide; N-[(2S,3R)-2-methyl-1-azabicyclo[2.2.2]oct-3-yl]-5-(5-fluoropyridin-2-yl)-furan-2-carboxamide; N-[(2S,3R)-2-methyl-1-azabicyclo[2.2.2]oct-3-yl]-5-(6-fluoropyridin-2-yl)-furan-2-carboxamide; N-[(2S,3R)-2-methyl-1-azabicyclo[2.2.2]oct-3-yl]-5-(2-fluoropyridin-3-yl)-furan-2-carboxamide; N-[(2S,3R)-2-methyl-1-azabicyclo[2.2.2]oct-3-yl]-5-(4-fluoropyridin-3-yl)-furan-2-carboxamide; N-[(2S,3R)-2-methyl-1-azabicyclo[2.2.2]oct-3-yl]-5-(5-fluoropyridin-3-yl)-furan-2-carboxamide; N-[(2S,3R)-2-methyl-1-azabicyclo[2.2.2]oct-3-yl]-5-(6-fluoropyridin-3-yl)-furan-2-carboxamide; N-[(2S,3R)-2-methyl-1-azabicyclo[2.2.2]oct-3-yl]-5-(2-fluoropyridin-4-yl)-furan-2-carboxamide; N-[(2S,3R)-2-methyl-1-azabicyclo[2.2.2]oct-3-yl]-5-(3-fluoropyridin-4-yl)-furan-2-carboxamide; N-[(2S,3R)-2-methyl-1-azabicyclo[2.2.2]oct-3-yl]-5-(3-chloropyridin-2-yl)-furan-2-carboxamide; N-[(2S,3R)-2-methyl-1-azabicyclo[2.2.2]oct-3-yl]-5-(4-chloropyridin-2-yl)-furan-2-carboxamide; N-[(2S,3R)-2-methyl-1-azabicyclo[2.2.2]oct-3-yl]-5-(5-chloropyridin-2-yl)-furan-2-carboxamide; N-[(2S,3R)-2-methyl-1-azabicyclo[2.2.2]oct-3-yl]-5-(6-chloropyridin-2-yl)-furan-2-carboxamide; N-[(2S,3R)-2-methyl-1-azabicyclo[2.2.2]oct-3-yl]-5-(2-chloropyridin-3-yl)-furan-2-carboxamide; N-[(2S,3R)-2-methyl-1-azabicyclo[2.2.2]oct-3-yl]-5-(4-chloropyridin-3-yl)-furan-2-carboxamide; N-[(2S,3R)-2-methyl-1-azabicyclo[2.2.2]oct-3-yl]-5-(5-chloropyridin-3-yl)-furan-2-carboxamide; N-[(2S,3R)-2-methyl-1-azabicyclo[2.2.2]oct-3-yl]-5-(6-chloropyridin-3-yl)-furan-2-carboxamide; N-[(2S,3R)-2-methyl-1-azabicyclo[2.2.2]oct-3-yl]-5-(2-chloropyridin-4-yl)-furan-2-carboxamide; N-[(2S,3R)-2-methyl-1-azabicyclo[2.2.2]oct-3-yl]-5-(3-chloropyridin-4-yl)-furan-2-carboxamide; N-[(2S,3R)-2-methyl-1-azabicyclo[2.2.2]oct-3-yl]-5-(2-piperidin-1-ylphenyl)-furan-2-carboxamide; N-[(2S,3R)-2-methyl-1-azabicyclo[2.2.2]oct-3-yl]-5-(3-piperidin-1-ylphenyl)-furan-2-carboxamide; N-[(2S,3R)-2-methyl-1-azabicyclo[2.2.2]oct-3-yl]-5-(4-piperidin-1-ylphenyl)-furan-2-carboxamide; N-[(2S,3R)-2-methyl-1-azabicyclo[2.2.2]oct-3-yl]-5-(2-morpholin-4-ylphenyl)-furan-2-carboxamide; N-[(2S,3R)-2-methyl-1-azabicyclo[2.2.2]oct-3-yl]-5-(3-morpholin-4-ylphenyl)-furan-2-carboxamide; N-[(2S,3R)-2-methyl-1-azabicyclo[2.2.2]oct-3-yl]-5-(4-morpholin-4-ylphenyl)-furan-2-carboxamide; N-[(2S,3R)-2-methyl-1-azabicyclo[2.2.2]oct-3-yl]-5-(2-pyrrolidin-1-ylphenyl)-furan-2-carboxamide; N-[(2S,3R)-2-methyl-1-azabicyclo[2.2.2]oct-3-yl]-5-(3-pyrrolidin-1-ylphenyl)-furan-2-carboxamide; N-[(2S,3R)-2-methyl-1-azabicyclo[2.2.2]oct-3-yl]-5-(4-pyrrolidin-1-ylphenyl)-furan-2-carboxamide; N-[(2S,3R)-2-methyl-1-azabicyclo[2.2.2]oct-3-yl]-5-[2-(1H-pyrrol-2-yl)phenyl]-furan-2-carboxamide; N-[(2S,3R)-2-methyl-1-azabicyclo[2.2.2]oct-3-yl]-5-[3-(1H-pyrrol-2-yl)phenyl]-furan-2-carboxamide; N-[(2S,3R)-2-methyl-1-azabicyclo[2.2.2]oct-3-yl]-5-[4-(1H-pyrrol-2-yl)phenyl]-furan-2-carboxamide; N-[(2S,3R)-2-methyl-1-azabicyclo[2.2.2]oct-3-yl]-5-[2-(2-furyl)phenyl]-furan-2-carboxamide; N-[(2S,3R)-2-methyl-1-azabicyclo[2.2.2]oct-3-yl]-5-[2-(3-furyl)phenyl]-furan-2-carboxamide; N-[(2S,3R)-2-methyl-1-azabicyclo[2.2.2]oct-3-yl]-5-[2-(5-methyl-2-furyl)phenyl]-furan-2-carboxamide; N-[(2S,3R)-2-methyl-1-azabicyclo[2.2.2]oct-3-yl]-5-[3-(2-furyl)phenyl]-furan-2-carboxamide; N-[(2S,3R)-2-methyl-1-azabicyclo[2.2.2]oct-3-yl]-5-[3-(3-furyl)phenyl]-furan-2-carboxamide; N-[(2S,3R)-2-methyl-1-azabicyclo[2.2.2]oct-3-yl]-5-[3-(5-methyl-2-furyl)phenyl]-furan-2-carboxamide; N-[(2S,3R)-2-methyl-1-azabicyclo[2.2.2]oct-3-yl]-5-[4-(2-furyl)phenyl]-furan-2-carboxamide; N-[(2S,3R)-2-m N-[(3R)-1-azabicyclo[2.2.2]oct-3-yl]-2-(2,3-difluorophenyl)-1,3-thiazole-5-carboxamide; N-[(3R)-1-azabicyclo[2.2.2]oct-3-yl]-2-(2,4-difluorophenyl)-1,3-thiazole-5-carboxamide; N-[(3R)-1-azabicyclo[2.2.2]oct-3-yl]-2-(2,5-difluorophenyl)-1,3-thiazole-5-carboxamide; N-[(3R)-1-azabicyclo[2.2.2]oct-3-yl]-2-(2,6-difluorophenyl)-1,3-thiazole-5-carboxamide; N-[(3R)-1-azabicyclo[2.2.2]oct-3-yl]-2-(1,3,4-difluorophenyl)-1,3-thiazole-5-carboxamide; N-[(3R)-1-azabicyclo[2.2.2]oct-3-yl]-2-(3,5-difluorophenyl)-1,3-thiazole-5-carboxamide; N-[(3R)-1-azabicyclo[2.2.2]oct-3-yl]-2-(2-chlorophenyl)-1,3-thiazole-5-carboxamide; N-[(3R)-1-azabicyclo[2.2.2]oct-3-yl]-2-(3-chlorophenyl)-1,3-thiazole-5-carboxamide; N-[(3R)-1-azabicyclo[2.2.2]oct-3-yl]-2-(4-chlorophenyl)-1,3-thiazole-5-carboxamide; N-[(3R)-1-azabicyclo[2.2.2]oct-3-yl]-2-(2-bromophenyl)-1,3-thiazole-5-carboxamide; N-[(3R)-1-azabicyclo[2.2.2]oct-3-yl]-2-(3-bromophenyl)-1,3-thiazole-5-carboxamide; N-[(3R)-1-azabicyclo[2.2.2]oct-3-yl]-2-(4-bromophenyl)-1,3-thiazole-5-carboxamide; N-[(3R)-1-azabicyclo[2.2.2]oct-3-yl]-2-(2-cyanophenyl)-1,3-thiazole-5-carboxamide; N-[(3R)-1-azabicyclo[2.2.2]oct-3-yl]-2-(3-cyanophenyl)-1,3-thiazole-5-carboxamide; N-[(3R)-1-azabicyclo[2.2.2]oct-3-yl]-2-(4-cyanophenyl) 1,3-thiazole-5-carboxamide; N-[(3R)-1-azabicyclo[2.2.2]oct-3-yl]-2-(2-nitrophenyl)-1,3-thiazole-5-carboxamide; N-[(3R)-

1-azabicyclo[2.2.2]oct-3-yl]-2-(3-nitrophenyl)-1,3-thiazole-5-carboxamide; N-[(3R)-1-azabicyclo[2.2.2]oct-3-yl]-2-(4-nitrophenyl)-1,3-thiazole-5-carboxamide; N-[(3R)-1-azabicyclo[2.2.2]oct-3-yl]-2-(2-methylphenyl)-1,3-thiazole-5-carboxamide; N-[(3R)-1-azabicyclo[2.2.2]oct-3-yl]-2-(3-methylphenyl)-1,3-thiazole-5-carboxamide; N-[(3R)-1-azabicyclo[2.2.2]oct-3-yl]-2-(2-aminophenyl) 1,3-thiazole-5-carboxamide; N-[(3R)-1-azabicyclo[2.2.2]oct-3-yl]-2-(3-aminophenyl)-1,3-thiazole-5-carboxamide; N-[(3R)-1-azabicyclo[2.2.2]oct-3-yl]-2-(4-aminophenyl)-1,3-thiazole-5-carboxamide; N-[(3R)-1-azabicyclo[2.2.2]oct-3-yl]-2-[2-(methylamino)phenyl]-1,3-thiazole-5-carboxamide; N-[(3R)-1-azabicyclo[2.2.2]oct-3-yl]-2-[3-(methylamino)phenyl]-1,3-thiazole-5-carboxamide; N-[(3R)-1-azabicyclo[2.2.2]oct-3-yl]-2-[4-(methylamino)phenyl]-1,3-thiazole-5-carboxamide; N-[(3R)-1-azabicyclo[2.2.2]oct-3-yl]-2-[2-(acetylamino)phenyl]-1,3-thiazole-5-carboxamide; N-[(3R)-1-azabicyclo[2.2.2]oct-3-yl]-2-[3-(acetylamino)phenyl]-1,3-thiazole-5-carboxamide; N-[(3R)-1-azabicyclo[2.2.2]oct-3-yl]-2-[4-(acetylamino)phenyl]-1,3-thiazole-5-carboxamide; N-[(3R)-1-azabicyclo[2.2.2]oct-3-yl]-2-(2-[(trifluoroacetyl)amino]phenyl)-1,3-thiazole-5-carboxamide; N-[(3R)-1-azabicyclo[2.2.2]oct-3-yl]-2-(3-[(trifluoroacetyl)amino]phenyl)-1,3-thiazole-5-carboxamide; N-[(3R)-1-azabicyclo[2.2.2]oct-3-yl]-2-(4-[(trifluoroacetyl)amino]phenyl)-1,3-thiazole-5-carboxamide; N-[(3R)-1-azabicyclo[2.2.2]oct-3-yl]-2-(2-[(methylsulfonyl)amino]phenyl)-1,3-thiazole-5-carboxamide; N-[(3R)-1-azabicyclo[2.2.2]oct-3-yl]-2-(3-[(methylsulfonyl)amino]phenyl)-1,3-thiazole-5-carboxamide; N-[(3R)-1-azabicyclo[2.2.2]oct-3-yl]-2-(4-[(methylsulfonyl)amino]phenyl)-1,3-thiazole-5-carboxamide; N-[(3R)-1-azabicyclo[2.2.2]oct-3-yl]-2-(3-hydroxyphenyl)-1,3-thiazole-5-carboxamide; N-[(3R)-1-azabicyclo[2.2.2]oct-3-yl]-2-(4-hydroxyphenyl)-1,3-thiazole-5-carboxamide; N-[(3R)-1-azabicyclo[2.2.2]oct-3-yl]-2-(2-methoxyphenyl)-1,3-thiazole-5-carboxamide; N-[(3R)-1-azabicyclo[2.2.2]oct-3-yl]-2-(3-methoxyphenyl)-1,3-thiazole-5-carboxamide; N-[(3R)-1-azabicyclo[2.2.2]oct-3-yl]-2-(4-methoxyphenyl)-1,3-thiazole-5-carboxamide; N-[(3R)-1-azabicyclo[2.2.2]oct-3-yl]-2-[2-(trifluoromethoxy)phenyl]-1,3-thiazole-5-carboxamide; N-[(3R)-1-azabicyclo[2.2.2]oct-3-yl]-2-[3-(trifluoromethoxy)phenyl]-1,3-thiazole-5-carboxamide; N-[(3R)-1-azabicyclo[2.2.2]oct-3-yl]-2-[4-(trifluoromethoxy)phenyl]-1,3-thiazole-5-carboxamide; N-[(3R)-1-azabicyclo[2.2.2]oct-3-yl]-2-pyridin-2-yl-1,3-thiazole-5-carboxamide; N-[(3R)-1-azabicyclo[2.2.2]oct-3-yl]-2-pyridin-3-yl-1,3-thiazole-5-carboxamide; N-[(3R)-1-azabicyclo[2.2.2]oct-3-yl]-2-pyridin-4-yl-1,3-thiazole-5-carboxamide; N-[(3R)-1-azabicyclo[2.2.2]oct-3-yl]-2-(6-fluoropyridin-2-yl)-1,3-thiazole-5-carboxamide; N-[(3R)-1-azabicyclo[2.2.2]oct-3-yl]-2-(5-fluoropyridin-2-yl)-1,3-thiazole-5-carboxamide; N-[(3R)-1-azabicyclo[2.2.2]oct-3-yl]-2-(4-fluoropyridin-2-yl)-1,3-thiazole-5-carboxamide; N-[(3R)-1-azabicyclo[2.2.2]oct-3-yl]-2-(3-fluoropyridin-2-yl)-1,3-thiazole-5-carboxamide; N-[(3R)-1-azabicyclo[2.2.2]oct-3-yl]-2-(2-fluoropyridin-2-yl)-1,3-thiazole-5-carboxamide; N-[(3R)-1-azabicyclo[2.2.2]oct-3-yl]-2-(6-fluoropyridin-3-yl)-1,3-thiazole-5-carboxamide; N-[(3R)-1-azabicyclo[2.2.2]oct-3-yl]-2-(5-fluoropyridin-3-yl)-1,3-thiazole-5-carboxamide; N-[(3R)-1-azabicyclo[2.2.2]oct-3-yl]-2-(4-fluoropyridin-3-yl)-1,3-thiazole-5-carboxamide; N-[(3R)-1-azabicyclo[2.2.2]oct-3-yl]-2-(2-fluoropyridin-3-yl)-1,3-thiazole-5-carboxamide; N-[(3R)-1-azabicyclo[2.2.2]oct-3-yl]-2-(2-fluoropyridin-4-yl)-1,3-thiazole-5-carboxamide; N-[(3R)-1-azabicyclo[2.2.2]oct-3-yl]-2-(3-fluoropyridin-4-yl)-1,3-thiazole-5-carboxamide;

N-[(3R)-1-azabicyclo[2.2.2]oct-3-yl]-5-(methylthio)-1,3-thiazole-2-carboxamide; N-[(3R)-1-azabicyclo[2.2.2]oct-3-yl]-5-chloro-1,3-thiazole-2-carboxamide; N-[(3R)-1-azabicyclo[2.2.2]oct-3-yl]-5-bromo-1,3-thiazole-2-carboxamide; N-[(3R)-1-azabicyclo[2.2.2]oct-3-yl]-5-(phenylthio)-1,3-thiazole-2-carboxamide; N-[(3R)-1-azabicyclo[2.2.2]oct-3-yl]-5-[(2-fluorophenyl)thio]-1,3-thiazole-2-carboxamide; N-[(3R)-1-azabicyclo[2.2.2]oct-3-yl]-5-[(3-fluorophenyl)thio]-1,3-thiazole-2-carboxamide; N-[(3R)-1-azabicyclo[2.2.2]oct-3-yl]-5-[(4-fluorophenyl)thio]-1,3-thiazole-2-carboxamide; N-[(3R)-1-azabicyclo[2.2.2]oct-3-yl]-5-[(2-chlorophenyl)thio]-1,3-thiazole-2-carboxamide; N-[(3R)-1-azabicyclo[2.2.2]oct-3-yl]-5-[(3-chlorophenyl)thio]-1,3-thiazole-2-carboxamide; N-[(3R)-1-azabicyclo[2.2.2]oct-3-yl]-5-[(4-chlorophenyl)thio]-1,3-thiazole-2-carboxamide; N-[(3R)-1-azabicyclo[2.2.2]oct-3-yl]-5-phenoxy-1,3-thiazole-2-carboxamide; N-[(3R)-1-azabicyclo[2.2.2]oct-3-yl]-5-(2-fluorophenoxy)-1,3-thiazole-2-carboxamide; N-[(3R)-1-azabicyclo[2.2.2]oct-3-yl]-5-(3-fluorophenoxy)-1,3-thiazole-2-carboxamide; N-[(3R)-1-azabicyclo[2.2.2]oct-3-yl]-5-(4-fluorophenoxy)-1,3-thiazole-2-carboxamide; N-[(3R)-1-azabicyclo[2.2.2]oct-3-yl]-5-(2-chlorophenoxy)-1,3-thiazole-2-carboxamide; N-[(3R)-1-azabicyclo[2.2.2]oct-3-yl]-5-(3-chlorophenoxy)-1,3-thiazole-2-carboxamide; N-[(3R)-1-azabicyclo[2.2.2]oct-3-yl]-5-(4-chlorophenoxy)-1,3-thiazole-2-carboxamide; N-[(3R)-1-azabicyclo[2.2.2]oct-3-yl)]-5-thien-3-yl-1,3-thiazole-2-carboxamide; N-[(3R)-1-azabicyclo[2.2.2]oct-3-yl]-5-(2,4-difluorophenyl)-1,3-thiazole-2-carboxamide; N-[(3R)-1-azabicyclo[2.2.2]oct-3-yl]-5-(3,5-difluorophenyl)-1,3-thiazole-2-carboxamide; N-[(3R)-1-azabicyclo[2.2.2]oct-3-yl]-5-(2,4-dichlorophenyl)-1,3-thiazole-2-carboxamide; N-[(3R)-1-azabicyclo[2.2.2]oct-3-yl]-5-(3,5-dichlorophenyl)-1,3-thiazole-2-carboxamide; N-[(3R)-1-azabicyclo[2.2.2]oct-3-yl]-5-(2-bromophenyl)-1,3-thiazole-2-carboxamide-N-[(3R)-1-azabicyclo[2.2.2]oct-3-yl]-5-(3-bromophenyl)-1,3-thiazole-2-carboxamide; N-[(3R)-1-azabicyclo[2.2.2]oct-3-yl]-5-(2-cyanophenyl)-1,3-thiazole-2-carboxamide; N-[(3R)-1-azabicyclo[2.2.2]oct-3-yl]-5-(3-cyanophenyl)-1,3-thiazole-2-carboxamide; N-[(3R)-1-azabicyclo[2.2.2]oct-3-yl]-5-(4-cyanophenyl)-1,3-thiazole-2-carboxamide; N-[(3R)-1-azabicyclo[2.2.2]oct-3-yl]-5-(2-hydroxyphenyl)-1,3-thiazole-2-carboxamide; N-[(3R)-1-azabicyclo[2.2.2]oct-3-yl]-5-(3-hydroxyphenyl)-1,3-thiazole-2-carboxamide; N-[(3R)-1-azabicyclo[2.2.2]oct-3-yl]-5-(4-hydroxyphenyl)-1,3-thiazole-2-carboxamide; N-[(3R)-1-azabicyclo[2.2.2]oct-3-yl]-5-(2-nitrophenyl) 1,3-thiazole-2-carboxamide-N-[(3R)-1-azabicyclo[2.2.2]oct-3-yl]-5-(4-nitrophenyl)-1,3-thiazole-2-carboxamide; N-[(3R)-1-azabicyclo[2.2.2]oct-3-yl]-5-(2-methylphenyl) 1,3- thiazole-2-carboxamide; N-[(3R)-1-azabicyclo[2.2.2]oct-3-yl]-5-(3-methylphenyl)-1,3-thiazole-2-carboxamide; N-[(3R)-1-azabicyclo[2.2.2]oct-3-yl]-5-(4-methylphenyl)-1,3-thiazole-2-carboxamide; N-[(3R)-1-azabicyclo[2.2.2]oct-3-yl]-5-(2-aminophenyl)-1,3-thiazole-2-carboxamide; N-[(3R)-1-azabicyclo[2.2.2]oct-3-yl]-5-(3-aminophenyl)-1,3-thiazole-2-carboxamide; N-[(3R)-1-azabicyclo[2.2.2]oct-3-yl]-5-(4-aminophenyl)-1,3-thiazole-2-carboxamide; N-[(3R)-1-azabicyclo[2.2.2]oct-3-yl]-5-[(2-(acetylamino)phenyl]-1,3-thiazole-2-carboxamide; N-[(3R)-1-azabicyclo[2.2.2]oct-3-yl]-5-[3-(acetylamino)phenyl]-1,3-thiazole-2-carboxamide; N-[(3R)-1-azabicyclo[2.2.2]oct-3-yl]-5-[4-(acetylamino)phenyl]-1,3-thiazole-2-carboxamide; N-[(3R)-1-azabicyclo[2.2.2]oct-3-yl]-5-(pyridin-2-yl)-1,3-thiazole-2-carboxamide; N-[(3R)-1-azabicyclo[2.2.2]oct-3-yl]-5-(pyridin-3-yl)-1,3-thiazole-2-carboxamide; N-[(3R)-1-azabicyclo[2.2.2]oct-3-yl]-5-(pyridin-4-yl)-1,3-thiazole-2-carboxamide; N-[(3R)-1-azabicyclo[2.2.2]oct-3-yl]-5-(3-fluoropyridin-2-yl)-1,3-thiazole-2-carboxamide; N-[(3R)-1-azabicyclo[2.2.2]oct-3-yl]-5-(4-fluoropyridin-2-yl)-1,3-thiazole-2-carboxamide; N-[(3R)-1-azabicyclo[2.2.2]oct-3-yl]-5-(5-fluoropyridin-2-yl)-1,3-thiazole-2-carboxamide; N-[(3R)-1-azabicyclo[2.2.2]oct-3-yl]-5-(6-fluoropyridin-2-yl)-1,3-thiazole-2-carboxamide; N-[(3R)-1-azabicyclo[2.2.2]oct-3-yl]-5-(2-fluoropyridin-3-yl)-1,3-thiazole-2-carboxamide; N-[(3R)-1-azabicyclo[2.2.2]oct-3-yl]-5-(4-fluoropyridin-3-yl)-1,3-thiazole-2-carboxamide; N-[(3R)-1-azabicyclo[2.2.2]oct-3-yl]-5-(5-fluoropyridin-3-yl)-1,3-thiazole-2-carboxamide; N-[(3R)-1-azabicyclo[2.2.2]oct-3-yl]-5-(6-fluoropyridin-3-yl)-1,3-thiazole-2-carboxamide; N-[(3R)-1-azabicyclo[2.2.2]oct-3-yl]-5-(2-fluoropyridin-4-yl)-1,3-thiazole-2-carboxamide; N-[(3R)-1-azabicyclo[2.2.2]oct-3-yl]-5-[(2-methoxyphenyl)thio]-1,3-thiazole-2-carboxamide; N-[(3R)-1-azabicyclo[2.2.2]oct-3-yl]-5-[(3-methoxyphenyl)thio]-1,3-thiazole-2-carboxamide; N-[(3R)-1-azabicyclo[2.2.2]oct-3-yl]-5-[(4-methoxyphenyl)thio]-1,3-thiazole-2-carboxamide; N-[(3R)-1-azabicyclo[2.2.2]oct-3-yl]-5-[(2-methylphenyl)thio]-1,3-thiazole-2-carboxamide; N-[(3R)-1-azabicyclo[2.2.2]oct-3-yl]-5-[(3-methylphenyl)thio]-1,3-thiazole-2-carboxamide; N-[(3R)-1-azabicyclo[2.2.2]oct-3-yl]-5-[(4-methylphenyl)thio]-1,3-thiazole-2-carboxamide; N-[(3R)-1-azabicyclo[2.2.2]oct-3-yl]-5-([4-(acetylamino)phenyl]thio)-1,3-thiazole-2-carboxamide; N-[(3R)-1-azabicyclo[2.2.2]oct-3-yl]-5-[(4-aminophenyl)thio]-1,3-thiazole-2-carboxamide; N-[(3R)-1-azabicyclo[2.2.2]oct-3-yl]-5-[(4-hydroxyphenyl)thio]-1,3-thiazole-2-carboxamide; N-[(3R)-1-azabicyclo[2.2.2]oct-3-yl]-5-(2-methylphenoxy)-1,3-thiazole-2-carboxamide; N-[(3R)-1-azabicyclo[2.2.2]oct-3-yl]-5-(3-methylphenoxy)-1,3-thiazole-2-carboxamide; N-[(3R)-1-azabicyclo[2.2.2]oct-3-yl]-5-(4-methylphenoxy)-1,3-thiazole-2-carboxamide; N-[(3R)-1-azabicyclo[2.2.2]oct-3-yl]-5-(2-methoxyphenoxy)-1,3-thiazole-2-carboxamide; N-[(3R)-1-azabicyclo[2.2.2]oct-3-yl]-5-(3-methoxyphenoxy)-1,3-thiazole-2-carboxamide; N-[(3R)-1-azabicyclo[2.2.2]oct-3-yl]-5-(4-methoxyphenoxy)-1,3-thiazole-2-carboxamide; N-[(3R)-1-azabicyclo[2.2.2]oct-3-yl]-5-(4-hydroxyphenoxy)-1,3-thiazole-2-carboxamide; N-[(3R)-1-azabicyclo[2.2.2]oct-3-yl]-5-(4-aminophenoxy)-1,3-thiazole-2-carboxamide; N-[(3R)-1-azabicyclo[2.2.2]oct-3-yl]-5-[4-(acetylamino)phenoxy]-1,3-thiazole-2-carboxamide; N-[(3R)-1-azabicyclo[2.2.2]oct-3-yl]-5-(2-fluorophenyl)-4-methyl-1,3-thiazole-2-carboxamide; N-[(3R)-1-azabicyclo[2.2.2]oct-3-yl]-5-(3-fluorophenyl)-4-methyl-1,3-thiazole-2-carboxamide; N-[(3R)-1-azabicyclo[2.2.2]oct-3-yl]-5-(2-chlorophenyl)-4-methyl-1,3-thiazole-2-carboxamide; N-[(3R)-1-azabicyclo[2.2.2]oct-3-yl]-5-(3-chlorophenyl)-4-methyl-1,3-thiazole-2-carboxamide; N-[(3R)-1-azabicyclo[2.2.2]oct-3-yl]-5-(2-methoxyphenyl)-4-methyl-1,3-thiazole-2-carboxamide; N-[(3R)-1-azabicyclo[2.2.2]oct-3-yl]-5-(3-methoxyphenyl)-4-methyl-1,3-thiazole-2-carboxamide; N-[(3R)-1-azabicyclo[2.2.2]oct-3-yl]-4-methyl-5-thien-2-yl-1,3-thiazole-2-carboxamide;

N-[(2S,3R)-2-methyl-1-azabicyclo[2.2.2]oct-3-yl]-2-(2,3-difluorophenyl)-1,3-thiazole-5-carboxamide; N-[(2S,3R)-2-methyl-1-azabicyclo[2.2.2]oct-3-yl]-2-(2,4-difluorophenyl)-1,3-thiazole-5-carboxamide; N-[(2S,3R)-2-methyl-1-azabicyclo[2.2.2]oct-3-yl]-2-(2,5-difluorophenyl)-1,3-thiazole-5-carboxamide; N-[(2S,3R)-2-methyl-1-azabicyclo[2.2.2]oct-3-yl]-2-(2,6-difluorophenyl)-1,3-thiazole-5-carboxamide; N-[(2S,3R)-2-methyl-1-azabicyclo[2.2.2]oct-3-yl]-2-(3,4-difluorophenyl)-1,3-thiazole-5-carboxamide; N-[(2S,3R)-2-methyl-1-azabicyclo[2.2.2]oct-3-yl]-2-(3,5-difluorophenyl)-1,3-thiazole-5-carboxamide; N-[(2S,3R)-2-methyl-1-azabicyclo[2.2.2]oct-3-yl]-2-(2-chlorophenyl)-1,3-thiazole-5-carboxamide; N-[(2S,3R)-2-methyl-1-azabicyclo[2.2.2]oct-3-yl]-2-(3-chlorophenyl)-1,3-thiazole-5-carboxamide; N-[(2S,3R)-2-methyl-1-azabicyclo[2.2.2]oct-3-yl]-2-(4-chlorophenyl)-1,3-thiazole-5-carboxamide; N-[(2S,3R)-2-methyl-1-azabicyclo[2.2.2]oct-3-yl]-2-(2-bromophenyl)-1,3-thiazole-5-carboxamide; N-[(2S,3R)-2-methyl-1-azabicyclo[2.2.2]oct-3-yl]-2-(3-bromophenyl)-1,3-thiazole-5-carboxamide; N-[(2S,3R)-2-methyl-1-azabicyclo[2.2.2]oct-3-yl]-2-(4-bromophenyl)-1,3-thiazole-5-carboxamide; N-[(2S,3R)-2-methyl-1-azabicyclo[2.2.2]oct-3-yl]-2-(2-cyanophenyl)-1,3-thiazole-5-carboxamide; N-[(2S,3R)-2-methyl-1-azabicyclo[2.2.2]oct-3-yl]-2-(3-cyanophenyl)-1,3-thiazole-5-carboxamide; N-[(2S,3R)-2-methyl-1-azabicyclo[2.2.2]oct-3-yl]-2-(4-cyanophenyl)-1,3-thiazole-5-carboxamide; N-[(2S,3R)-2-methyl-1-azabicyclo[2.2.2]oct-3-yl]-2-(2-nitrophenyl)-1,3-thiazole-5-carboxamide; N-[(2S,3R)-2-methyl-1-azabicyclo[2.2.2]oct-3-yl]-2-(3-nitrophenyl)-1,3-thiazole-5-carboxamide; N-[(2S,3R)-2-methyl-1-azabicyclo[2.2.2]oct-3-yl]-2-(4-nitrophenyl)-1,3-thiazole-5-carboxamide; N-[(2S,3R)-2-methyl-1-azabicyclo[2.2.2]oct-3-yl]-2-(2-methylphenyl)-1,3-thiazole-5-carboxamide; N-[(2S,3R)-2-methyl-1-azabicyclo[2.2.2]oct-3-yl]-2-(3-methylphenyl)-1,3-thiazole-5-carboxamide; N-[(2S,3R)-2-methyl-1-azabicyclo[2.2.2]oct-3-yl]-2-(2-aminophenyl)-1,3-thiazole-5-carboxamide; N-[(2S,3R)-2-methyl-1-azabicyclo[2.2.2]oct-3-yl]-2-(3-aminophenyl)-1,3-thiazole-5-carboxamide; N-[(2S,3R)-2-methyl-1-azabicyclo[2.2.2]oct-3-yl]-2-(4-aminophenyl)-1,3-thiazole-5-carboxamide; N-[(2S,3R)-2-methyl-1-azabicyclo[2.2.2]oct-3-yl]-2-[2-(methylamino)phenyl]-1,3-thiazole-5-carboxamide;

N-[(2S,3R)-2-methyl-1-azabicyclo[2.2.2]oct-3-yl]-2-[3-(methylamino)phenyl]-1,3-thiazole-5-carboxamide; N-[(2S,3R)-2-methyl-1-azabicyclo[2.2.2]oct-3-yl]-2-[4-(methylamino)phenyl]-1,3-thiazole-5-carboxamide; N-[(2S,3R)-2-methyl-1-azabicyclo[2.2.2]oct-3-yl]-2-[2-(acetylamino)phenyl]-1,3-thiazole-5-carboxamide; N-[(2S,3R)-2-methyl-1-azabicyclo[2.2.2]oct-3-yl]-2-[3-(acetylamino)phenyl]-1,3-thiazole-5-carboxamide; N-[(2S,3R)-2-methyl-1-azabicyclo[2.2.2]oct-3-yl]-2-[4-(acetylamino)phenyl]-1,3-thiazole-5-carboxamide; N-[(2S,3R)-2-methyl-1-azabicyclo[2.2.2]oct-3-yl]-2-(2-[(trifluoroacetyl)amino]phenyl)-1,3-thiazole-5-carboxamide; N-[(2S,3R)-2-methyl-1-azabicyclo[2.2.2]oct-3-yl]-2-(3-[(trifluoroacetyl)amino]phenyl)-1,3-thiazole-5-carboxamide; N-[(2S,3R)-2-methyl-1-azabicyclo[2.2.2]oct-3-yl]-2-(4-[(trifluoroacetyl)amino]phenyl)-1,3-thiazole-5-carboxamide; N-[(2S,3R)-2-methyl-1-azabicyclo[2.2.2]oct-3-yl]-2-(2-[(methylsulfonyl)amino]phenyl)-1,3-thiazole-5-carboxamide; N-[(2S,3R)-2-methyl-1-azabicyclo[2.2.2]oct-3-yl]-2-(3-[(methylsulfonyl)amino]phenyl)-1,3-thiazole-5-carboxamide; N-[(2S,3R)-2-methyl-1-azabicyclo[2.2.2]oct-3-yl]-2-(4-[(methylsulfonyl)amino]phenyl)-1,3-thiazole-5-carboxamide; N-[(2S,3R)-2-methyl-1-azabicyclo[2.2.2]oct-3-yl]-2-(3-hydroxyphenyl)-1,3-thiazole-5-carboxamide; N-[(2S,3R)-2-methyl-1-azabicyclo[2.2.2]oct-3-yl]-2-(4-hydroxyphenyl)-1,3-thiazole-5-carboxamide; N-[(2S,3R)-2-methyl-1-azabicyclo[2.2.2]oct-3-yl]-2-(2-methoxyphenyl)-1,3-thiazole-5-carboxamide; N-[(2S,3R)-2-methyl-1-azabicyclo[2.2.2]oct-3-yl]-2-(3-methoxyphenyl)-1,3-thiazole-5-carboxamide; N-[(2S,3R)-2-methyl-1-azabicyclo[2.2.2]oct-3-yl]-2-(4-methoxyphenyl)-1,3-thiazole-5-carboxamide; N-[(2S,3R)-2-methyl-1-azabicyclo[2.2.2]oct-3-yl]-2-[2-(trifluoromethoxy)phenyl]-1,3-thiazole-5-carboxamide; N-[(2S,3R)-2-methyl-1-azabicyclo[2.2.2]oct-3-yl]-2-[3-(trifluoromethoxy)phenyl]-1,3-thiazole-5-carboxamide; N-[(2S,3R)-2-methyl-1-azabicyclo[2.2.2]oct-3-yl]-2-[4-(trifluoromethoxy)phenyl]-1,3-thiazole-5-carboxamide; N-[(2S,3R)-2-methyl-1-azabicyclo[2.2.2]oct-3-yl]-2-pyridin-2-yl-1,3-thiazole-5-carboxamide; N-[(2S,3R)-2-methyl-1-azabicyclo[2.2.2]oct-3-yl]-2-pyridin-3-yl-1,3-thiazole-5-carboxamide; N-[(2S,3R)-2-methyl-1-azabicyclo[2.2.2]oct-3-yl]-2-pyridin-4-yl-1,3-thiazole-5-carboxamide; N-[(2S,3R)-2-methyl-1-azabicyclo[2.2.2]oct-3-yl]-2-(6-fluoropyridin-2-yl)-1,3-thiazole-5-carboxamide; N-[(2S,3R)-2-methyl-1-azabicyclo[2.2.2]oct-3-yl]-2-(5-fluoropyridin-2-yl)-1,3-thiazole-5-carboxamide; N-[(2S,3R)-2-methyl-1-azabicyclo[2.2.2]oct-3-yl]-2-(4-fluoropyridin-2-yl)-1,3-thiazole-5-carboxamide; N-[(2S,3R)-2-methyl-1-azabicyclo[2.2.2]oct-3-yl]-2-(3-fluoropyridin-2-yl)-1,3-thiazole-5-carboxamide; N-[(2S,3R)-2-methyl-1-azabicyclo[2.2.2]oct-3-yl]-2-(2-fluoropyridin-2-yl)-1,3-thiazole-5-carboxamide; N-[(2S,3R)-2-methyl-1-azabicyclo[2.2.2]oct-3-yl]-2-(6-fluoropyridin-3-yl)-1,3-thiazole-5-carboxamide; N-[(2S,3R)-2-methyl-1-azabicyclo[2.2.2]oct-3-yl]-2-(5-fluoropyridin-3-yl)-1,3-thiazole-5-carboxamide; N-[(2S,3R)-2-methyl-1-azabicyclo[2.2.2]oct-3-yl]-2-(4-fluoropyridin-3-yl)-1,3-thiazole-5-carboxamide; N-[(2S,3R)-2-methyl-1-azabicyclo[2.2.2]oct-3-yl]-2-(2-fluoropyridin-3-yl)-1,3-thiazole-5-carboxamide; N-[(2S,3R)-2-methyl-1-azabicyclo[2.2.2]oct-3-yl]-2-(2-fluoropyridin-4-yl)-1,3-thiazole-5-carboxamide; N-[(2S,3R)-2-methyl-1-azabicyclo[2.2.2]oct-3-yl]-2-(3-fluoropyridin-4-yl)-1,3-thiazole-5-carboxamide;

N-[(2S,3R)-2-methyl-1-azabicyclo(2.2.2)oct-3-yl]-5-(methylthio)-1,3-thiazole-2-carboxamide; N-[(2S,3R)-2-methyl-1-azabicyclo[2.2.2]oct-3-yl]-5-chloro-1,3-thiazole-2-carboxamide; N-[(2S,3R)-2-methyl-1-azabicyclo[2.2.2]oct-3-yl]-5-bromo-1,3-thiazole-2-carboxamide, N-[(2S,3R)-2-methyl-1-azabicyclo[2.2.2]oct-3-yl]-5-(phenylthio)-1,3-thiazole-2-carboxamide; N-[(2S,3R)-2-methyl-1-azabicyclo[2.2.2]oct-3-yl]-5-[(2-fluorophenyl)thio]-1,3-thiazole-2-carboxamide; N-[(2S,3R)-2-methyl-1-azabicyclo[2.2.2]oct-3-yl]-5-[(3-fluorophenyl)thio]-1,3-thiazole-2-carboxamide; N-[(2S,3R)-2-methyl-1-azabicyclo[2.2.2]oct-3-yl]-5-[(4-fluorophenyl)thio]-1,3-thiazole-2-carboxamide; N-[(2S,3R)-2-methyl-1-azabicyclo[2.2.2]oct-3-yl]-5-[(2-chlorophenyl)thio]-1,3-thiazole-2-carboxamide; N-[(2S,3R)-2-methyl-1-azabicyclo[2.2.2]oct-3-yl]-5-[(3-chlorophenyl)thio]-1,3-thiazole-2-carboxamide; N-[(2S,3R)-2-methyl-1-azabicyclo[2.2.2]oct-3-yl]-5-[(4-chlorophenyl)thio]-1,3-thiazole-2-carboxamide; N-[(2S,3R)-2-methyl-1-azabicyclo[2.2.2]oct-3-yl]-5-phenoxy-1,3-thiazole-2-carboxamide; N-[(2S,3R)-2-methyl-1-azabicyclo[2.2.2]oct-3-yl]-5-(2-fluorophenoxy)-1,3-thiazole-2-carboxamide; N-[(2S,3R)-2-methyl-1-azabicyclo[2.2.2]oct-3-yl]-5-(3-fluorophenoxy)-1,3-thiazole-2-carboxamide; N-[(2S,3R)-2-methyl-1-azabicyclo[2.2.2]oct-3-yl]-5-(4-fluorophenoxy)-1,3-thiazole-2-carboxamide; N-[(2S,3R)-2-methyl-1-azabicyclo[2.2.2]oct-3-yl]-5-(2-chlorophenoxy)-1,3-thiazole-2-carboxamide; N-[(2S,3R)-2-methyl-1-azabicyclo[2.2.2]oct-3-yl]-5-(3-chlorophenoxy)-1,3-thiazole-2-carboxamide; N-[(2S,3R)-2-methyl-1-azabicyclo[2.2.2]oct-3-yl]-5-(4-chlorophenoxy)-1,3-thiazole-2-carboxamide; N-[(2S,3R)-2-methyl-1-azabicyclo[2.2.2]oct-3-yl]-5-thien-3-yl-1,3-thiazole-2-carboxamide; N-[(2S,3R)-2-methyl-1-azabicyclo[2.2.2]oct-3-yl]-5-(2,4-difluorophenyl)-1,3-thiazole-2-carboxamide; N-[(2S,3R)-2-methyl-1-azabicyclo[2.2.2]oct-3-yl]-5-(3,5-difluorophenyl)-1,3-thiazole-2-carboxamide; N-[(2S,3R)-2-methyl-1-azabicyclo[2.2.2]oct-3-yl]-5-(2,4-dichlorophenyl)-1,3-thiazole-2-carboxamide; N-[(2S,3R)-2-methyl-1-azabicyclo[2.2.2]oct-3-yl]-5-(3,5-dichlorophenyl)-1,3-thiazole-2-carboxamide; N-[(2S,3R)-2-methyl-1-azabicyclo[2.2.2]oct-3-yl]-5-(2-bromophenyl)-1,3-thiazole-2-carboxamide; N-[(2S,3R)-2-methyl-1-azabicyclo[2.2.2]oct-3-yl]-5-(3-bromophenyl)-1,3-thiazole-2-carboxamide; N-[(2S,3R)-2-methyl-1-azabicyclo[2.2.2]oct-3-yl]-5-(2-cyanophenyl)-1,3-thiazole-2-carboxamide; N-[(2S,3R)-2-methyl-1-azabicyclo[2.2.2]oct-3-yl]-5-(3-cyanophenyl)-1,3-thiazole-2-carboxamide; N-[(2S,3R)-2-methyl-1-azabicyclo[2.2.2]oct-3-yl]-5-(4-cyanophenyl)-1,3-thiazole-2-carboxamide; N-[(2S,3R)-2-methyl-1-azabicyclo[2.2.2]oct-3-yl]-5-(2-hydroxyphenyl)-1,3-thiazole-2-carboxamide; N-[(2S,3R)-2-methyl-1-azabicyclo[2.2.2]oct-3-yl]-5-(3-hydroxyphenyl)-1,3-thiazole-2-carboxamide; N-[(2S,3R)-2-methyl-1-azabicyclo[2.2.2]oct-3-yl]-5-(4-hydroxyphenyl)-1,3-thiazole-2-carboxamide; N-[(2S,3R)-2-methyl-1-azabicyclo[2.2.2]oct-3-yl]-5-(2-nitrophenyl)-1,3-thiazole-2-carboxamide; N-[(2S,3R)-2-methyl-1-azabicyclo[2.2.2]oct-3-yl]-5-(4-nitrophenyl)-1,3-thiazole-2-carboxamide; N-[(2S,3R)-2-methyl-1-azabicyclo[2.2.2]oct-3-yl]-5-(2-methylphenyl)-1,3-thiazole-2- carboxamide; N-[(2S,3R)-2-methyl-1-azabicyclo[2.2.2]oct-3-yl]-5-(3-methylphenyl)-1,3-thiazole-2-carboxamide; N-[(2S,3R)-2-methyl-1-azabicyclo[2.2.2]oct-3-yl]-5-(4-methylphenyl)-1,3-thiazole-2-carboxamide; N-[(2S,3R)-2-methyl-1-azabicyclo[2.2.2]oct-3-yl]-5-(2-aminophenyl)-1,3-thiazole-2-carboxamide; N-[(2S,3R)-2-methyl-1-azabicyclo[2.2.2]oct-3-yl]-5-(3-aminophenyl)-1,3-thiazole-2-carboxamide; N-[(2S,3R)-2-methyl-1-azabicyclo[2.2.2]oct-3-yl]-5-(4-aminophenyl)-1,3-thiazole-2-carboxamide; N-[(2S,3R)-2-methyl-1-azabicyclo[2.2.2]oct-3-yl]-5-[2-(acetylamino)phenyl]-1,3-thiazole-2-carboxamide; N-[(2S,3R)-2-methyl-1-azabicyclo[2.2.2]oct-3-yl]-5-[3-(acetylamino)phenyl]-1,3-thiazole-2-carboxamide; N-[(2S,3R)-2-methyl-1-azabicyclo[2.2.2]oct-3-yl]-5-[4-(acetylamino)phenyl]-1,3-thiazole-2-carboxamide; N-[(2S,3R)-2-methyl-1-azabicyclo[2.2.2]oct-3-yl]-5-(pyridin-2-yl)-1,3-thiazole-2-carboxamide; N-[(2S,3R)-2-methyl-1-azabicyclo[2.2.2]oct-3-yl]-5-(pyridin-3-yl)-1,3-thiazole-2-carboxamide; N-[(2S,3R)-2-methyl-1-azabicyclo[2.2.2]oct-3-yl]-5-(pyridin-4-yl)-1,3-thiazole-2-carboxamide; N-[(2S,3R)-2-methyl-1-azabicyclo[2.2.2]oct-3-yl]-5-(3-fluoropyridin-2-yl)-1,3-thiazole-2-carboxamide; N-[(2S,3R)-2-methyl-1-azabicyclo[2.2.2]oct-3-yl]-5-(4-fluoropyridin-2-yl)-1,3-thiazole-2-carboxamide; N-[(2S,3R)-2-methyl-1-azabicyclo[2.2.2]oct-3-yl]-5-(5-fluoropyridin-2-yl)-1,3-thiazole-2-carboxamide; N-[(2S,3R)-2-methyl-1-azabicyclo[2.2.2]oct-3-yl]-5-(6-fluoropyridin-2-yl)-1,3-thiazole-2-carboxamide; N-[(2S,3R)-2-methyl-1-azabicyclo[2.2.2]oct-3-yl]-5-(2-fluoropyridin-3-yl)-1,3-thiazole-2-carboxamide; N-[(2S,3R)-2-methyl-1-azabicyclo[2.2.2]oct-3-yl]-5-(4-fluoropyridin-3-yl)-1,3-thiazole-2-carboxamide; N-[(2S,3R)-2-methyl-1-azabicyclo[2.2.2]oct-3-yl]-5-(5-fluoropyridin-3-yl)-1,3-thiazole-2-carboxamide; N-[(2S,3R)-2-methyl-1-azabicyclo[2.2.2]oct-3-yl]-5-(6-fluoropyridin-3-yl)-1,3-thiazole-2-carboxamide; N-[(2S,3R)-2-methyl-1-azabicyclo[2.2.2]oct-3-yl]-5-(2-fluoropyridin-4-yl)-1,3-thiazole-2-carboxamide; N-[(2S,3R)-2-methyl-1-azabicyclo[2.2.2]oct-3-yl]-5-[(2-methoxyphenyl)thio]-1,3-thiazole-2-carboxamide; N-[(2S,3R)-2-methyl-1-azabicyclo[2.2.2]oct-3-yl]-5-[(3-methoxyphenyl)thio]-1,3-thiazole-2-carboxamide; N-[(2S,3R)-2-methyl-1-azabicyclo[2.2.2]oct-3-yl]-5-[(4-methoxyphenyl)thio]-1,3-thiazole-2-carboxamide; N-[(2S,3R)-2-methyl-1-azabicyclo[2.2.2]oct-3-yl]-5-[(2-methylphenyl)thio]-1,3-thiazole-2-carboxamide; N-[(2S,3R)-2-methyl-1-azabicyclo[2.2.2]oct-3-yl]-5-[(3-methylphenyl)thio]-1,3-thiazole-2-carboxamide; N-[(2S,3R)-2-methyl-1-azabicyclo[2.2.2]oct-3-yl]-5-[(4-methylphenyl)thio]-1,3-thiazole-2-carboxamide; N-[(2S,3R)-2-methyl-1-azabicyclo[2.2.2]oct-3-yl]-5-([4-(acetylamino)phenyl]thio)-1,3-thiazole-2-carboxamide; N-[(2S,3R)-2-methyl-1-azabicyclo[2.2.2]oct-3-yl]-5-[(4-aminophenyl)thio]-1,3-thiazole-2-carboxamide; N-[(2S,3R)-2-methyl-1-azabicyclo[2.2.2]oct-3-yl]-5-[(4-hydroxyphenyl)thio]-1,3-thiazole-2-carboxamide; N-[(2S,3R)-2-methyl-1-azabicyclo[2.2.2]oct-3-yl]-5-(2-methylphenoxy)-1,3-thiazole-2-carboxamide; N-[(2S,3R)-2-methyl-1-azabicyclo[2.2.2]oct-3-yl]-5-(3-methylphenoxy)-1,3-thiazole-2-carboxamide; N-[(2S,3R)-2-methyl-1-azabicyclo[2.2.2]oct-3-yl]-5-(4-methylphenoxy)-1,3-thiazole-2-carboxamide; N-[(2S,3R)-2-methyl-1-azabicyclo[2.2.2]oct-3-yl]-5-(2-methoxyphenoxy)-1,3-thiazole-2-carboxamide; N-[(2S,3R)-2-methyl-1-azabicyclo[2.2.2]oct-3-yl]-5-(3-methoxyphenoxy)-1,3-thiazole-2-carboxamide; N-[(2S,3R)-2-methyl-1-azabicyclo[2.2.2]oct-3-yl]-5-(4-methoxyphenoxy)-1,3-thiazole-2-carboxamide; N-[(2S,3R)-2-methyl-1-azabicyclo[2.2.2]oct-3-yl]-5-(4-hydroxyphenoxy)-1,3-thiazole-2-carboxamide; N-[(2S,3R)-2-methyl-1-azabicyclo[2.2.2]oct-3-yl]-5-(4-aminophenoxy)-1,3-thiazole-2-carboxamide; N-[(2S,3R)-2-methyl-1-azabicyclo[2.2.2]oct-3-yl]-5-[4-(acetylamino)phenoxy]-1,3-thiazole-2-carboxamide; N-[(2S,3R)-2-methyl-1-azabicyclo[2.2.2]oct-3-yl]-5-(2-fluorophenyl)-4-methyl-1,3-thiazole-2-carboxamide; N-[(2S,3R)-2-methyl-1-azabicyclo[2.2.2]oct-3-yl]-5-(3-fluorophenyl)-4-methyl-1,3-thiazole-2-carboxamide; N-[(2S,3R)-2-methyl-1-azabicyclo[2.2.2]oct-3-yl]-5-(2-chlorophenyl)-4-methyl-1,3-thiazole-2-carboxamide; N-[(2S,3R)-2-methyl-1-azabicyclo[2.2.2]oct-3-yl]-5-(3-chlorophenyl)-4-methyl-1,3-thiazole-2-carboxamide; N-[(2S,3R)-2-methyl-1-azabicyclo[2.2.2]oct-3-yl]-5-(2-methoxyphenyl)-4-methyl-1,3-thiazole-2-carboxamide; N-[(2S,3R)-2-methyl-1-azabicyclo[2.2.2]oct-3-yl]-5-(3-methoxyphenyl)-4-methyl-1,3-thiazole-2-carboxamide; N-[(2S,3R)-2-methyl-1-azabicyclo[2.2.2]oct-3-yl]-4-methyl-5-thien-2-yl-1,3-thiazole-2-carboxamide, N-[(2S,3R)-2-methyl-1-azabicyclo[2.2.2]oct-3-yl]-5-phenyl-1,3-thiazole-2-carboxamide; N-[(2S,3R)-2-methyl-1-azabicyclo[2.2.2]oct-3-yl]-5-phenyl-4-methyl-1,3-thiazole-2-carboxamide; N-[(2S,3R)-2-methyl-1-azabicyclo[2.2.2]oct-3-yl]-5-(2-fluorophenyl)-1,3-thiazole-2-carboxamide; N-[(2S,3R)-2-methyl-1-azabicyclo[2.2.2]oct-3-yl]-5-(3-fluorophenyl)-1,3-thiazole-2-carboxamide; N-[(2S,3R)-2-methyl-1-azabicyclo[2.2.2]oct-3-yl]-5-(4-fluorophenyl)-1,3-thiazole-2-carboxamide; N-[(2S,3R)-2-methyl-1-azabicyclo[2.2.2]oct-3-yl]-5-thien-2-yl-1,3-thiazole-2-carboxamide; N-[(2S,3R)-2-methyl-1-azabicyclo[2.2.2]oct-3-yl]-5-(2-chlorophenyl)-1,3-thiazole-2-carboxamide; N-[(2S,3R)-2-methyl-1-azabicyclo[2.2.2]oct-3-yl]-5-(3-chlorophenyl)-1,3-thiazole-2-carboxamide; N-[(2S,3R)-2-methyl-1-azabicyclo[2.2.2]oct-3-yl]-5-(4-chlorophenyl)-1,3-thiazole-2-carboxamide; N-[(2S,3R)-2-methyl-1-azabicyclo[2.2.2]oct-3-yl]-5-(4-bromophenyl)-1,3-thiazole-2-carboxamide; N-[(2S,3R)-2-methyl-1-azabicyclo[2.2.2]oct-3-yl]-5-(3-nitrophenyl)-1,3-thiazole-2-carboxamide; N-[(2S,3R)-2-methyl-1-azabicyclo[2.2.2]oct-3-yl]-5-(2-methoxyphenyl)-1,3-thiazole-2-carboxamide; N-[(2S,3R)-2-methyl-1-azabicyclo[2.2.2]oct-3-yl]-5-(3-methoxyphenyl)-1,3-thiazole-2-carboxamide; N-[(2S,3R)-2-methyl-1-azabicyclo[2.2.2]oct-3-yl]-5-(4-methoxyphenyl)-1,3-thiazole-2-carboxamide; N-[(2S,3R)-2-methyl-1-azabicyclo[2.2.2]oct-3-yl]-2-(2-hydroxyphenyl)-1,3-thiazole-5-carboxamide; N-[(2S,3R)-2-methyl-1-azabicyclo[2.2.2]oct-3-yl]-2-(4-methylphenyl)-1,3-thiazole-5-carboxamide; N-[(2S,3R)-2-methyl-1-azabicyclo[2.2.2]oct-3-yl]-2-phenyl-1,3-thiazole-5-carboxamide; N-[(2S,3R)-2-methyl-1-azabicyclo[2.2.2]oct-3-yl]-2-(2-fluorophenyl)-1,3-thiazole-5-carboxamide; N-[(2S,3R)-2-methyl-1-azabicyclo[2.2.2]oct-3-yl]-2-(3-fluorophenyl)-1,3-thiazole-5-carboxamide; N-[(2S,3R)-2-methyl-1-azabicyclo[2.2.2]oct-3-yl]-2-(4-fluorophenyl)-1,3-thiazole-5-carboxamide;
N-[(3R)-1-azabicyclo[2.2.2]oct-3-yl]-5-phenylsulfanyl-1,3-oxazole-2-carboxamide; N-[(3R)-1-azabicyclo

[2.2.2]oct-3-yl]-5-(2-fluorophenylsulfanyl)-1,3-oxazole-2-carboxamide; N-[(3R)-1-azabicyclo[2.2.2]oct-3-yl]-5-(3-fluorophenylsulfanyl)-1,3-oxazole-2-carboxamide; N-[(3R)-1-azabicyclo[2.2.2]oct-3-yl]-5-(4-fluorophenylsulfanyl)-1,3-oxazole-2-carboxamide; N-[(3R)-1-azabicyclo[2.2.2]oct-3-yl]-5-(3,4-difluorophenylsulfanyl)-1,3-oxazole-2-carboxamide; N-[(3R)-1-azabicyclo[2.2.2]oct-3-yl]-5-(2,4-difluorophenylsulfanyl)-1,3-oxazole-2-carboxamide; N-[(3R)-1-azabicyclo[2.2.2]oct-3-yl]-5-(3,5-difluorophenylsulfanyl)-1,3-oxazole-2-carboxamide; N-[(3R)-1-azabicyclo[2.2.2]oct-3-yl]-5-(2-chlorophenylsulfanyl)-1,3-oxazole-2-carboxamide; N-[(3R)-1-azabicyclo[2.2.2]oct-3-yl]-5-(3-chlorophenylsulfanyl)-1,3-oxazole-2-carboxamide; N-[(3R)-1-azabicyclo[2.2.2]oct-3-yl]-5-(4-chlorophenylsulfanyl)-1,3-oxazole-2-carboxamide; N-[(3R)-1-azabicyclo[2.2.2]oct-3-yl]-5-(3,4-dichlorophenylsulfanyl)-1,3-oxazole-2-carboxamide; N-[(3R)-1-azabicyclo[2.2.2]oct-3-yl]-5-(2,4-dichlorophenylsulfanyl)-1,3-oxazole-2-carboxamide; N-[(3R)-1-azabicyclo[2.2.2]oct-3-yl]-5-(3,5-dichlorophenylsulfanyl)-1,3-oxazole-2-carboxamide; N-[(3R)-1-azabicyclo[2.2.2]oct-3-yl]-5-(2-fluorophenyl)-1,3-oxazole-2-carboxamide; N-[(3R)-1-azabicyclo[2.2.2]oct-3-yl]-5-(3-fluorophenyl)-1,3-oxazole-2-carboxamide; N-[(3R)-1-azabicyclo[2.2.2]oct-3-yl]-5-(3,4-difluorophenyl)-1,3-oxazole-2-carboxamide; N-[(3R)-1-azabicyclo[2.2.2]oct-3-yl]-5-(2,4-difluorophenyl)-1,3-oxazole-2-carboxamide; N-[(3R)-1-azabicyclo[2.2.2]oct-3-yl]-5-(3,5-difluorophenyl)-1,3-oxazole-2-carboxamide; N-[(3R)-1-azabicyclo[2.2.2]oct-3-yl]-5-(4-chlorophenyl)-1,3-oxazole-2-carboxamide; N-[(3R)-1-azabicyclo[2.2.2]oct-3-yl]-5-(3,4-dichlorophenyl)-1,3-oxazole-2-carboxamide; N-[(3R)-1-azabicyclo[2.2.2]oct-3-yl]-5-(2,4-dichlorophenyl)-1,3-oxazole-2-carboxamide; N-[(3R)-1-azabicyclo[2.2.2]oct-3-yl]-5-(3,5-dichlorophenyl)-1,3-oxazole-2-carboxamide; N-[(3R)-1-azabicyclo[2.2.2]oct-3-yl]-5-(2-bromophenyl)-1,3-oxazole-2-carboxamide; N-[(3R)-1-azabicyclo[2.2.2]oct-3-yl]-5-(3-bromophenyl)-1,3-oxazole-2-carboxamide; N-[(3R)-1-azabicyclo[2.2.2]oct-3-yl]-5-(2-cyanophenyl)-1,3-oxazole-2-carboxamide; N-[(3R)-1-azabicyclo[2.2.2]oct-3-yl]-5-(4-cyanophenyl)-1,3-oxazole-2-carboxamide; N-[(3R)-1-azabicyclo[2.2.2]oct-3-yl]-5-(2-hydroxyphenyl)-1,3-oxazole-2-carboxamide; N-[(3R)-1-azabicyclo[2.2.2]oct-3-yl]-5-(3-hydroxyphenyl)-1,3-oxazole-2-carboxamide; N-[(3R)-1-azabicyclo[2.2.2]oct-3-yl]-5-(4-hydroxyphenyl)-1,3-oxazole-2-carboxamide; N-[(3R)-1-azabicyclo[2.2.2]oct-3-yl]-5-(4-nitrophenyl)-1,3-oxazole-2-carboxamide; N-[(3R)-1-azabicyclo[2.2.2]oct-3-yl]-5-(2-methylphenyl)-1,3-oxazole-2-carboxamide; N-[(3R)-1-azabicyclo[2.2.2]oct-3-yl]-5-(3-methylphenyl)-1,3-oxazole-2-carboxamide; N-[(3R)-1-azabicyclo[2.2.2]oct-3-yl]-5-(4-methylphenyl)-1,3-oxazole-2-carboxamide; N-[(3R)-1-azabicyclo[2.2.2]oct-3-yl]-5-(2-methylaminophenyl)-1,3-oxazole-2-carboxamide; N-[(3R)-1-azabicyclo[2.2.2]oct-3-yl]-5-(3-methylaminophenyl)-1,3-oxazole-2-carboxamide; N-[(3R)-1-azabicyclo[2.2.2]oct-3-yl]-5-(4-methylaminophenyl)-1,3-oxazole-2-carboxamide; N-[(3R)-1-azabicyclo[2.2.2]oct-3-yl]-5-(2-aminophenyl)-1,3-oxazole-2-carboxamide; N-[(3R)-1-azabicyclo[2.2.2]oct-3-yl]-5-(3-aminophenyl)-1,3-oxazole-2-carboxamide; N-[(3R)-1-azabicyclo[2.2.2]oct-3-yl]-5-(4-aminophenyl)-1,3-oxazole-2-carboxamide; N-[(3R)-1-azabicyclo[2.2.2]oct-3-yl]-5-[2-(acetylamino)phenyl]-1,3-oxazole-2-carboxamide; N-[(3R)-1-azabicyclo[2.2.2]oct-3-yl]-5-[3-(acetylamino)phenyl]-1,3-oxazole-2-carboxamide; N-[(3R)-1-azabicyclo[2.2.2]oct-3-yl]-5-[4-(acetylamino)phenyl]-1,3-oxazole-2-carboxamide; N-[(3R)-1-azabicyclo[2.2.2]oct-3-yl]-5-(pyridin-2-yl)-1,3-oxazole-2-carboxamide; N-[(3R)-1-azabicyclo[2.2.2]oct-3-yl]-5-(pyridin-3-yl)-1,3-oxazole-2-carboxamide; N-[(3R)-1-azabicyclo[2.2.2]oct-3-yl]-5-(pyridin-4-yl)-1,3-oxazole-2-carboxamide; N-[(3R)-1-azabicyclo[2.2.2]oct-3-yl]-5-(3-fluoropyridin-2-yl)-1,3-oxazole-2-carboxamide; N-[(3R)-1-azabicyclo[2.2.2]oct-3-yl]-5-(4-fluoropyridin-2-yl)-1,3-oxazole-2-carboxamide; N-[(3R)-1-azabicyclo[2.2.2]oct-3-yl]-5-(5-fluoropyridin-2-yl)-1,3-oxazole-2-carboxamide; N-[(3R)-1-azabicyclo[2.2.2]oct-3-yl]-5-(6-fluoropyridin-2-yl)-1,3-oxazole-2-carboxamide; N-[(3R)-1-azabicyclo[2.2.2]oct-3-yl]-5-(2-fluoropyridin-3-yl)-1,3-oxazole-2-carboxamide; N-[(3R)-1-azabicyclo[2.2.2]oct-3-yl]-5-(4-fluoropyridin-3-yl)-1,3-oxazole-2-carboxamide; N-[(3R)-1-azabicyclo[2.2.2]oct-3-yl]-5-(5-fluoropyridin-3-yl)-1,3-oxazole-2-carboxamide; N-[(3R)-1-azabicyclo[2.2.2]oct-3-yl]-5-(6-fluoropyridin-3-yl)-1,3-oxazole-2-carboxamide; N-[(3R)-1-azabicyclo[2.2.2]oct-3-yl]-5-(2-fluoropyridin-4-yl)-1,3-oxazole-2-carboxamide; N-[(3R)-1-azabicyclo[2.2.2]oct-3-yl]-5-(2-fluoropyridin-3-yl)-1,3-oxazole-2-carboxamide; N-[(3R)-1-azabicyclo[2.2.2]oct-3-yl]-5-phenoxy-1,3-oxazole-2-carboxamide; N-[(3R)-1-azabicyclo[2.2.2]oct-3-yl]-5-(2-fluorophenoxy)-1,3-oxazole-2-carboxamide; N-[(3R)-1-azabicyclo[2.2.2]oct-3-yl]-5-(3-fluorophenoxy)-1,3-oxazole-2-carboxamide; N-[(3R)-1-azabicyclo[2.2.2]oct-3-yl]-5-(4-fluorophenoxy)-1,3-oxazole-2-carboxamide; N-[(3R)-1-azabicyclo[2.2.2]oct-3-yl]-5-(3,4-difluorophenoxy)-1,3-oxazole-2-carboxamide; N-[(3R)-1-azabicyclo[2.2.2]oct-3-yl]-5-(2,4-difluorophenoxy)-1,3-oxazole-2-carboxamide; N-[(3R)-1-azabicyclo[2.2.2]oct-3-yl]-5-(3,5-difluorophenoxy)-1,3-oxazole-2-carboxamide; N-[(3R)-1-azabicyclo[2.2.2]oct-3-yl]-5-(2-chlorophenoxy)-1,3-oxazole-2-carboxamide; N-[(3R)-1-azabicyclo[2.2.2]oct-3-yl]-5-(3-chlorophenoxy)-1,3-oxazole-2-carboxamide; N-[(3R)-1-azabicyclo[2.2.2]oct-3-yl]-5-(4-chlorophenoxy)-1,3-oxazole-2-carboxamide; N-[(3R)-1-azabicyclo[2.2.2]oct-3-yl]-5-(3,4-dichlorophenoxy)-1,3-oxazole-2-carboxamide; N-[(3R)-1-azabicyclo[2.2.2]oct-3-yl]-5-(2,4-dichlorophenoxy)-1,3-oxazole-2-carboxamide; N-[(3R)-1-azabicyclo[2.2.2]oct-3-yl]-5-(3,5-dichlorophenoxy)-1,3-oxazole-2-carboxamide;

N-[(2S,3R)-2-methyl-1-azabicyclo[2.2.2]oct-3-yl]-5-phenylsulfanyl-1,3-oxazole-2-carboxamide; N-[(2S,3R)-2-methyl-1-azabicyclo[2.2.2]oct-3-yl]-5-(2-fluorophenylsulfanyl)-1,3-oxazole-2-carboxamide; N-[(2S,3R)-2-methyl-1-azabicyclo[2.2.2]oct-3-yl]-5-(3-fluorophenylsulfanyl)-1,3-oxazole-2-carboxamide; N-[(2S,3R)-2-methyl-1-azabicyclo[2.2.2]oct-3-yl]-5-(4-fluorophenylsulfanyl)-1,3-oxazole-2-carboxamide; N-[(2S,3R)-2-methyl-1-azabicyclo[2.2.2]oct-3-yl]-5-(3,4-difluorophenylsulfanyl)-1,3-oxazole-2-carboxamide; N-[(2S,3R)-2-methyl-1-azabicyclo[2.2.2]oct-3-yl]-5-(2,4-difluorophenylsulfanyl)-1,3- oxazole-2-carboxamide; N-[(2S,3R)-2-methyl-1-azabicyclo[2.2.2]oct-3-yl]-5-(3,5-difluorophenylsulfanyl)-1,3-oxazole-2-carboxamide; N-[(2S,3R)-2-methyl-1-azabicyclo[2.2.2]oct-3-yl]-5-(2-chlorophenylsulfanyl)-1,3-oxazole-2-carboxamide; N-[(2S,3R)-2-methyl-1-azabicyclo[2.2.2]oct-3-yl]-5-(3-chlorophenylsulfanyl)-1,3-oxazole-2-carboxamide; N-[(2S,3R)-2-methyl-1-azabicyclo[2.2.2]oct-3-yl]-5-(4-chlorophenylsulfanyl)-1,3-oxazole-2-carboxamide; N-[(2S,3R)-2-methyl-1-azabicyclo[2.2.2]oct-3-yl]-5-(3,4-dichlorophenylsulfanyl)-1,3-oxazole-2-carboxamide; N-[(2S,3R)-2-methyl-1-azabicyclo[2.2.2]oct-3-yl]-5-(2,4-dichlorophenylsulfanyl)-1,3-oxazole-2-carboxamide; N-[(2S,3R)-2-methyl-1-azabicyclo[2.2.2]oct-3-yl]-5-(3,5-dichlorophenylsulfanyl)-1,3-oxazole-2-carboxamide; N-[(2S,3R)-2-methyl-1-azabicyclo[2.2.2]oct-3-yl]5-(2-fluorophenyl)-1,3-oxazole-2-carboxamide; N-[(2S,3R)-2-methyl-1-azabicyclo[2.2.2]oct-3-yl]-5-(3-fluorophenyl)-1,3-oxazole-2-carboxamide; N-[(2S,3R)-2-methyl-1-azabicyclo[2.2.2]oct-3-yl]-5-(3,4-difluorophenyl)-1,3-oxazole-2-carboxamide; N-[(2S,3R)-2-methyl-1-azabicyclo[2.2.2]oct-3-yl]-5-(2,4-difluorophenyl)-1,3-oxazole-2-carboxamide; N-[(2S,3R)-2-methyl-1-azabicyclo[2.2.2]oct-3-yl]-5-(3,5-difluorophenyl)-1,3-oxazole-2-carboxamide; N-[(2S,3R)-2-methyl-1-azabicyclo[2.2.2]oct-3-yl]-5-(4-chlorophenyl)-1,3-oxazole-2-carboxamide; N-[(2S,3R)-2-methyl-1-azabicyclo[2.2.2]oct-3-yl]-5-(3,4-dichlorophenyl)-1,3-oxazole-2-carboxamide; N-[(2S,3R)-2-methyl-1-azabicyclo[2.2.2]oct-3-yl]-5-(2,4-dichlorophenyl)-1,3-oxazole-2-carboxamide; N-[(2S,3R)-2-methyl-1-azabicyclo[2.2.2]oct-3-yl]-5-(3,5-dichlorophenyl)-1,3-oxazole-2-carboxamide; N-[(2S,3R)-2-methyl-1-azabicyclo[2.2.2]oct-3-yl]-5-(2-bromophenyl)-1,3-oxazole-2-carboxamide; N-[(2S,3R)-2-methyl-1-azabicyclo[2.2.2]oct-3-yl]-5-(3-bromophenyl)-1,3-oxazole-2-carboxamide; N-[(2S,3R)-2-methyl-1-azabicyclo[2.2.2]oct-3-yl]-5-(2-cyanophenyl)-1,3-oxazole-2-carboxamide; N-[(2S,3R)-2-methyl-1-azabicyclo[2.2.2]oct-3-yl]-5-(4-cyanophenyl)-1,3-oxazole-2-carboxamide; N-[(2S,3R)-2-methyl-1-azabicyclo[2.2.2]oct-3-yl]-5-(2-hydroxyphenyl)-1,3-oxazole-2-carboxamide; N-[(2S,3R)-2-methyl-1-azabicyclo[2.2.2]oct-3-yl]-5-(3-hydroxyphenyl)-1,3-oxazole-2-carboxamide; N-[(2S,3R)-2-methyl-1-azabicyclo[2.2.2]oct-3-yl]-5-(4-hydroxyphenyl)-1,3-oxazole-2-carboxamide; N-[(2S,3R)-2-methyl-1-azabicyclo[2.2.2]oct-3-yl]-5-(4-nitrophenyl)-1,3-oxazole-2-carboxamide; N-[(2S,3R)-2-methyl-1-azabicyclo[2.2.2]oct-3-yl]-5-(2-methylphenyl)-1,3-oxazole-2-carboxamide; N-[(2S,3R)-2-methyl-1-azabicyclo[2.2.2]oct-3-yl]-5-(3-methylphenyl)-1,3-oxazole-2-carboxamide; N-[(2S,3R)-2-methyl-1-azabicyclo[2.2.2]oct-3-yl]-5-(4-methylphenyl)-1,3-oxazole-2-carboxamide; N-[(2S,3R)-2-methyl-1-azabicyclo[2.2.2]oct-3-yl]-5-(2-methylaminophenyl)-1,3-oxazole-2-carboxamide; N-[(2S,3R)-2-methyl-1-azabicyclo[2.2.2]oct-3-yl]-5-(3-methylaminophenyl)-1,3-oxazole-2-carboxamide; N-[(2S,3R)-2-methyl-1-azabicyclo[2.2.2]oct-3-yl]-5-(4-methylaminophenyl)-1,3-oxazole-2-carboxamide; N-[(2S,3R)-2-methyl-1-azabicyclo[2.2.2]oct-3-yl]-5-(2-aminophenyl)-1,3-oxazole-2-carboxamide; N-[(2S,3R)-2-methyl-1-azabicyclo[2.2.2]oct-3-yl]-5-(3-aminophenyl)-1,3-oxazole-2-carboxamide; N-[(2S,3R)-2-methyl-1-azabicyclo[2.2.2]oct-3-yl]-5-(4-aminophenyl)-1,3-oxazole-2-carboxamide; N-[(2S,3R)-2-methyl-1-azabicyclo[2.2.2]oct-3-yl]-5-[2-(acetylamino)phenyl]-1,3-oxazole-2-carboxamide; N-[(2S,3R)-2-methyl-1-azabicyclo[2.2.2]oct-3-yl]-5-[3-(acetylamino)phenyl]-1,3-oxazole-2-carboxamide; N-[(2S,3R)-2-methyl-1-azabicyclo[2.2.2]oct-3-yl]-5-[4-(acetylamino)phenyl]-1,3-oxazole-2-carboxamide; N-[(2S,3R)-2-methyl-1-azabicyclo[2.2.2]oct-3-yl]-5-(pyridin-2-yl)-1,3-oxazole-2-carboxamide; N-[(2S,3R)-2-methyl-1-azabicyclo[2.2.2]oct-3-yl]-5-(pyridin-3-yl)-1,3-oxazole-2-carboxamide; N-[(2S,3R)-2-methyl-1-azabicyclo[2.2.2]oct-3-yl]-5-(pyridin-4-yl)-1,3-oxazole-2-carboxamide; N-[(2S,3R)-2-methyl-1-azabicyclo[2.2.2]oct-3-yl]-5-(3-fluoropyridin-2-yl)-1,3-oxazole-2-carboxamide; N-[(2S,3R)-2-methyl-1-azabicyclo[2.2.2]oct-3-yl]-5-(4-fluoropyridin-2-yl)-1,3-oxazole-2-carboxamide; N-[(2S,3R)-2-methyl-1-azabicyclo[2.2.2]oct-3-yl]-5-(5-fluoropyridin-2-yl)-1,3-oxazole-2-carboxamide; N-[(2S,3R)-2-methyl-1-azabicyclo[2.2.2]oct-3-yl]-5-(6-fluoropyridin-2-yl)-1,3-oxazole-2-carboxamide; N-[(2S,3R)-2-methyl-1-azabicyclo[2.2.2]oct-3-yl]-5-(2-fluoropyridin-3-yl)-1,3-oxazole-2-carboxamide; N-[(2S,3R)-2-methyl-1-azabicyclo[2.2.2]oct-3-yl]-5-(4-fluoropyridin-3-yl)-1,3-oxazole-2-carboxamide; N-[(2S,3R)-2-methyl-1-azabicyclo[2.2.2]oct-3-yl]-5-(5-fluoropyridin-3-yl)-1,3-oxazole-2-carboxamide; N-[(2S,3R)-2-methyl-1-azabicyclo[2.2.2]oct-3-yl]-5-(6-fluoropyridin-3-yl)-1,3-oxazole-2-carboxamide; N-[(2S,3R)-2-methyl-1-azabicyclo[2.2.2]oct-3-yl]-5-(2-fluoropyridin-4-yl)-1,3-oxazole-2-carboxamide; N-[(2S,3R)-2-methyl-1-azabicyclo[2.2.2]oct-3-yl]-5-(2-fluoropyridin-3-yl)-1,3-oxazole-2-carboxamide; N-[(2S,3R)-2-methyl-1-azabicyclo[2.2.2]oct-3-yl]-5-phenoxy-1,3-oxazole-2-carboxamide; N-[(2S,3R)-2-methyl-1-azabicyclo[2.2.2]oct-3-yl]-5-(2-fluorophenoxy)-1,3-oxazole-2-carboxamide; N-[(2S,3R)-2-methyl-1-azabicyclo[2.2.2]oct-3-yl]-5-(3-fluorophenoxy)-1,3-oxazole-2-carboxamide; N-[(2S,3R)-2-methyl-1-azabicyclo[2.2.2]oct-3-yl]-5-(4-fluorophenoxy)-1,3-oxazole-2-carboxamide; N-[(2S,3R)-2-methyl-1-azabicyclo[2.2.2]oct-3-yl]-5-(3,4-difluorophenoxy)-1,3-oxazole-2-carboxamide; N-[(2S,3R)-2-methyl-1-azabicyclo[2.2.2]oct-3-yl]-5-(2,4-difluorophenoxy)-1,3-oxazole-2-carboxamide; N-[(2S,3R)-2-methyl-1-azabicyclo[2.2.2]oct-3-yl]-5-(3,5-difluorophenoxy)-1,3-oxazole-2-carboxamide; N-[(2S,3R)-2-methyl-1-azabicyclo[2.2.2]oct-3-yl]-5-(2-chlorophenoxy)-1,3-oxazole-2-carboxamide; N-[(2S,3R)-2-methyl-1-azabicyclo[2.2.2]oct-3-yl]-5-(3-chlorophenoxy)-1,3-oxazole-2-carboxamide; N-[(2S,3R)-2-methyl-1-azabicyclo[2.2.2]oct-3-yl]-5-(4-chlorophenoxy)-1,3-oxazole-2-carboxamide; N-[(2S,3R)-2-methyl-1-azabicyclo[2.2.2]oct-3-yl]-5-(3,4-dichlorophenoxy)-1,3-oxazole-2-carboxamide; N-[(2S,3R)-2-methyl-1-azabicyclo[2.2.2]oct-3-yl]-5-(2,4-dichlorophenoxy)-1,3-oxazole-2-carboxamide; N-[(2S,3R)-2-methyl-1-azabicyclo[2.2.2]oct-3-yl]-5-(3,5-dichlorophenoxy)-1,3-oxazole-2-carboxamide;

N-[(3R)-1-azabicyclo[2.2.2]oct-3-yl]-5-bromo-1-methyl-1H-pyrrole-2-carboxamide; N-[(3R)-1-azabicyclo[2.2.2]oct-3-yl]-5-[2-(methylthio)phenyl]-1-methyl-1H-pyrrole-2-carboxamide; N-[(3R)-1-azabicyclo[2.2.2]oct-3-yl]-5-[4-(methylthio)phenyl]-1-methyl-1H-pyrrole-2-carboxamide; N-[(3R)-1-azabicyclo[2.2.2]oct-3-yl]-5-phenyl-1H-pyrrole-2-carboxamide; N-[(3R)-1-azabicyclo[2.2.2]oct-3-yl]-5-(2- fluorophenyl)-1-methyl-1H-pyrrole-2-carboxamide;
N-[(3R)-1-azabicyclo[2.2.2]oct-3-yl]-5-(3-fluorophenyl)-1-methyl-1H-pyrrole-2-carboxamide;
N-[(3R)-1-azabicyclo[2.2.2]oct-3-yl]-5-(4-fluorophenyl)-1-methyl-1H-pyrrole-2-carboxamide;
N-[(3R)-1-azabicyclo[2.2.2]oct-3-yl]-5-(2,3-difluorophenyl)-1-methyl-1H-pyrrole-2-carboxamide;
N-[(3R)-1-azabicyclo[2.2.2]oct-3-yl]-5-(2,4-difluorophenyl)-1-methyl-1H-pyrrole-2-carboxamide;
N-[(3R)-1-azabicyclo[2.2.2]oct-3-yl]-5-(2,6-difluorophenyl)-1-methyl-1H-pyrrole-2-carboxamide;
N-[(3R)-1-azabicyclo[2.2.2]oct-3-yl]-5-(3,4-difluorophenyl)-1-methyl-1H-pyrrole-2-carboxamide;
N-[(3R)-1-azabicyclo[2.2.2]oct-3-yl]-5-(3,5-difluorophenyl)-1-methyl-1H-pyrrole-2-carboxamide;
N-[(3R)-1-azabicyclo[2.2.2]oct-3-yl]-5-(2,4,6-trifluorophenyl)-1-methyl-1H-pyrrole-2-carboxamide;
N-[(3R)-1-azabicyclo[2.2.2]oct-3-yl]-5-(2-chlorophenyl)-1-methyl-1H-pyrrole-2-carboxamide;
N-[(3R)-1-azabicyclo[2.2.2]oct-3-yl]-5-(3-chlorophenyl)-1-methyl-1H-pyrrole-2-carboxamide;
N-[(3R)-1-azabicyclo[2.2.2]oct-3-yl]-5-(4-chlorophenyl)-1-methyl-1H-pyrrole-2-carboxamide;
N-[(3R)-1-azabicyclo[2.2.2]oct-3-yl]-5-(2,4-dichlorophenyl)-1-methyl-1H-pyrrole-2-carboxamide;
N-[(3R)-1-azabicyclo[2.2.2]oct-3-yl]-5-(3,4-dichlorophenyl)-1-methyl-1H-pyrrole-2-carboxamide;
N-[(3R)-1-azabicyclo[2.2.2]oct-3-yl]-5-(3,5-dichlorophenyl)-1-methyl-1H-pyrrole-2-carboxamide;
N-[(3R)-1-azabicyclo[2.2.2]oct-3-yl]-5-(2-bromophenyl)-1-methyl-1H-pyrrole-2-carboxamide;
N-[(3R)-1-azabicyclo[2.2.2]oct-3-yl]-5-(3-bromophenyl) 1-methyl-1H-pyrrole-2-carboxamide;
N-[(3R)-1-azabicyclo[2.2.2]oct-3-yl]-5-(4-bromophenyl)-1-methyl-1H-pyrrole-2-carboxamide;
N-[(3R)-1-azabicyclo[2.2.2]oct-3-yl]-5-(2-hydroxyphenyl)-1-methyl-1H-pyrrole-2-carboxamide;
N-[(3R)-1-azabicyclo[2.2.2]oct-3-yl]-5-(3-hydroxyphenyl)-1-methyl-1H-pyrrole-2-carboxamide;
N-[(3R)-1-azabicyclo[2.2.2]oct-3-yl]-5-(4-hydroxyphenyl)-1-methyl-1H-pyrrole-2-carboxamide;
N-[(3R)-1-azabicyclo[2.2.2]oct-3-yl]-5-(2-methoxyphenyl)-1-methyl-1H-pyrrole-2-carboxamide;
N-[(3R)-1-azabicyclo[2.2.2]oct-3-yl]-5-(3-methoxyphenyl)-1-methyl-1H-pyrrole-2-carboxamide;
N-[(3R)-1-azabicyclo[2.2.2]oct-3-yl]-5-(4-methoxyphenyl)-1-methyl-1H-pyrrole-2-carboxamide;
N-[(3R)-1-azabicyclo[2.2.2]oct-3-yl]-5-(2-methylphenyl)-1-methyl-1H-pyrrole-2-carboxamide;
N-[(3R)-1-azabicyclo[2.2.2]oct-3-yl]-5-(3-methylphenyl)-1-methyl-1H-pyrrole-2-carboxamide;
N-[(3R)-1-azabicyclo[2.2.2]oct-3-yl]-5-(4-methylphenyl)-1-methyl-1H-pyrrole-2-carboxamide;
N-[(3R)-1-azabicyclo[2.2.2]oct-3-yl]-5-(2-methylaminophenyl)-1-methyl-1H-pyrrole-2-carboxamide;
N-[(3R)-1-azabicyclo[2.2.2]oct-3-yl]-5-(3-methylaminophenyl)-1-methyl-1H-pyrrole-2-carboxamide;
N-[(3R)-1-azabicyclo[2.2.2]oct-3-yl]-5-(4-methylaminophenyl)-1-methyl-1H-pyrrole-2-carboxamide;
N-[(3R)-1-azabicyclo[2.2.2]oct-3-yl]-5-(2-nitrophenyl)-1-methyl-1H-pyrrole-2-carboxamide;
N-[(3R)-1-azabicyclo[2.2.2]oct-3-yl]-5-(3-nitrophenyl)-1-methyl-1H-pyrrole-2-carboxamide;
N-[(3R)-1-azabicyclo[2.2.2]oct-3-yl]-5-(4-nitrophenyl)-1-methyl-1H-pyrrole-2-carboxamide;
N-[(3R)-1-azabicyclo[2.2.2]oct-3-yl]-5-(2-aminophenyl)-1-methyl-1H-pyrrole-2-carboxamide;
N-[(3R)-1-azabicyclo[2.2.2]oct-3-yl]-5-(3-aminophenyl)-1-methyl-1H-pyrrole-2-carboxamide;
N-[(3R)-1-azabicyclo[2.2.2]oct-3-yl]-5-(4-aminophenyl)-1-methyl-1H-pyrrole-2-carboxamide;
N-[(3R)-1-azabicyclo[2.2.2]oct-3-yl]-5-[2-(acetylamino)phenyl]-1-methyl-1H-pyrrole-2-carboxamide;
N-[(3R)-1-azabicyclo[2.2.2]oct-3-yl]-5-[3-(acetylamino)phenyl]-1-methyl-1H-pyrrole-2-carboxamide;
N-[(3R)-1-azabicyclo[2.2.2]oct-3-yl]-5-[4-(acetylamino)phenyl]-1-methyl-1H-pyrrole-2-carboxamide;
N-[(3R)-1-azabicyclo[2.2.2]oct-3-yl]-5-(pyrid-2-yl)-1-methyl-1H-pyrrole-2-carboxamide;
N-[(3R)-1-azabicyclo[2.2.2]oct-3-yl]-5-(pyrid-3-yl)-1-methyl-1H-pyrrole-2-carboxamide;
N-[(3R)-1-azabicyclo[2.2.2]oct-3-yl]-5-(pyridin-4-yl)-1-methyl-1H-pyrrole-2-carboxamide;
N-[(3R)-1-azabicyclo[2.2.2]oct-3-yl]-5-(3-fluoropyrid-2-yl)-1-methyl-1H-pyrrole-2-carboxamide;
N-[(3R)-1-azabicyclo[2.2.2]oct-3-yl]-5-(4-fluoropyrid-2-yl)-1-methyl-1H-pyrrole-2-carboxamide;
N-[(3R)-1-azabicyclo[2.2.2]oct-3-yl]-5-(5-fluoropyrid-2-yl)-1-methyl-1H-pyrrole-2-carboxamide;
N-[(3R)-1-azabicyclo[2.2.2]oct-3-yl]-5-(6-fluoropyrid-2-yl)-1-methyl-1H-pyrrole-2-carboxamide;
N-[(3R)-1-azabicyclo[2.2.2]oct-3-yl]-5-(2-fluoropyrid-3-yl)-1-methyl-1H-pyrrole-2-carboxamide;
N-[(3R)-1-azabicyclo[2.2.2]oct-3-yl]-5-(4-fluoropyrid-3-yl)-1-methyl-1H-pyrrole-2-carboxamide;
N-[(3R)-1-azabicyclo[2.2.2]oct-3-yl]-5-(5-fluoropyrid-3-yl)-1-methyl-1H-pyrrole-2-carboxamide;
N-[(3R)-1-azabicyclo[2.2.2]oct-3-yl]-5-(6-fluoropyrid-3-yl)-1-methyl-1H-pyrrole-2-carboxamide;
N-[(3R)-1-azabicyclo[2.2.2]oct-3-yl]-5-(2-fluoropyrid-4-yl)-1-methyl-1H-pyrrole-2-carboxamide;
N-[(3R)-1-azabicyclo[2.2.2]oct-3-yl]-5-(3-fluoropyrid-4-yl)-1-methyl-1H-pyrrole-2-carboxamide;
N-[(3R)-1-azabicyclo[2.2.2]oct-3-yl]-5-(2-cyanophenyl)-1-methyl-1H-pyrrole-2-carboxamide;
N-[(3R)-1-azabicyclo[2.2.2]oct-3-yl]-5-(3-cyanophenyl)-1-methyl-1H-pyrrole-2-carboxamide;
N-[(3R)-1-azabicyclo[2.2.2]oct-3-yl]-5-(4-cyanophenyl)-1-methyl-1H-pyrrole-2-carboxamide;
N-[(3R)-1-azabicyclo[2.2.2]oct-3-yl]-5-(2-fluorophenyl)-1H-pyrrole-2-carboxamide;
N-[(3R)-1-azabicyclo[2.2.2]oct-3-yl]-5-(3-fluorophenyl)-1H-pyrrole-2-carboxamide;
N-[(3R)-1-azabicyclo[2.2.2]oct-3-yl]-5-(4-fluorophenyl)-1H-pyrrole-2-carboxamide;
N-[(3R)-1-azabicyclo[2.2.2]oct-3-yl]-5-(3,5-difluorophenyl)-1H-pyrrole-2-carboxamide;
N-[(3R)-1-azabicyclo[2.2.2]oct-3-yl]-5-(3,4-difluorophenyl)-1H-pyrrole-2-carboxamide;
N-[(3R)-1-azabicyclo[2.2.2]oct-3-yl]-5-(2,4-difluorophenyl)-1H-pyrrole-2-carboxamide;
N-[(3R)-1-azabicyclo[2.2.2]oct-3-yl]-5-(2-chlorophenyl)-1H-pyrrole-2-carboxamide;
N-[(3R)-1-azabicyclo[2.2.2]oct-3-yl]-5-(3-chlorophenyl)-1H-pyrrole-2-carboxamide;
N-[(3R)-1-azabicyclo[2.2.2]oct-3-yl]-5-(4-chlorophenyl)-1H-pyrrole-2-carboxamide;
N-[(3R)-1-azabicyclo[2.2.2]oct-3-yl]-5-(3,5-dichlorophenyl)-1H-pyrrole-2-carboxamide;
N-[(3R)-1-azabicyclo[2.2.2]oct-3-yl]-5-(3,4-dichlorophenyl)-1H-pyrrole-2-carboxamide;
N-[(3R)-1-azabicyclo[2.2.2]oct-3-yl]-5-(2,4-dichlorophenyl)-1H-pyrrole-2-carboxamide;
N-[(3R)-1-azabicyclo[2.2.2]oct-3-yl]-5-(2-bromophenyl)-1H-pyrrole-2-carboxamide;
N-[(3R)-1-azabicyclo[2.2.2]oct-3-yl]-5-(3-bromophenyl)-1H-pyrrole-2-carboxamide;
N-[(3R)-1-azabicyclo[2.2.2]oct-3-yl]-5-(4-bromophenyl)-1H-pyrrole-2-carboxamide; N-[(3R)-

1-azabicyclo[2.2.2]oct-3-yl]-5-(2-hydroxyphenyl)-1H-pyrrole-2-carboxamide; N-[(3R)-1-azabicyclo[2.2.2]oct-3-yl]-5-(3-hydroxyphenyl)-1H-pyrrole-2-carboxamide; N-[(3R)-1-azabicyclo[2.2.2]oct-3-yl]-5-(4-hydroxyphenyl)-1H-pyrrole-2-carboxamide; N-[(3R)-1-azabicyclo[2.2.2]oct-3-yl]-5-(2-methoxyphenyl)-1H-pyrrole-2-carboxamide; N-[(3R)-1-azabicyclo[2.2.2]oct-3-yl]-5-(3-methoxyphenyl)-1H-pyrrole-2-carboxamide; N-[(3R)-1-azabicyclo[2.2.2]oct-3-yl]-5-(4-methoxyphenyl)-1H-pyrrole-2-carboxamide; N-[(3R)-1-azabicyclo[2.2.2]oct-3-yl]-5-(2-methylphenyl)-1H-pyrrole-2-carboxamide; N-[(3R)-1-azabicyclo[2.2.2]oct-3-yl]-5-(3-methylphenyl)-1H-pyrrole-2-carboxamide; N-[(3R)-1-azabicyclo[2.2.2]oct-3-yl]-5-(4-methylphenyl)-1H-pyrrole-2-carboxamide; N-[(3R)-1-azabicyclo[2.2.2]oct-3-yl]-5-(2-methylaminophenyl)-1H-pyrrole-2-carboxamide; N-[(3R)-1-azabicyclo[2.2.2]oct-3-yl]-5-(3-methylaminophenyl)-1H-pyrrole-2-carboxamide; N-[(3R)-1-azabicyclo[2.2.2]oct-3-yl]-5-(4-methylaminophenyl)-1H-pyrrole-2-carboxamide; N-[(3R)-1-azabicyclo[2.2.2]oct-3-yl]-5-(2-nitrophenyl)-1H-pyrrole-2-carboxamide; N-[(3R)-1-azabicyclo[2.2.2]oct-3-yl]-5-(3-nitrophenyl)-1H-pyrrole-2-carboxamide; N-[(3R)-1-azabicyclo[2.2.2]oct-3-yl]-5-(4-nitrophenyl)-1H-pyrrole-2-carboxamide; N-[(3R)-1-azabicyclo[2.2.2]oct-3-yl]-5-(2-aminophenyl)-1H-pyrrole-2-carboxamide; N-[(3R)-1-azabicyclo[2.2.2]oct-3-yl]-5-(3-aminophenyl)-1H-pyrrole-2-carboxamide; N-[(3R)-1-azabicyclo[2.2.2]oct-3-yl]-5-(4-aminophenyl)-1H-pyrrole-2-carboxamide; N-[(3R)-1-azabicyclo [2.2.2]oct-3-yl]-5-[2-(acetylamino)phenyl]-1H-pyrrole-2-carboxamide; N-[(3R)-1-azabicyclo[2.2.2]oct-3-yl]-5-[3-(acetylamino)phenyl]-1H-pyrrole-2-carboxamide; N-[(3R)-1-azabicyclo[2.2.2]oct-3-yl]-5-[4-(acetylamino)phenyl]-1H-pyrrole-2-carboxamide; N-[(3R)-1-azabicyclo[2.2.2]oct-3-yl]-5-(pyrid-2-yl)-1H-pyrrole-2-carboxamide; N-[(3R)-1-azabicyclo[2.2.2]oct-3-yl]-5-(pyrid-3-yl)-1H-pyrrole-2-carboxamide; N-[(3R)-1-azabicyclo[2.2.2]oct-3-yl]-5-(pyrid-4-yl)-1H-pyrrole-2-carboxamide; N-[(3R)-1-azabicyclo[2.2.2]oct-3-yl]-5-(3-fluoropyrid-2-yl)-1H-pyrrole-2-carboxamide; N-[(3R)-1-azabicyclo[2.2.2]oct-3-yl]-5-(4-fluoropyrid-2-yl)-1H-pyrrole-2-carboxamide; N-[(3R)-1-azabicyclo[2.2.2]oct-3-yl]-5-(5-fluoropyrid-2-yl)-1H-pyrrole-2-carboxamide; N-[(3R)-1-azabicyclo[2.2.2]oct-3-yl]-5-(6-fluoropyrid-2-yl)-1H-pyrrole-2-carboxamide; N-[(3R)-1-azabicyclo[2.2.2]oct-3-yl]-5-(2-fluoropyrid-3-yl)-1H-pyrrole-2-carboxamide; N-[(3R)-1-azabicyclo[2.2.2]oct-3-yl]-5-(4-fluoropyrid-3-yl)-1H-pyrrole-2-carboxamide; N-[(3R)-1-azabicyclo[2.2.2]oct-3-yl]-5-(5-fluoropyrid-3-yl)-1H-pyrrole-2-carboxamide; N-[(3R)-1-azabicyclo[2.2.2]oct-3-yl]-5-(6-fluoropyrid-3-yl)-1H-pyrrole-2-carboxamide; N-[(3R)-1-azabicyclo[2.2.2]oct-3-yl]-5-(2-fluoropyrid-4-yl)-1H-pyrrole-2-carboxamide; N-[(3R)-1-azabicyclo[2.2.2]oct-3-yl]-5-(3-fluoropyrid-4-yl)-1H-pyrrole-2-carboxamide; N-[(3R)-1-azabicyclo[2.2.2]oct-3-yl]-5-(2-cyanophenyl)-1H-pyrrole-2-carboxamide; N-[(3R)-1-azabicyclo[2.2.2]oct-3-yl]-5-(3-cyanophenyl)-1H-pyrrole-2-carboxamide; N-[(3R)-1-azabicyclo[2.2.2]oct-3-yl]-5-(4-cyanophenyl)-1H-pyrrole-2-carboxamide;

N-[(2S,3R)-2-methyl-1-azabicyclo[2.2.2]oct-3-yl]-5-bromo-1-methyl-1H-pyrrole-2-carboxamide; N-[(2S,3R)-2-methyl-1-azabicyclo[2.2.2]oct-3-yl]-5-[2-(methylthio)phenyl]-1-methyl-1H-pyrrole-2-carboxamide; N-[(2S,3R)-2-methyl-1-azabicyclo[2.2.2]oct-3-yl]-5-[4-(methylthio)phenyl]-1-methyl-1H-pyrrole-2-carboxamide; N-[(2S,3R)-2-methyl-1-azabicyclo[2.2.2]oct-3-yl]-5-phenyl-1H-pyrrole-2-carboxamide; N-[(2S,3R)-2-methyl-1-azabicyclo[2.2.2]oct-3-yl]-5-(2-fluorophenyl)-1-methyl-1H-pyrrole-2-carboxamide; N-[(2S,3R)-2-methyl-1-azabicyclo[2.2.2]oct-3-yl]-5-(3-fluorophenyl)-1-methyl-1H-pyrrole-2-carboxamide; N-[(2S,3R)-2-methyl-1-azabicyclo[2.2.2]oct-3-yl]-5-(4-fluorophenyl)-1-methyl-1H-pyrrole-2-carboxamide; N-[(2S,3R)-2-methyl-1-azabicyclo[2.2.2]oct-3-yl]-5-(2,3-difluorophenyl)-1-methyl-1H-pyrrole-2-carboxamide; N-[(2S,3R)-2-methyl-1-azabicyclo[2.2.2]oct-3-yl]-5-(2,4-difluorophenyl)-1-methyl-1H-pyrrole-2-carboxamide; N-[(2S,3R)-2-methyl-1-azabicyclo[2.2.2]oct-3-yl]-5-(2,6-difluorophenyl)-1-methyl-1H-pyrrole-2-carboxamide; N-[(2S,3R)-2-methyl-1-azabicyclo[2.2.2]oct-3-yl]-5-(3,4-difluorophenyl)-1-methyl-1H-pyrrole-2-carboxamide; N-[(2S,3R)-2-methyl-1-azabicyclo[2.2.2]oct-3-yl]-5-(3,5-difluorophenyl)-1-methyl-1H-pyrrole-2-carboxamide; N-[(2S,3R)-2-methyl-1-azabicyclo[2.2.2]oct-3-yl]-5-(2,4,6-trifluorophenyl)-1-methyl-1H-pyrrole-2-carboxamide; N-[(2S,3R)-2-methyl-1-azabicyclo[2.2.2]oct-3-yl]-5-(2-chlorophenyl)-1-methyl-1H-pyrrole-2-carboxamide; N-[(2S,3R)-2-methyl-1-azabicyclo[2.2.2]oct-3-yl]-5-(3-chlorophenyl)-1-methyl-1H-pyrrole-2-carboxamide; N-[(2S,3R)-2-methyl-1-azabicyclo[2.2.2]oct-3-yl]-5-(4-chlorophenyl)-1-methyl-1H-pyrrole-2-carboxamide; N-[(2S,3R)-2-methyl-1-azabicyclo[2.2.2]oct-3-yl]-5-(2,4-dichlorophenyl)-1-methyl-1H-pyrrole-2-carboxamide; N-[(2S,3R)-2-methyl-1-azabicyclo[2.2.2]oct-3-yl]-5-(3,4-dichlorophenyl)-1-methyl-1H-pyrrole-2-carboxamide; N-[(2S,3R)-2-methyl-1-azabicyclo[2.2.2]oct-3-yl]-5-(3,5-dichlorophenyl)-1-methyl-1H-pyrrole-2-carboxamide; N-[(2S,3R)-2-methyl-1-azabicyclo[2.2.2]oct-3-yl]-5-(2-bromophenyl)-1-methyl-1H-pyrrole-2-carboxamide; N-[(2S,3R)-2-methyl-1-azabicyclo[2.2.2]oct-3-yl]-5-(3-bromophenyl)-1-methyl-1H-pyrrole-2-carboxamide; N-[(2S,3R)-2-methyl-1-azabicyclo[2.2.2]oct-3-yl]-5-(4-bromophenyl)-1-methyl-1H-pyrrole-2-carboxamide; N-[(2S,3R)-2-methyl-1-azabicyclo[2.2.2]oct-3-yl]-5-(2-hydroxyphenyl)-1-methyl-1H-pyrrole-2-carboxamide; N-[(2S,3R)-2-methyl-1-azabicyclo[2.2.2]oct-3-yl]-5-(3-hydroxyphenyl)-1-methyl-1H-pyrrole-2-carboxamide; N-[(2S,3R)-2-methyl-1-azabicyclo[2.2.2]oct-3-yl]-5-(4-hydroxyphenyl)-1-methyl-1H-pyrrole-2-carboxamide; N-[(2S,3R)-2-methyl-1-azabicyclo[2.2.2]oct-3-yl]-5-(2-methoxyphenyl)-1-methyl-1H-pyrrole-2-carboxamide; N-[(2S,3R)-2-methyl-1-azabicyclo[2.2.2]oct-3-yl]-5-(3-methoxyphenyl)-1-methyl-1H-pyrrole-2-carboxamide; N-[(2S,3R)-2-methyl-1-azabicyclo[2.2.2]oct-3-yl]-5-(4-methoxyphenyl)-1-methyl-1H-pyrrole-2-carboxamide; N-[(2S,3R)-2-methyl-1-azabicyclo[2.2.2]oct-3-yl]-5-(2-methylphenyl)-1-methyl-1H-pyrrole-2-carboxamide; N-[(2S,3R)-2-methyl-1-azabicyclo[2.2.2]oct-3-yl]-5-(3-methylphenyl)-1-methyl-1H-pyrrole-2-carboxamide; N-[(2S,3R)-2-methyl 1-azabicyclo[2.2.2]oct-3-yl]-5-(4-methylphenyl)-1-methyl-1H-pyrrole-2-carboxamide;

N-[(2S,3R)-2-methyl-1-azabicyclo[2.2.2]oct-3-yl]-5-(2-methyaminophenyl)-1-methyl-1H-pyrrole-2-carboxamide; N-[(2S,3R)-2-methyl-1-azabicyclo[2.2.2]oct-3-yl]-5-(3-methylaminophenyl)-1-methyl-1H-pyrrole-2-carboxamide; N-[(2S,3R)-2-methyl-1-azabicyclo[2.2.2]oct-3-yl]-5-(4-methylaminophenyl)-1-methyl-1H-pyrrole-2-carboxamide; N-[(2S,3R)-2-methyl-1-azabicyclo[2.2.2]oct-3-yl]-5-(2-nitrophenyl)-1-methyl-1H-pyrrole-2-carboxamide; N-[(2S,3R)-2-methyl-1-azabicyclo[2.2.2]oct-3-yl]-5-(3-nitrophenyl)-1-methyl-1H-pyrrole-2-carboxamide; N-[(2S,3R)-2-methyl-1-azabicyclo[2.2.2]oct-3-yl]-5-(4-nitrophenyl)-1-methyl-1H-pyrrole-2-carboxamide; N-[(2S,3R)-2-methyl-1-azabicyclo[2.2.2]oct-3-yl]-5-(2-aminophenyl)-1-methyl-1H-pyrrole-2-carboxamide; N-[(2S,3R)-2-methyl-1-azabicyclo[2.2.2]oct-3-yl]-5-(3-aminophenyl)-1-methyl-1H-pyrrole-2-carboxamide; N-[(2S,3R)-2-methyl-1-azabicyclo[2.2.2]oct-3-yl]-5-(4-aminophenyl)-1-methyl-1H-pyrrole-2-carboxamide; N-[(2S,3R)-2-methyl-1-azabicyclo[2.2.2]oct-3-yl]-5-[2-(acetylamino)phenyl]-1-methyl-1H-pyrrole-2-carboxamide; N-[(2S,3R)-2-methyl-1-azabicyclo[2.2.2]oct-3-yl]-5-[3-(acetylamino)phenyl]-1-methyl-1H-pyrrole-2-carboxamide; N-[(2S,3R)-2-methyl-1-azabicyclo[2.2.2]oct-3-yl]-5-[4-(acetylamino)phenyl]-1-methyl-1H-pyrrole-2-carboxamide; N-[(2S,3R)-2-methyl-1-azabicyclo[2.2.2]oct-3-yl]-5-(pyrid-2-yl)-1-methyl-1H-pyrrole-2-carboxamide; N-[(2S,3R)-2-methyl-1-azabicyclo[2.2.2]oct-3-yl]-5-(pyrid-3-yl)-1-methyl-1H-pyrrole-2-carboxamide; N-[(2S,3R)-2-methyl-1-azabicyclo[2.2.2]oct-3-yl]-5-pyridin-4-yl-1-methyl-1H-pyrrole-2-carboxamide; N-[(2S,3R)-2-methyl-1-azabicyclo[2.2.2]oct-3-yl]-5-(3-fluoropyrid-2-yl)-1-methyl-1H-pyrrole-2-carboxamide; N-[(2S,3R)-2-methyl-1-azabicyclo[2.2.2]oct-3-yl]-5-(4-fluoropyrid-2-yl)-1-methyl-1H-pyrrole-2-carboxamide; N-[(2S,3R)-2-methyl-1-azabicyclo[2.2.2]oct-3-yl]-5-(5-fluoropyrid-2-yl)-1-methyl-1H-pyrrole-2-carboxamide; N-[(2S,3R)-2-methyl-1-azabicyclo[2.2.2]oct-3-yl]-5-(6-fluoropyrid-2-yl)-1-methyl-1H-pyrrole-2-carboxamide; N-[(2S,3R)-2-methyl-1-azabicyclo[2.2.2]oct-3-yl]-5-(2-fluoropyrid-3-yl)-1-methyl-1H-pyrrole-2-carboxamide; N-[(2S,3R)-2-methyl-1-azabicyclo[2.2.2]oct-3-yl]-5-(4-fluoropyrid-3-yl)-1-methyl-1H-pyrrole-2-carboxamide; N-[(2S,3R)-2-methyl-1-azabicyclo[2.2.2]oct-3-yl]-5-(5-fluoropyrid-3-yl)-1-methyl-1H-pyrrole-2-carboxamide; N-[(2S,3R)-2-methyl-1-azabicyclo[2.2.2]oct-3-yl]-5-(6-fluoropyrid-3-yl)-1-methyl-1H-pyrrole-2-carboxamide; N-[(2S,3R)-2-methyl-1-azabicyclo[2.2.2]oct-3-yl]-5-(2-fluoropyrid-4-yl)-1-methyl-1H-pyrrole-2-carboxamide; N-[(2S,3R)-2-methyl-1-azabicyclo[2.2.2]oct-3-yl]-5-(3-fluoropyrid-4-yl)-1-methyl-1H-pyrrole-2-carboxamide; N-[(2S,3R)-2-methyl-1-azabicyclo[2.2.2]oct-3-yl]-5-(2-cyanophenyl)-1-methyl-1H-pyrrole-2-carboxamide; N-[(2S,3R)-2-methyl-1-azabicyclo[2.2.2]oct-3-yl]-5-(3-cyanophenyl)-1-methyl-1H-pyrrole-2-carboxamide; N-[(2S,3R)-2-methyl-1-azabicyclo[2.2.2]oct-3-yl]-5-(4-cyanophenyl)-1-methyl-1H-pyrrole-2-carboxamide; N-[(2S,3R)-2-methyl-1-azabicyclo[2.2.2]oct-3-yl]-5-(2-fluorophenyl)-1H-pyrrole-2-carboxamide; N-[(2S,3R)-2-methyl-1-azabicyclo[2.2.2]oct-3-yl]-5-(3-fluorophenyl)-1H-pyrrole-2-carboxamide; N-[(2S,3R)-2-methyl-1-azabicyclo[2.2.2]oct-3-yl]-5-(4-fluorophenyl)-1H-pyrrole-2-carboxamide; N-[(2S,3R)-2-methyl-1-azabicyclo[2.2.2]oct-3-yl]-5-(3,5-difluorophenyl)-1H-pyrrole-2-carboxamide; N-[(2S,3R)-2-methyl-1-azabicyclo[2.2.2]oct-3-yl]-5-(3,4-difluorophenyl)-1H-pyrrole-2-carboxamide; N-[(2S,3R)-2-methyl-1-azabicyclo[2.2.2]oct-3-yl]-5-(2,4-difluorophenyl)-1H-pyrrole-2-carboxamide; N-[(2S,3R)-2-methyl-1-azabicyclo[2.2.2]oct-3-yl]-5-(2-chlorophenyl)-1H-pyrrole-2-carboxamide; N-[(2S,3R)-2-methyl-1-azabicyclo[2.2.2]oct-3-yl]-5-(3-chlorophenyl)-1H-pyrrole-2-carboxamide; N-[(2S,3R)-2-methyl-1-azabicyclo[2.2.2]oct-3-yl]-5-(4-chlorophenyl)-1H-pyrrole-2-carboxamide; N-[(2S,3R)-2-methyl-1-azabicyclo[2.2.2]oct-3-yl]-5-(3,5-dichlorophenyl)-1H-pyrrole-2-carboxamide; N-[(2S,3R)-2-methyl-1-azabicyclo[2.2.2]oct-3-yl]-5-(3,4-dichlorophenyl)-1H-pyrrole-2-carboxamide; N-[(2S,3R)-2-methyl-1-azabicyclo[2.2.2]oct-3-yl]-5-(2,4-dichlorophenyl)-1H-pyrrole-2-carboxamide; N-[(2S,3R)-2-methyl-1-azabicyclo[2.2.2]oct-3-yl]-5-(2-bromophenyl)-1H-pyrrole-2-carboxamide; N-[(2S,3R)-2-methyl-1-azabicyclo[2.2.2]oct-3-yl]-5-(3-bromophenyl)-1H-pyrrole-2-carboxamide; N-[(2S,3R)-2-methyl-1-azabicyclo[2.2.2]oct-3-yl]-5-(4-bromophenyl)-1H-pyrrole-2-carboxamide; N-[(2S,3R)-2-methyl-1-azabicyclo[2.2.2]oct-3-yl]-5-(2-hydroxyphenyl)-1H-pyrrole-2-carboxamide; N-[(2S,3R)-2-methyl-1-azabicyclo[2.2.2]oct-3-yl]-5-(3-hydroxyphenyl)-1H-pyrrole-2-carboxamide; N-[(2S,3R)-2-methyl-1-azabicyclo[2.2.2]oct-3-yl]-5-(4-hydroxyphenyl)-1H-pyrrole-2-carboxamide; N-[(2S,3R)-2-methyl-1-azabicyclo[2.2.2]oct-3-yl]-5-(2-methoxyphenyl)-1H-pyrrole-2-carboxamide; N-[(2S,3R)-2-methyl-1-azabicyclo[2.2.2]oct-3-yl]-5-(3-methoxyphenyl)-1H-pyrrole-2-carboxamide; N-[(2S,3R)-2-methyl-1-azabicyclo[2.2.2]oct-3-yl]-5-(4-methoxyphenyl)-1H-pyrrole-2-carboxamide; N-[(2S,3R)-2-methyl-1-azabicyclo[2.2.2]oct-3-yl]-5-(2-methylphenyl)-1H-pyrrole-2-carboxamide; N-[(2S,3R)-2-methyl-1-azabicyclo[2.2.2]oct-3-yl]-5-(3-methylphenyl)-1H-pyrrole-2-carboxamide; N-[(2S,3R)-2-methyl-1-azabicyclo[2.2.2]oct-3-yl]-5-(4-methylphenyl)-1H-pyrrole-2-carboxamide; N-[(2S,3R)-2-methyl-1-azabicyclo[2.2.2]oct-3-yl]-5-(2-methyaminophenyl)-1H-pyrrole-2-carboxamide; N-[(2S,3R)-2-methyl-1-azabicyclo[2.2.2]oct-3-yl]-5-(3-methylaminophenyl)-1H-pyrrole-2-carboxamide; N-[(2S,3R)-2-methyl-1-azabicyclo[2.2.2]oct-3-yl]-5-(4-methylaminophenyl)-1H-pyrrole-2-carboxamide; N-[(2S,3R)-2-methyl-1-azabicyclo[2.2.2]oct-3-yl]-5-(2-nitrophenyl)-1H-pyrrole-2-carboxamide; N-[(2S,3R)-2-methyl-1-azabicyclo[2.2.2]oct-3-yl]-5-(3-nitrophenyl)-1H-pyrrole-2-carboxamide; N-[(2S,3R)-2-methyl-1-azabicyclo[2.2.2]oct-3-yl]-5-(4-nitrophenyl)-1H-pyrrole-2-carboxamide; N-[(2S,3R)-2-methyl-1-azabicyclo[2.2.2]oct-3-yl]-5-(2-aminophenyl)-1H-pyrrole-2-carboxamide; N-[(2S,3R)-2-methyl-1-azabicyclo[2.2.2]oct-3-yl]-5-(3-aminophenyl)-1H-pyrrole-2-carboxamide; N-[(2S,3R)-2-methyl-1-azabicyclo[2.2.2]oct-3-yl]-5-(4-aminophenyl)-1H-pyrrole-2-carboxamide; N-[(2S,3R)-2-methyl-1-azabicyclo[2.2.2]oct-3-yl]-5-[2-(acetylamino)phenyl]-1H-pyrrole-2-carboxamide; N-[(2S,3R)-2-methyl-1-azabicyclo[2.2.2]oct-3-yl]-5-[3-(acetylamino)phenyl]-1H-pyrrole-2-carboxamide; N-[(2S,3R)-2-methyl-1-azabicyclo[2.2.2]oct-3-yl]-5-[4-(acetylamino)phenyl]-1H-pyrrole-2-carboxamide; N-[(2S,3R)-2-methyl-1-azabicyclo[2.2.2]oct-3-yl]-5-

(pyrid-2-yl)-1H-pyrrole-2-carboxamide; N-[(2S,3R)-2-methyl-1-azabicyclo[2.2.2]oct-3-yl]-5-(pyrid-3-yl)-1H-pyrrole-2-carboxamide; N-[(2S,3R)-2-methyl-1-azabicyclo[2.2.2]oct-3-yl]-5-(pyrid-4-yl)-1H-pyrrole-2-carboxamide; N-[(2S,3R)-2-methyl-1-azabicyclo[2.2.2]oct-3-yl]-5-(3-fluoropyrid-2-yl)-1H-pyrrole-2-carboxamide; N-[(2S,3R)-2-methyl-1-azabicyclo[2.2.2]oct-3-yl]-5-(4-fluoropyrid-2-yl)-1H-pyrrole-2-carboxamide; N-[(2S,3R)-2-methyl-1-azabicyclo[2.2.2]oct-3-yl]-5-(5-fluoropyrid-2-yl)-1H-pyrrole-2-carboxamide; N-[(2S,3R)-2-methyl-1-azabicyclo[2.2.2]oct-3-yl]-5-(6-fluoropyrid-2-yl)-1H-pyrrole-2-carboxamide; N-[(2S,3R)-2-methyl-1-azabicyclo[2.2.2]oct-3-yl]-5-(2-fluoropyrid-3-yl)-1H-pyrrole-2-carboxamide; N-[(2S,3R)-2-methyl-1-azabicyclo[2.2.2]oct-3-yl]-5-(4-fluoropyrid-3-yl)-1H-pyrrole-2-carboxamide; N-[(2S,3R)-2-methyl-1-azabicyclo[2.2.2]oct-3-yl]-5-(5-fluoropyrid-3-yl)-1H-pyrrole-2-carboxamide; N-[(2S,3R)-2-methyl-1-azabicyclo[2.2.2]oct-3-yl]-5-(6-fluoropyrid-3-yl)-1H-pyrrole-2-carboxamide; N-[(2S,3R)-2-methyl-1-azabicyclo[2.2.2]oct-3-yl]-5-(2-fluoropyrid-4-yl)-1H-pyrrole-2-carboxamide; N-[(2S,3R)-2-methyl-1-azabicyclo[2.2.2]oct-3-yl]-5-(3-fluoropyrid-4-yl)-1H-pyrrole-2-carboxamide; N-[(2S,3R)-2-methyl-1-azabicyclo[2.2.2]oct-3-yl]-5-(2-cyanophenyl)-1H-pyrrole-2-carboxamide; N-[(2S,3R)-2-methyl-1-azabicyclo[2.2.2]oct-3-yl]-5-(3-cyanophenyl)-1H-pyrrole-2-carboxamide; N-[(2S,3R)-2-methyl-1-azabicyclo[2.2.2]oct-3-yl]-5-(4-cyanophenyl)-1H-pyrrole-2-carboxamide; or a pharmaceutically acceptable salt thereof.

50. The method according to claim 49, wherein said compound(s) is(are) administered rectally, topically, orally, sublingually, or parenterally.

51. The method according to claim 49, wherein said compound(s) is(are) administered from about 0.001 to about 100 mg/kg of body weight of said mammal per day.

52. The method according to claim 49, wherein said compound(s) is(are) administered from about 0.1 to about 50 mg/kg of body weight of said mammal per day.

* * * * *